US006395734B1

(12) United States Patent
Tang et al.

(10) Patent No.: US 6,395,734 B1
(45) Date of Patent: *May 28, 2002

(54) PYRROLE SUBSTITUTED 2-INDOLINONE PROTEIN KINASE INHIBITORS

(75) Inventors: Peng Cho Tang, Moraga; Li Sun, Foster City; Gerald McMahon, Kenwood, all of CA (US)

(73) Assignee: Sugen, Inc., South San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/322,297

(22) Filed: May 28, 1999

Related U.S. Application Data

(60) Provisional application No. 60/087,310, filed on May 29, 1998, and provisional application No. 60/116,106, filed on Jan. 15, 1999.

(51) Int. Cl.[7] ............... A61K 31/4045; A61K 31/5375; C07D 413/04; C07D 209/14

(52) U.S. Cl. .................... 514/235.2; 514/414; 544/144; 548/468

(58) Field of Search .................. 544/144; 548/468; 514/235.2, 414

(56) References Cited

U.S. PATENT DOCUMENTS

| | | |
|---|---|---|
| 3,308,134 A | 3/1967 | Janis |
| 4,002,749 A | 1/1977 | Rovnyak .................... 424/246 |
| 4,053,613 A | 10/1977 | Rovnyak et al. |
| 4,966,849 A | 10/1990 | Vallee et al. ................. 435/199 |
| 5,217,999 A | 6/1993 | Levitzki et al. ............. 514/613 |
| 5,302,606 A | 4/1994 | Spada et al. ................ 514/357 |
| 5,330,992 A | 7/1994 | Eissenstat et al. .......... 514/312 |
| 5,786,488 A | 7/1998 | Tang ........................... 548/455 |
| 5,792,783 A | 8/1998 | Tang ........................... 514/397 |
| 5,840,745 A | 11/1998 | Buzzetti et al. ............. 514/414 |
| 5,880,141 A | 3/1999 | Tang ........................... 514/339 |
| 5,883,113 A | 3/1999 | Tang ........................... 514/418 |
| 5,883,116 A | 3/1999 | Tang ........................... 514/418 |
| 5,886,020 A | 3/1999 | Tang ........................... 514/418 |
| RE36,256 E | 7/1999 | Spada et al. ................. 514/249 |

FOREIGN PATENT DOCUMENTS

| | | |
|---|---|---|
| EP | 0 252 731 A1 | 1/1988 |
| EP | 0 566 226 A1 | 10/1993 |
| WO | 91/15495 | 10/1991 |
| WO | 92/07830 | 5/1992 |
| WO | 92/20642 | 11/1992 |
| WO | 92/21660 | 12/1992 |
| WO | 93/23040 | 11/1993 |
| WO | 94/03427 | 2/1994 |
| WO | 94/10202 | 5/1994 |
| WO | 94/14808 | 7/1994 |
| WO | 95/24190 | 9/1995 |
| WO | 96/00226 | 1/1996 |
| WO | 96/16964 | 6/1996 |
| WO | 96/40116 | 12/1996 |
| WO | 98/07695 | 2/1998 |
| WO | 98/07835 | 2/1998 |
| WO | 98/24432 | 6/1998 |
| WO | 98/38984 | 9/1998 |
| WO | 98/45708 | 10/1998 |
| WO | 98-50356 | 11/1998 |
| WO | 98/56376 | 12/1998 |
| WO | 99/61422 | 2/1999 |
| WO | 99/10325 | 9/1999 |
| WO | 9948868 | 9/1999 |

OTHER PUBLICATIONS

Akbasak et al., "Oncogenes: cause of conquence in the development of glial tumors," *J. Neurol. Sci.* 111:119–133 (1992).

Andreani et al., "Synthesis and potential coanthracyclinic activity of substituted 3–(5–imidazo[2,1–b] thiazolylmethylene–2–indolinones," *Eur. J. Med. Chem.* 32:919–924 (1997).

Andreani et al., "In vivo cardiotonic activity ofpyridylmethylene–2–indolinines"*Arzneimittel–Forschung Drug Research* 48(11):727–729 (1998).

Arteaga et al., "Blockade of the Type I Somatomedin Receptor Inhibits Growth of Human Breast Cancer Cells in Athymic Mice," *J. Clin. Invest.* 84:1418–1423 (1989).

Arvidsson et al., "Tyr–716 in the Platelet–Derived Growth Factor β–Receptor Kinase Insert is Involved in GRB2 Binding and Ras Activation," *Molecular and Cellular Biology* 14:6715–6726 (1994).

Baserga, "Oncogenes and the Strategy of Growth Factors," *Cell* 79:927–930 (1994).

Baserga, "The Insulin–like Growth Factor I Receptor: A Key to Tumor Growth?" *Cancer Research* 55:249–252 (1995).

Bolen et al., "The Src family of tyrosine protein kinases in hemopoietic signal transduction," *FASEB J.* 6:3403–3409 (1992).

Bolen, "Nonreceptor tyrosine protein kinases," *Oncogene* 8:2025–2031 (1993).

Bonner et al., "Structure and Biological Activity of Human Homologs of the raf/mil Oncogene," *Molecular and Cellular Biology* 5:1400–1407 (1985).

Cance et al., "Novel Protein Kinases Expressed in Human Breast Cancer," *Int. J. Cancer* 54:571–577 (1993).

Carpenedo et al., "Identification and Measurement of Oxindole (2–indolinone) in the Mammalian Brain and Other Rat Organs"*Analytical Biochemistry* 244:74–79 (1997).

(List continued on next page.)

Primary Examiner—Robert W. Ramsuer
Assistant Examiner—Sonya Wright
(74) Attorney, Agent, or Firm—Brobeck Phleger & Harrison

(57) ABSTRACT

The present invention relates to novel pyrrole substituted 2-indolinone compounds and physiologically acceptable salts and prodrugs thereof which modulate the activity of protein kinases and therefore are expected to be useful in the prevention and treatment of protein kinase related cellular disorders such as cancer.

23 Claims, No Drawings-

OTHER PUBLICATIONS

Claesson–Welsh, "Signal Transduction by the PDGF Receptors," *Progress in Growth Factor Research* 5:37–54 (1994).

Coppola et al., "A Functional Insulin–Like Growth Factor I Receptor is Required for the Mitogenic and Transforming Activities of the Epidermal Growth Factor Receptor," *Molecular and Cellular Biology* 14:4588–4595 (1994).

Damiani et al., "Inhibition of Copper–Mediated Low Density Lipoprotein Peroxidation by Quinoline and Indolinone Nitroxide Radicals" *Biochemical Pharmacology* 48(6):1155–1161 (1994).

Davis et al., "Synthesis and Microbiological Properties of 3–Amino–1–Hydroxy–2–Indolinone and Related Compounds,"*Journal of Medicinal Chemistry* 16(9):1043–1045 (1973).

De Vries et al., "The fms–Like Tyrosine Kinase, a Receptor for Vascular Endothelial Growth Factor," *Science* 255:989–991 (1992).

Decker et al., "A quick and simple method for the quantitation of lactate dehydrogenase release in measurements of cellular cytotoxicity and tumor necrosis factor (TNF) activity," *Journal of Immunological Methods* 15:61–69 (1988).

Dickson et al., "Tyrosine kinase receptor—nuclear protooncogene interactions in breast cancer," *Cancer Treatment Res.* 61:249–273 (1992).

Fantl et al., "Distinct Phosphotyrosines on a Growth Factor Receptor Bind to Specific Molecules That Mediate Different Signaling Pathways," *Cell* 69:413–423 (1992).

Fendly et al., "Characteristerization of Murine Monoclonal Antibodies Reactive to Either the Human Epidermal Growth Factor Receptor or HER2–neu Gene Product," *Cancer Research* 50:1550–1558 (1990) mistakenly referredto as Fendley).

Ferrara and Henzel, "Pituitary Fillicular Cells Secrete a Novel Heparin–Binding Growth Factor Specific for Vascular Endothelial Cells," *Biochemical and Biophysical Research Communications* 161:851–858 (1989).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Floege et al., "Heparin suppresses mesangial cell proliferation and matrix expansion in experimental mesangioproliferative glomerulonephritis," *Kidney International* 43:369–380 (1993).

Folkman and Shing, "Angiogenesis," *J. Biol. Chem.* 267:10931–10934 (1992).

Folkman, "Ch. 24. Angiogenesis," *Congress of Thrombosis and Haemostasis* (Verstraete et al., eds.) Leuven University Press, Leuven pp. 583–596 (1987).

Folkman, "Tumor Angiogenesis, Therapeutic Implications," *New England J. Medicine* 285:1182–1186 (1971).

Folkman, "What is evidence that tumors are angiogenesis dependent?" Journal of National Cancer Institute 82:4–6 (1990).

Gazit et al., "Tyrphostins. 2. Heterocyclic and alpha–substituted benzylidenmalononitrile tyrphostins as potent inhibitors of EGF receptor and ErbB2–neu tyrosine kinases," *J. Med. Chem.* 34(6):1896–1907 (1991).

Gennaro (editor), *Remington's Pharmaceutical Sciences* (1990) (Table of Contents Only).

Goldring and Goldring, "Cytokines and Cell Growth Control," *Critical Reviews in Eukaryotic Gene Expression* 1:301–326 (1991).

Graziani et al., "Hepatocyte Growth Factor/Scatter Factor Stimulates the Ras–Guanine Nucleotide Exchanger", *The Journal of Biological Chemistry* 268(13):9165–9168 (1993).

Honegger et al., "Point Mutation at the ATP Binding Site of EGF Receptor Abolishes Protein–Tyrosine Kinase Activity and Alters Cellular Routing," *Cell* 51:199–209 (1987).

Houck et al., "Dual Regulation of Vascular Endothelial Growth Factor Bioavailability by Genetic and Proteolytic Mechanisms," *J. Biol. Chem.* 267:26031–26037 (1992).

Hu et al., "Interaction of Phosphatidylinositol 3–Kinase–Associated p85 with Epidermal Growth Factor and Platelet–Derived Growth Factor Receptors," *Molecular and Cellular Biology* 12(3):981–990 (1992).

Jellinek et al., "Inhibition of Receptor Binding by High–Affinity RNA Ligands to Vascular Endothelial Growth Factor," *Biochemistry* 33:10450–10456 (1994).

Kashishian and Cooper, "Phosphorylation Sites at the C–terminus of the Platelet–Derived Growth Factor Receptor Bind Phospholipase Cγ1," *Molecular Biology of the Cell* 4:49–57 (1993).

Kashishian et al., "Phosphorylation sites in the PDGF receptor with different specificities for binding GAP and P13 kinase in vivo," *The EMBO Journal* 11(4):1373–1382 (1992).

Kato et al., "Simultaneous Determination of Amfenac Sodium and its Metabolite (7–Benzoyl–2–Oxindole) in Human Plasma by High–Performance Liquid Chromatography," *Journal of Chromatography* 616:67–71 (1993).

Kazlauskas et al., "The 64–kDa protein that associates with the platelet–derived growth factor receptor β subunit via Tyr–1009 is the SH2–containing phosphotyrosine phosphatase Syp," *Proc. Natl. Acad. Sci. USA* 90:6939–6942 (1993).

Kendall and Thomas, "Inhibition of vascular endothelial cell growth factor activity by an endogenously encoded soluble receptor," *Proc. Natl. Acad. Sci. USA* 90:10705–10709 (1993).

Kim et al., "Inhibition of vascular endothelial growth factor–induced angiogenesis suppresses tumour growth in vivo," *Nature* 362:841–844 (1993).

Kinsella et al., "Protein Kinase C Regulates Endothelial Cell Tube Formation on Basement Membrane Matrix, Matrigel," *Exp. Cell Research* 199:56–62 (1992).

Klagsbrun and Soker, "VEGF/VPF: the angiogenesis factor found?" *Current Biology* 3:699–702 (1993).

Koch et al., "SH2 and SH3 Domains: Elements That Control Interactions of Cytoplasmic Signaling Proteins," *Science* 252:668–674 (1991).

Komada and Kitamura, "The cell dissociation and motility triggered by scatter factor/hepatocyte growth factor are mediated through the cytoplasmic domain of the c–Met receptor," *Oncogene* 8:2381–2390 (1993).

Korc et al., "Overexpression of the Epidermal Growth Factor Receptor in Human Pancreatic Cancer is Associated with Concomitant Increases in the Levels of Epidermal Growth Factor and Transforming Growth Factor Alpha," *J. Clin. Invest.* 90:1352–1360 (1992).

Korzeniewski and Callewaert, "An Enzyme–Release Assay for Natural Cytotoxicity[1]," *J. Immunol. Methods* 64:313–320 (1983).

Kumabe et al., "Amplification of α–platelet–derived growth factor receptor gene lacking an exon coding for a portion of the extracellular region in a primary brain tumor of glial origin," *Oncogene* 7:627–633 (1992).

Lee and Donoghue, "Intracellular retention of membrane–anchored v–sis protein abrogates autocrine signal transduction," *Journal of Cell Biology* 118:1057–1070 (1992).

Levitzki et al., "Tyrosine kinase inhibition: An approach to drug development," *Science* 267:1782–1788 (1995).

Maass et al., "Viral resistance to the thiazolo–iso–indolinoes, a new class of nonnucleoside inhibitors of human immunodeficiency virus type 1 reverse transcriptase", *Antimicrobial Agents and Chemotherapy* 37(12) 2612–2617 (1993).

Macauley et al., "Autocrine function for insulin–like growth factor I in human small cell lung cancer cell lines and fresh tumor cells," *Cancer Research* 50:2511–2517 (1990).

Mariani et al., "Inhibition of angiogenesis by PCE 26806, a potent tyrosine kinase inhibitor," Experimental Therapeutics—Proceedings of the American Association for Cancer Research 35:381 at abstract No. 2268 (Mar. 1994).

Millauer et al., "High Affintiy VEGF Binding and Developmental Expression Suggest Flk–1 as a Major Regulator of Vasculogenesis and Angiogenesis," *Cell* 72:835–846 (1993).

Mohammadi et al., "Structures of the tyrosine kinase domain of fibroblast growth factor receptor in complex with inhibitors,"*Science* 276(5314):955–960 (1997).

Moreto et al., "3,3–bis(4–hydroxyphenyl)–7–methyl–2indolinone (BHMI), the active metabolite of the laxative sulisatin" *Arzneimittel–Forschung Drug Research* 29(11): 1561–1567 (1979).

Morrison et al., "Signal Transduction From Membrane to Cytoplasm: Growth Factors and Membrane–Bound Oncogene Products Increase Raf–1 Phosphorylation and Associated Protein Kinase Activity," *Proc. Natl. Acad. Sci. USA* 85:8855–8859 (1988).

Mosmann, "Rapid Colorimetric Assay for Cellular Growth and Survival: Application to Proliferation and Cytotoxicity Assays," *J. Immunol. Methods* 65:55–63 (1983).

Nishimura et al., "Two Signaling Molecules Share a Phosphotyrosine–Containing Binding Site in the Platelet–Derived Growth Factor Receptor," *Molecular and Cellular Biology* 13:6889–6896 (1993).

Plowman et al., "Receptor Tyrosine Kinases as Targets for Drug Intervention," *DN&P* 7(6):334–339 (1994).

Quinn et al., "Fetal liver kinase 1 is a receptor for vascular endothelial growth factor and is selectively expressed in vascular endothelium," *Proc. Natl. Acad. Sci. USA* 90:7533–7537 (1993).

Rozakis–Adcock et al., "Association of the Shc and Grb2/Sem5 SH2–containing proteins is implicated in activation of the Ras pathway by tyrosine kinases," *Nature* 360:689–692 (1992).

Rygaard and Povlsen, "Heterotransplantation of a Human Malignant Tumour to 'Nude' Mice," *Act path. Microbiol. scand.* 77:758–760 (1969).

Sandberg–Nordqvist et al., "Characterization of Insulin–Like Growth Factor 1 in Human Primary Brain Tumors," *Cancer Research* 53:2475–2478 (1993).

Schlessinger and Ullrich, "Growth Factor Signalling by Receptor Tyrosine Kinases," *Neuron* 9:383–391 (1992).

Shibuya et al., "Nucleotide sequence and expression of a novel human receptor–type tyrosine kinase gene (flt) closely realted to the fms family," *Oncogene* 5:519–524 (1990).

Singh et al., "Small molecule inhibitors of tyrosine kinase activity," *Expert Opinion on Therapeutic Patent* 5(8):805–817 (1995).

Singh et al., "Synthesis and Anticonvulsant Activity of the New 1 Substituted 1'–Methyl–3–Chloro–2–Oxosprio(Azetidin–3', 4–Indol–2'Ones)," *Bollettino Chimico Farmaceutico* 133:76–79 (1994).

Slamon et al., "Studies of the HER–2/neu Proto–oncogene in Human Breast and Ovarian Cancer," *Science* 244:707–712 (1989).

Songyang et al., "SH2 Domains Recognize Specific Phosphopeptide Sequences," *Cell* 72:767–778 (1993).

Songyang et al., "Specific Motifs Recognized by the SH2 Domains of Csk, 3BP2, fps/fes, GRB–2, HCP, SHC, Syk and Vav," *Molecular and Cellular Biology* 14:2777–2785 (1994).

Superti–Furga et al., "A functional screen in yeast for regulators and antagonizers of heterologous protein tyrosine kinases," *Nature Biotech* 14:600–605 (1996).

Superti–Furga et al., "Csk inhibition of c–Src activity requires both the SH2 and SH3 domains of Src," *EMBO J.* 12:2625–2634 (1993).

Takano et al., "Inhibition of angiogenesis by a novel diaminoanthraquinone that inhibits protein kinase C," *Mol. Bio. Cell* 4:358A at abstract No. 2076 (1993).

Torp et al., "Expression of the Epidermal Growth Factor Receptor Gene in Human Brain Metastases," *AMPIS* 100:713–719 (1992).

Tuzi et al., "Expression of growth factor receptors in human brain tumours," *Br. J. Cancer* 63:227–233 (1991).

Twamley–Stein et al., "The Src family tyrosine kinases are required for platelet–derived growth factor–mediated signal transduction in NIH 3T3 cells," *Proc. Natl. Acad. Sci.* 90:7696–7700 (1993).

Vaisman et al., "Characterization of the Receptors for Vascular Endothelial Growth Factor," *J. Biol. Chem.* 265:19461–19466 (1990).

Voller et al., "Ch. 45—Enzyme–Linked Immunosorbent Assay," in *Manual of Clinical Immunology*, $2^{nd}$ edition, Rose and Friedman editors, American Society of Microbiology, Washington, D.C., pp. 359–371 (1980).

Weidner et al., "Tumor angiogenesis and metastasis–correlation in invasive breast carcinoma," *New England Journal of Medicine* 324(1):1–8 (1991).

Wright et al., "Inhibition of Angiogenesis in Vitro and In Ovo With an Inhibitor of Cellular Protein Kinases, MDL 27032," *J. Cellular Physiology* 152:448–457 (1992).

Spada et al., "Small molecule inhibitors of tyrosine kinase activity," *Expert Opinion on Therapeutic Patent* 5(8):805–817(1995).

European Search Report of 99927120.

Sun, et al. "Design, Synthesis, and Evaluation of Substituted 3–[(3–or 4–Carbonxyethylpyrrol–2–yl)methylidenyl]indolin–2–ones as lnhibitors of VEGF,FGF, and PDGF Receptor Tyrosine Kinases," *J. Med. Chem.* 42:5120–5130 (1999)©American Chemical Society.

Database Caplus, An 1998: 151222, abstract for Mohammadi et al., Crystal structures of a parotein tyrosine kinasem WO 98/07835 (Feb. 26, 1998).

Database Caplus, on STN, An 1998; 147306, abstract for Tang et al. Indolinone combinatorial libraries and related products and mathods for the treatment of disease, WO 98/07695 (Feb. 26, 1998).

Database Caplus on STN, An 1997: 140244, abstract for Tang et al., Indolinone compounds capable of modulating tyrosine kinase signal trasductio, WO 96/40116 (Dec. 19, 1996).

Sun et al., "Synthesis and biological evaluations of 3–substituted indolin–2–ones: A novel class of tyrosine kinase inhibitors that exhibit selectivity toward particular receptor tyrosine kinases,", *J. Med. Chem.*41(14):2588–2603 (1998).

Traxler, "Protein tyrosine kinase inhibitors in cancer treatment", *Expert Opinion on Therapeutic Patents* 7(6):571–588 (1997).

Tsai et al., "The effect of 3,3–Di–Pyridyl–Methyl–1–Phenyl–2–indoline on the nerver Terminal Currents of Mouse Skeletal Muscles," *Neuropharmacology* 31(9);943–947 (1992).

Varma and Gupta, "Nucleophilic Reactions of 23–Methl–3–(4'–carbomethoxyphenyl)–4–quinazolinones with 2–Indolinones," *J. Indian Chem. Soc.*66:804–805 (1989).

Walker, "The Reduction of Insoindogenides, Nitro Compounds, and Pyridines in a Series of 2–Indolines," *J. Med. Chem.* 8(5):626–637 (1965).

Zaman et al., "Tyrosine Kinase Activity of Purified Recombinant Cytoplasmic Domain of Platelet–Derived Growth Factor β–Receptor (β–PDGFR) and Discovery of A Novel Inhibitor of Receptor Tyrosine Kinases," *Biochemical Pharmacology* 57(1):57–64 (1999).

Zhang et al., "Microtubule Effects of Welwistatin, a Cyanobacterial Indolinone that Circumvents Multiple Drugs Resistance," *Molecular Pharmacology* 49:228–294 (1996).

PYRROLE SUBSTITUTED 2-INDOLINONE PROTEIN KINASE INHIBITORS

RELATED APPLICATIONS

This application is related to and claims priority from U.S. Provisional patent application Ser. No. 60/087,310 filed May 29, 1998, and U.S. Provisional patent application Ser. No. 60/116,106, filed Jan. 15, 1999, both of which are incorporated by reference as if fully set forth herein.

INTRODUCTION

The present invention relates generally to organic chemistry, biochemistry, pharmacology and medicine. More particularly, it relates to novel pyrrole substituted 2-indolinone compounds, and their physiologically acceptable salts and prodrugs, which modulate the activity of protein kinases ("PKs") and thus are expected to exhibit a salutary effect against disorders related to abnormal PK activity.

BACKGROUND OF THE INVENTION

The following is offered as background information only and is not admitted to be prior art to the present invention.

PKs are enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on PK activity. Furthermore, abnormal PK activity has been related to a host of disorders, ranging from relatively non-life threatening diseases such as psoriasis to extremely virulent diseases such as glioblastoma (brain cancer).

The PKs can be conveniently be broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc. For a more complete discussion, see Schlessinger and Ullrich, *Neuron*, 9:303–391 (1992) which is incorporated by reference, including any drawings, as if fully set forth herein.

Growth factor receptors with PTK activity are known as receptor tyrosine kinases ("RTKs"). They comprise a large family of transmembrane receptors with diverse biological activity. At present, at least nineteen (19) distinct subfamilies of RTKs have been identified. An example of these is the subfamily designated the "HER" RTKs, which include EGFR (epithelial growth factor receptor), HER2, HER3 and HER4. These RTKs consist of an extracellular glycosylated ligand binding domain, a transmembrane domain and an intracellular cytoplasmic catalytic domain that can phosphorylate tyrosine residues on proteins.

Another RTK subfamily consists of insulin receptor (IR), insulin-like growth factor I receptor (IGF-1R) and insulin receptor related receptor (IRR). IR and IGF-1R interact with insulin, IGF-I and IGF-II to form a heterotetramer of two entirely extracellular glycosylated α subunits and two β subunits which cross the cell membrane and which contain the tyrosine kinase domain.

A third RTK subfamily is referred to as the platelet derived growth factor receptor ("PDGFR") group, which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences.

Another group which, because of its similarity to the PDGFR subfamily, is sometimes subsumed into the later group is the fetus liver kinase ("flk") receptor subfamily. This group is believed to be made of up of kinase insert domain-receptor fetal liver kinase-1 (KDR/FLK-1), flk-1R, flk-4 and fms-like tyrosine kinase 1 (flt-1).

A further member of the tyrosine kinase growth factor receptor family is the fibroblast growth factor ("FGF") receptor subgroup. This group consists of four receptors, FGFR1–4, and seven ligands, FGF1–7. While not yet well defined, it appears that the receptors consist of a glycosylated extracellular domain containing a variable number of immunoglobin-like loops and an intracellular domain in which the tyrosine kinase sequence is interrupted by regions of unrelated amino acid sequences.

Still another member of the tyrosine kinase growth factor receptor family is the vascular endothelial growth factor ("VEGF") receptor subgroup. VEGF is a dimeric glycoprotein similar to PDGF but has different biological functions and target cell specificity in vivo. In particular, VEGF is presently thought to play an essential role is vasculogenesis and angiogenesis.

A more complete listing of the known RTK subfamilies is described in Plowman et al., *DN&P*, 7(6):334–339 (1994) which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK," will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appear so far to be the largest group of CTKs and includes Src, Yes, Fyn, Lyn, Lck, Blk, Hck, Fgr and Yrk. For a more detailed discussion of CTKs, see Bolen, *Oncogene*, 8:2025–2031 (1993), which is incorporated by reference, including any drawings, as if fully set forth herein.

The serine/threonine kinases, STKs, like the CTKs, are predominantly intracellular although there are a few receptor kinases of the STK type. STKs are the most common of the cytosolic kinases; i.e., kinases that perform their function in that part of the cytoplasm other than the cytoplasmic organelles and cytoskelton. The cytosol is the region within the cell where much of the cell's intermediary metabolic and biosynthetic activity occurs; e.g., it is in the cytosol that proteins are synthesized on ribosomes.

RTKs, CTKs and STKs have all been implicated in a host of pathogenic conditions including, significantly, cancer. Other pathogenic conditions which have been associated with PTKs include, without limitation, psoriasis, hepatic cirrhosis, diabetes, angiogenesis, restenosis, ocular diseases, rheumatoid arthritis and other inflammatory disorders, immunological disorders such as autoimmune disease, cardiovascular disease such as atherosclerosis and a variety of renal disorders.

With regard to cancer, two of the major hypotheses advanced to explain the excessive cellular proliferation that drives tumor development relate to functions known to be PK regulated. That is, it has been suggested that malignant cell growth results from a breakdown in the mechanisms that control cell division and/or differentiation. It has been shown that the protein products of a number of proto-oncogenes are involved in the signal transduction pathways that regulate cell growth and differentiation. These protein products of proto-oncogenes include the extracellular growth factors, transmembrane growth factor PTK receptors (RTKs), cytoplasmic PTKs (CTKs) and cytosolic STKs, discussed above.

In view of the apparent link between PK-related cellular activities and wide variety of human disorders, it is no surprise that a great deal of effort is being expended in an attempt to identify ways to modulate PK activity. Some of these have involved biomimetic approaches using large molecules patterned on those involved in the actual cellular processes (e.g., mutant ligands (U.S. Pat. No. 4,966,849); soluble receptors and antibodies (App. No. WO 94/10202, Kendall and Thomas, *Proc. Nat'l Acad. Sci.*, 90:10705–09 (1994), Kim, et al., *Nature*, 362:841–844 (1993)); RNA ligands (Jelinek, et al., *Biochemistry*, 33:10450–56); Takano, et al., *Mol. Bio. Cell* 4:358A (1993); Kinsella, et al., *Exp. Cell Res.* 199:56–62 (1992); Wright, et al., *J. Cellular Phys.*, 152:448–57) and tyrosine kinase inhibitors (WO 94/03427; WO 92/21660; WO 91/15495; WO 94/14808; U.S. Pat. No. 5,330,992; Mariani, et al., *Proc. Am. Assoc. Cancer Res.*, 35:2268 (1994)).

In addition to the above, attempts have been made to identify small molecules which act as PK inhibitors. For example, bis-monocylic, bicyclic and heterocyclic aryl compounds (PCT WO 92/20642), vinylene-azaindole derivatives (PCT WO 94/14808) and 1-cyclopropyl-4-pyridylquinolones (U.S. Pat. No. 5,330,992) have been described as tyrosine kinase inhibitors. Styryl compounds (U.S. Pat. No. 5,217,999), styryl-substituted pyridyl compounds (U.S. Pat. No. 5,302,606), quinazoline derivatives (EP App. No. 0 566 266 A1), selenaindoles and selenides (PCT WO 94/03427), tricyclic polyhydroxylic compounds (PCT WO 92/21660) and benzylphosphonic acid compounds (PCT WO 91/15495) have all been described as PTK inhibitors useful in the treatment of cancer.

SUMMARY OF THE INVENTION

Our own efforts to identify small organic molecules which modulate PK activity and which, therefore, are expected to be useful in the treatment and prevention of disorders involving abnormal PK activity, has led us to the discovery of a family of novel pyrrole substituted 2-indolinone compounds which exhibit PK modulating ability and are thereby expected to have a salutary effect against disorders related to abnormal PK activity; it is these compounds which is the subject of this invention.

Thus, the present invention relates generally to novel pyrrole substituted 2-indolinones which modulate the activity of receptor tyrosine kinases (RTKs), non-receptor protein tyrosine kinases (CTKs) and serine/threonine protein kinases (STKs). In addition, the present invention relates to the preparation and use of pharmaceutical compositions of the disclosed compounds and their physiologically acceptable salts and prodrugs in the treatment or prevention of PK driven disorders such as, by way of example and not limitation, cancer, diabetes, hepatic cirrhosis, cardiovasacular disease such ase atherosclerosis, angiogenesis, immunological disease such as autoimmune disease and renal disease.

The terms "2-indolinone," indolin-2-one and "2-oxindole" are used interchangeably herein to refer to a molecule having the chemical structure:

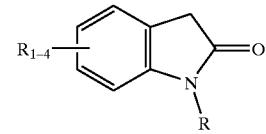

A "pyrrole" refers to a molecule having the chemical structure:

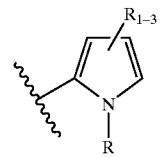

"Pyrrole substituted 2-indolinone" and "3-pyrrolidenyl-2-indolinone" are used interchangeably herein to refer to a chemical compound having the general structure shown in Formula 1.

A "pharmaceutical composition" refers to a mixture of one or more of the compounds described herein, or physiologically acceptable salts or prodrugs thereof, with other chemical components, such as physiologically acceptable carriers and excipients. The purpose of a pharmaceutical composition is to facilitate administration of a compound to an organism.

A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

A further example of a prodrug might be a short polypeptide, for example, without limitation, a 2–10 amino acid polypeptide, bonded through a terminal amino group to a carboxy group of a compound of this invention wherein the polypeptide is hydrolyzed or metabolized in vivo to release the active molecule.

A "pyrrole aldehyde" refers to a molecule having the chemical structure:

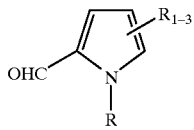

As used herein, a "physiologically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

1. CHEMISTRY

A. General Structural Features

In one aspect, the the present invention relate to pyrrole substituted 2-indolinones which, in addition to being otherwise optionally substituted on both the pyrrole and 2-indolinone portions of the compound, are necessarily substituted on the pyrrole moiety with one or more hydrocarbon chains which themselves are substituted with at least one polar group. Physiologically acceptable salts and prodrugs of the claimed compounds are also within the scope of this invention.

A "hydrocarbon chain" refers to an alkyl, alkenyl or alkynyl group, as defined herein.

A "polar" group refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitation, hydroxy, alkoxy, carboxy, nitro, cyano, amino, ammonium, amido, ureido, sulfonamido, sulfinyl, sulfonyl, phosphono, morpholino, piperazinyl and tetrazolo.

While not being bound to any particular theory, applicants at this time believe that the polar groups may interact electronically, for example, but without limitation, through hydrogen bonds, Van der Walls forces and/or ionic bonds (but not covalent bonding), with the amino acids at a PTK active site. These interactions may assist the molecules of this invention to bind to an active site with sufficient tenacity to interfere with or prevent the natural substrate from entering the site. Polar groups may also contribute to the selectivity of the compounds; i.e., one polar group may have greater affinity for a PTK binding domain than other polar groups so that the compound containing the first particular polar group is more potent than the compounds containing the other polar groups.

Thus, one aspect of the present invention relates to compounds having the following chemical structure:

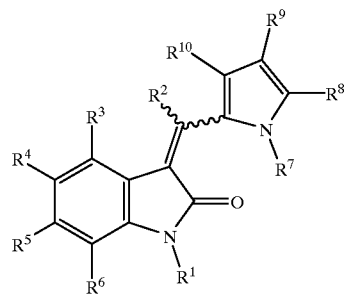

$R^1$ is selected from the group consisting of hydrogen, alkyl, alkenyl, alkynyl, cycloalkyl, aryl, hydroxy, alkoxy, C-carboxy, O-carboxy, acetyl, C-amido, C-thioamido, sulfonyl and trihalomethanesulfonyl.

$R^2$ is selected from the group consisting of hydrogen, halo, alkyl, cycloalkyl, aryl, heteroaryl and heteroalicyclic.

$R^3$, $R^4$, $R^5$ and $R^6$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, trihalomethanesulfonamido, carbonyl, C-carboxy, O-carboxy, C-amido, N-amido, cyano, nitro, halo, O-carbamyl, N-carbamyl, O-thiocarbamyl, N-thiocarbamyl, amino and —$NR^{11}R^{12}$.

$R^{11}$ and $R^{12}$ are independently selected from the group consisting of hydrogen, alkyl, cycloalkyl, aryl, carbonyl, acetyl, sulfonyl, trifluoromethanesulfonyl and, combined, a five- or six-member heteroalicyclic ring.

$R^3$ and $R^4$, $R^4$ and $R^5$, or $R^4$ and $R^5$ may combine to form a six-member aryl ring, a methylenedioxy group or an ethylenedioxy group.

$R^7$ is selected from the group consisting of hydrogen, alkyl, cycloalkyl, alkenyl, alkynyl, aryl, heteroaryl, heteroalicyclic, hydroxy, alkoxy, aryloxy, carbonyl, acetyl, C-amido, C-thioamido, amidino, C-carboxy, O-carboxy, sulfonyl and trihalomethane-sulfonyl.

$R^8$, $R^9$ and $R^{10}$ are independently selected from the group consisting of hydrogen, alkyl, trihaloalkyl, cycloalkyl, alkenyl, alkynyl, aryl, heteroaryl, heteroalicyclic, hydroxy, alkoxy, aryloxy, mercapto, alkylthio, arylthio, sulfinyl, sulfonyl, S-sulfonamido, N-sulfonamido, carbonyl, C-carboxy, O-carboxy, cyano, nitro, halo, O-carbamyl, N-carbamyl, O-thiocarbamyl, N-thiocarbamyl, C-amido, N-amido, amino and —$NR^{11}R^{12}$, providing, however that at least one of $R^8$, $R^9$ or $R^{10}$ is a group having the formula —$(alk_1)Z$.

$Alk_1$ is selected from the group consisting of alkyl, alkenyl or alkynyl.

Z is a polar group.

As used herein, the term "alkyl" refers to a saturated aliphatic hydrocarbon including straight chain and branched chain groups. Preferably, the alkyl group has 1 to 20 carbon atoms (whenever a numerical range; e.g. "1–20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^{11}$R$^{12}$, with R$^{11}$ and R$^{12}$ as defined above.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, the substituent group(s) is preferably one or more individually selected from alkyl, aryl, heteroaryl, heteroalycyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —NR$^{11}$R$^{12}$, with R$^{11}$ and R$^{12}$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituted group(s) is preferably one or more selected from halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —NR$^{11}$R$^{12}$, with R$^{11}$ and R$^{12}$ as defined herein.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more selected from alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —NR$^{11}$R$^{12}$ with R$^{11}$ and R$^{12}$ as defined above.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted. When substituted, the substituted group(s) is preferably one or more selected from alkyl, cycloaklyl, halo, trihalomethyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and —NR$^{11}$R$^{12}$ with R$^{11}$ and R$^{12}$ as defined above.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "mercapto" group refers to an —SH group.

A "alkylthio" group refers to both an S-alkyl and an —S-cycloalkyl group, as defined herein.

A "arylthio" group refers to both an —S-aryl and an —S-heteroaryl group, as defined herein.

A "carbonyl" group refers to a —C(=O)—R" group, where R" is selected from the group consisting of hydrogen, alkyl, cycloalkyl, aryl, heteroaryl (bonded through a ring carbon) and heteroalicyclic (bonded through a ring carbon), as defined herein.

An "aldehyde" group refers to a carbonyl group where R" is hydrogen.

A "thiocarbonyl" group refers to a —C(=S)—R" group, with R" as defined herein.

A "C-carboxy" group refers to a —C(=O)O—R" group, with R" as defined herein.

An "O-carboxy" group refers to a —OC(=O)R" group, with R" as defined herein.

An "ester" group refers to a —C(=O)O—R" group with R" as defined herein except that R" cannot be hydrogen.

An "acetyl" group refers to a —C(=O)CH$_3$ group.

A "carboxylic acid" group refers to a C-carboxy group in which R" is hydrogen.

A "halo" group refers to fluorine, chlorine, bromine or iodine.

A "trihalomethyl" group refers to a —CX$_3$ group wherein X is a halo group as defined herein.

A "trihalomethanesulfonyl" group refers to a X$_3$CS(=O)$_2$— groups with X as defined above.

A "cyano" group refers to a —C≡N group.

A "sulfinyl" group refers to a —S(=O)—R" group wherein, in addition to being as defined above, R" may also be a hydroxy group.

A "sulfonyl" group refers to a —S(=O)$_2$R" group wherein, in addition to being as defined above, R" may also be a hydroxy group.

A "methylenedioxy" group refers to a —OCH$_2$O— group where the two oxygen atoms are bonded to adjacent carbon atoms.

An "ethylenedioxy" group refers to a —OCH$_2$CH$_2$O— where the two oxygen atoms are bonded to adjacent carbon atoms.

An "S-sulfonamido" group refers to a —S(=O)$_2$NR$^{11}$R$^{12}$ group, with R$^{11}$ and R$^{12}$ as defined herein.

An "N-sulfonamido" group refers to a —NR$^{11}$S(=O)$_2$R$^{12}$ group, with R$^{11}$ and R$^{12}$ as defined herein.

An "O-carbamyl" group refers to a —OC(=O)NR$^{11}$R$^{12}$ group with R$^{11}$ and R$^{12}$ as defined herein.

An "N-carbamyl" group refers to a R$^{12}$OC(=O)NR$^{11}$— group, with R$^{11}$ and R$^{12}$ as defined herein.

An "O-thiocarbamyl" group refers to a —OC(=S)NR$^{11}$R$^{12}$ group with R$^{11}$ and R$^{12}$ as defined herein.

An "N-thiocarbamyl" group refers to a R$^{12}$OC(=S)NR$^{11}$— group, with R$^{11}$ and R$^{12}$ as defined herein.

An "amino" group refers to an —NR$^{11}$R$^{12}$ group, wherein R$^{11}$ and R$^{12}$ are both hydrogen.

A "C-amido" group refers to a —C(=O)NR$^{11}$R$^{12}$ group with R$^{11}$ and R$^{12}$ as defined herein.

An "N-amido" group refers to a R$^{12}$C(=O)NR$^{11}$— group, with R$^{11}$ and R$^{12}$ as defined herein.

A "ammonium" group refers to a —$^{+}$NHR$^{11}$R$^{12}$ group wherein R$^{11}$ and R$^{12}$ are independently selected from the group consisting of alkyl, cycloalkyl, aryl, and heteroaryl.

A "ureido" group refers to a —NR$^{11}$C(=O)NR$^{12}$R$^{13}$ group, with R$^{11}$ and R$^{12}$ as defined herein and R$^{13}$ defined the same as R$^{11}$ and R$^{12}$.

A "guanidino" group refers to a —R$^{11}$NC(=N)NR$^{12}$R$^{13}$ group, with R$^{11}$, R$^{12}$ and R$^{13}$ as defined herein.

A "amidino" group refers to a R$^{11}$R$^{12}$NC(=N)— group, with R$^{11}$ and R$^{12}$ as defined herein.

A "nitro" group refers to a —NO$_2$ group.

A "phosphonyl" group refers to a —OP(=O)$_2$OR", with R" as defined herein.

A "morpholino" group refers to a group having the chemical structure:

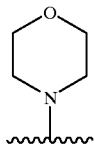

A "piperazinyl" group refers to a group having the chemical structure:

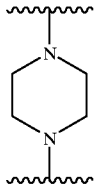

A "tetrazolo" group refers to a group having the chemical structure:

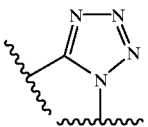

B. Preferred Structural Features

It is a presently preferred feature of this invention that R$^1$ is hydrogen.

It is also a presently preferred feature of this invention that R$^2$ is hydrogen.

It is likewise a presently preferred feature of this invention that R$^7$ is hydrogen.

It is a presently preferred feature of this invention that all three of the above limitations exist in the same molecule; i.e., that, in a compound of this invention, R$^1$, R$^2$ and R$^7$ are hydrogen.

It is also presently preferred that R$^3$, R$^4$, R$^5$ and R$^6$ are selected from the group consisting of hydrogen, unsubstituted lower alkyl, lower alkyl substituted with a group selected from the group consisting of hydroxy, halo, C-carboxy substituted with a group selected from the group consisting of hydrogen and unsubstituted lower alkyl, amino or —NR$^{11}$R$^{12}$; unsubstituted lower alkyl alkoxy, lower alkoxy substituted with one or more halo groups, lower alkoxy substituted with a group consisting of unsubstituted aryl or aryl substituted with one or more groups independently selected from the group consisting of unsubstituted lower alkyl, hydroxy, unsubstituted lower alkyl alkoxy, halo, amino, unsubstituted lower alkyl S-sulfonamido or —NR$^{11}$R$^{12}$, unsubstituted aryl or aryl substituted with one or more groups independently selected from the group consisting of unsubstituted lower alkyl, unsubstituted lower alkyl alkoxy, lower alkoxy substituted with one or more halo groups, lower alkoxy substituted with a group selected from the group consisting of unsubstituted aryl or aryl substituted with one or more groups independently selected from the group consisting of unsubstituted lower alkyl, hydroxy, unsubstituted lower alkyl alkoxy, halo, amino, unsubstituted lower alkyl S-sulfonamido or —NR$^{11}$R$^{12}$, hydroxy, amino, unsubstituted lower alkyl sulfonamido, C-carboxy substituted with a groups selected from the group consisting of hydrogen or unsubstituted lower alkyl, morpholino, —NR$^{11}$R$^{12}$, trihalomethyl, aryl, aryl substituted with one or more groups independently selected from the group consisting of hydroxy, halo, trihalomethyl, amino, —NR$^{11}$R$^{12}$, sulfonamido, C-carboxy substituted with a group selected from the group consisting of hydrogen or unsubstituted lower alkyl, unsubstituted lower alkyl or lower alkyl substituted with a group selected from the group consisting of hydroxy, halo, C-carboxy substituted with a group selected from the group consisting of hydrogen or unsubstituted lower alkyl, amino or —NR$^{11}$R$^{12}$, unsubstituted heteroalicyclic, heteroalicyclic substituted with one or more groups independently selected from the group consisting of halo, hydroxy, unsubstituted lower alkyl, unsubstituted lower alkyl carbonyl, hydroxy, unsubstituted lower alkyl alkoxy or alkoxy substituted with one or more halo groups, unsubstituted aryloxy, aryloxy substituted with one or more groups independently selected from the group consisting of unsubstituted lower alkyl, trihalomethyl, halo, hydroxy, amino or —NR$^{11}$R$^{12}$, mercapto, unsubstituted lower alkyl alkylthio, unsubstituted arylthio, arylthio substituted with one or more groups selected from the group consisting of halo, hydroxy, amino or —NR$^{11}$R$^{12}$, C-carboxy substituted with a group selected from the group consisting of hydrogen and unsubstituted lower alkyl, unsubstituted lower alkyl O-carboxy, unsubstituted lower alkyl S-sulfonamido, nitro, unsubstituted lowe alkyl C-amido, unsubstituted lower alkyl N-amido, amino and —R$^{11}$R$^{12}$.

In another presently preferred embodiments of this invention, R$^3$, R$^4$, R$^5$ and R$^6$ are independently selected from the group consisting of hydrogen, halo, unsubstituted lower alkyl, lower alkyl substituted with one or more groups selected from the group consisting of hydroxy, halo, C-carboxy substituted with a group selected from the group consisting of hydrogen or unsubstituted lower alkyl, amino or —NR$^{11}$R$^{12}$, unsubstituted lower alkyl alkoxy, lower alkyl alkoxy substituted with one or more halo groups, unsubstituted aryloxy, aryloxy substituted with one or more groups indepedently selected from the group consisting of unsubstituted lower alkyl, lower alkyl substituted with one or more halo groups, hydroxy, unsubstituted lower alkyl alkoxy, halo, amino or —NR$^{11}$R$^{12}$, S-sulfonamido wherein R$^{11}$ and R$^{12}$ are independently selected from the group consisting of hydrogen and unsubstituted lower alkyl, unsubstituted aryl, aryl substituted with one or more groups independently selected from the group consisting of halo, unsubstituted lower alkyl, lower alkyl substituted with one or more halo groups, unsubstituted lower alkyl alkoxy, amino or —NR$^{11}$R$^{12}$, unsubstituted heteroaryl, heteroaryl substituted with one or more groups independently selected from the group consisting of unsubstituted lower alkyl, lower alkyl substituted with one or more halo groups, unsubstituted lower alkyl alkoxy, hydroxy, halo, amino or —NR$^{11}$R$^{12}$, unsubstituted heteroalicyclic, heteroalicyclic substituted with one or more groups independently selected from the group consisting of halo, hydroxy, unsubstituted lower alkyl, lower alkyl substituted with one or more halo groups, unsubstituted lower alkyl alkoxy, amino or —NR$^{11}$R$^{12}$, unsubstituted lower alkyl O-carboxy, C-amido wherein R$^{11}$ and R$^{12}$ are independently selected from the group consisting of hydrogen, unsubstituted lower alkyl and unsubstituted aryl, and, N-amido wherein R$^{11}$ and R$^{12}$ are independently selected from the group consisting of hydrogen, unsubstituted lower alkyl and unsubstituted aryl.

It is a presently preferred feature of this invention that one of R$^8$, R$^9$ and R$^{10}$ is —(alk$_1$)Z while the other two are independently selected from the group consisting of hydrogen, hydroxy, unsubstituted lower alkyl, unsubstituted lower alkenyl, unsubstituted lower alkynyl, unsubstituted lower alkyl alkoxy, lower alkoxy substituted with one or more halo groups, unsubstituted aryl alkoxy, amino, —NR$^{11}$R$^{12}$, halo, C-carboxy substituted with a groups selected from the group consisting of hydrogen or unsubstituted lower alkyl, unsubstituted lower alkyl O-carboxy, unsubstituted lower alkyl C-amido, unsubstituted lower alkyl N-amido, acetyl, unsubstituted lower alkyl S-sulfonamido, unsubstituted aryl or aryl substituted with a group selected from the group consisting of halo, hydroxy, unsubstituted lower alkyl alkoxy, alkoxy substituted with one or more halo groups, C-carboxy substituted with a groups selected from the group consisting of hydrogen or unsubstituted lower alkyl, unsubstituted lower alkyl O-carboxy, amino, unsubstituted lower alkyl S-sulfonamido and —NR$^{11}$R$^{12}$.

It is a presently preferred feature of this invention that R$^8$ and R$^{10}$ are selected from the groups consisting of hydrogen and unsubstituted lower alkyl.

It is also a presently preferred feature of this invention that alk$_1$ is an unsubstituted lower alkyl group.

In yet another presently preferred feature of this invention, Z is selected from the group consisting of hydroxy, amino, —NR$^{11}$R$^{12}$, quarternary ammonium, C-carboxy substituted with a group selected from the group consisting of hydrogen or unsubstituted lower alkyl, C-amido substituted with groups selected from the group consisting of hydrogen and unsubstituted lower alkyl, morpholino, piperadinyl, tetrazolo and phosphonyl.

A further presently preferred feature of this invention is that alk$_1$ is a two to four carbon unsubstituted lower alkyl group and Z is a carboxylic acid.

It is a presently preferred feature of this invention that R$^9$ is alk$_1$Z.

It is likewise a presently preferred feature of this invention that R$^{11}$ and R$^{12}$ are independently selected from the group comprising hydrogen, unsubstituted lower alkyl, hydroxy, unsubstituted lower alkyl alkoxy, unsubstituted lower alkyl carbonyl, unsubstituted lower alkyl O-carboxy and acetyl.

In another presently preferred embodiment of this invention R$^1$, R$^2$, R$^3$, R$^4$, R$^5$, R$^6$ and R$^7$ are hydrogen, R$^8$ and R$^{10}$ are methyl and R$^9$ is —CH$_2$CH$_2$C(=O)OH.

It is also a presently preferred embodiment of this invention that R$^1$, R$^2$, R$^3$, R$^4$, R$^5$, R$^6$, R$^7$ and R$^8$ are hydrogen, R$^{10}$ is methyl and R$^9$ is —CH$_2$CH$_2$C(=O)OH.

In yet another presently preferred embodiment of this invention R$^7$ is selected from the group consisting of: hydrogen, unsubstituted lower alkyl, and lower alkyl substituted with a group selected from the group consisting of unsubstituted cycloalkyl, unsubstituted aryl, and, aryl substituted with a group selected from hydroxy, unsubstituted lower alkyl alkoxy and halo.

It is also a presently preferred embodiment of this invention that z is selected from the group consisting of —C(=O)NR$^{13}$R$^{14}$ wherein R$^{13}$ and R$^{14}$ are independently selected from the group consisting of hydrogen, unsubstituted lower alkyl, lower alkyl substituted with a group selected from the group consisting of amino and —NR$^{11}$R$^{12}$, unsubstituted aryl, aryl substituted with one or more groups selected from the group consisting of halo, hydroxy, unsubstituted lower alkyl alkoxy and trihalomethyl, unsubstituted heteroaryl, unsubstituted heteroalicyclic, and, combined, a five-member or a six-member unsubstituted heteroalicyclic, and, —NR$^{11}$R$^{12}$, wherein, R$^{11}$ and R$^{12}$ are independently selected from the group consisting of unsubstituted lower alkyl and, combined, a five-member or a six-member unsubstituted heteroalicyclic ring.

Yet another presently preferred embodiment of this invention is that R$^7$ is selected from the group consisting of unsubstituted lower alkyl, lower alkyl substituted with one or more groups selected from the group consisting of unsubstituted cycloalkyl, unsubstituted aryl, aryl substituted with one or more groups independently selected from the group consisting of halo and unsubstituted lower alkyl alkoxy and unsubstituted lower alkyl carboxyalkyl, and Z is selected from the group consisting of unsubstituted C-carboxy and unsubstituted lower alkyl C-carboxy.

Finally, it is a presently preferred embodiment of this invention that R$^3$ R$^4$, R$^5$, and R$^6$ are independently selected from the group consisting of hydrogen, halo, unsubstituted lower alkyl, lower alkyl substituted with one or more hydroxy groups, unsubstituted lower alkoxy, unsubstituted aryl, aryl substituted with one or more unsubstituted lower alkoxy groups, and —S(O)$_2$NR$^{11}$R$^{12}$, R$^5$ is hydrogen, R$^6$ is —NR$^{11}$R$^{12}$, and R$^{11}$ and R$^{12}$ are independently selected from the group consisting of hydrogen, unsubstituted lower alkyl and, combined, a five-member or a six-member unsubstituted heteroalicyclic ring.

The chemical formulae referred to herein may exhibit the phenomena of tautomerism and structural isomerism. For example, the compounds described herein may adopt an E or a Z configuration about the double bond connecting the 2-indolinone moiety to the pyrrole moiety or they may be a mixture of E and Z. This invention encompasses any tautomeric or structural isomeric form and mixtures thereof which possess the ability to modulate RTK, CTK and/or STK activity and is not limited to any one tautomeric or structural isomeric form.

2. SYNTHESIS/COMBINATORIAL LIBRARIES

An additional aspect of this invention is a combinatorial library of at least ten 3-pyrrolidinyl-2-indolinone compounds that can be formed by reacting oxindoles of structure 2 with aldehydes of structure 3.

2

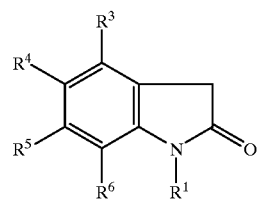

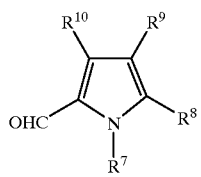

wherein R¹–R¹⁰ have the meanings set forth above.

As used herein, a "combinatorial library" refers to all the compounds formed by the reaction of each compound of one dimension with a compound in each of the other dimensions in a multi-dimensional array of compounds. In the context of the present invention, the array is two dimensional and one dimension represents all the oxindoles of the invention and the second dimension represents all the aldehydes of the invention. Each oxindole may be reacted with each and every aldehyde in order to form a 3-pyrrolidinyl-2-indolinone compound. All 3-pyrrolidinyl-2-indolinone compounds formed in this way are within the scope of the present invention. Also within the scope of the present invention are smaller combinatorial libraries formed by the reaction of some of the oxindoles with all of the aldehydes, all of the oxindoles with some of the aldehydes, or some of the oxindoles with some of the aldehydes.

The oxindole in the above combinatorial library is preferably selected from the group consisting of oxindole itself and substituted oxindoles such as, without limitation, 6-bromooxindole, 5-hydroxyoxindole, 5-methoxyoxindole, 6-methoxyoxindole, 5-phenylaminosulfonyloxindole, 4-[2-(2-isopropylphenoxy)-ethyl]oxindole, 4-[2-(3-isopropylphenoxy)ethyl]oxindole, 4-[2-(4-isopropylphenoxy)ethyl]oxindole, 5-fluorooxindole, 6-fluorooxindole, 7-fluorooxindole, 6-trifluoromethyloxindole, 5-chlorooxindole, 6-chlorooxindole, indole-4-carboxylic acid, 5-bromooxindole, 6-(N-acetamido)-oxindole, 4-methyloxindole, 5-methyloxindole, 4-methyl-5-chlorooxindole, 5-ethyloxindole, 6-hydroxyoxindole, 5-acetyloxindole, oxindole-5-carboxylic acid, 5-methoxyoxindole, 6-methoxyoxindole, 5-aminooxindole, 6-aminooxindole, 4-(2-N-morpholinoethyl)oxindole, 7-azaoxindole, oxindole-4-carabamic acid t-butyl ester, oxindole-6-carbamic acid t-butyl ester, 4-(2-carboxyethyl)oxindole, 4-n-butyloxindole, 4,5-dimethoxyoxindole, 6-(methanesulfonamido)oxindole, 6-(benzamido)oxindole, 5-ethoxyoxindole, 6-phenyloxindole, 6-(2-methoxyphen-1-yl)oxindole, 6-(3-methoxyphen-1-yl)oxindole, 6-(4-methoxyphen-1-yl)oxindole, 5-aminosulfonyloxindole, 5-isopropylaminosulfonyloxindole, dimethylaminosulfonyloxindole, 5-(N-morpholinosulfonyl)oxindole and 4-(2-hydroxyethyl)oxindole.

The aldehyde in the above combinatorial library is preferably selected from the group consisting of, without limitation, 3-(5-formyl-2,4-dimethyl-1H-pyrrol-3-yl) propionic acid, 3-(5-formyl-4-methyl-1H-pyrrol-3-yl) propionic acid, 3-(1-benzyl-5-formyl-2,4-dimethyl-1H-pyrrol-3-yl) propionic acid, 3-(5-formyl-1-methoxycarbonylmethyl-2,4-dimethyl-1H-pyrrol-3-yl) propionic acid, 3-(5-formyl-1,2,4-trimethyl-1H-pyrrol-3-yl) propionic acid, 3-[5-formyl-1-(3-methoxy-benzyl)-2,4-dimethyl-1H-pyrrol-3-yl] propionic acid methyl ester, 3-(1-cyclohexylmethyl-5-formyl-2,4-dimethyl-1H-pyrrol-3-yl) propionic acid methyl ester, 3-[1-(2,2-dimethyl-propyl)-5-formyl-2,4-dimethyl-1H-pyrrol-3-yl] propionic acid methyl ester, 1,3,5-trimethyl-4-(3-morpholin-4-yl-3-oxo-propyl)-1H-pyrrole-2-carbaldehyde, 3-(5-formyl-1,2,4-trimethyl-1H-pyrrol-3-yl)-N-(2-morpholin-4-yl-ethyl)propionamide, 3-(5-formyl-1,2,4-trimethyl-1H-pyrrol-3-yl)-N-phenylpropionamide, 1,3,5-trimethyl-4-(3-oxo-3-piperidin-1-yl-propyl)-1H-pyrrole-2-carbaldehyde, 1,3,5-trimethyl-4-(3-oxo-3-pyrrolidin-1-yl-propyl)-1H-pyrrole-2-carbaldehyde, 3-(5-formyl-1,2,4-trimethyl-1H-pyrrol-3-yl)-N-(4-methoxy-phenyl)propionamide, 3-(5-formyl-1,2,4-trimethyl-1H-pyrrol-3-yl)-N-(4-methoxyphenyl)propionamide, N-(4-fluoro-phenyl)-3-(5-formyl-1,2,4-trimethyl-1H-pyrrol-3-yl)propionamide, 3-(5-formyl-1,2,4-trimethyl-1H-pyrrol-3-yl)-N-(4-trifluoromethylphenyl)propionamide, 3-[5-formyl-1-(3-methoxy-benzyl)-2,4-dimethyl-1H-pyrrol-3-yl] propionic acid, 3-(1-cyclohexylmethyl-5-formyl-2,4-dimethyl-1H-pyrrol-3-yl) propionic acid, 3-[1-(3-fluoro-benzyl)-5-formyl-2,4-dimethyl-1H-pyrrol-3-yl] propionic acid methyl ester, 3-(1-benzyl-5-formyl-2,4-dimethyl-1H-pyrrol-3-yl) propionic acid, 3-[1-(4-fluorobenzyl)-5-formyl-2,4-dimethyl-1H-pyrrol-3-yl] propionic acid methyl ester, 3-[1-(4-fluorobenzyl)-5-formyl-2,4-dimethyl-1H-pyrrol-3-yl] propionic acid, 3-[1-(3-fluoro-benzyl)-5-formyl-2,4-dimethyl-1H-pyrrol-3-yl] propionic acid, 3,5-dimethyl-4-(3-morpholin-4-yl-propyl)-1H-pyrrole-2-carbaldehyde, 4-(3-dimethylamino-propyl)-3,5-dimethyl-1H-pyrrole-2-carbaldehyde, 5-formyl-2,4-dimethyl-1H-pyrrole-3-carboxylic acid, 3,5-dimethyl-4-(4-methyl-piperazine-1-carbonyl)-1H-pyrrole-2-carbaldehyde, 5-formyl-2,4-dimethyl-1H-pyrrole-3-carboxylic acid (2-dimethylaminoethyl) amide.

Another aspect of this invention provides a method for the synthesis of a 3-pyrrolidinyl-2-indolinone of formula 1 comprising reacting an oxindole of formula 2 with an aldehyde of formula 3 in a solvent, preferably in the presence of a base.

Examples of the oxindoles of formula 2 which may be reacted with an aldehyde of formula 3 to give the 3-pyrrolidinyl-2-indolinones of formula 1 are oxindole itself and substituted oxindoles such as, without limitation, 6-bromooxindole, 5-hydroxyoxindole, 5-methoxyoxindole, 6-methoxyoxindole, 5-phenylaminosulfonyloxindole, 4-[2-(2-isopropylphenoxy)-ethyl]oxindole, 4-[2-(3-isopropylphenoxy)ethyl]oxindole, 4-[2-(4-isopropylphenoxy)ethyl]oxindole, 5-fluorooxindole, 6-fluorooxindole, 7-fluorooxindole, 6-trifluoromethyloxindole, 5-chlorooxindole, 6-chlorooxindole, indole-4-carboxylic acid, 5-bromooxindole, 6-(N-acetamido)-oxindole, 4-methyloxindole, 5-methyloxindole, 4-methyl-5-chlorooxindole, 5-ethyloxindole, 6-hydroxyoxindole, 5-acetyloxindole, oxindole-5-carboxylic acid, 5-methoxyoxindole, 6-methoxyoxindole, 5-aminooxindole, 6-aminooxindole, 4-(2-N-morpholinoethyl)oxindole, 7-azaoxindole, oxindole-4-carabamic acid t-butyl ester, oxindole-6-carbamic acid t-butyl ester, 4-(2-carboxyethyl)oxindole, 4-n-butyloxindole, 4,5-dimethoxyoxindole, 6-(methanesulfonamido)oxindole, 6-(benzamido)oxindole, 5-ethoxyoxindole, 6-phenyloxindole, 6-(2-methoxyphen-1-yl)oxindole, 6-(3-methoxyphen-1-yl)oxindole, 6-(4-methoxyphen-1-yl)oxindole, 5-aminosulfonyloxindole, 5-isopropylaminosulfonyloxindole, dimethylaminosulfonyloxindole, 5-(N-morpholinosulfonyl)oxindole and 4-(2-hydroxyethyl)oxindole.

Examples of aldehydes of structure 3 which may be reacted with oxindoles of structure 2 are, without limitation, 3-(5-formyl-2,4-dimethyl-1H-pyrrol-3-yl) propionic acid, 3-(5-formyl-4-methyl-1H-pyrrol-3-yl) propionic acid, 3-(1- benzyl-5-formyl-2,4-dimethyl-1H-pyrrol-3-yl) propionic acid, 3-(5-formyl-1-methoxycarbonylmethyl-2,4-dimethyl-1H-pyrrol-3-yl) propionic acid, 3-(5-formyl-1,2,4-trimethyl-1H-pyrrol-3-yl) propionic acid, 3-[5-formyl-1-(3-methoxy-benzyl)-2,4-dimethyl-1H-pyrrol-3-yl] propionic acid methyl ester, 3-(1-cyclohexylmethyl-5-formyl-2,4-dimethyl-1H-pyrrol-3-yl) propionic acid methyl ester, 3-[1-(2,2-dimethyl-propyl)-5-formyl-2,4-dimethyl-1H-pyrrol-3-yl] propionic acid methyl ester, 1,3,5-trimethyl-4-(3-morpholin-4-yl-3-oxopropyl)-1H-pyrrole-2-carbaldehyde, 3-(5-formyl-1,2,4-trimethyl-1H-pyrrol-3-yl)-N-(2-morpholin-4-yl-ethyl)propionamide, 3-(5-formyl-1,2,4-trimethyl-1H-pyrrol-3-yl)-N-phenylpropionamide, 1,3,5-trimethyl-4-(3-oxo-3-piperidin-1-yl-propyl)-1H-pyrrole-2-carbaldehyde, 1,3,5-trimethyl-4-(3-oxo-3-pyrrolidin-1-yl-propyl)-1H-pyrrole-2-carbaldehyde, 3-(5-formyl-1,2,4-trimethyl-1H-pyrrol-3-yl)-N-(4-methoxy-phenyl) propionamide, 3-(5-formyl-1,2,4-trimethyl-1H-pyrrol-3-yl)-N-(4-methoxy-phenyl)propionamide, N-(4-fluoro-phenyl)-3-(5-formyl-1,2,4-trimethyl-1H-pyrrol-3-yl)propionamide, 3-(5-formyl-1,2,4-trimethyl-1H-pyrrol-3-yl)-N-(4-trifluoromethyl-phenyl)propionamide, 3-[5-formyl-1-(3-methoxybenzyl)-2,4-dimethyl-1H-pyrrol-3-yl] propionic acid, 3-(1-cyclohexylmethyl-5-formyl-2,4-dimethyl-1H-pyrrol-3-yl) propionic acid, 3-[1-(3-fluoro-benzyl)-5-formyl-2,4-dimethyl-1H-pyrrol-3-yl] propionic acid methyl ester, 3-(1-benzyl-5-formyl-2,4-dimethyl-1H-pyrrol-3-yl) propionic acid, 3-[1-(4-fluorobenzyl)-5-formyl-2,4-dimethyl-1H-pyrrol-3-yl] propionic acid methyl ester, 3-[1-(4-fluoro-benzyl)-5-formyl-2,4-dimethyl-1H-pyrrol-3-yl] propionic acid, 3-[1-(3-fluoro-benzyl)-5-formyl-2,4-dimethyl-1H-pyrrol-3-yl] propionic acid, 3,5-dimethyl-4-(3-morpholin-4-yl-propyl)-1H-pyrrole-2-carbaldehyde, 4-(3-dimethylamino-propyl)-3,5-dimethyl-1H-pyrrole-2-carbaldehyde, 5-formyl-2,4-dimethyl-1H-pyrrole-3-carboxylic acid, 3,5-dimethyl-4-(4-methyl-piperazine-1-carbonyl)-1H-pyrrole-2-carbaldehyde, 5-formyl-2,4-dimethyl-1H-pyrrole-3-carboxylic acid (2-dimethylaminoethyl) amide.

The reaction may be carried out in the presence of a base. The base may be an organic or an inorganic base. If an organic base is used, preferably it is a nitrogen base. Examples of organic nitrogen bases include, but are not limited to, diisopropylamine, trimethylamine, triethylamine, aniline, pyridine, 1,8-diazabicyclo[5.4.1]undec-7-ene, pyrrolidine and piperidine.

Examples of inorganic bases are, without limitation, ammonia, alkali metal or alkaline earth hydroxides, phosphates, carbonates, bicarbonates, bisulfates and amides. The alkali metals include, lithium, sodium and potassium while the alkaline earths include calcium, magnesium and barium.

In a presently preferred embodiment of this invention, when the solvent is a protic solvent, such as water or alcohol, the base is an alkali metal or an alkaline earth inorganic base, preferably, a alkali metal or an alkaline earth hydroxide.

It will be clear to those skilled in the art, based both on known general principles of organic synthesis and on the disclosures herein which base would be most appropriate for the reaction contemplated.

The solvent in which the reaction is carried out may be a protic or an aprotic solvent, preferably it is a protic solvent. A "protic solvent" is a solvent which has hydrogen atom(s) covalently bonded to oxygen or nitrogen atoms which renders the hydrogen atoms appreciably acidic and thus capable of being "shared" with a solute through hydrogen bonding. Examples of protic solvents include, without limitation, water and alcohols.

An "aprotic solvent" may be polar or non-polar but, in either case, does not contain acidic hydrogens and therefore is not capable of hydrogen bonding with solutes. Examples, without limitation, of non-polar aprotic solvents, are pentane, hexane, benzene, toluene, methylene chloride and carbon tetrachloride. Examples of polar aprotic solvents are chloroform, tetrahydrofuran, dimethylsulfoxide and dimethylformamide.

In a presently preferred embodiment of this invention, the solvent is a protic solvent, preferably water or an alcohol such as ethanol.

The reaction is carried out at temperatures greater than room temperature. The temperature is generally from about 30° C. to about 150° C., preferably about 80° C. to about 100° C., most preferable about 75° C. to about 85° C., which is about the boiling point of ethanol. By "about" is meant that the temperature range is preferably within 10 degrees Celcius of the indicated temperature, more preferably within 5 degrees Celcius of the indicated temperature and, most preferably, within 2 degrees Celcius of the indicated temperature. Thus, for example, by "about 75° C." is meant 75° C.±10° C., preferably 75° C.±5° C. and most preferably, 75° C.±2° C.

3. BIOCHEMISTRY/PHARMACOTHERAPY

Another aspect of this invention relates to a method for the modulation of the catalytic activity of a PK by contacting a PK with a compound of this invention or a physiologically acceptable salt or prodrug thereof.

As used herein, "PK" refers to receptor protein tyrosine kinase (RTKs), non-receptor or "cellular" tyrosine kinase (CTKs) and serine-threonine kinases (STKs).

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

The term "catalytic activity" as used herein refers to the rate of phosphorylation of tyrosine under the influence, direct or indirect, of RTKs and/or CTKs or the phosphorylation of serine and threonine under the influence, direct or indirect, of STKs.

The term "contacting" as used herein refers to bringing a compound of this invention and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, defined below, can be determined before use of the compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

A further aspect of this invention is that the modulation of the catalytic activity of PKs using a compound of this invention may be carried out in vitro or in vivo.

"In vitro" refers to procedures performed in an artificial environment such as, e.g., without limitation, in a test tube or culture medium.

As used herein, "in vivo" refers to procedures performed within a living organism such as, without limitation, a mouse, rat or rabbit.

A still further aspect of this invention is that the protein kinase whose catalytic activity is being modulated by a compound of this invention is selected from the group consisting of receptor protein tyrosine kinases, cellular tyrosine kinases and serine-threonine kinases.

It is an aspect of this invention that the receptor protein kinase whose catalytic activity is modulated by a compound of this invention is selected from the group consisting of EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R.

In addition, it is an aspect of this invention that the cellular tyrosine kinase whose catalytic activity is modulated by a compound of this invention is selected from the group consisting of Src, Frk, Btk, Csk, Abl, ZAP70, Fes/Fps, Fak, Jak, Ack, Yes, Fyn, Lyn, Lck, Blk, Hck, Fgr and Yrk.

Another aspect of this invention is that the serine-threonine protein kinase whose catalytic activity is modulated by a compound of this invention is selected from the group consisting of CDK2 and Raf.

A pharmaceutical composition of a compound of this invention with a pharmaceutically acceptable carrier is yet another aspect of this invention. Such pharmaceutical composition may contain excipients as well.

A method for treating or preventing a protein kinase related disorder in an organism comprising administering a therapeutically effective amount of a compound, salt or prodrug that is a 3-pyrrolidenyl-2-indolinone of the present invention to the organism is another aspect of this invention.

As used herein, "PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

As used herein, the terms "prevent", "preventing" and "prevention" refer to a method for barring an organism from acquiring a PK related disorder in the first place.

As used herein, the terms "treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal, including a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

It is an aspect of this invention that the above-referenced protein kinase related disorder is selected from the group consisting of a receptor protein tyrosine kinase related disorder, a cellular tyrosine kinase disorder and a serine-threonine kinase related disorder.

In yet another aspect of this invention, the above referenced protein kinase related disorder is selected from the group consisting of an EGFR related disorder, a PDGFR related disorder, an IGFR related disorder and a flk related disorder.

The above referenced protein kinase related disorder is a cancer selected from the group consisting of squamous cell carcinoma, sarcomas such as Kaposi's sarcoma, astrocytoma, glioblastoma, lung cancer, bladder cancer, colorectal cancer, gastrointestinal cancer, head and neck cancer, melanoma, ovarian cancer, prostate cancer, breast cancer, small-cell lung cancer and glioma in a further aspect of this invention.

The above referenced protein kinase related disorder is selected from the group consisting of diabetes, a hyperproliferation disorder, von Hippel-Lindau disease, restenosis, fibrosis, psoriasis, osteoarthritis, rheumatoid arthritis, an inflammatory disorder and angiogenesis in yet another aspect of this invention.

Additional disorders which may be treated or prevented using the compounds of this invention are immunological disorders such as autoimmune disease (AIDS) and cardiovasular disorders such as atherosclerosis.

It is as aspect of this invention that a chemical compound that modulates the catalytic activity of a protein kinase may be identified by contacting cells expressing said protein kinase with a compound, salt or prodrug that is a 3-pyrrolidenyl-2-indolinone of the present invention and then monitoring said cells for an effect.

By "monitoring" is meant observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art.

The above-referenced effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

It is also an aspect of this invention that a compound described herein, or its salt or prodrug, might be combined with other chemotherapeutic agents for the treatment of the diseases and disorders discussed above. For instance, a compound, salt or prodrug of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound, salt or prodrug of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound, salt or prodrug of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound, salt or prodrug of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as anastrozole.

Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia.

A presently preferred compound of this invention which might be expected to have a beneficial effect in combination with one or more of the above chemotherapeutic agents is 3-[2,4-Dimethyl-5-(2-oxo-1,2-dihydroindol-3-ylidenemethyl)-1H-pyrrol-3-yl]propionic acid.

DETAILED DESCRIPTION OF THE INVENTION

1. BRIEF DESCRIPTION OF THE TABLES

TABLE 1 shows the chemical structures and biological activity of some exemplary compounds of this invention. The compound numbers correspond to the Example numbers in the Examples section. That is, the synthesis of Compound 1 in Table 1 is described in Example 1. The bioassays used are described in detail below. The results are reported in terms of $IC_{50}$, the micromolar ($\mu$m) concentration of the compound being tested which causes a 50% change in the activity of the target PKT compared to the activity of the PTK in a control to which no test compound has been added. Specifically, the results shown indicate the concentration of a test compound needed to cause a 50% reduction of the activity of the target PTK. The compounds presented in Table 1 are exemplary only and are not to be construed as limiting the scope of this invention in any manner.

TABLE 1

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 1 | 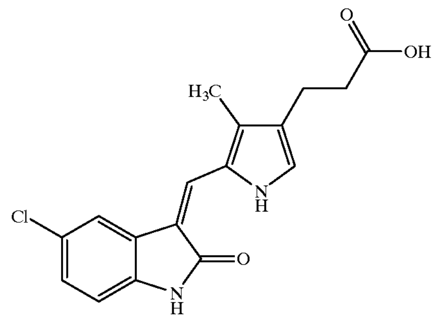 | 1.3 | <0.78 | 20.2 | 0.38 | 21.4 | 8.4 | 8.8 | 12 |
| 2 | 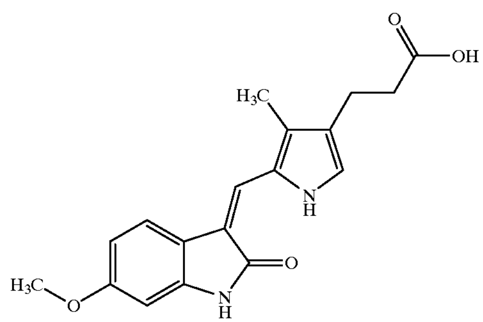 | 89.1 | 0.14 | 12.1 | 1.6 | 31.6 | 1.2 | >50 | >50 |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 3 | 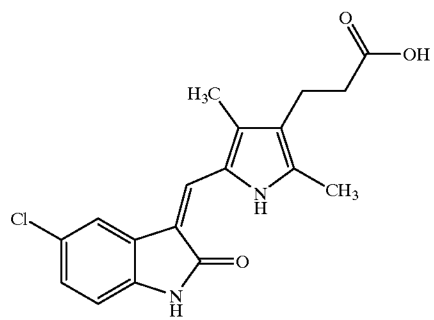 | 1.2 | 0.042 | 0.86 | 0.05 | 2.8 | 2.5 | 30 | >50 |
| 4 | 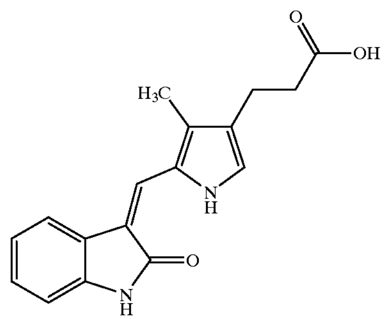 | 1.2 | 13 | 9 | 0.11 | 7.1 | 8.2 | >50 | >50 |
| 5 | 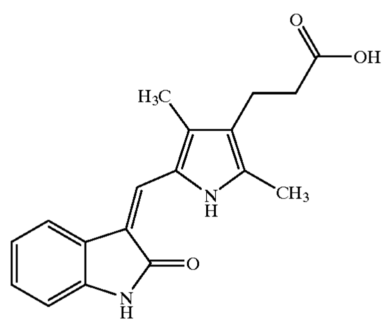 | 0.13 | <1.2 | 8.81 | 0.42 | 9.3 | 10.7 | 46.8 | 95.9 |

TABLE 1-continued
| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 6 | 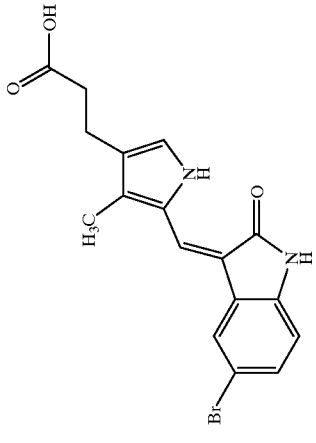 | 6.8 | 0.26 | | 0.63 | 18.4 | 8.6 | >50 | >50 |
| 7 | 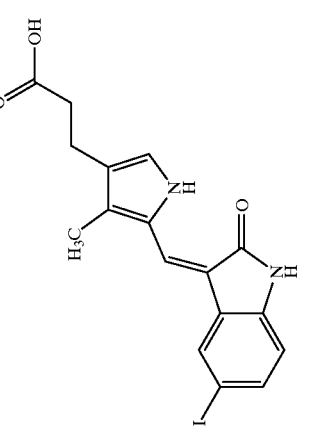 | 19.2 | 2.2 | | 1.34 | 12.3 | 11.4 | >50 | >50 |
| 8 | 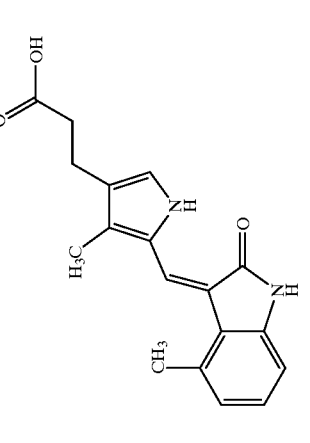 | 0.77 | 0.37 | 0.68 | 0.74 | 4.52 | 8.2 | >50 | >50 |

TABLE 1-continued

| Example # | Structure | bio-FLK-1 IC$_{50}$ (mM) | bio-PDGFr IC$_{50}$ (mM) | bio-FGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 9 | 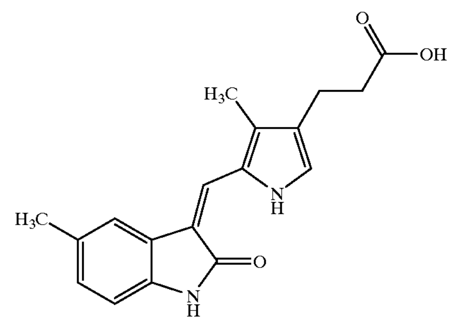 | 1.06 | 0.13 | 1.63 | 0.33 | 13.4 | 6.3 | >50 | >50 |
| 10 | 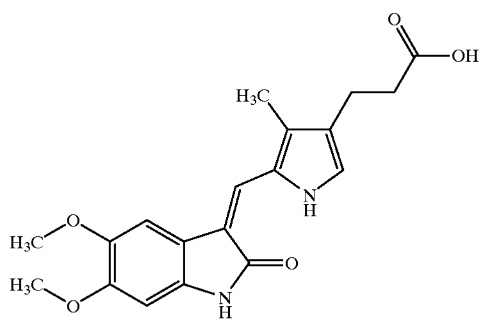 | 11 | <0.78 | 7.73 | 10.62 | >50 | 5.1 | >50 | >50 |
| 11 | 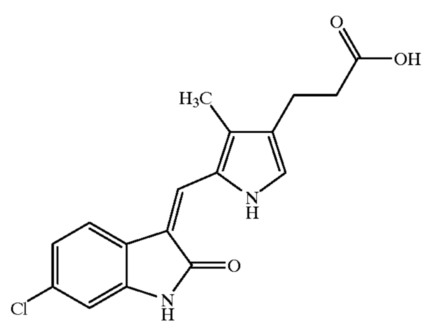 | 0.7 | 0.13 | 1.4 | 1.4 | 9.6 | 11.1 | >50 | >50 |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 12 | 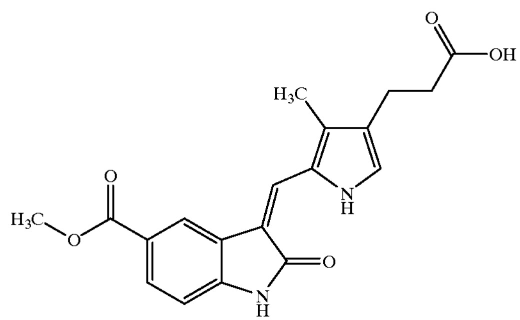 | 52.3 | 13.6 | 3.3 | 11 | 24.6 | 1 | >50 | >50 |
| 13 | 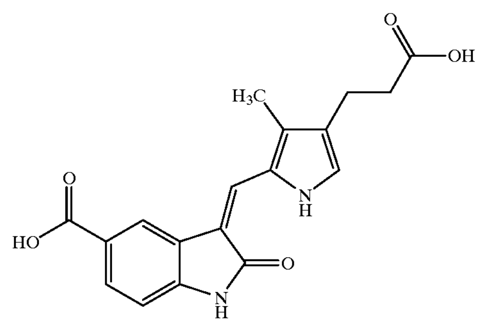 | 31 | 4.2 | | | | | | |
| 14 | 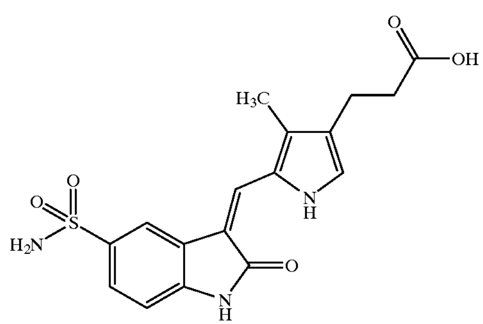 | 17 | 6 | | | | | | |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 15 | 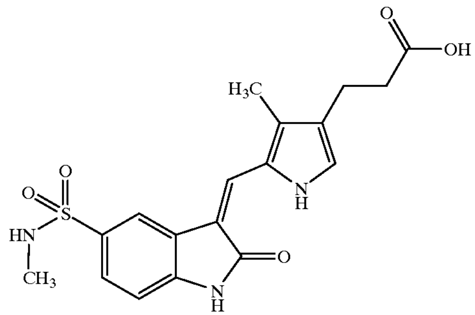 | 6.6 | <0.78 | | | | | | |
| 16 | 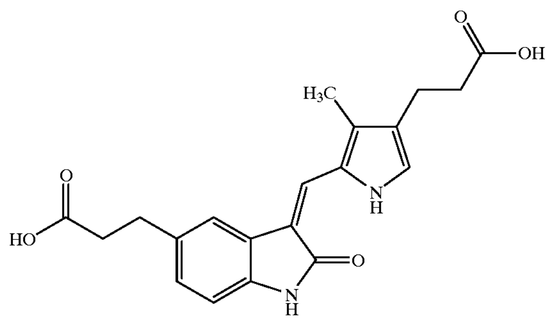 | >100 | 8.7 | | | | | | |
| 17 | 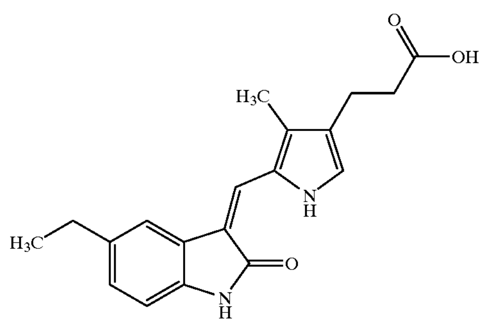 | 10 | 10.3 | | 1.2 | 20 | 6.3 | 44.3 | >50 |

TABLE 1-continued
| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 18 | 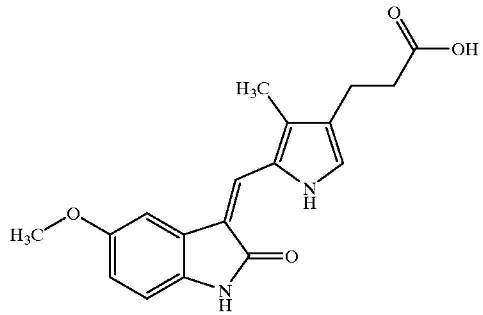 | 2.9 | 2 | | 2.4 | 18.4 | 14.3 | 46 | >50 |
| 19 | 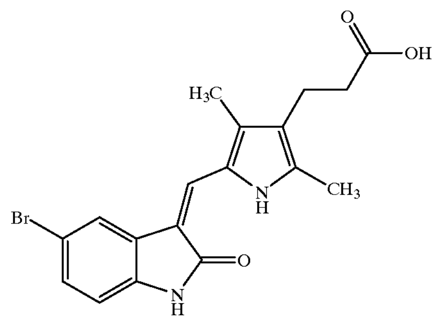 | 0.006 | 0.063 | | 0.07 | 3.6 | 3.7 | 39.6 | >50 |
| 20 | 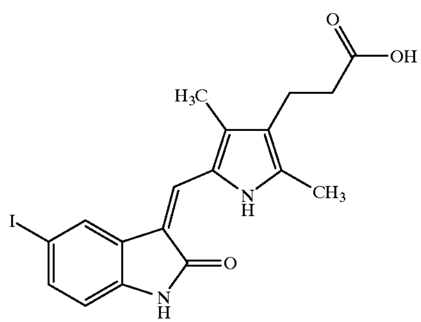 | 0.027 | 0.7 | | 0.29 | 5 | 7.4 | >50 | >50 |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 21 | 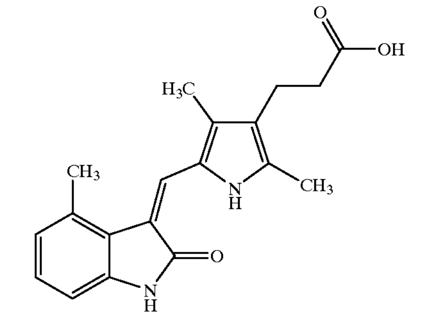 | 0.02 | 0.68 | 4 | 4 | 5.6 | 24.4 | >50 | >50 |
| 22 | 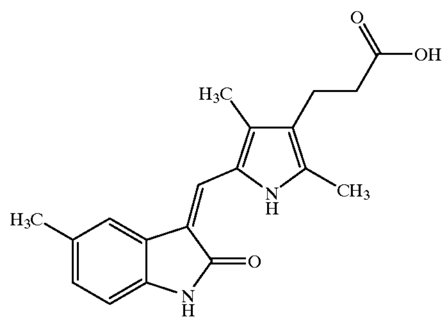 | 0.61 | 0.73 | 0.68 | 0.13 | 15.8 | 5 | 18 | >50 |
| 23 | 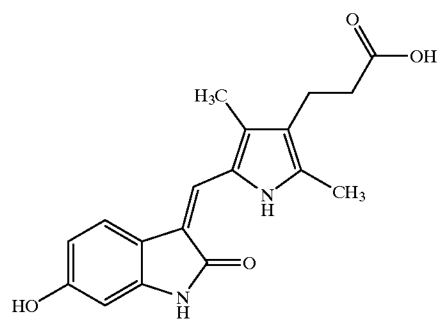 | 5.2 | 0.8 | | 3 | 1.1 | 10.8 | >50 | >50 |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 24 | 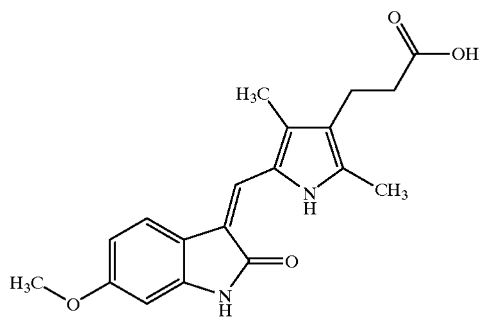 | <0.78 | 0.55 | 17.9 | 0.67 | 25.1 | 2.4 | 21 | >50 |
| 25 | 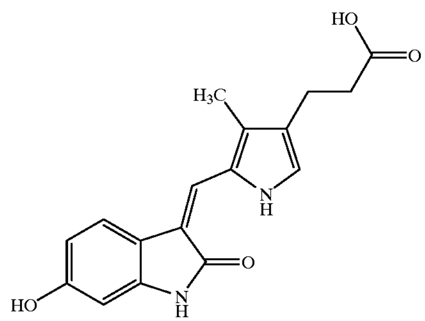 | 0.8 | 1.2 | | | | | | |

TABLE 1-continued
| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 26 | 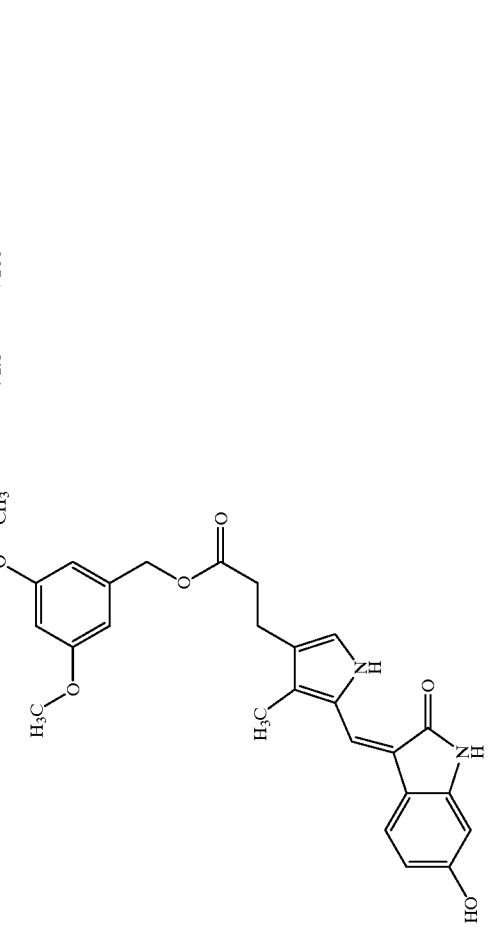 | 91.8 | >100 | | | | | | |
| 27 | 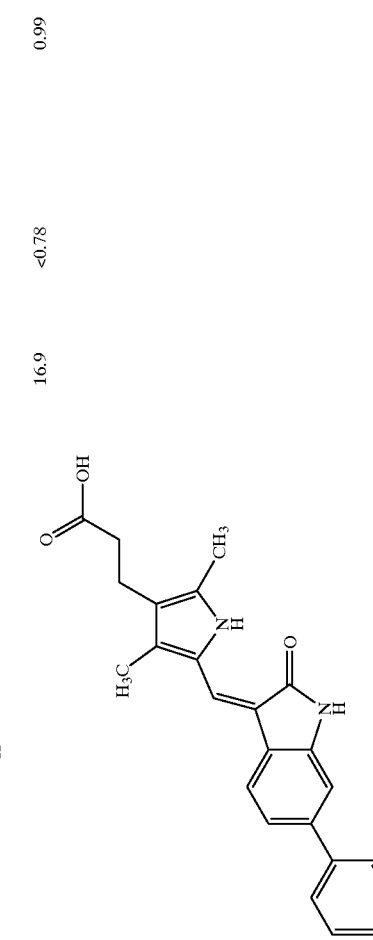 | 16.9 | <0.78 | | 0.99 | 1.5 | | | |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 28 | 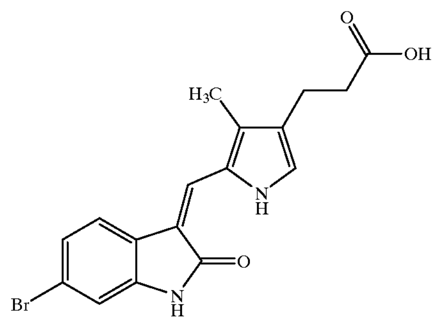 | <0.78 | 0.16 | 0.04 | 0.15 | 1.9 | 3.4 | 37 | >50 |
| 29 | 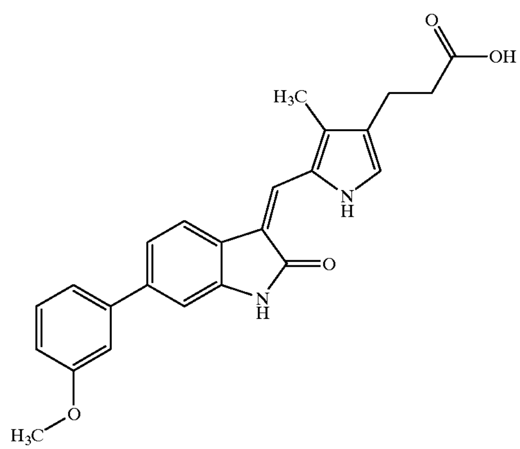 | 5.9 | 1.18 | 6.89 | 0.18 | 0.13 | 0.29 | 13.2 | 30.6 |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 30 | 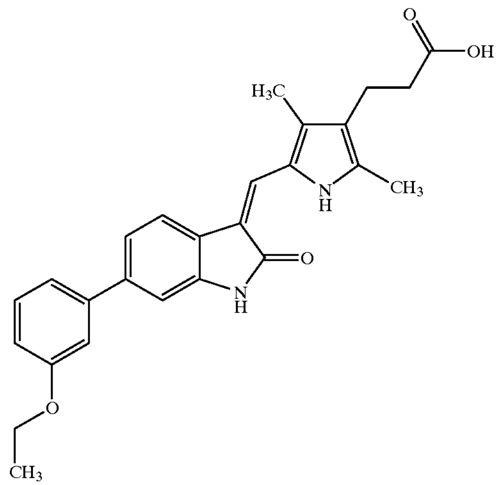 | 2.6 | 0.52 | 3.5 | 0.25 | 0.64 | 0.4 | 22 | 24.7 |
| 31 | 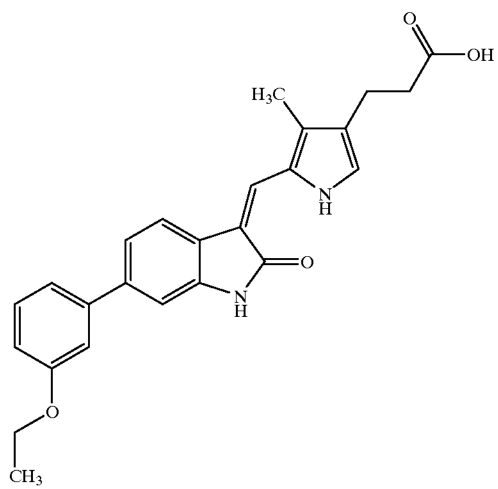 | 3.1 | 1.53 | | 0.09 | 0.18 | 2.1 | 35.9 | 37.2 |

TABLE 1-continued
| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 32 | 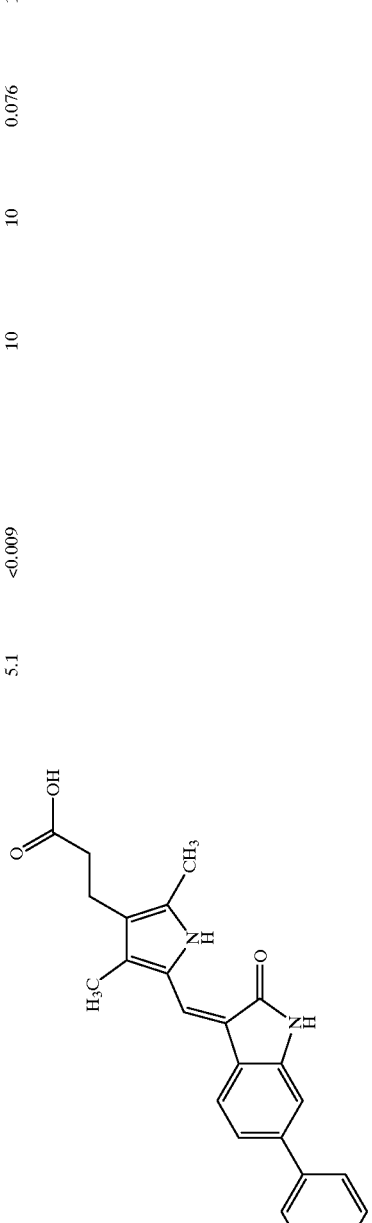 | 5.1 | <0.009 | | 10 | 10 | 0.076 | 12 | 32.7 |
| 33 | 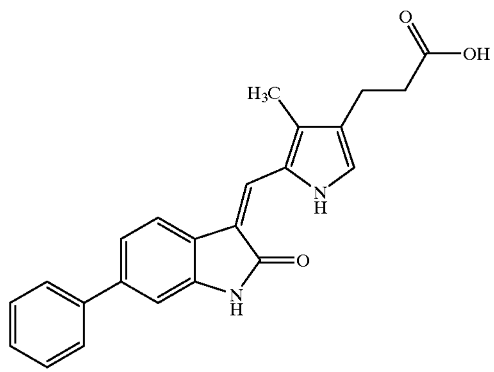 | 4.6 | 0.16 | | 0.81 | 1 | 0.1 | 21 | 30.5 |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 34 | 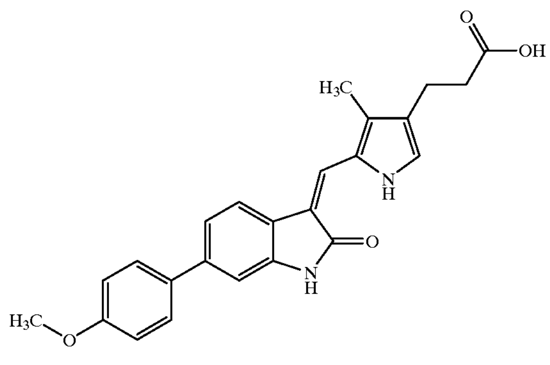 | 24.7 | 3.1 | | | | 3.8 | 34.7 | 36.8 |
| 35 | 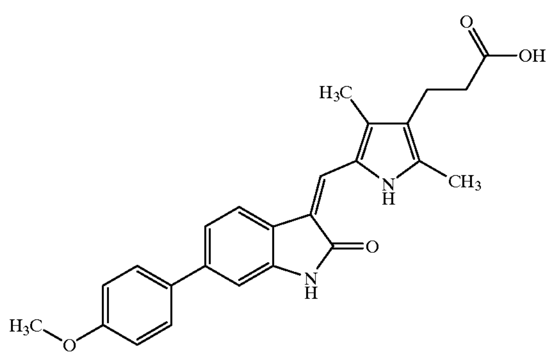 | 14.4 | 1.2 | | | | 1.59 | 35.8 | >50 |

TABLE 1-continued
| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 36 | 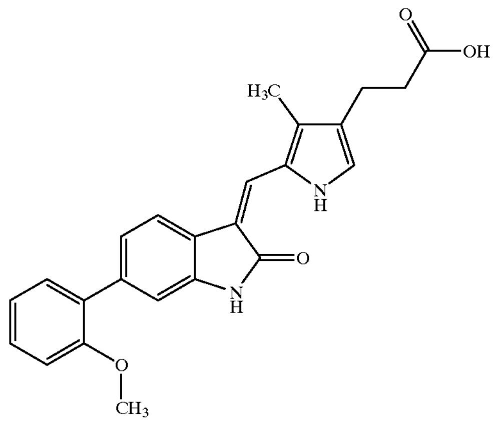 | 89.7 | 1.4 | | | | | | |
| 37 | 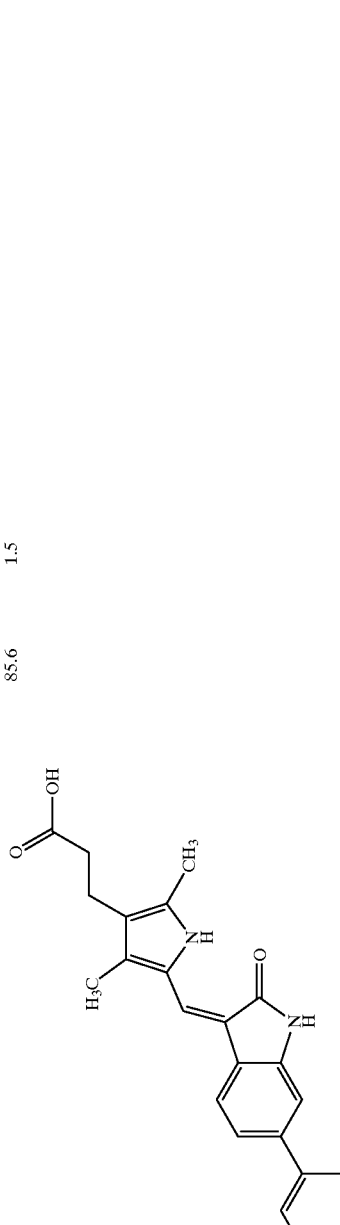 | 85.6 | 1.5 | | | | | | |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 38 | (structure) | | | | | | | | |
| 39 | (structure) | | | | | | | | |

TABLE 1-continued

| Example # | Structure | bio-FLK-1 IC$_{50}$ (mM) | bio-PDGFr IC$_{50}$ (mM) | bio-FGFR IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 40 | 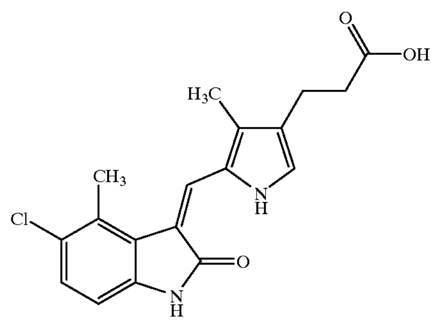 | | | | | | | | |
| 41 | 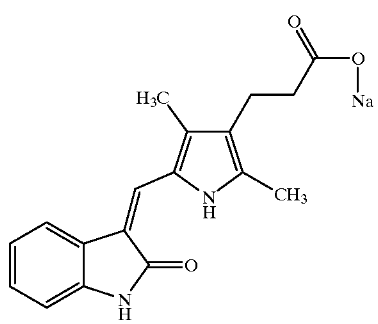 | 0.01 | 0.09 | 3.2 | | | | | |

TABLE 2
| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 42 | 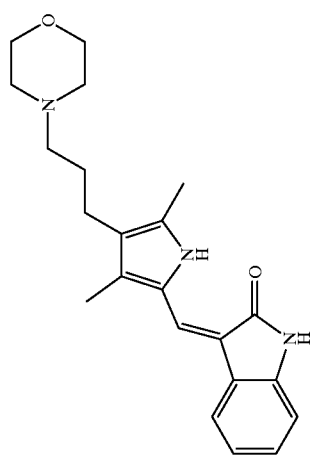 | <0.78 | >100 | 2.31 | | | 0.38 | 34.93 | >50 |
| 43 | 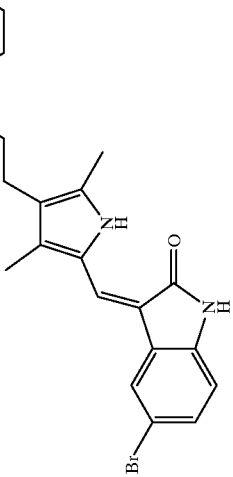 | <0.78 | >100 | 1.59 | | | 0.37 | 45.48 | 44.63 |

TABLE 2-continued
| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 44 | 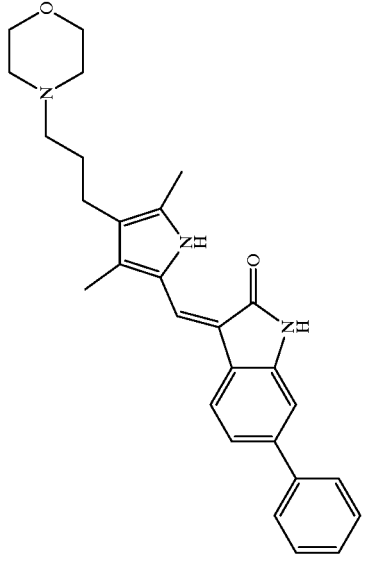 | 42.82 | >100 | 0.27 | | | 0.44 | >50 | >50 |
| 45 | 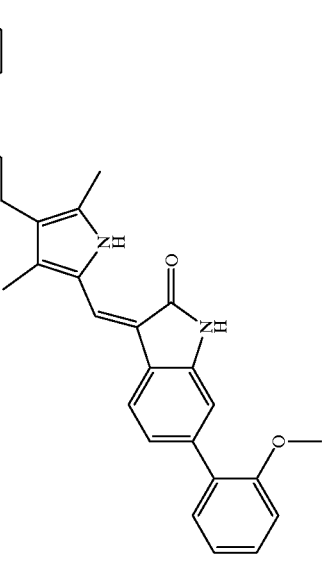 | >100 | >100 | 7.53 | | | 1.02 | 4.96 | 3.9 |

TABLE 2-continued
| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 46 | 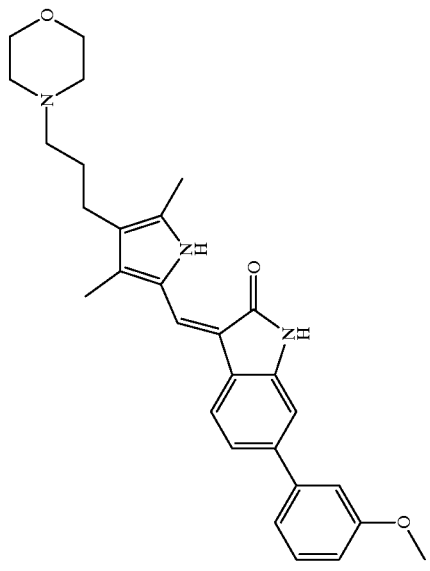 | >100 | >100 | >100 | | | 0.52 | 15.42 | 41.9 |
| 47 | 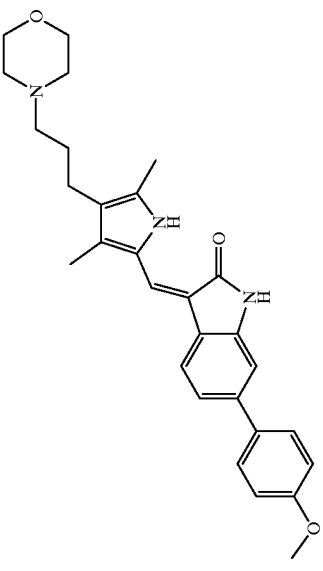 | >100 | >100 | 0.75 | | | >50 | >50 | >50 |

TABLE 2-continued

| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 48 | 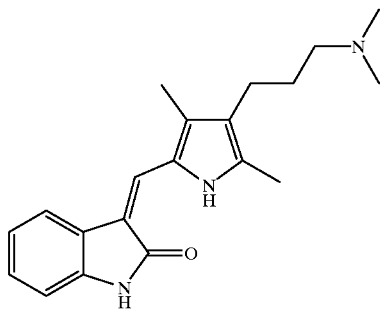 | <0.78 | >100 | 0.053 | | | 0.079 | 9.93 | 12.6 |
| 49 | 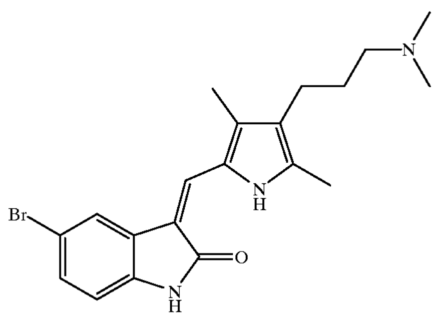 | <0.78 | >100 | <0.046 | | | <0.069 | 1.26 | 4.1 |

TABLE 2-continued

| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 50 | 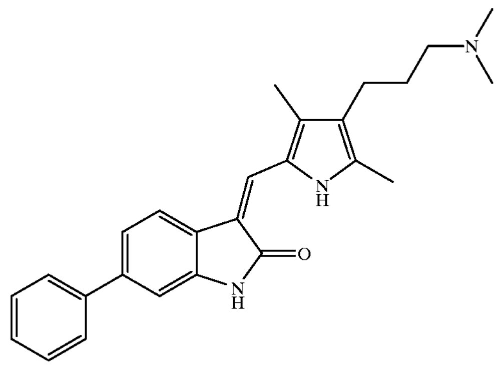 | 5.16 | >100 | 0.1 | | | 0.103 | 3.42 | 4 |
| 51 | 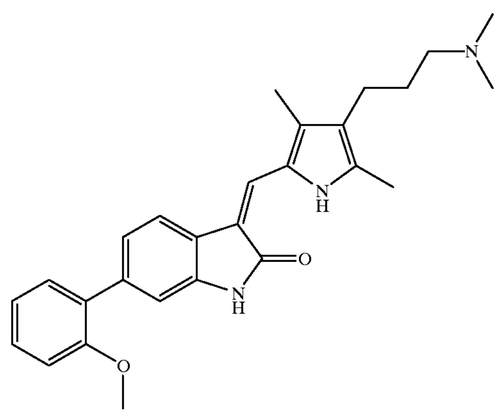 | 42.36 | 22.83 | 1.02 | | | 1.54 | 3.9 | 9.56 |

TABLE 2-continued

| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 52 | 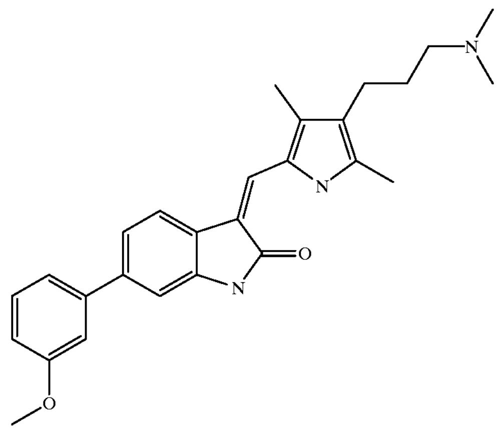 | 9.77 | 28.06 | 0.11 | | | 0.7 | 10.9 | 9.57 |
| 53 | 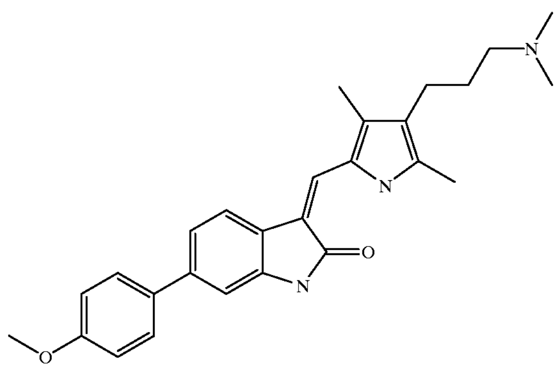 | 99.55 | >100 | 4.35 | | | 0.48 | 3.1 | 3.86 |

TABLE 2-continued

| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 54 | 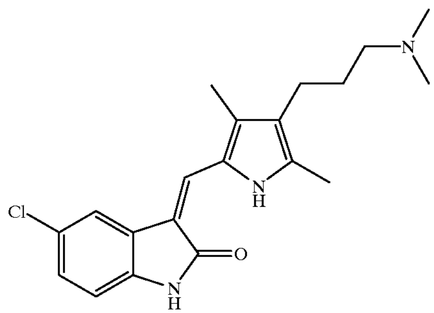 | <0.78 | >100 | <0.0078 | | | <0.069 | 3.01 | 7.49 |
| 55 | 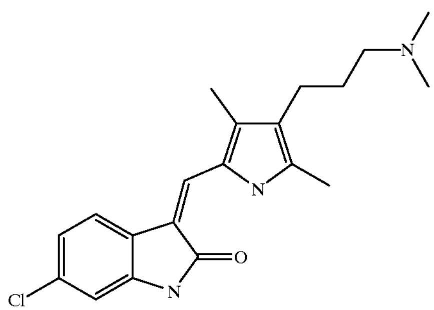 | <0.78 | 86.56 | <0.0078 | | | <0.069 | 13.85 | 25.37 |
| 56 | 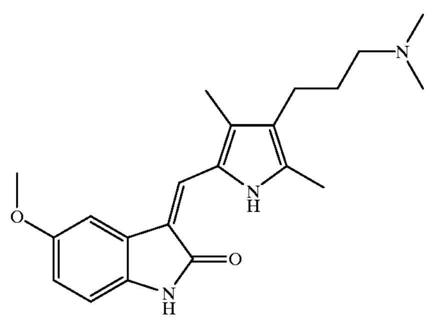 | <0.78 | >100 | 0.16 | | | 0.55 | 4.86 | 11.01 |

TABLE 2-continued

| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 57 | 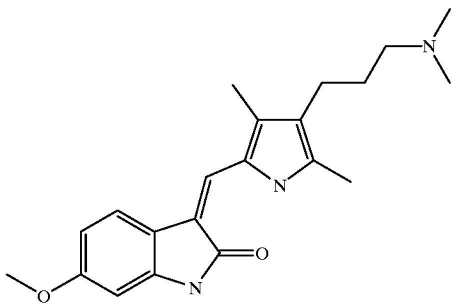 | <0.78 | >100 | 0.05 | | | 0.29 | 15.7 | 27.47 |
| 58 | 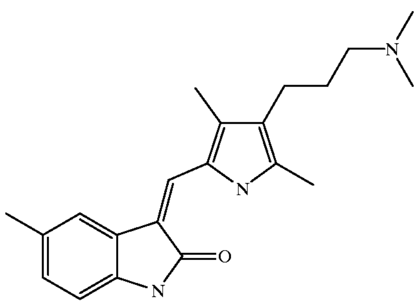 | <0.78 | >100 | <0.0078 | | | <0.069 | 9.18 | 25.35 |
| 59 | 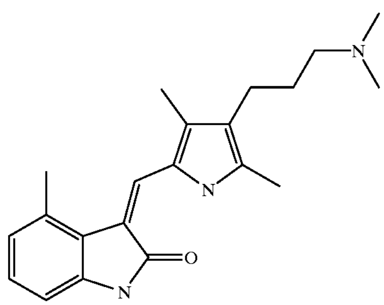 | <0.78 | >100 | 0.067 | | | 0.32 | 9.95 | 20.2 |

TABLE 2-continued

| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 60 | 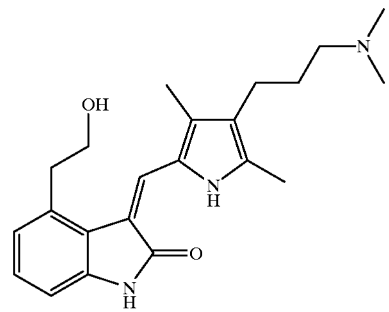 | <0.78 | >100 | 0.43 | | | 0.56 | 3 | 25.34 |
| 61 | 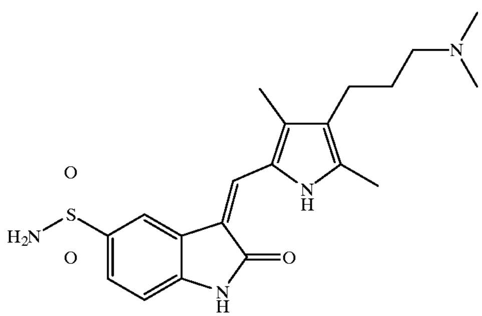 | 0.91 | >100 | 0.44 | | | 1.04 | 11.31 | 6.59 |
| 62 | 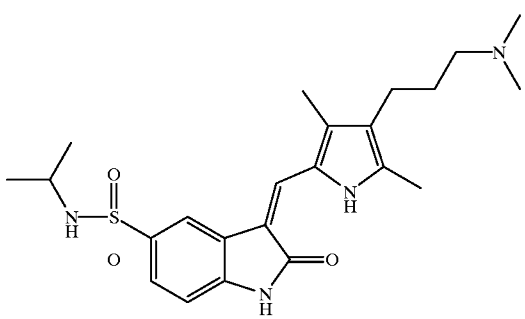 | 1.97 | >100 | 2.35 | | | 0.57 | 2.14 | 8.38 |

TABLE 2-continued

| Example # | Structure | bio-FLK-1 IC$_{50}$ (mM) | bio-EGFr IC$_{50}$ (mM) | bio-PDGFr IC$_{50}$ (mM) | HUVEC-VEGF IC$_{50}$ (mM) | HUVEC-aFGF IC$_{50}$ (mM) | BrdU-PDGFr IC$_{50}$ (mM) | BrdU-FGFr IC$_{50}$ (mM) | BrdU-EGFr IC$_{50}$ (mM) |
|---|---|---|---|---|---|---|---|---|---|
| 63 | 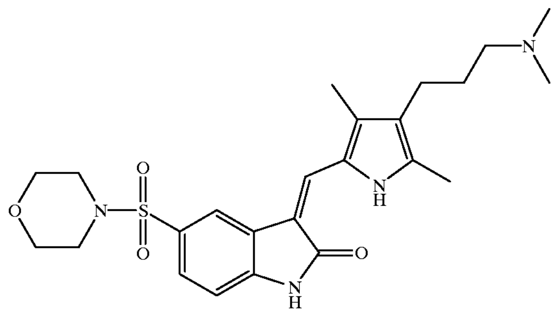 | 12.08 | >100 | 2.41 | | | 10.32 | 29.09 | 29.77 |
| 64 | 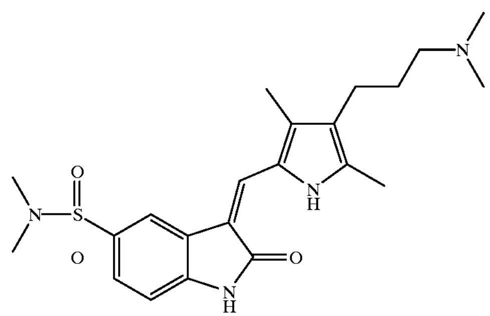 | 15.07 | >100 | 2.86 | | | 1.45 | 4.58 | 11.24 |

TABLE 2 shows the chemical structures of some additional compounds of this invention. As in Table 1, the compound numbers correspond to Example numbers. The general description of the bioassays above applies as well to the bioassays shown in Table 2.

2. INDICATIONS/TARGET DISEASES

The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK mediated signal transduction, is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See, Schlessinger and Ullrich, 1992, Neuron 9:303–391.

It has been shown that tyrosine phosphorylation sites on growth factor receptors function as high-affinity binding sites for SH2 (src homology) domains of signaling molecules. Fantl et al., 1992, *Cell* 69:413–423, Songyang et al., 1994, *Mol. Cell. Biol.* 14:2777–2785), Songyang et al., 1993, *Cell* 72:767–778, and Koch et al., 1991, *Science* 252:668–678. Several intracellular substrate proteins that associate with RTKs have been identified. They may be divided into two principal groups: (1) substrates that have a catalytic domain, and (2) substrates which lack such domain but which serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each RTK is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

STKs, being primarily cytosolic, affect the internal biochemistry of the cell, often as a down-line response to a PTK event. STKs have been implicated in the signaling process which initiates DNA synthesis and subsequent mitosis leading to cell proliferation.

Thus, PK signal transduction results in, among other responses, cell proliferation, differentiation, growth and metabolism. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs. More specifically, it is thought that the 2-indolinone component of the compounds of this invention binds in the general space normally occupied by the adenine ring of ATP. Specificity of a particular molecule for a particular PK may then arise as the result of additional interactions between the various substituents on the 2-indolinone core and the amino acid domains specific to particular PKs. Thus, different indolinone substituents may contribute to preferential binding to particular PKs. The ability to select compounds active at different ATP (or other nucleotide) binding sites makes the compounds of this invention useful for targeting any protein with such a site. The compounds disclosed herein may thus have utility as in vitro assays for such proteins as well as exhibiting in vivo therapeutic effects through interaction with such proteins.

In another aspect, the protein kinase, the catalytic activity of which is modulated by contact with a compound of this invention, is a protein tyrosine kinase, more particularly, a receptor protein tyrosine kinase. Among the receptor protein tyrosine kinases whose catalytic activity can be modulated with a compound of this invention, or salt thereof, are, without limitation, EGF, HER2, HER3, HER4, IR, IGF-1R, IRR, PDGFRα, PDGFRβ, CSFIR, C-Kit, C-fms, Flk-1R, Flk4, KDR/Flk-1, Flt-1, FGFR-1R, FGFR-2R, FGFR-3R and FGFR-4R.

The protein tyrosine kinase whose catalytic activity is modulated by contact with a compound of this invention, or a salt or a prodrug thereof, can also be a non-receptor or cellular protein tyrosine kinase (CTK). Thus, the catalytic activity of CTKs such as, without limitation, Src, Frk, Btk, Csk, Abl, ZAP70, Fes, Fps, Fak, Jak, Ack, Yes, Fyn, Lyn, Lck, Blk, Hck, Fgr and Yrk, may be modulated by contact with a compound or salt of this invention.

Still another group of PKs which may have their catalytic activity modulated by contact with a compound of this invention are the serine-threonine protein kinases such as, without limitation, CDK2 and Raf.

In another aspect, this invention relates to a method for treating or preventing a PK related disorder by administering a therapeutically effective amount of a compound of this invention, or a salt or a prodrug thereof, to an organism.

It is also an aspect of this invention that a pharmaceutical composition containing a compound of this invention or a salt or prodrug thereof is administered to an organism for the purpose of preventing or treating a PK related disorder.

This invention is therefore directed to compounds that modulate PK signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to cure many kinds of solid tumors, including but not limited to carcinomas, sarcomas including Kaposi's sarcoma, erythroblastoma, glioblastoma, meningioma, astrocytoma, melanoma and myoblastoma. Treatment or prevention of non-solid tumor cancers such as leukemia are also contemplated by this invention. Indications may include, but are not limited to brain cancers, bladder cancers, ovarian cancers, gastric cancers, pancreas cancers, colon cancers, blood cancers, lung cancers and bone cancers.

Further examples, without limitation, of the types of disorders related to inappropriate PK activity that the compounds described herein may be useful in preventing, treating and studying, are cell proliferative disorders, fibrotic disorders and metabolic disorders.

Cell proliferative disorders, which may be prevented, treated or further studied by the present invention include cancer, blood vessel proliferative disorders and mesangial cell proliferative disorders.

Blood vessel proliferative disorders refer to disorders related to abnormal vasculogenesis (blood vessel formation) and angiogenesis (spreading of blood vessels). While vasculogenesis and angiogenesis play important roles in a variety of normal physiological processes such as embryonic development, corpus luteum formation, wound healing and organ regeneration, they also play a pivotal role in cancer development where they result in the formation of new capillaries needed to keep a tumor alive. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness.

Two structurally related RTKs have been identified to bind VEGF with high affinity: the fms-like tyrosine 1 (flt-1) receptor (Shibuya et al., 1990, *Oncogene*,5:519–524; De Vries et al., 1992, *Science*, 255:989–991) and the KDR/FLK-1 receptor, also known as VEGF-R2. Vascular endothelial growth factor (VEGF) has been reported to be an endothelial cell specific mitogen with in vitro endothelial cell growth promoting activity. Ferrara & Henzel, 1989, *Biochein. Biophys. Res. Comm.*, 161:851–858; Vaisman et al., 1990, *J. Biol. Chem.*, 265:19461–19566. Information set forth in U.S. application Ser. Nos. 08/193,829, 08/038,596 and 07/975,750, strongly suggest that VEGF is not only responsible for endothelial cell proliferation, but also is the prime regulator of normal and pathological angiogenesis. See generally, Klagsburn & Soker, 1993, *Current Biology*, 3(10)699–702; Houck, et al., 1992, *J. Biol. Chem.*, 267:26031–26037.

Normal vasculogenesis and angiogenesis play important roles in a variety of physiological processes such as embryonic development, wound healing, organ regeneration and female reproductive processes such as follicle development in the corpus luteum during ovulation and placental growth after pregnancy. Folkman & Shing, 1992, *J. Biological Chem.*, 267(16):10931–34. Uncontrolled vasculogenesis and/or angiogenesis has been associated with diseases such as diabetes as well as with malignant solid tumors that rely on vascularization for growth. Klagsburn & Soker, 1993, *Current Biology*, 3(10):699–702; Folkham, 1991, *J. Natl. Cancer Inst.*, 82:4–6; Weidner, et al., 1991, *New Engl. J. Med.*, 324:1–5.

The surmised role of VEGF in endothelial cell proliferation and migration during angiogenesis and vasculogenesis indicates an important role for the KDR/FLK-1 receptor in these processes. Diseases such as diabetes mellitus (Folkman, 198, in *XIth Congress of Thrombosis and Haemostasis* (Verstraeta, et al., eds.), pp. 583–596, Leuven University Press, Leuven) and arthritis, as well as malignant tumor growth may result from uncontrolled angiogenesis. See e.g., Folkman, 1971, *N. Engl. J. Med.*, 285:1182–1186. The receptors to which VEGF specifically binds are an important and powerful therapeutic target for the regulation and modulation of vasculogenesis and/or angiogenesis and a variety of severe diseases which involve abnormal cellular growth caused by such processes. Plowman, et al., 1994, *DN&P*, 7(6):334–339. More particularly, the KDR/FLK-1 receptor's highly specific role in neovascularization make it a choice target for therapeutic approaches to the treatment of cancer and other diseases which involve the uncontrolled formation of blood vessels.

Thus, one aspect of the present invention relates to compounds capable of regulating and/or modulating tyrosine kinase signal transduction including KDR/FLK-1 receptor signal transduction in order to inhibit or promote angiogenesis and/or vasculogenesis, that is, compounds that inhibit, prevent, or interfere with the signal transduced by KDR/FLK-1 when activated by ligands such as VEGF. Although it is believed that the compounds of the present invention act on a receptor or other component along the tyrosine kinase signal transduction pathway, they may also act directly on the tumor cells that result from uncontrolled angiogenesis.

Although the nomenclature of the human and murine counterparts of the generic "flk-I" receptor differ, they are, in many respects, interchangeable. The murine receptor, Flk-1, and its human counterpart, KDR, share a sequence homology of 93.4% within the intracellular domain. Likewise, murine FLK-I binds human VEGF with the same affinity as mouse VEGF, and accordingly, is activated by the ligand derived from either species. Millauer et al., 1993, *Cell*, 72:835–846; Quinn et al., 1993, *Proc. Natl. Acad. Sci. USA*, 90:7533–7537. FLK-1 also associates with and subsequently tyrosine phosphorylates human RTK substrates (e.g., PLC-γ or p85) when co-expressed in 293 cells (human embryonal kidney fibroblasts).

Models which rely upon the FLK-1 receptor therefore are directly applicable to understanding the KDR receptor. For example, use of the murine FLK-1 receptor in methods which identify compounds that regulate the murine signal transduction pathway are directly applicable to the identification of compounds which may be used to regulate the human signal transduction pathway, that is, which regulate activity related to the KDR receptor. Thus, chemical compounds identified as inhibitors of KDR/FLK-1 in vitro, can be confirmed in suitable in vivo models. Both in vivo mouse and rat animal models have been demonstrated to be of excellent value for the examination of the clinical potential of agents acting on the KDR/FLK-1 induced signal transduction pathway.

Thus, in one aspect, this invention is directed to compounds that regulate, modulate and/or inhibit vasculogenesis and/or angiogenesis by affecting the enzymatic activity of the KDR/FLK-1 receptor and interfering with the signal transduced by KDR/FLK-1. In another aspect, the present invention is directed to compounds which regulate, modulate and/or inhibit the KDR/FLK-1 mediated signal transduction pathway as a therapeutic approach to the treatment of many kinds of solid tumors including, but not limited to, glioblastoma, melanoma and Kaposi's sarcoma, and ovarian, lung, mammary, prostate, pancreatic, colon and epidermoid carcinoma. In addition, data suggest the administration of compounds which inhibit the KDR/Flk-1 mediated signal transduction pathway may also be used in the treatment of hemangioma, restenois and diabetic retinopathy.

A further aspect of this invention relates to the inhibition of vasculogenesis and angiogenesis by other receptor-mediated pathways, including the pathway comprising the flt-1 receptor.

Receptor tyrosine kinase mediated signal transduction is initiated by extracellular interaction with a specific growth factor (ligand), followed by receptor dimerization, transient stimulation of the intrinsic protein tyrosine kinase activity and autophosphorylation. Binding sites are thereby created for intracellular signal transduction molecules which leads to the formation of complexes with a spectrum of cytoplasmic signalling molecules that facilitate the appropriate cellular response, e.g., cell division and metabolic effects to the extracellular microenvironment. See, Schlessinger and Ullrich, 1992, *Neuron,* 9:1–20.

The close homology of the intracellular regions of KDR/FLK-1 with that of the PDGF-β receptor (50.3% homology) and/or the related flt-1 receptor indicates the induction of overlapping signal transduction pathways. For example, for the PDGF-β receptor, members of the src family (Twamley et al., 1993, *Proc. Natl. Acad. Sci. USA,* 90:7696–7700), phosphatidylinositol-3'-kinase (Hu et al., 1992, *Mol. Cell. Biol.,* 12:981–990), phospholipase cγ (Kashishian & Cooper, 1993, *Mol. Cell. Biol.,* 4:49–51), ras-GTPase-activating protein, (Kashishian et al., 1992, *EMBO J.,* 11:1373–1382), PTP-ID/syp (Kazlauskas et al., 1993, *Proc. Natl. Acad. Sci. USA,* 10 90:6939–6943), Grb2 (Arvidsson et al., 1994, *Mol. Cell. Biol.,* 14:6715–6726), and the adapter molecules Shc and Nck (Nishimura et al., 1993, *Mol. Cell. Biol.,* 13:6889–6896), have been shown to bind to regions involving different autophosphorylation sites. See generally, Claesson-Welsh, 1994, *Prog. Growth Factor Res.,* 5:37–54. Thus, it is likely that signal transduction pathways activated by KDR/FLK-1 include the ras pathway (Rozakis et al., 1992, *Nature,* 360:689–692), the PI-3'-kinase, the src-mediated and the plcγ-mediated pathways. Each of these pathways may play a critical role in the angiogenic and/or vasculogenic effect of KDR/FLK-1 in endothelial cells. Consequently, a still further aspect of this invention relates to the use of the organic compounds described herein to modulate angiogenesis and vasculogenesis as such processes are controlled by these pathways.

Conversely, disorders related to the shrinkage, contraction or closing of blood vessels, such as restenosis, are also implicated and may be treated or prevented by the methods of this invention.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar. An increased extracellular matrix resulting in a hepatic scar can also be caused by a viral infection such as hepatitis. Lipocytes appear to play a major role in hepatic cirrhosis. Other fibrotic disorders implicated include atherosclerosis.

Mesangial cell proliferative disorders refer to disorders brought about by abnormal proliferation of mesangial cells. Mesangial proliferative disorders include various human renal diseases such as glomerulonephritis, diabetic nephropathy and malignant nephrosclerosis as well as such disorders as thrombotic microangiopathy syndromes, transplant rejection, and glomerulopathies. The RTK PDGFR has been implicated in the maintenance of mesangial cell proliferation. Floege et al., 1993, *Kidney International* 43:47S–54S.

Many cancers are cell proliferative disorders and, as noted previously, PKs have been associated with cell proliferative disorders. Thus, it is not surprising that PKs such as, for example, members of the RTK family have been associated with the development of cancer. Some of these receptors, like EGFR (Tuzi et al., 1991, *Br. J. Cancer* 63:227–233, Torp et al., 1992, *APMIS* 100:713–719) HER2/neu (Slamon et al., 1989, *Science* 244:707–712) and PDGF-R (Kumabe et al., 1992, *Oncogene,* 7:627–633) are over-expressed in many tumors and/or persistently activated by autocrine loops. In fact, in the most common and severe cancers these receptor over-expressions (Akbasak and Suner-Akbasak et al., 1992, *J. Neurol. Sci.,* 111:119–133, Dickson et al., 1992, *Cancer Treatment Res.* 61:249–273, Korc et al., 1992, *J. Clin. Invest.* 90:1352–1360) and autocrine loops (Lee and Donoghue, 1992, *J. Cell. Biol.,* 118:1057–1070, Korc et al., supra, Akbasak and Suner-Akbasak et al., supra) have been demonstrated. For example, EGFR has been associated with squamous cell carcinoma, astrocytoma, glioblastoma, head and neck cancer, lung cancer and bladder cancer. HER2 has been associated with breast, ovarian, gastric, lung, pancreas and bladder cancer. PDGFR has been associated with glioblastoma and melanoma as well as lung, ovarian and prostate cancer. The RTK c-met has also been associated with malignant tumor formation. For example, c-met has been associated with, among other cancers, colorectal, thyroid, pancreatic, gastric and hepatocellular carcinomas and lymphomas. Additionally c-met has been linked to leukemia. Over-expression of the c-met gene has also been detected in patients with Hodgkins disease and Burkitts disease.

IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.,* 50:2511–2517). In addition, IGF-I, while integrally involved in the normal growth and differentiation of the nervous system, also appears to be an autocrine stimulator of human gliomas. Sandberg-Nordqvist et al., 1993, *Cancer Res.* 53:2475–2478. The importance of IGF-IR and its ligands in cell proliferation is further supported by the fact that many cell types in culture (fibroblasts, epithelial cells, smooth muscle cells, T-lymphocytes, myeloid cells, chondrocytes and osteoblasts (the stem cells of the bone marrow)) are stimulated to grow by IGF-I. Goldring and Goldring, 1991, *Eucaryotic Gene Expression,* 1:301–326. In a series of recent publications, Baserga suggests that IGF-IR plays a central role in the mechanism of transformation and, as such, could be a preferred target for therapeutic interventions for a broad spectrum of human malignancies. Baserga, 1995, *Cancer Res.,* 55:249–252, Baserga, 1994, *Cell* 79:927–930, Coppola et al., 1994, *Mol. Cell. Biol.,* 14:4588–4595.

STKs have been implicated in many types of cancer including, notably, breast cancer (Cance, et al., *Int. J. Cancer,* 54:571–77 (1993)).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, von Hippel-Lindau disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., 1994, *DN&P* 7:334–339.

As noted previously, not only RTKs but CTKs including, but not limited to, src, abl, fps, yes, fyn, lyn, lck, blk, hck, fgr and yrk (reviewed by Bolen et al., 1992, *FASEB J.,* 6:3403–3409) are involved in the proliferative and metabolic signal transduction pathway and thus could be expected, and have been shown, to be involved in many PTK-mediated disorders to which the present invention is directed. For example, mutated src (v-src) has been shown to be an oncoprotein ($pp60^{v\text{-}src}$) in chicken. Moreover, its cellular homolog, the proto-oncogene $pp60^{c\text{-}src}$ transmits oncogenic signals of many receptors. Over-expression of EGFR or HER2/neu in tumors leads to the constitutive activation of $pp60^{c\text{-}src}$, which is characteristic of malignant cells but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflamation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents.

Finally, both RTKs and CTKs are currently suspected as being involved in hyperimmune disorders.

A method for identifying a chemical compound that modulates the catalytic activity of one or more of the above discussed protein kinases is another aspect of this invention. The method involves contacting cells expressing the desired protein kinase with a compound of this invention (or its salt or prodrug) and monitoring the cells for any effect that the compound has on them. The effect may be any observable, either to the naked eye or through the use of instrumentation, change or absence of change in a cell phenotype. The change or absence of change in the cell phenotype monitored may be, for example, without limitation, a change or absence of change in the catalytic activity of the protein kinase in the cells or a change or absence of change in the interaction of the protein kinase with a natural binding partner.

Examples of the effect of a number of exemplary compounds of this invention on several PTKs are shown in Tables 1 and 2 and in the Biological Examples section, below. The compounds and data presented are not to be construed as limiting the scope of this invention in any manner whatsoever.

5. PHARMACEUTICAL COMPOSITIONS AND USE

A compound of the present invention, a prodrug thereof or a physiologically acceptable salt of either the compound or its prodrug, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

As used herein, "administer" or "administration" refers to the delivery of a compound, salt or prodrug of the present invention or of a pharmaceutical composition containing a compound, salt or prodrug of this invention to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration ary oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethylcellulose, sodium carboxymethylcellulose, and/or polyvinylpyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the fomulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharamcologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80™, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80™, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addtion, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, succinate wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of the PK activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50–90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

6. SYNTHESIS

The compounds of this invention, as well as the precursor 2-oxindoles and aldehydes, may be readily synthesized using techniques well known in the chemical arts. It will be appreciated by those skilled in the art that other synthetic pathways for forming the compounds of the invention are available and that the following is offered by way of example and not limitation.

A. General Synthetic Procedure

The following general methodology may be employed to prepare the compounds of this invention:

The appropriately substituted 2-oxindole (1 equiv.), the appropriately substituted aldehyde (1.2 equiv.) and piperidine (0.1 equiv.) are mixed with ethanol (1–2 ml/mmol 2-oxindole) and the mixture is then heated at 90° C. for 3 to 5 hours After cooling, the reaction mixture is concentrated and acidified to pH 3. The precipitate that forms is filtered, washed with water to pH 7 and then cold ethanol, ethyl acetate and/or hexane and vacuum dried to yield the target compound. The product may optionally be further purified by chromatography.

B. 2-oxindoles

The following examples are representative syntheses of 2-oxindole precursors to the compounds of this invention. These 2-oxindoles will form the claimed compounds by reaction with an appropriately substituted pyrrole aldehyde using the above general synthetic procedure or the procedures exemplified in section C, below. It is to be understood that the following syntheses are not to be construed as limiting either with regard to synthetic approach or to the oxindoles whose syntheses are exemplified.

5-Amino-2-oxindole

5-Nitro-2-oxindole (6.3 g) was hydrogenated in methanol over 10% palladium on carbon to give 3.0 g (60% yield) of the title compound as a white solid.

5-Bromo-2-oxindole

2-Oxindole (1.3 g) in 20 mL acetonitrile was cooled to −10° C. and 2.0 g N-bromosuccinimide was slowly added with stirring. The reaction was stirred for 1 hour at −10° C. and 2 hours at 0° C. The precipitate was collected, washed with water and dried to give 1.9 g (90% yield) of the title compound.

4-Methyl-2-oxindole

Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6 N hydrochloric acid. The resulting precipitate was collected by vacuum filtration, washed with water, and dried under vacuum to give 9.8 g (45% yield) of 2-methyl-6-nitrophenylacetic acid as an off-white solid. The solid was hydrogenated in methanol over 10% palladium on carbon to give 9.04 g of the title compound as a white solid.

7-Bromo-5-chloro-2-oxindole

5-Chloro-2-oxindole (16.8 g) and 19.6 g of N-bromosuccinimide were suspended in 140 mL of acetonitrile and refluxed for 3 hours. Thin layer chromatography (silica, ethyl acetate) at 2 hours of reflux showed 5-chloro-2-oxindole or N-bromosuccinimide (Rf 0.8), product (Rf 0.85) and a second product (Rf 0.9) whose proportions did not change after another hour of reflux. The mixture was cooled to 10° C., the precipitate was collected by vacuum filtration, washed with 25 mL of ethanol and sucked dry for 20 minutes in the funnel to give 14.1 g of wet product (56% yield). The solid was suspended in 200 mL of denatured ethanol and slurry-washed by stirring and refluxing for 10 minutes. The mixture was cooled in an ice bath to 10° C. The solid product was collected by vacuum filtration, washed with 25 mL of ethanol and dried under vacuum at 40° C. to give 12.7 g (51% yield) of 7-bromo-5-chloro-2-oxindole.

5-Fluoro-2-oxindole

5-Fluoroisatin (8.2 g) was dissolved in 50 mL of hydrazine hydrate and refluxed for 1.0 hr. The reaction mixtures were then poured in ice water. The precipitate was then filtered, washed with water and dried in a vacuum oven to afford the title compound.

5-Nitro-2-oxindole

2-Oxindole (6.5 g) was dissolved in 25 mL concentrated sulfuric acid and the mixture maintained at −10 to −15° C. while 2.1 mL of fuming nitric acid was added dropwise. After the addition of the nitric acid the reaction mixture was stirred at 0 ° C. for 0.5 hr and poured into ice-water. The precipitate was collected by filtration, washed with water and crystallized from 50% acetic acid. The crystalline product was then filtered, washed with water and dried under vacuum to give 6.3 g (70%) of 5-nitro-2-oxindole.

5-Iodo-2-oxindole

2-Oxindole (82.9 g) was suspended in 630 mL of acetic acid with mechanical stirring and the mixture cooled to 10° C. in an ice water bath. Solid N-iodosuccinimide (175 g) was added in portions over 10 minutes. After the addition was complete the mixture was stirred for 1.0 hour at 10° C. The suspended solid, which had always been present, became very thick at this time. The solid was collected by vacuum filtration, washed with 100 mL of 50% acetic acid in water and then with 200 mL of water and sucked dry for 20 minutes in the funnel. The product was dried under vacuum to give 93.5 g (36%) of 5-iodo-2-oxindole containing about 5% 2-oxindole by proton NMR.

5-Methyl-2-oxindole

5-Methylisatin (15.0 g) and 60 mL of hydrazine hydrate were heated at 140 to 160° C. for 4 hours. Thin layer chromatography (ethyl acetate:hexane 1:2, silica gel) showed no starting material remaining. The reaction mixture was cooled to room temperature, poured into 300 mL of ice water and acidified to pH 2 with 6 N hydrochloric acid. After standing at room temperature for 2 days the precipitate was collected by vacuum filtration, washed with water and dried under vacuum to give 6.5 g (47% yield) of 5-methyl-2-oxindole.

5-Bromo-4-methyloxindole and 5,7-Dibromo-4-methyloxindole

4-Methyl-2-oxindole (5 g) in 40 mL of acetonitrile was treated with 7.26 g of N-bromosuccinimide and stirred at room temperature for 4 hours. Thin layer chromatography (ethyl acetate:hexane 1:2, silica gel) showed a mixture of 5-bromo (Rf 0.3) and 5,7-dibromo (Rf 0.5) products. Another 7.26 g of N-bromosuccinimide was added and the mixture stirred for 4 additional hours. The solid was collected by vacuum filtration, washed with 20 mL of acetonitrile and dried to give a 1:1 mixture of mono and dibromo compounds. The filtrate was concentrated and chromatographed on silica gel (ethyl acetate:hexane (1:2)) to give 1.67 g of 5-bromo-4-methyl-2-oxindole as a beige solid. The remaining 1:1 mixture of solids was recrystallized twice from glacial acetic acid to give 3.2 g of 5,7-dibromo-4-methyl-2-oxindole as a light orange solid. The filtrates from this material were chromatographed as above to give 0.6 g of 5-bromo-4-methyl-2-oxindole and 0.5 g of 5,7-dibromo-4-methyl-2-oxindole.

6-Fluoro-2-oxindole

Sodium hydride (2.6 g) and 14.5 g of dimethylmalonate was stirred and heated to 100° C. in 160 mL dimethylsulfoxide for 1.0 hour. The mixture was cooled to room temperature, 7.95 g of 2,5-difluoronitrobenzene were added and the mixture was stirred for 30 minutes. The mixture was then heated to 100° C. for 1.0 hour, cooled to room temperature and poured into 400 mL of saturated ammonium chloride solution. The mixture was extracted with 200 mL of ethyl acetate and the organic layer washed with brine, dried over anhydrous sodium sulfate and concentrated under vacuum. The residue was crystallized from methanol to give 24.4 g (80% yield) of dimethyl 4-fluoro-2-nitrophenylmalonate as a white solid, Rf 0.2 on thin layer chromatography (ethyl acetate:hexane 1:6, silica gel). The filtrate was concentrated and chromatographed on a column of silica gel (ethyl acetate:hexane 1:8) to give an additional 5.03 g of dimethyl 4-fluoro-2-nitrophenylmalonate, for a total of 29.5 g (96% yield).

Dimethyl 4-fluoro-2-nitrophenylmalonate (5.0 g) was refluxed in 20 mL of 6 N hydrochloric acid for 24 hours. The reaction was cooled and the white solid collected by vacuum filtration, washed with water and dried to give 3.3 g (87% yield) of 4-fluoro-2-nitrophenylacetic acid, Rf 0.6 on thin layer chromatography (ethyl acetate:hexane 1:2, silica gel).

4-Fluoro-2-nitrophenylacetatic acid (3.3 g) dissolved in 15 mL of acetic acid was hydrogenated over 0.45 g of 10% palladium on carbon at 60 psi $H_2$ for 2 hours. The catalyst was removed by filtration and washed with 15 mL of methanol. The combined filtrates were concentrated and diluted with water. The precipitate was collected by vacuum filtration, washed with water and dried to give 1.6 g (70% yield) of 6-fluoro-2-oxindole, Rf 0.24 on thin layer chromatography. The filtrate was concentrated to give a purple solid with an NNM spectrum similar to the first crop. Chromatography of the purple solid (ethyl acetate:hexane 1:2, silica gel) gave a second crop of 6-fluoro-2-oxindole as a white solid.

5-Aminosulfonyl-2-oxindole

To a 100 mL flask charged with 27 mL of chlorosulfonic acid was added slowly 13.3 g of 2-oxindole. The reaction temperature was maintained below 30° C. during the addition. After the addition, the reaction mixture was stirred at room temperature for 1.5 hr, heated to 68° C. for 1 hr, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL of ammonium hydroxide in 10 mL of ethanol and stirred at room temperature overnight. The mixture was concentrated and the solid collected by vacuum filtration to give 0.4 g (20% yield) of the title compound as an off-white solid.

5-Methylaminosulfonyl-2-oxindole

A suspension of 3.38 g of 5-chlorosulfonyl-2-oxindole in 10 mL 2 M methylamine in tetrahydrofuran was stirred at room temperature for 4 hours during which time a white solid formed. The precipitate was collected by vacuum filtration, washed twice with 5 mL of water and dried under vacuum at 40° C. overnight to give 3.0 g (88% yield) of 5-methylaminosulfonyl-2-oxindole.

5-(4-Trifluoromethylphenylaminosulfonyl)-2-oxindole

A suspension of 2.1 g of 5-chlorosulfonyl-2-oxindole, 1.6 g of 4-trifluoromethylaniline and 1.4 g of pyridine in 20 mL of dichloromethane was stirred at room temperature for 4 hours. The precipitate which formed was collected by vacuum filtration, washed twice with 5 mL of water and dried under vacuum at 40° C. overnight to give 2.4 g of crude product containing some impurities by thin layer chromatography. The crude product was chromatographed on silica gel eluting with ethyl acetate:hexane (1:2) to give 1.2 g (37% yield) of 5-(4-trifluoromethylphenylaminosulfonyl)-2-oxindole.

5-(Morpholinosulfonyl)-2-oxindole

A suspension of 2.3 g of 5-chlorosulfonyl-2-oxindole and 2.2 g of morpholine in 50 mL of dichloromethane was stirred at room temperature for 3 hours. The white precipitate was collected by vacuum filtration, washed with ethyl acetate and hexane and dried under vacuum at 40° C. overnight to give 2.1 g (74% yield) of 5-(morpholinosulfonyl)-2-oxindole.

6-Trifluoromethyl-2-oxindole

Dimethylsulfoxide (330 mL) was added to 7.9 g of sodium hydride followed by dropwise addition of 43.6 g diethyloxalate. The mixture was heated to 100° C. for 1.0 hour and cooled to room temperature. 2-Nitro-4-trifluoromethyltoluene (31.3 g) was added, the reaction stirred for 30 minutes at room temperature and then heated to 100° C. for 1 hour. The reaction was cooled and poured into a mixture of saturated aqueous ammonium chloride, ethyl acetate and hexane. The organic layer was washed with saturated ammonium chloride, water and brine, dried, and concentrated to give dimethyl 2-(2-nitro-4-trifluoromethylphenyl)malonate.

The diester was dissolved in a mixture of 6.4 g of lithium chloride and 2.7 mL of water in 100 mL of dimethylsulfoxide and heated to 100° C. for 3 hours. The reaction was cooled and poured into a mixture of ethyl acetate and brine. The organic phase was washed with brine, dried with sodium sulfate, concentrated and chromatographed on silica gel (10% ethyl acetate in hexane). The fractions containing product were evaporated to give 25.7 g of methyl 2-nitro-4-trifluoromethylphenylacetate.

Methyl 2-nitro-4-trifluoromethylphenylacetate (26 mg) was hydrogenated over 10% palladium on carbon and then heated at 100° C. for 3 hours. The catalyst was removed by filtration and the solvent evaporated to give the title compound.

5-(2-Chloroethyl)oxindole

5-Chloroacetyl-2-oxindole(4.18 g) in 30 mL of trifluoroacetic acid in an ice bath was treated with 4.65 g of triethylsilane and stirred at room temperature for 3 hours. The mixture was poured into 150 mL of water and the precipitate collected by vacuum filtration, washed with 50 mL of water and dried to give 2.53 g (65% yield) of 5-(2-chloroethyl)-2-oxindole as a reddish-brown solid.

5-Methoxycarbonyl-2-oxindole

5-Iodo-2-oxindole (17 g) was refluxed with 2 g of palladium diacetate, 18.2 g of triethylamine, 150 mL of methanol, 15 mL of dimethylsulfoxide and 2.6 g of DPPP in an atmosphere saturated with carbon monoxide. After 24 hours, the reaction was filtered to remove the catalyst and the filtrate concentrated. The concentrate was chromatographed on silica gel (30% ethyl acetate in hexane). The fractions containing product were concentrated and allowed to stand. The precipitated product was collected by vacuum filtration to give 0.8 g (7%) of the title compound as an off-white solid.

4-Carboxy-2-oxindole

A solution of trimethylsilyldiazomethane in hexane (2 M) was added dropwise to a solution of 2.01 g of 2-chloro-3-carboxynitrobenzene in 20 mL methanol at room temperature until no further gas evolution occurred. The excess trimethylsilyldiazomethane was quenched with acetic acid. The reaction mixture was dried by rotary pump and the residue was further dried in a vacuum oven overnight. The product (2-chloro-3-methoxycarbonylnitrobenzene) was pure enough for the following reaction.

Dimethyl malonate (6.0 mL) was added to an ice-cold suspension of 2.1 g of sodium hydride in 15 mL of DMSO. The reaction mixture was then stirred at 100° C. for 1.0 h and then cooled to room temperature. 2-Chloro-3-methoxycarbonylnitrobenzene (2.15 g) was added to the above mixture in one portion and the mixture was heated to 100° C. for 1.5 h. The reaction mixture was then cooled to room temperature and poured into ice water, acidified to pH 5, and extracted with ethyl acetate. The organic layer was washed with brine, dried over anhydrous sodium sulfate and concentrated to give 3.0 g of the dimethyl 2-methoxycarbonyl-6-nitrophenylmalonate.

Dimethyl 2-methoxycarbonyl-6-nitrophenylmalonate (3.0 g) was refluxed in 50 mL of 6 N hydrochloric acid overnight. The mixture was concentrated to dryness and refluxed for 2 hours with 1.1 g of tin(II) chloride in 20 mL of ethanol. The mixture was filtered through Celite, concentrated and chromatographed on silica gel (ethyl acetate:hexane:acetic acid) to give 0.65 g (37% yield) of 4-carboxy-2-oxindole as a white solid.

5-Carboxy-2-oxindole

2-Oxindole (6.7 g) was added to a stirred suspension of 23 g of aluminum chloride in 30 mL of dichloroethane in an ice bath. Chloroacetyl chloride (11.3 g) was slowly added and hydrogen chloride gas was evolved. After ten minutes of stirring, the reaction was warmed at 40 to 50° C. for 1.5 hours. Thin layer chromatography (ethyl acetate, silica gel) showed no remaining starting material. The mixture was cooled to room temperature and poured into ice water. The precipitate was collected by vacuum filtration, washed with water and dried under vacuum to give 10.3 g (98%) of 5-chloroacetyl-2-oxindole as an off-white solid.

A suspension of 9.3 g of 5-chloroacetyl-2-oxindole was stirred in 90 mL pyridine at 80 to 90° C. for 3 hours then cooled to room temperature. The precipitate was collected by vacuum filtration and washed with 20 mL ethanol. The solid was dissolved in 90 mL 2.5 N sodium hydroxide and stirred at 70 to 80° C. for 3 hours. The mixture was cooled to room temperature and acidified to pH 2 with 0.5 N hydrochloric acid. The precipitate was collected by vacuum filtration and washed thoroughly with water to give crude 5-carboxy-2-oxindole as a dark brown solid. After standing overnight the filtrate yielded 2 g of 5-carboxy-2-oxindole as a yellow solid. The crude dark brown product was dissolved in hot methanol, the insoluble material removed by filtration and the filtrate concentrated to give 5.6 g of 5-carboxy-2-oxindole as a brown solid. The combined yield was 97%.

5-Carboxyethyl-2-oxindole

5-Cyanoethyl-2-oxindole (4.02 g) in 10 mL of water containing 25 mL of concentrated hydrochloric acid was refluxed for 4 hours. The mixture was cooled, water added and the resulting solid collected by vacuum filtration, washed with water and dried to give 1.9 g (44% yield) of the title compound as a yellow solid.

5-Iodo-4-methyl-2-oxindole

To 2 g of 4-methyl-2-oxindole in 40 mL of glacial acetic acid in an ice bath was added 3.67 g N-iodosuccinimide. The mixture was stirred for 1 hour, diluted with 100 mL 50% acetic acid in water and filtered. The resulting white solid was dried under high vacuum to give 3.27 g (88% yield) of the title compound as an off-white solid.

5-Chloro-4-methyl-2-oxindole

A suspension of 3.0 g of 4-methyl-2-oxindole was stirred in 50 mL of acetonitrile at room temperature while 3.3 g of N-chlorosuccinimide was added in portions. Trifluoroacetic acid (1 mL) was then added. The suspension was stirred at room temperature for 3 days during which time solid was always present. The white solid was collected by vacuum filtration, washed with a small amount of cold acetone and dried overnight in a vacuum oven at 40° C. to give 2.5 g (68%) of 5-chloro-4-methyl-2-oxindole.

5-Butyl-2-oxindole

Triethylsilane (2.3 g) was added to 2 g 4-butanoyl-2-oxindole in 20 mL of trifluoroacetic acid at room temperature and the solution stirred for 3 hours. The reaction was poured into ice water to give a red oil which solidified after standing. The solid was collected by vacuum filtration, washed with water and hexane and dried to give 1.7 g (91% yield) of the title compound as an off-white solid.

5-Ethyl-2-oxindole

To 5-Acetyl-2-oxindole (2 g) in 15 mL of trifluoroacetic acid in an ice bath was slowly added 1.8 g of triethylsilane; the reaction was then stirred at room temperature for 5 hours. One mL of triethylsilane was added and the stirring continued overnight. The reaction mixture was poured into ice water and the resulting precipitate collected by vacuum filtration, washed copiously with water and dried under vacuum to give 1.3 g (71% yield) of the title compound as a yellow solid.

5-(Morpholin-4-ethyl)-2-oxindole

5-Chloroethyl-2-oxindole (2.3 g), 1.2 mL of morpholine and 1.2 mL of diisopropylethylamine were heated overnight at 100° C. in 10 mL of dimethylsulfoxide. The mixture ws cooled, poured into water and extacted with ethyl acetate. The organic layer was washed with brine, dried and evaporated. The residue was chromatographed on silica gel (5% methanol in chloroform) to give 0.9 g (31%) of the title compound as a white solid.

5-(4-Methoxycarbonylbenzamido)-2-oxindole

A mixture of 82.0 mg 5-amino-2-oxindole and 131.0 mg 4-methoxycarbonylbenzoyl chloride in pyridine was stirred at room temperature for 3 hr and poured into ice water. The precipitate was filtered, washed with water and dried in a vacuum oven to give 138.0 mg of 5-(4-methoxycarbonylbenzamido)-2-oxindole (81% yield).

5-(4-Carboxybenzamido)-2-oxindole 5-(4-Methoxycarbonylbenzamido)-2-oxindole (0.9 g) and 0.4 g of sodium hydroxide in 25 mL of methanol were refluxed for 3 hours. The mixture was concentrated, water added, and the mixture acidified with 6 N hydrochloric acid. The precipitate was collected by vacuum filtration to give 0.75 g (87%) of the title compound as a white solid.

5-Methoxy-2-oxindole

Chloral hydrate (9.6 g) was dissolved in 200 mL of water containing 83 g of sodium sulfate. The solution was warmed to 60° C., a solution of 11.4 g of hydroxylamine hydrochloride in 50 mL of water was added and the mixture was held at 60° C. In a separate flask, 6.4 g of 4-anisidine and 4.3 mL of concentrated hydrochloric acid in 80 mL of water was warmed to 80° C. The first solution was added to the second and the mixture refluxed for 2 minutes after which it was cooled slowly to room temperature and then cooled in an ice bath. The tan precipitate was collected by vacuum filtration, washed with water and dried under vacuum to give 8.6 g (85% yield) of N-(2-hydroximinoacetyl)anisidine.

Concentrated sulfuric acid (45 mL) containing 5 mL of water was warmed to 60° C. and 8.6 g of N-(2-hydroximinoacetyl)anisidine was added in one portion. The stirred mixture was heated to 93° C. for 10 minutes and then allowed to cool to room temperature. The mixture was poured into 500 g of ice and extracted 3 times with ethyl acetate. The combined extracts were dried over anhydrous sodium sulfate and concentrated to give 5.1 g (65% yield) of 5-methoxyisatin as a dark red solid. 5-Methoxyisatin (5.0 g) and 30 mL of hydrazine hydrate were heated to reflux for 15 minutes. The reaction mixture was cooled to room temperature and 50 mL of water was added. The mixture was extracted 3 times with 25 mL of ethyl acetate each time, the organic layers combined, dried over anhydrous sodium sulfate and concentrated to give a yellow solid. The solid was stirred in ethyl acetate and 1.1 g of insoluble material was removed by vacuum filtration and saved. This material proved to be 2-hydrazinocarbonylmethyl-4-anisidine. The filtrate was concentrated and chromatographed on silica gel eluting with ethyl acetate:hexane (1:1) to give 0.7 g of 5-methoxy-2-oxindole as a yellow solid. The 1. 1 g of 2-hydrazinocarbonylmethyl-4-anisidine was refluxed for 1 hour in 20 mL of 1 N sodium hydroxide. The mixture was cooled, acidified to pH 2 with concentrated hydrochloric acid and extracted 3 times with 25 mL of ethyl acetate each time. The organic extracts were combined, washed with brine, dried over anhydrous sodium sulfate and concentrated to give 0.8 g of 5-methoxy-2-oxindole as a yellow solid. The combined yield was 1.5 g or 33%.

7-Azaoxindole 3,3-Dibromo-7-azaoxindole (2.9 g) was dissolved in a mixture of 20 mL of acetic acid and 30 mL of acetonitrile. To the solution was added 6.5 g of zinc dust. The mixture was stirred for 2 hrs at room temperature. The solid was filtered from the mixture and the solvent evaporated. The residue was slurried with ethyl acetate. The ethyl acetate solution containing insoluble solid was passed through a short column of silica gel. The collected ethyl acetate solution was evaporated and the residue dried under vacuum to give 1.8 g (yield 91%) of 7-azaoxindole acetic acid salt.

5-Dimethylaminosulfonyl-2-oxindole

A suspension of 2.3 g 5-chlorosulfonyl-2-oxindole in 10 mL 2 M dimethylamine in methanol was stirred at room temperature for 4 hours at which time a white solid formed. The precipitate was collected by vacuum filtration, washed with 5 mL 1 N sodium hydroxide and 5 mL of 1 N hydrochloric acid and dried under vacuum at 40° C. overnight to give 1.9 g (79% yield) of 5-dimethylaminosulfonyl-2-oxindole.

6-Phenyl-2-oxindole

Dimethyl malonate (10 mL) in 25 mL of dimethylsulfoxide was added dropwise to 3.5 g sodium hydride suspended in 25 mL dimethylsulfoxide and the mixture heated at 100° C. for 10 minutes. The mixture was cooled to room temperature and 4.7 g of 4-fluoro-3-nitrobiphenyl in 25 mL dimethylsulfoxide was added. The mixture was heated at 100° C. for 2 hours, cooled and quenched with 300 mL of saturated ammonium chloride solution. The mixture was extracted three times with ethyl acetate and the combined organic layers washed with water and brine and evaporated to give, as a yellow oil, crude dimethyl-3-nitrobiphenyl-4-malonate.

Crude dimethyl-3-nitrobiphenyl-4-malonate was refluxed in 30 mL of 6 N hydrochloric acid for 24 hours. The precipitate was collected by filtration, washed with water and dried to give 4.5 g of 3-nitrobiphenyl-4-acetic acid as a cream colored solid.

Iron powder (2.6 g) was added all at once to 4.5 g of 3-nitrobiphenyl-4-acetic acid in 40 mL of acetic acid. The mixture was refluxed for 2 hours, concentrated to dryness and taken up in ethyl acetate. The solids were removed by filtration and the filtrate washed twice with 1 N hydrochloric acid and brine and dried over anhydrous sodium sulfate. The filtrate was concentrated to give 3.4 g (93% yield) of 6-phenyl-2-oxindole as a light brown solid.

6-(2-Methoxyphenyl)-2-oxindole

Tetrakis(triphenylphosphine)palladium (I g) was added to a mixture of 5 g 2-methoxyphenylboronic acid, 6.6 g 5-bromo-2-fluoronitrobenzene and 30 mL of 2 M sodium carbonate solution in 50 mL of toluene and 50 mL of ethanol. The mixture was refluxed for 2 hours, concentrated, and the residue extracted twice with ethyl acetate. The ethyl acetate layer was washed with water and brine, then dried, and concentrated to give a dark green oil which solidified on standing, crude 4-fluoro-2'-methoxy-3-nitrobiphenyl.

Dimethyl malonate (14 mL) was added dropwise to 2.9 g of sodium hydride suspended in 50 mL of dimethylsulfoxide. The mixture was heated at 100° C. for 15 minutes and cooled to room temperature. Crude 4-fluoro-2'-methoxy-3-nitrobiphenyl in 60 mL of dimethylsulfoxide was added and the mixture was heated at 100° C. for 2 hours. The reaction mixture was cooled and quenched with 300 mL of saturated sodium chloride solution and extracted twice with ethyl acetate. The extracts were combined, washed with saturated ammonium chloride, water and brine, dried over anhydrous sodium sulfate and concentrated to give crude dimethyl 2'-methoxy-3-nitrobiphenyl-4-malonate as a yellow oil.

Crude dimethyl 2'-methoxy-3-nitrobiphenyl-4-malonate was heated at 100° C. in 50 mL of 6 N hydrochloric acid for 24 hours and cooled. The precipitate was collected by filtration, washed with water and hexane, and dried to give 9.8 of 2'-methoxy-2-nitrobiphenyl-4acetic acid as a light tan solid.

Iron powder (5 g) was added in one portion to 9.8 g of 2'-methoxy-3-nitrobiphenyl-4-acetic acid in 50 mL of glacial acetic acid was heated to 100° C. for 3 hours. The reaction mixture was concentrated to dryness, sonicated in ethyl acetate and filtered to remove the insolubles. The filtrate was washed twice with 1 N hydrochloric acid, water and then brine, dried over anhydrous sodium sulfate and concentrated. The residue was chromatographed on silica gel in ethyl acetate:hexane (1:2) to give 5.4 g of 6-(2-methoxyphenyl)-2-oxindole as a rose colored solid.

6-(3-Methoxyphenyl)-2-oxindole

Tetrakis(triphenylphosphine)palladium (0.8 g) was added to a mixture of 5 g 3-methoxyphenylboronic acid, 5 g 5-bromo-2-fluoronitrobenzene and 11 mL of 2 M sodium carbonate solution in 100 mL of toluene. The mixture was refluxed for 2 hours, diluted with water and extracted with ethyl acetate. The ethyl acetate was washed with saturated sodium bicarbonate and brine and then dried and concentrated to give an oily solid. The solid was chromatographed on silica gel (ethyl acetate:hexane (1:6)) to give 4.3 g (77% yield) of 4-fluoro-3'-methoxy-3-nitrobiphenyl.

Dimethyl malonate (9.7 mL) was added dropwise to 2.0 g sodium hydride suspended in 50 mL dimethylsulfoxide. The mixture was heated to 100° C. for 35 minutes and cooled to room temperature. 4-Fluoro-2'-methoxy-3-nitrobiphenyl (4.2 g) in 50 mL dimethylsulfoxide was added and the mixture was heated at 100° C. for 1 hour. The reaction mixture was cooled and quenched with 300 mL of saturated ammonium chloride solution and extracted twice with ethyl acetate. The extracts were combined, washed with brine, dried over anhydrous sodium sulfate and concentrated to give crude dimethyl 3'-methoxy-3-nitrobiphenyl-4-malonate as a pale yellow solid.

Crude dimethyl 3'-methoxy-3-nitrobiphenyl-4-malonate was heated at 110° C. in 45 mL 6 N hydrochloric acid for 4 days and then cooled. The precipitate was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g of 10% palladium on carbon for 3 hours at room temperature. The catalyst was removed by filtration, washed with methanol and the filtrates combined and concentrated to give a brown solid. The solid was chromatographed on silica gel in ethyl acetate:hexane:acetic acid (33:66:1) to give 3.0 g of 6-(3-methoxypheny)-2-oxindole as a pink solid.

6-(4-Methoxyphenyl)-2-oxindole

Tetrakis(triphenylphosphine)palladium (I g) was added to a mixture of 5 g of 4methoxyphenylboronic acid, 6.6 g of 5-bromo-2-fluoronitrobenzene and 30 mL of 2 M sodium carbonate solution in 50 mL of toluene and 50 mL of ethanol. The mixture was refluxed for 2 hours, concentrated, and the residue extracted twice with ethyl acetate. The ethyl acetate layer was washed with water and brine, dried, and concentrated to give a brown oily solid. The solid was chromatographed on silica gel (5% ethyl acetate in hexane) to give crude 4-fluoro-4'-methoxy-3-nitrobiphenyl as a pale yellow solid.

Dimethyl malonate (10 mL) was added dropwise to 2.0 g of sodium hydride suspended in 60 mL of dimethylsulfoxide. The mixture was heated to 100° C. for 10 minutes and cooled to room temperature. Crude 4-fluoro-2'-methoxy-3-nitrobiphenyl (5.2 g) in 50 mL dimethylsulfoxide was added and the mixture was heated at 100° C. for 2 hours. The reaction mixture was cooled and quenched with 300 mL of saturated sodium chloride solution and extracted three times with ethyl acetate. The extracts were combined, washed with saturated ammonium chloride, water and brine, dried over anhydrous sodium sulfate and concentrated to give crude dimethyl 4'-methoxy-3-nitrobiphenyl-4malonate as a yellow oil.

Crude dimethyl 4'-methoxy-3-nitro-biphenyl-4-malonate was heated at 100° C. in 60 mL of 6 N hydrochloric acid for 15 hours and cooled. The precipitate was collected by filtration, washed with water and hexane, and dried to give 7.2 g of crude 4'-methoxy-3nitrobiphenyl-4-acetic acid as a light tan solid.

Iron powder (3.6 g) was added in one portion to 7.2 g of 4'-methoxy-3-nitrobiphenyl-4-acetic acid in 50 mL of glacial acetic acid and heated at 100° C. overnight. The reaction mixture was concentrated to dryness, sonicated in ethyl acetate and filtered to remove the insolubles. The filtrate was washed twice with 1 N hydrochloric acid and brine, dried over anhydrous sodium sulfate and concentrated to give 2.7 g of 6-(4-methoxyphenyl)-2-oxindole as a rose colored solid.

6-(3-Ethoxyphenyl)-2-oxindole

Tetrakis(triphenylphosphine)palladium (0.8 g) was added to a mixture of 4.2 g of 3-ethoxyphenylboronic acid, 5.0 g of 5-bromo-2-fluoronitrobenzene and 22 mL of 2 M sodium carbonate solution in 50 mL of toluene and 50 mL of ethanol. The mixture was refluxed for 2 hours, concentrated, water was added and the mixture was extracted twice with ethyl acetate. The ethyl acetate layer was washed with water and brine, then dried, and concentrated. The residue was chromatographed on silica gel (5% ethyl acetate in hexane) to give 5.3 g (90% yield) of crude 4-fluoro-3'-ethoxy-3-nitrobiphenyl as a yellow oil.

Dimethyl malonate (11.4 mL) was added dropwise to 4.0 g sodium hydride suspended in 20 mL dimethylsulfoxide. The mixture was heated to 100° C. for 10 minutes and then cooled to room temperature. Crude 4-fluoro-3'-ethoxy-3-nitrobiphenyl (5.3 g) in 25 mL of dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with water and brine and then dried over anhydrous sodium sulfate and concentrated to give crude dimethyl 3'-ethoxy-3-nitrobiphenyl-4-malonate as a yellow oil.

Crude dimethyl 3'-ethoxy-3-nitrobiphenyl-4-malonate was heated at 100° C. in 60 mL of 6 N hydrochloric acid for 4 days and then cooled. The precipitate was collected by filtration, washed with water and hexane, and dried to give 4.7 g of crude 3'-ethoxy-3-nitrobiphenyl-4-acetic acid as a light tan solid.

Iron powder (2.4 g) was added in one portion to 4.6 g of 3'-ethoxy-3-nitrobiphenyl-4-acetic acid in 40 mL of glacial acetic acid and refluxed for 2 hours. The reaction mixture was concentrated to dryness, treated repeatedly with ethyl acetate and filtered to remove the insolubles. The filtrate was washed twice with 1 N hydrochloric acid and brine and then dried over anhydrous sodium sulfate and concentrated to give 3.5 g (91% yield) of 6-(3-ethoxyphenyl)-2-oxindole as a light brown solid.

6-Bromo-2-oxindole

Dimethyl malonate (13 mL) was added dropwise to 2.7 g sodium hydride suspended in 20 mL dimethylsulfoxide. The mixture was heated to 100° C. for 10 minutes and then cooled to room temperature. 5-Bromo-2-fluoronitrobenzene (5.0 g) in 25 mL of dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium chloride, water and brine, dried over anhydrous sodium sulfate and concentrated to give crude dimethyl 4-bromo-2-nitrophenylmalonate as a pale yellow oil.

Crude dimethyl 4-bromo-2-nitrophenylmalonate was heated at 110° C. in 40 mL of 6 N hydrochloric acid for 24 hours and then cooled. The precipitate was collected by filtration, washed with water and dried to give 5.3 g (89% yield) of 4-bromo-2-nitrophenylacetic acid as an off white solid.

4-Bromo-2-nitrophenylacetic acid (0.26 g), 0.26 g zinc powder and 3 mL 50% sulfuric acid in 5 mL of ethanol were heated at 100° C. overnight. The reaction mixture was filtered, diluted with a little acetic acid, concentrated to remove ethanol, diluted with water and extracted twice with ethyl acetate. The combined extracts were washed with brine, dried over anhydrous sodium sulfate and concentrated to give 0.19 g (90% yield) of 6-bromo-2-oxindole as a yellow solid.

5-Acetyl-2-oxindole

2-Oxindole (3 g) was suspended in 1,2-dichloroethane and 3.2 mL acetyl chloride were slowly added. The resulting suspension was heated to 50° C. for 5 hours, cooled, and poured into water. The resulting precipitate was collected by vacuum filtration, washed copiously with water and dried under vacuum to give 2.9 g (73% yield) of the title compound as a brown solid.

5-Butanoyl-2-oxindole

To 15 g aluminum chloride suspended in 30 mL 1,2-dichloroethane in an ice bath was added 7.5 g of 2-oxindole and then 12 g of butanoyl chloride. The resulting suspension was heated to 50° C. overnight. The mixture was poured into ice water and extracted 3 times with ethyl acetate. The combined ethyl acetate layers were washed with brine, dried over sodium sulfate, and concentrated to dryness to give a brown solid. The solid was chromatographed on silica gel (50% ethyl acetate in hexane) to give 3 g (25%) of the title compound as a yellow solid.

5-Cyanoethyl-2-oxindole

Potassium cyanide (2.0 g) was added to 15 mL of dimethylsulfoxide and heated to 90° C. 5-Chloroethyl-2-oxindole (3.0 g) dissolved in 5 mL dimethyl sulfoxide was added slowly with stirring, and the reaction heated to 150° C. for 2 hours. The mixture was cooled, poured into ice water and the precipitate collected by vacuum filtration, washed with water, dried and then chromatographed on silica gel (5% methanol in chloroform) to give 1.2 g (42% yield) of the title compound.

6-Morpholin-4-yl)-2-oxindole

6-Amino-2-oxindole (2.2 g), 4.0 g 2, 2'-dibromoethyl ether and 7.9 g sodium carbonate were refluxed in 20 ml ethanol overnight, concentrated and diluted with 50 ml of water. The mixture was extracted three times with 50 ml of ethyl acetate and the organic extracts combined, washed with 20 ml of brine, dried over anhydrous sodium sulfate and concentrated to dryness. The solid was chromatographed on a column of silica gel (ethyl acetate:hexane (1:1) containing 0.7% acetic acid) to give 1.2 g (37% yield) of the title compound as a beige solid.

6-(3-Trifluoroacetylphenyl)-2-oxindole

3-Aminophenylboronic acid (3.9 g), 5 g 5-bromo-2-fluoronitrobenzene, 0.8 g tetrakis(triphenylphosphine) palladium and 23 mL of 2 M sodium bicarbonate solution in 50 mL of toluene were refluxed under nitrogen for 2.5 hours. The reaction mixture was poured into 200 mL of ice water and the mixture extracted three times with 50 mL of ethyl acetate. The combined organic layers were washed with 50 mL of water and 20 mL of brine, dried over anhydrous sodium sulfate and concentrated to give 9.7 g (92% yield) of 2-fluoro-5-(3-aminophenyl)nitrobenzene as a dark brown oil.

Trifluoroacetic anhydride (5.4 mL) was slowly added to a stirred solution of 9.7 g 2-fluoro-5-(3-aminophenyl) nitrobenzene and 5.3 mL of triethylamine in 50 mL of dichloromethane at 0° C. and the mixture was stirred for an additional 20 minutes. The mixture was concentrated and the residue chromatographed on a column of silica gel (10% ethyl acetate in hexane) to give 8.6 g (65% yield) of 2-fluoro-5-(3-trifluoroacetamidophenyl)nitrobenzene as a pale orange oil which solidified on standing.

Dimethyl malonate (9.6 mL) was added dropwise to a stirred suspension of 3.2 g of 60% sodium hydride in mineral oil in 40 mL anhydrous dimethylsulfoxide under nitrogen. The mixture was stirred for 10 minutes and 2-fluoro-5-(3-trifluoroacetamidophenyl)nitrobenzene in 20 mL dimethylsulfoxide was added. The resulting dark red mixture was heated to 100° C. for 2 hours. The reaction was quenched by pouring into 100 mL of saturated ammonium chloride solution and extracted twice with 50 mL of ethyl acetate. The organic phase was washed with 50 mL each of saturated ammonium chloride solution, water, and brine, dried over anhydrous sodium sulfate and concentrated to a yellow oil. The oil was chromatographed on a column of silica gel (ethyl acetate:hexane (1:4)) to give 4.4 g (50% yield) of dimethyl 2-[2-nitro-4-(3-trifluoroacetamidophenyl)phenyl]-malonate as a pale yellow solid.

Dimethyl 2-[2-nitro-4-(3-trifluoroacetamidophenyl) phenyl]malonate (4.4 g) was refluxed overnight in 50 mL 6 N hydrochloric acid. The reaction mixture was cooled to room temperature and the solids were collected by vacuum filtration, washed with water, and dried under vacuum to give 2.7 g (73% yield) of 2-[2-nitro-4-(3-trifluoroacetamidophenyl)phenyl] acetic acid.

2-[2-Nitro-4-(3-trifluoroacetamidophenyl)phenyl]acetic acid (100 mg) and 50 mg iron powder in 3 mL acetic acid was heated at 100° C. for 2 hours. The reaction mixture was concentrated and the residue sonicated in 5 mL ethyl acetate. The insoluble solids were removed by vacuum filtration and the filtrate washed with 1 N hydrochloric acid, water and brine, dried over anhydrous sodium sulfate and concentrated to give 10 mg (14% yield) of the title compound as a rose-colored solid.

B. Aldehydes
5-Formyl-2,4-dimethyl-1H-pyrrole-3-carboxylic acid t-Butyl-3-oxobutyrate (158 g, 1 mol) was dissolved in 200 mL of acetic acid in a 500 mL 3-neck round bottom flask equipped with a thermometer, addition funnel and mechanical stirring. The mixture was cooled in an ice bath to about 10° C. Sodium nitrite (69 g, 1 mol) was added over 75 minutes keeping the temperature under 15° C. The cold bath was removed and the mixture stirred for 30 minutes and then allowed to stand for 3.5 hours to give t-butyl-2-hydroximino-3-oxobutyrate.

Ethyl-3-oxobutyrate (130 g, 1 mol) was dissolved in 400 mL of acetic acid in a 2 L 3-neck round bottom flask equipped with a thermometer, an addition funnel, mechanical stirring and placed in an oil bath. Zinc dust (50 g, 0.76 mol) was added and the mixture heated to 60° C. with stirring. The t-butyl-2-hydroximino-3-oxobutyrate solution prepared above was slowly added, the temperature of the reaction mixture being maintained at about 65° C. More zinc dust was then added (4×50 g, 3.06 mol) with the last portion added after all the t-butyl ester had been added. At the end of the additions the temperature was 64° C. The temperature was increased to 70–75° C., stirred for one hour and then poured into 5 L of water. The gray floating precipitate was collected by vacuum filtration and washed with 2 L of water to give 354 g of wet crude product. The crude product was dissolved in 1 L of hot methanol and filtered hot to remove zinc. The filtrate was cooled upon which a precipitate formed. The precipitate that was collected by vacuum filtration and dried to give 118 g of product. The filtrate was put in the refrigerator overnight uon which additional product precipated. A total of 173.2 g of 3,5-dimethyl-1H-pyrrole-2,4-dicarboxylic acid 2-tert-butyl ester 4-ethyl ester was obtained.

3,5-Dimethyl-1H-pyrrole-2,4-dicarboxylic acid 2-tert-butyl ester 4-ethyl ester (80.1 g, 0.3 mol) and 400 mL trifluoroacetic acid were stirred for 5 minutes in a 2 L 3-neck round bottom flask equipped with mechanical stirring and warmed to 40° C. in an oil bath. The mixture was then cooled to −5° C. and triethyl orthoformate (67.0 g, 0.45 mol) was added all at once. The temperature increased to 15° C. The mixture was stirred for about 1 minute, removed from the cold bath and then stirred for 1 hour. The trifluoroacetic acid was removed by rotary evaporation and the residue put in the refrigerator where it solidified. The solid was dissolved by warming and poured into 500 g of ice. The mixture was extracted with 800 mL of dichloromethane to give a red solution and a brown precipitate, both of which were saved. The precipitate was isolated and washed with 150 mL of saturated sodium bicarbonate solution. The dichoromethane phase was also washed with 150 mL of sodium bicarbonate. The dichloromethane solution was washed 3 more times with 100 mL of water. The dichloromethane solution was evaporated to dryness. The dark residue which remained was recrystallized twice from ethyl acetate containing Darco carbon black to give golden yellow needles. The brown precipitate was recrystallized from 350 mL ethyl acetate likewise containing Darco to give a yellow-red solid. All the recrystallized solids were combined and recrystallized from 500 mL of ethanol to give 37.4 g (63.9%) of 5-formyl-2,4-dimethyl-1H-pyrrole-3-carboxylic acid ethyl ester as yellow needles (mp 165.6–166.3° C., lit. 163–164° C.). The residues obtained after evaporationg of the ethyl acetate and ethanol mother liquors were combined and recrystallized from 500 mL of ethanol to give a second crop (10.1 g) or product as dirty yellow needles.

5-Formyl-2,4-dimethyl-1H-pyrrole-3-carboxylic acid ethyl ester (2 g, 10 mmol) was added to a solution of potassium hydroxide (3 g, 53 mmol) dissolved in methanol (3 mL) and water (10 mL). The mixture was refluxed for 3 hours, cooled to room temperature and acidified with 6 N hydrochloric acid to pH 3. The solid which formed was collected by filtration, washed with water and dried in a vacuum oven overnight to give 1.6 g (93%) of 5-formyl-2,4-dimethyl-1H-pyrrole-3-carboxylic acid.

$^1$H NMR (300 MHz, DMSO-d6)δ: 12.09 (s, br, 2 H, NH & COOH), 9.59 (s, 1 H, CHO), 2.44 (s, 3 H, CH$_3$), 2.40 (s, 3 H, CH$_3$).

5-Formyl-2,4-dimethyl-1H-pyrrole-3-carboxylic acid (2-dimethylaminoethyl) amide

To a mixture of 5-formyl-2,4-dimethyl-1H-pyrrole-3-carboxylic acid (1.67 g, 10 mmol) in dimethylformamide (10 mL) was added benzotriazol-1-yloxytris(dimethylamino)-phosphonium hexafluorophosphate (BOP reagent, 6 g, 13.5 mmol) followed by 3 mL diisopropylethylamine. After stirring for 5 minutes, 1 mL of N,N-dimethylethylendiamine was added and the mixture was stirred at room temperature for 24 hours. To the reaction mixture was added 25 mL of 1 N sodium hydroxide and 25 mL of brine. After stirring for 30 minutes, the reaction mixture was poured into water (100 mL) and extracted (3×200 mL) with 10% of methanol in dichloromethane. The organic layers were combined, dried over anhydrous sodium sulfate and evaporated using a rotary evaporator. The residue which remained was purified by chromatography (silica gel column, 5%–10% methanol in dichloromethane) to give 1 g (42%) of 5-formyl-2,4-dimethyl-1H-pyrrole-3-carboxylic acid (2-dimethylaminoethyl)-amide.

$^1$H NMR (360 MHz, DMSO-d6) δ: 11.77 (s, 1 H, NH), 9.53 (s, 1 H, CHO), 7.34 (t, J=5.6 Hz, 1 H, CONH), 3.27 (m, 2 H, CONCH$_2$CH$_2$), 2.37 (t, J=6.8 Hz, 2 H, CONCH$_2$CH$_2$), 2.35 (s, 3 H, CH$_3$), 2.3 (s, 3 H, CH$_3$), 2.17 (s, 6 H, 2×CH$_3$).

MS m/z 238.3 [M+1]$^+$.

3,5-dimethyl-4-(4-methyl-piperazine-1-carbonyl)-1H-pyrrole-2-carboxaldehyde

To a mixture of 5-formyl-2,4-dimethyl-1H-pyrrole-3-carboxylic acid (1.67 g, 10 mmol) in dimethylformamide (10 mL) was added benzotriazol-1-yloxytris (dimethylamino)-phosphonium hexafluorophosphate (BOP reagent, 6 g, 13.5 mmol) followed by 3 mL of diisopropylethylamine. After stirring for 5 minutes, 2 mL of 1-methylpiperazine was added and the mixture was stirred at room temperature for 24 hours. To the reaction was then added 25 mL of 1 N sodium hydroxide and 25 mL of brine. After stirring for 30 minutes, the reaction mixture was poured into water (100 mL) and extracted (3×200 mL) with 10% of methanol in dichloromethane. The organic layers were combined, dried over anhydrous sodium sulfate and evaporated on a rotary evaporator. The residue which remained was purified by chromatography(silica gel column, 5%–10% of methanol in dichloromethane) to give 1 g (40%) of 3,5-dimethyl-4-(4-methyl-piperazine-1-carbonyl)-1H-pyrrole-2-carboxaldehyde.

$^1$H NMR (360 MHz, DMSO-d6)δ: 11.82 (s, 1 H, NH), 9.50 (s, 1 H, CHO), 3.14 (br m, 4 H, 2×CH$_2$), 2.29 (br m, 4 H, 2×CH$_2$), 2.19 (s, 3 H, CH$_3$), 2.17 (s, 3 H, CH$_3$), 2.14 (s, 3 H, CH$_3$).

MS EI 249 [M]$^+$.

C. EXAMPLES

Synthesis of pyrrole substituted 2-indolinones

The following syntheses of representative compounds of this invention are shown by way of example only and are not to be construed as limiting the scope of this invention as to synthetic approach or as to the compounds which comprises this ivention.

EXAMPLE 1

3-[5-(5-Chloro-2-oxo-1,2-dihydroindol-3-ylidenemethyl)-4-methyl-1H-pyrrol-3-yl]-propionic acid 4-(2-Carboxyethyl)-2-formyl-3-methylpyrrole (4.5 g), 4.2 g of 5-chloro-2-oxindole, and 2.9 mL of piperidine in 50 mL of ethanol were heated to 95° C. for 5 hours. The reaction mixture was cooled and concentrated. The residue was suspended in acetone and the yellow precipitate was filtered, washed with cold ethanol, 2 N aqueous hydrochloric acid and water to pH 6 then dried in a vacuum oven overnight to give 7.2 g of the title compound (88%) as a yellow solid.

$^1$HNMR (360 MHz, DMSO-d6): δ 13.31 (s, br, 1 H, NH-1'), 12.06 (s, br, 1 H, COOH), 10.88 (s, br, 1 H, NH-1), 7.93 (d, J=1.88 Hz, 1 H, H-4), 7.75 (s, 1 H, H-vinyl), 7.19 (d, J=3.1 Hz, 1 H, H-2'), 7.1 (dd, b, J=1.88,8.40 Hz, 1 H, H-6), 6.84 (d, J=8.40 Hz, 1 H, H-7), 2.65 (t, J=7.44 Hz, 2 H, CH$_2$CH$_2$COOH), 2.46 (t, J=7.44 Hz, 2 H, CH$_2$CH$_2$COOH), 2.28 (s, 3 H, CH$_3$).

EXAMPLE 2

3-[5-(6-Methoxy-2-oxo-1,2-dihydroindol-3-ylidenemethyl)-4-methyl-1H-pyrrol-3-yl]-propionic acid 4-(2-Carboxyethyl)-2-formyl-3-methylpyrrole (190 mg), 163 mg of 6-methoxy-2-oxindole, and 2 drops of piperidine in 2 mL of ethanol were heated to 90° C. for 3 hours. The reaction mixture was cooled and concentrated. The residue was suspended in 6N aqueous hydrochloric acid. The precipitate was filtered, washed with water to pH 6 and dried in a vacuum oven to give 140 mg of the title compound (43%) as a brown solid.

$^1$HNMR (360 MHz, DMSO-d6): δ 13.1 (s, br, 1 H, NH-1'), 12.04 (s, br, 1 H, COOH), 10.76 (s, br, 1 H, NH-1), 7.63 (d, J=8.29 Hz, 1 H, H-4), 7.46 (s, 1 H, H-vinyl), 7.07 (d, J=3.03 Hz, 1 H, H-2'), 6.55 (dd, J=2.32, 8.29 Hz, 1 H, H-5), 6.43 (d, J=2.32 Hz, 1 H, H-7), 3.74 (s, 3 H, OCH$_3$), 2.63 (t, J=7.31 Hz, 2 H, CH$_2$CH$_2$COOH), 2.45 (t, J=7.31 Hz, 2 H, CH$_2$CH$_2$COOH), 2.23 (s, 3 H, CH$_3$); MS m/z (relative intensity, %) 327 ([M+1]$^{30}$, 100).

EXAMPLE 3

3-[5-(5-Chloro-2-oxo-1,2-dihydroindol-3-ylidenemethyl)-2,4-dimethyl-1H-pyrrol-3-yl]-propionic acid 3-(2-Carboxyethyl)-2,4-dimethyl-5-formylpyrrole (220 mg), 147 mg 5-chloro-2-oxindole, and 2 drops of piperidine in 2 mL of ethanol were heated to 90° C. for 3 hours. The reaction mixture was cooled and concentrated. The residue was suspended in 6 N of aqueous hydrochloric acid. The precipitate was filtered, washed with water to pH 6 and dried in a vacuum oven to give 172 mg of the title compound (50%) as a brown solid.

$^1$HNMR (360 MHz, DMSO-d6): δ 13.42 (s, br, 1 H, NH-1'), 12.03 (s, br, 1 H, COOH), 10.80 (s, br, 1 H, NH-1), 7.87 (d, J=2.06 Hz, 1 H, H-4), 7.67 (s, 1 H, H-vinyl), 7.06 (dd, J=2.06, 8.3 Hz, 1 H, H-6), 6.83 (d, J=8.3 Hz, 1 H, H-7), 2.64 (t, J=7.6 Hz, 2 H, CH$_2$CH$_2$COOH), 2.34 (t, J=7.6 Hz, 2 H, CH$_2$CH$_2$COOH), 2.29 (s, 3 H, CH$_3$), 2.27 (s, 3 H, CH$_3$); MS m/z (relative intensity, %) 345 ([M+1]$^+$, 64).

EXAMPLE 4

3-[4-Methyl-5-(2-oxo-1,2-dihydroindol-3-ylidenemethyl)-1H-pyrrol-3-yl]-propionic acid Sodium metal (1.5 g) was placed in a 3 L 3-neck round bottom flask equipped with a thermometer, reflux condenser and mechanical stirring and placed in an oil bath. Absolute ethanol (1 L) was added with stirring. When the sodium had dissolved, 350 g of pentan-2,4-dione was added all at once and then 310 g of ethyl acrylate added over 30 minutes. The mixture was refluxed for 2.5 hours and then allowed to cool to room temperature overnight. Glacial acetic acid (3 mL) was added and the solvent removed by rotary evaporation. The residue was filtered through a pad of diatomaceous earth and distilled in a wiped film still at 0.1 mm. The distillate was redistilled using a 10 inch vacuum jacketed Vigreux column to give 518 g of ethyl 5-acetyl-4-oxohexanoate, BP 84–92° C. at 0.2–0.7 mm.

To a 5 L three-neck flask equipped with a thermometer and a mechanical stirrer and heated on a steam bath was added 350 g ethyl 5-acetyl-4-oxohexanoate, 329 g ethyl aminomalonate hydrochloride, 133 g sodium acetate and 1.2 L acetic acid. The mixture was heated to 99° C. over 37 minutes. By 62° C., carbon dioxide evolution was already rapid. After a total of 35 minutes at 99° C. gas, CO$_2$ evolution had greatly slowed. After another hour, the mixture was cooled, sodium chloride removed by vacuum filtration, and the solvent evaporated. The residue was mixed with 1 L of cold water. The precipitate was collected by vacuum filtration, washed with 400 mL water, and dissolved in 1 L of hot 95% ethanol. The solution was treated with 20 g of Darco G-60, hot-filtered, and cooled to room temperature. The crystalline solid was collected by vacuum filtration, washed twice on the filter with 200 mL of 50% ethanol and dried under vacuum at 70° C. to give 285 g (64% yield) of 2-ethoxycarbonyl-4-(2-ethoxycarbonylethyl)-3,5-dimethylpyrrole. The filtrate was refrigerated overnight to give another 53.1 g (11.9% yield) of product for a total yield of 75.9%).

2-Ethoxycarbonyl-4-(2-ethoxycarbonylethyl)-3,5-dimethylpyrrole (285 g) and 3500 mL of ethyl ether was placed in a 5 L, 3 neck flask equipped with a mechanical stirrer, a reflux condenser and an addition funnel and cooled in an ice bath. Sulfuryl chloride (435 g) was added dropwise over 145 minutes. As the addition proceeded the mixture turned cloudy and green, then cleared. At the end of the addition the mixture was clear and faintly yellow. The mixture was stirred for 1 additional hour and then heated to reflux for 1 hour. The mixture was cooled and rotary evaporated, diluted with 1500 mL of ether, and rotary evaporated again. The dilution and evaporation was repeated again. The residue was added to 8 L of water containing 802 g of acetic acid and 535 g of sodium hydroxide. The mixture was briefly heated to 85° C. and then allowed to cool overnight with stirring. The aqueous layer, which contained solids, was separated and extracted with 800 mL of ether. The solids and the ether layer were added to 2.5 L of water containing 300 g of sodium carbonate, stirred for 1 hour and filtered to remove a small amount (~7 g) of solid. Sulfurous acid (137 g) was added to the mixture and the resulting precipitate washed twice with 250 mL of water and dried under vacuum to give 56.4 g of product. Sulfurous acid (92 g) was added to the filtrate and the resulting precipitate washed twice with 0.5 L of water and dried under vacuum to give 220 g of product for a total of 276.4 g (86.8% yield) of 2-carboxy-5-ethoxycarbonyl-3-(2-ethoxycarbonylethyl)-4-methylpyrrole.

2-Carboxy-5-ethoxycarbonyl-3-(2-ethoxycarbonylethyl)-4-methylpyrrole (50.5 g) and 400 ml 10% sodium hydroxide solution was heated to 180° C. in a Parr autoclave for 90 minutes. This process was repeated 4 more times until a total of 252.5 g of 2-carboxy-5-ethoxycarbonyl-3-(2-ethoxycarbonylethyl)-4-methylpyrrole had been treated. The five solutions were combined and rotary evaporated to a volume of about 1.8 L of thick black residue. The mixture was cooled to 10° C. in a water bath and 50% sulfuric acid was slowly added so as to keep the temperature at <20° C. until the pH was 2. Ethyl ether (1400 mL) was added, the mixture filtered and the precipitate saved. The precipitate was extracted in a Soxhlet extractor with 500 mL of ether. The combined ether layers were washed with 250 mL water followed by 150 mL of water. The combined water layers were back extracted with 150 mL of ether. All the ether layers were rotary evaporated and the residue dried to give 123.5 g of 3-(2-carboxyethyl)-4-methylpyrrole.

3-(2-Carboxyethyl)-4-methylpyrrole (123 g) was mixed with 1500 mL of ethyl ether and 250 mL of methanol in a magnetically stirred receiver flask. A separate 3 L, 3 neck round bottom flask was equipped with magnetic stirring, a distillation head and condenser leading to the inlet of the receiver flask, and heated in a water bath. Into the 3 L flask was placed 240 g of Diazald dissolved in 1800 mL of ethyl ether and a solution of 73 g of potassium hydroxide dissolved in 360 mL of 95% ethanol and 112 mL of water. The 3 L flask was stirred and heated to 65–75° C. in a water bath and the diazomethane-ether mixture was distilled into the stirred receiver flask over about 2.5 hours. Ethyl ether (200 mL) was added to the 3 L flask and the distillation continued until complete. The receiver flask was stirred for another 30 minutes and then 10 mL of acetic acid was added. The mixture was extracted twice with 500 mL of water, then twice with 200 mL of saturated sodium bicarbonate. The ether layer was dried over anhydrous sodium sulfate and distilled to leave a dark fluid residue. The residue was distilled twice through a 4 inch Vigreux column and once through a 10 inch vacuum-jacketed Vigreux column to give 108 g (80.6% yield) of 3-(2-ethoxycarbonylethyl)-4-methylpyrrole. BP 108–113° C. at 0.5 mm.

Dimethylformamide was charged to a 500 mL, 3 neck round bottom flask equipped with mechanical stirring, a thermometer and a dropping funnel and maintained under a nitrogen atmosphere. The flask was cooled to 0° C. and 58.4 mL of phosphorus oxychloride was added dropwise over 80 minutes. Dichloroethane (280 mL) was added and the mixture allowed to warm to room temperature and then cooled to −10° C. 3-(2-methoxycarbonylethyl)-4-methylpyrrole (55.7 g) dissolved in 80 mL dichloroethane was added dropwise over 1 hour and the mixture stirred for another 35 minutes. The mixture was rotary evaporated at <30° C. The fluid residue was poured into 2700 mL of ice-cold 2 N sodium hydroxide solution. The resulting solution was heated to 88° C. over 20 minutes and then maintained at this temperature for an additional 30 minutes. The solution was cooled to ambient temperature and extracted with 200 mL of ethyl ether. The aqueous solution was cooled to 0° C. and acidified to pH 3.5 by slowly adding about 1350 mL of 5 N hydrochloric acid. The yellow precipitate was collected by vacuum filtration, washed four times with 100 mL of water, and dried in a vacuum oven at ambient temperature to give 54.4 g (90.2% yield) of crude 4-(2-carboxyethyl)-2-formyl-3-methylpyrrole.

The crude material was placed in a refluxing mixture of 425 mL of ethanol and 700 mL of ethyl ether and hot filtered to remove an insoluble residue, which was retained. The filtrate was put in the freezer and the resulting precipitate collected by vacuum filtration and washed with 50 mL of ether. The filtrate was used to again extract the insoluble residue, hot filtered and put in the freezer. The resulting precipitate and the first precipitate were combined to give 26.1 g of 4-(2-carboxyethyl)-2-formyl-3-methylpyrrole as a brown powder, MP 149.0–150.3° C. The filtrate was combined with the filtrate from a previous preparation and concentrated to give 43 g of a brown solid. The solid was put into a refluxing mixture of 500 ml ether and 100 mL ethanol, filtered. The filtrate treated with Norit at reflux and hot filtered again. The filtrate was put in the freezer to give 3 additional crops of 4-(2-carboxyethyl)-2-formyl-3-ethylpyrrole, 7.7 g, MP 148–151° C., 3.2 g MP 128–134° C. and 4.1 g, MP 148.2–150.0° C.

4-(2-Carboxyethyl)-2-formyl-3-methylpyrrole (9.0 g) and 6.0 g of 2-oxindole in 50 mL of ethanol were heated to 70° C. in a 250 mL, 3-neck round bottom flask equipped with a thermometer, a reflux condenser and magnetic stirring. When most of the solids had dissolved, 4.5 g of piperidine was slowly added and the mixture refluxed for 4 hours. Acetic acid (12 mL) was slowly added resulting in a copious precipitate. The mixture was refluxed for 5 minutes, cooled to room temperature and the precipitate collected by vacuum filtration and washed with 30 mL of ethanol. The precipitate was slurry-washed at reflux in 30 mL of ethanol, cooled to room temperature, collected by vacuum filtration, washed with 20 mL of ethanol and dried under vacuum to give 11.9 g (80% yield) of 3-[4-(2-carboxyethyl)-3-methylpyrrol-2-methylidenyl]-2-indolinone, SU6663, as an orange solid.

$^1$HNMR (360 MHz, DMSO-d6): δ 13.29 (s, br, 1 H, NH-1'), 12.05 (s, br, 1 H, COOH), 10.78 (s, br, 1 H, NH-1), 7.73 (d, J=7.43 Hz, 1 H, H-4), 7.61 (s, 1 H, H-vinyl), 7.13 (d, J=2.75 Hz, 1 H, H-2'), 7.10 (t, J=7.43 Hz, 1 H, H-6), 6.97 (t, J=7.43 Hz, 1 H, H-5), 6.85 (d, J=7.43 Hz, 1 H, H-7), 2.64 (t, J=7.38 Hz, 2 H, CH$_2$CH$_2$COOH), 2.46 (t, J=7.38 Hz, 2 H, CH$_2$CH$_2$COOH), 2.25 (s, 3 H, CH$_3$); MS m/z (relative intensity, %) 297 ([M+1]$^+$, 100).

EXAMPLE 5

3-[2,4-Dimethyl-5-(2-oxo-1,2-dihydroindol-3-ylidenemethyl)-1H-pyrrol-3-yl]-propionic acid 2,4-Dimethyl-5-ethoxycarbonyl-3-(2-ethoxycarbonylethyl)pyrrole (1.07 kg) and 3.2 L 5 N sodium hydroxide were mechanically stirred in a 12 L three-neck round bottom flask equipped with a reflux condenser and an addition funnel and heated in an oil bath. The mixture was refluxed for 3 hours after which time the internal temperature was 96° C., all solids were dissolved and thin layer chromatography showed hydrolysis to be complete. The heating bath was removed and the mixture cooled to 50° C. in a water bath. 12 N Hydrochloric acid (~1.3 L) was slowly added. After about 50% of the acid was added gas evolution began and the temperature reached 60° C. As more acid was added, gas evolution increased and a yellow precipitate formed. The final pH was adjusted to 3.5 with hydrochloric acid. The mixture was cooled in an ice bath to 8° C. The solids were collected by vacuum filtration, washed twice with 0.5 L of distilled water and dried for 48 hours in a vacuum oven at 55–60° C. to give 677 g (101% yield) of 3-(2-carboxyethyl)-2,4-dimethylpyrrole.

$^1$HNMR (d$_6$-DMSO) δ 11.9 (s, 1 H, COOH), 9.9 (s, 1 H, NH), 6.2 (s, 1 H, aromatic), 2.5 (t, 2 H, CH$_2$), 2.2 (t, 2 H, CH$_2$), 2.0 (s, 3 H, CH$_3$), 1.9 (s, 3 H, CH$_3$); MP 134–136° C.

Dimethylformamide (28.5 g) in 250 mL of dichloromethane in a 1 L three neck round bottom flask equipped with magnetic stirring, a thermometer and a dropping funnel was cooled in an ice-salt bath to −1° C. Phosphorus oxychloride (59.3 g) was placed in the dropping funnel and slowly added to the reaction mixture. The funnel was flushed with 25 mL of dichloromethane to be sure all the phosphorus oxychloride. The maximum temperature reached by the mixture was 5° C. The mixture was stirred for 15 minutes at which time the temperature was −3° C. Solid 3-(2-Carboxyethyl)-2,4-dimethylpyrrole (32.6 g) was added in portions over 15 minutes. The maximum temperature reached by the mixture was 7° C. The reddish-black mixture was stirred for 30 minutes more and then heated to reflux for 1 hour. The mixture was cooled to 15° C. and 300 mL of water was added leading to a vigorous reaction during which the temperature increased. The mixture was stirred and cooled to 22° C. and the layers separated and saved. The organic layer was extracted with 100 mL of water and the aqueous layers combined and washed with 50 ml of dichloromethane. The organic layers were discarded. The aqueous layer was adjusted to pH 11 with ~180 mL of 10 N sodium hydroxide. The temperature increased to 40° C. The mixture was stirred for 30 minutes at which time the temperature was 27° C. The mixture was acidified to pH 2 with ~120 mL of 10 N hydrochloric acid which increased the temperature to 30° C. Ethyl acetate (150 mL) was added and the mixture was stirred to extract the product. During stirring a considerable amount of black solid appeared on top of the water layer. The ethyl acetate layer was separated and the aqueous layer and solid was extracted twice with 100 mL of ethyl acetate. The solid still present was collected by vacuum filtration, washed thoroughly with water and dried under vacuum at 40° C. to give 12 g (31% yield) of 3-(2-carboxyethyl)-2,4-dimethyl-5-formylpyrrole as a brownish-black solid. Thin layer chromatography (dichloromethane:acetic acid, 95:5, silica gel) showed a spot at Rf 0.7 and a colored spot at the origin. The ethyl acetate layers were combined, dried over anhydrous sodium sulfate, and evaporated to a brownish-black solid which was dried under vacuum at 40° C. to give 21 g (55% yield, total yield 86%) of 3-(2-carboxyethyl)-2,4-dimethyl-5-formylpyrrole, identical in appearance to the previous solid by thin layer chromatography.

Alternatively, dimethylformamide (124 mL) in 750 mL of dichloromethane in a 5 L three-neck round bottom flask equipped with mechanical stirring, a thermometer and a dropping funnel was cooled in an ice-salt bath to −9° C. Phosphorus oxychloride (114 mL) was added rapidly via the dropping funnel which was flushed into the reaction mixture with 50 mL of dichloromethane. The maximum temperature reached by the mixture was −4° C. Solid 3-(2-carboxyethyl)-2,4-dimethylpyrrole (133.6 g) was added in portions over 20 minutes. The maximum temperature reached by the mixture was 3° C. The dark reddish mixture was heated to reflux for 1 minute and then cooled to −1° C. The mixture was cooled to 1° C. and 800 mL of ice water was rapidly added. The maximum temperature reached was 15° C. The organic layer was separated and discarded. The aqueous layer was slowly adjusted to pH 12–13 with ~800 mL of 10 N potassium hydroxide, adding ice to control the temperature. The temperature increased to 37° C. The mixture was stirred for 90 minutes at ambient temperature at which time thin layer chromatography showed only a trace of light-colored material at the origin with the product at Rf 0.3. The mixture was cooled to 0° C. The mixture was acidified to pH 3 with ~600 mL of 10 N hydrochloric acid ice being added to control the temperature. The maximum temperature reached was 10° C. The mixture was stirred for 1 hour in the cold. The solid was collected by vacuum filtration, washed 4 times with 100 mL of water and dried under vacuum at 50–60° C. to give 140.6 g (90% yield) of 3-(2-carboxyethyl)-2,4-dimethyl-5-formylpyrrole as a brown solid.

$^1$HNMR (d$_6$-DMSO): δ 12.0 (s, 1 H, COOH), 11.3 (s, 1 H, NH), 9.4 (s, 1 H, CHO), 2.6 (t, 2 H, CH$_2$), 2.3 (t, 2 H, CH$_2$), 2.2 (s, 3 H, CH$_3$), 2.1 (s, 3 H, CH$_3$). MP 145–147° C.

3-(2-Carboxyethyl)-2,4-dimethyl-5-formylpyrrole (18.2 g) and 11.7 g 2-oxindole were dissolved in 100 mL of ethanol by heating in a 250 mL round bottom flask equipped with a magnetic stirrer and a reflux condenser in an oil bath. Pyrrolidine (7.0 g) was added and the reaction mixture refluxed for 2 hours at which time a large quantity of brown-black solid was present. Thin layer chromatography (ethyl acetate:ethanol:acetic acid 96:2:2, silica gel) showed the absence of oxindole starting material. Eight mL of acetic acid was added and the mixture refluxed for 15 minutes. The thick mixture was diluted with 50 mL of ethanol and cooled to 10° C. The solid was collected by vacuum filtration and washed with 50 mL of ethanol. The solid was stirred in 125 ml of ethanol at reflux for 10 minutes, cooled to 10° C., collected by vacuum filtration and washed with 50 mL of ethanol. The product was dried overnight at 45° C. under vacuum to give 25.5 g (88% yield) of 3-[2,4-dimethyl-3-(2-carboxyethyl) pyrrol-5-methylidenyl]-2-indolinone as an orange solid.

Alternatively, a mixture of 3-(5-formyl-2,4-dimethyl-1H-pyrrol-3-yl)-propionic acid (10 g, 51 mmol), 2-oxindole (6.5 g, 49 mmol) and sodium hydroxide (40 g, 58 mmol) dissolved in 50 ml of water was stirred at 50° C. for 4 hours. The reaction mixture was cooled to room temperature, filtered and the filtrate acidified with to pH 3 with 12 N hydrochloric acid. The solid which precipitated was collected by vacuum filtration, washed with 10 ml of water and dried under vacuum overnight. The crude solid slurry washed with hot ethanol twice. The solid was then collected by vacuum filtration, washed with 10 ml of ethanol and dried under vacuum to give 13.8 g (91%) of 3-[2,4-dimethyl-5-(2-oxo-1,2-dihydro-indol-3-ylidenemethyl)-1H-pyrrol-3-yl]-propionic acid.

$^1$HNMR (360 MHz, DMSO-d6): δ 13.38 (s, br, 1 H, NH-1'), 12.05 (s, br, 1 H, COOH), 10.70 (s, br, 1 H, NH-1), 7.69 (d, J=7.39 Hz, 1 H, H-4), 7.53 (s, 1 H, H-vinyl), 7.06 (t, J=7.39 Hz, 1 H, H-6), 6.95 (t, J=7.39 Hz, 1 H, H-5), 6.85 (d, J=7.39 Hz, 1 H, H-7), 2.63 (t, J=7.45 Hz, 2 H, CH$_2$CH$_2$COOH), 2.34 (t, J=7.45 Hz, 2 H, CH$_2$CH$_2$COOH), 2.28 (s, 3 H, CH$_3$), 2.24 (s, 3 H, CH$_3$); MS m/z (relative intensity, %) 311 ([M+1]$^+$, 100).

EXAMPLE 6

3-[5-(5-Bromo-2-oxo-1,2-dihydroindol-3-ylidenemethyl)-4-methyl-1H-pyrrol-3-yl]-propionic acid 2-Oxindole (53.3 g) was suspended in 640 mL acetonitrile and the mixture cooled to 7° C. in an ice bath with mechanical stirring. Solid N-bromosuccinimide (74.8 g) was added in portions over 20 minutes. After about one-third of the N-bromosuccinimide had been added (over 5 minutes), the temperature had increased to 12° C. The addition was halted until the temperature of the mixture had dropped to 10° C. The addition was resumed keeping the temperature below 12° C. After the addition was complete, the mixture was stirred for 1 hour at 10° C. and then for 1 additional hour during which the mixture was allowed to warm to ambient temperature. The precipitate was collected by vacuum filtration, washed with 80 mL of ethanol and sucked dry for 20 minutes in the filtration funnel to give product containing 6.4% of 2-oxindole by HPLC. The solid was suspended in 1440 mL of denatured ethanol and slurry-washed by stirring and refluxing for 5 minutes at which time most of the solid had dissolved. The mixture was cooled in an ice bath to 13° C. The solid product was collected by vacuum filtration, washed with 80 mL of ethanol and dried under vacuum to give 57.7 g (68.0%) of 5-bromo-2-oxindole containing 1.13% 2-oxindole by HPLC. Slurry-washing with 30% less ethanol gave a better yield (88%) but contained more 2-oxindole (1.76%).

$^1$HNMR (360 MHz, DMSO-d6): δ 10.44 (s, br, 1 H, NH-1), 7.32–7.36 (m, 2 H), 6.76 (d, J=8.50 Hz, 1 H, H-7), 3.5 (s, 2 H, CH$_2$); MS m/z 212.1/214.1 (M$^+$/[M+2]$^+$).

4-(2-Carboxyethyl)-2-formyl-3-methylpyrrole (90 mg), 106 mg 5-bromo-2-oxindole, and 75 μL piperidine in 2 mL ethanol were heated to 95° C. for 5 hours. The reaction mixture was cooled and concentrated. The residue was suspended in 2 N aqueous hydrochloric acid. The precipitate was filtered, washed with water to pH 6 and dried in a vacuum oven to give 120 mg (64%) of the title compound as a brown solid.

$^1$HNMR (360 MHz, DMSO-d6): δ 13.31 (s, br, 1 H, NH-1'), 12.06 (s, br, 1 H, COOH), 10.90 (s, br, 1 H, NH-1), 8.06 (s, br, 1 H, H-4), 7.75 (s, 1 H, H-vinyl), 7.23 (d, br, J=8.50 Hz, 1 H, H-6), 7.19 (d, J=2.84 Hz, 1 H, H-2'), 6.80 (d, br, J=8.50 Hz, 1 H, H-7), 2.65 (t, J=7.65 Hz, 2 H, CH$_2$CH$_2$COOH), 2.46 (t, J=7.65 Hz, 2 H, CH$_2$CH$_2$COOH), 2.28 (s, 3 H, CH$_3$); MS m/z 375.1/377.2 (M$^+$/[M+2]$^+$).

EXAMPLE 7

3-[5-(5-Iodo-2-oxo-1,2-dihydroindol-3-ylidenemethyl)-4-methyl-1H-pyrrol-3-yl]-propionic acid 2-Oxindole (82.9 g) was suspended in 630 mL acetic acid and the misture was mechanically stirred and cooled to 10° C. in an ice water bath. Solid N-iodosuccinimide (175 g) was added in portions over 10 minutes. After the addition was complete the mixture was stirred for 1 hour at 10° C. The suspended solid which was always present became very thick at this time. The solid was collected by vacuum filtration, washed with 100 mL of 50% acetic acid in water and then with 200 mL of water and sucked dry for 20 minutes in the filtration funnel. The product was dried under vacuum to give 93.5 g (36%) of 5-iodo-2-oxindole containing about 5% 2-oxindole by proton NMR.

$^1$HNMR (360 MHz, DMSO-d6): δ 10.45 (s, 1 H, NH-1), 7.49 (s, 1 H, H-4), 7.48 (d, J=8.10 Hz, 1 H, H-6), 6.64 (d, J=8.10 Hz, 1 H, H-7), and 3.46 (s, 2 H, CH$_2$—3); MS m/z 258 [M−1]$^+$.

4-(2-Carboxyethyl)-2-formyl-3-methylpyrrole (90 mg), 130 mg 5-iodo-2-oxindole, and 75 L piperidine in 2 mL ethanol were heated at 95° C. for 5 hours. The reaction mixture was cooled and concentrated. The residue was suspended in 2 N aqueous hydrochloric acid. The precipitate was filtered, washed with water to pH 6 and dried in a vacuum oven to give 162 mg (77%) of the title compound as a brown solid.

$^1$HNMR (360 MHz, DMSO-d6): δ 13.30 (s, br, 1 H, NH-1'), 12.06 (s, br, 1 H, COOH), 10.88 (s, br, 1 H, NH-1), 8.18 (s, br, 1 H, H-4), 7.73 (s, 1 H, H-vinyl), 7.40 (d, br, J=8.03 Hz, 1 H, H-6), 7.19 (d, J=2.94 Hz, 1 H, H-2'), 6.69 (d, br, J=8.03 Hz, 1 H, H-7), 2.65 (t, J=7.40 Hz, 2 H, CH$_2$CH$_2$COOH), 2.46 (t, J=7.40 Hz, 2 H, CH$_2$CH$_2$COOH), 2.28 (s, 3 H, CH$_3$); MS m/z 423 [M+1]$^+$.

EXAMPLE 8

3-[4-Methyl-5-(4-methyl-2-oxo-1,2-dihydroindol-3-ylidenemethyl)-1H-pyrrol-3-yl]-propionic acid Diethyl oxalate (30 mL) in 20 mL dry ether was added with stirring to 19 g potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered and the filtrate acidified with 6 N hydrochloric acid. The resulting precipitate was collected by vacuum filtration, washed with water, and dried under vacuum to give 9.8 g (45% yield) of 2-methyl-6-nitrophenylacetic acid as an off-white solid. The solid was hydrogenated in methanol over 10% palladium on carbon to give 9.04 g of 4-methyl-2-oxindole as a white solid.

$^1$HNMR (360 MHz, DMSO-d6): δ 10.27 (s, br, 1 H, NH-1), 7.06 (t J=7.71 Hz, 1 H, H-6), 6.74 (d, J=7.73 Hz, H-5), 6.63 (d, J=7.73 Hz, 1 H, H-7), 3.36 (s, 2 H, CH$_2$), 2.18 (s, 3 H, CH$_3$).

4-(2-Carboxyethyl)-2-formyl-3-methylpyrrole (90 mg), 74 mg 4-methyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 80 mg (52%) of the title compound as a brown solid.

$^1$HNMR (360 MHz, DMSO-d6): δ 13.33 (s, br, 1 H, NH-1'), 10.84 (s, br, 1 H, NH-1), 7.54 (s, 1 H, H-vinyl), 7.12 (d, J=2.0 Hz, 1 H, H-2'), 7.01 (t, J=7.75 Hz, 1 H, H-6), 6.79 (d, J=7.75 Hz, H-5), 6.74 (d, J=7.75 Hz, 1 H, H-7), 2.64 (t, J=7.65 Hz, 2 H, CH$_2$CH$_2$COOH), 2.57 (s, 3 H, CH$_3$), 2.42 (t, J=7.65 Hz, 2 H, CH$_2$CH$_2$COOH), 2.19 (s, 3 H, CH$_3$); MS m/z (relative intensity, %) 311 ([M+1]$^+$, 100).

EXAMPLE 9

3-[4-Methyl-5-(5-methyl-2-oxo-1,2-dihydroindol-3-ylidenemethyl)-1H-pyrrol-3-yl]-propionic acid 5-Methylisatin (15.0 g) and 60 mL hydrazine hydrate were heated at 140–160° C. for 4 hours. Thin layer chromatography (ethyl acetate:hexane 1:2, silica gel) showed no starting material remaining. The reaction mixture was cooled to room temperature, poured into 300 mL of ice water and acidified to pH 2 with 6 N hydrochloric acid. After standing at room temperature for 2 days the precipitate was collected by vacuum filtration, washed with water and dried under vacuum to give 6.5 g (47% yield) of 5-methyl-2-oxindole.

¹HNMR (360 MHz, DMSO-d6): δ 10.20 (s, br, 1 H, NH-1), 6.99 (s, 1 H, H-4), 6.94 (d, J=8.11 Hz, 1 H, H-6), 6.68 (d, J=8.11 Hz, 1 H, H-7), 3.39 (s, 2 H, $CH_2$—3), and 2.22 (s, 3 H, $CH_3$—5).

4-(2-Carboxyethyl)-2-formyl-3-methylpyrrole (90 mg), 74 mg 5-methyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 65 mg (42%) of the title compound as a brown solid.

¹HNMR (360 MHz, DMSO-d6): δ 13.30 (s, br, 1 H, NH-1'), 12.05 (s, br, 1 H, COOH), 10.67 (s, br, 1 H, NH-1), 7.57 (s, 2 H, H-vinyl, H-4), 7.12 (d, J=2.65 Hz, 1 H, H-2'), 6.91 (d, J=7.82 Hz, 1 H, H-6), 6.74 (d, J=7.82 Hz, 1 H, H-7), 2.65 (t, J=6.94 Hz, 2 H, $CH_2CH_2COOH$), 2.46 (t, J=6.94 Hz, 2 H, $CH_2CH_2COOH$), 2.30 (s, 3 H, $CH_3$), 2.25 (s, 3 H, $CH_3$); MS m/z (relative intensity, %) 311 ([M+1]⁺, 100).

EXAMPLE 10

3-[5-(5,6-Dimethoxy-2-oxo-1,2-dihydroindol-3-ylidenemethyl)-4-methyl-1H-pyrrol-3-yl]-propionic acid 4-(2-Carboxyethyl)-2-formyl-3-methylpyrrole (90 mg), 97 mg 5,6-dimethoxy-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 104 mg (58%) of the title compound as a brown solid.

¹HNMR (360 MHz, DMSO-d6): δ 13.19 (s, br, 1 H, NH-1'), 12.05 (s, br, 1 H, COOH), 10.53 (s, br, 1 H, NH-1), 7.46 (s, 1 H), 7.41 (s, 1 H), 7.02 (s, 1 H, H-2'), 6.45 (s, 1 H), 3.74 (s, 3 H, $OCH_3$), 3.70 (s, 3 H, $OCH_3$), 2.59 (t, J=7.43 Hz, 2 H, $CH_2CH_2COOH$), 2.44 (t, J=7.43 Hz, 2 H, $CH_2CH_2COOH$), 2.22 (s, 3 H, $CH_3$); MS m/z 357 [M+1]⁺.

EXAMPLE 11

3-[5-(6-Chloro-2-oxo-1,2-dihydroindol-3-ylidenemethyl)-4-methyl-1H-pyrrol-3-yl]-propionic acid 4-(2-Carboxyethyl)-2-formyl-3-methylpyrrole (200 mg), 167.6 mg 6-chloro-2-oxindole, and 166 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 246 mg (74%) of the title compound as a brown solid.

¹HNMR (360 MHz, DMSO-d6): δ 13.22 (s, br, 1 H, NH-1'), 12.09 (s, br, 1 H, COOH), 10.95 (s, br, 1 H, NH-1), 7.78 (d, J=7.95 Hz, 1 H, H-4), 7.66 (s, 1 H, H-vinyl), 7.18 (d, J=2.64 Hz, 1 H, H-2'), 7.01 (dd, J=1.90, 7.95 Hz, 1 H, H-5), 6.86 (d, J=1.90 Hz, 1 H, H-7), 2.65 (t, J=7.14 Hz, 2 H, $CH_2CH_2COOH$), 2.45 (t, J=7.14 Hz, 2 H, $CH_2CH_2COOH$), 2.26 (s, 3 H, $CH_3$).

EXAMPLE 12

3-[4-(2-Carboxyethyl)-3-methyl-1H-pyrrol-2-ylmethylene]-2-oxo-2,3-dihydro-1H-indole-5-carboxylic acid methyl ester 5-Iodo-2-oxindole (17 g) was refluxed with 2 g palladium diacetate, 18.2 triethylamine, 150 mL methanol, 15 mL dimethylsulfoxide and 2.6 g DPPP in an atmosphere saturated with carbon monoxide. After 24 hours, the reaction mixture was filtered to remove the catalyst and the filtrate was concentrated. The concentrate was chromatographed on silica gel using 30% ethyl acetate in hexane. The fractions containing product were concentrated and allowed to stand. The product precipitated and collected by vacuum filtration to give 0.8 g (7%) of 5-methoxycarbonyl-2-oxindole as an off-white solid.

¹HNMR (360 MHz, DMSO-d6) δ 10.70 (s, br, 1 H, NH-1), 7.83 (dd, J=1.77, 8.29 Hz, 1 H, H-6), 7.77 (s, br, 1 H, H-4), 6.89 (d, J=8.29 (Hz, 1 H, H-7), 3.80 (s, 3 H, $COOCH_3$—5), 3.51 (s, 2 H, $CH_2$—3).

4-(2-Carboxyethyl)-2-formyl-3-methylpyrrole (90.6 mg), 88.6 mg 5-methoxycarbonyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 123 mg (69%) of the title compound as a yellow solid.

¹HNMR (360 MHz, DMSO-d6): δ 13.27 (s, br, 1 H, NH-1'), 12.0 (s, vbr, 1 H, COOH), 11.16 (s, br, 1 H, NH-1), 8.36 (s, br, 1 H, H-4), 7.80 (s, 1 H, H-vinyl), 7.40 (dd, J=1.80, 8.14 Hz, 1 H, H-6), 7.20 (d, J=2.91 Hz, 1 H, H-5'), 6.96 (d, J=8.14 Hz, 1 H, H-7), 3.84 (s, 3 H, $COOCH_3$), 2.66 (t, J=7.55 Hz, 2 H, $CH_2CH_2COOH$), 2.46 (t, J=7.55 Hz, 2 H, $CH_2CH_2COOH$), 2.30 (s, 3 H, $CH_3$); MS m/z (relative intensity, %) 355 ([M+1]⁺, 100).

EXAMPLE 13

3-[4-(2-Carboxy-ethyl)-3-methyl-1H-pyrrol-2-ylmethylene]-2-oxo-2,3-dihydro-1H-indole-5-carboxylic acid 2-Oxindole (6.7 g) was added to a stirred suspension of 23 g aluminum chloride in 30 mL dichloroethane in an ice bath. Chloroacetyl chloride (11.3 g) was slowly added and hydrogen chloride gas was evolved. After ten minutes of stirring, the reaction was warmed to 40–50° C. for 1.5 hours. Thin layer chromatography (ethyl acetate, silica gel) showed no remaining starting material. The mixture was cooled to room temperature and poured into ice water. The precipitate was collected by vacuum filtration, washed with water and dried under vacuum to give 10.3 g (98%) of 5-chloroacetyl-2-oxindole as an off-white solid.

A suspension of 9.3 g 5-chloroacetyl-2-oxindole was stirred in 90 mL pyridine at 80–90° C. for 3 hours then cooled to room temperature. The precipitate was collected by vacuum filtration and washed with 20 mL of ethanol. The solid was dissolved in 90 mL of 2.5 N sodium hydroxide and stirred at 70–80° C. for 3 hours. The mixture was cooled to room temperature and acidified to pH 2 with 0.5 N hydrochloric acid. The precipitate was collected by vacuum filtration and washed thoroughly with water to give crude 5-carboxy-2-oxindole as a dark brown solid. After standing overnight the filtrate yielded 2 g of 5-carboxy-2-oxindole as a yellow solid. The crude dark brown product was dissolved in hot methanol, the insoluble material removed by filtration and the filtrate concentrated to give 5.6 g of 5-carboxy-2-oxindole as a brown solid. The combined yield was 97%.

¹HNMR (360 MHz, DMSO-d6) δ 12.56 (s, br, 1 H, COOH-5), 10.70 (s, 1 H, NH-1), 7.82 (dd, J=1.57, 7.79 Hz, 1 H, H-6), 7.74 (s, br, 1 H, H-4), 6.87 (d, J=7.79 Hz, 1 H, H-7), and 3.53 (s, 2 H, $CH_2$—3). MS m/z (relative intensity, %) 178 ([M+1]⁺, 100).

4-(2-Carboxyethyl)-2-formyl-3-methylpyrrole (90.6 mg), 88.6 mg 5-carboxy-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven. The crude product was purified by chromatography on a silica gel column using ethyl acetate-hexane-acetic acid as the eluant to give 51 mg(30%) of the title compound as a yellow solid.

$^1$HNMR (360 MHz, DMSO-d6): δ 13.27 (s, br, 1 H, NH-1), 12.28 (s, vbr, 2 H, 2×COOH), 11.11 (s, br, 1 H, NH-1), 8.34 (d, J=1.36 Hz, 1 H, H-4), 7.78 (s, 1 H, H-vinyl), 7.40 (dd, J=1.36, 8.20 Hz, 1 H, H-6), 7.19 (d, J=3.07 Hz, 1 H, H-5'), 6.93 (d, J=8.20 Hz, 1 H, H-7), 2.65 (t, J=7.56 Hz, 2 H, CH$_2$CH$_2$COOH), 2.46 (t, J=7.56 Hz, 2 H, CH$_2$CH$_2$COOH), 2.29 (s, 3 H, CH$_3$); MS m/z 341.0 [M+1]$^+$.

EXAMPLE 14

3-[4-Methyl-5-(2-oxo-5-sulfamoyl-1,2-dihydroindol-3-ylidenemethyl)-1H-pyrrol-3-yl]-propionic acid To a 100 mL flask charged with 27 mL of chlorosulfonic acid was added slowly 13.3 g 2-oxindole. The reaction temperature was maintained below 30° C. during the addition. After the addition, the reaction mixture was stirred at room temperature for 1.5 hr, heated to 68° C. for 1 hr, cooled, and poured into water. The precipitate was washed with water and dried in a vacuum oven to give 11.0 g of 5-chlorosulfonyl-2-oxindole (50% yield) which was used without further purification.

5-Chlorosulfonyl-2-oxindole (2.1 g) was added to 10 mL ammonium hydroxide in 10 mL ethanol and stirred at room temperature overnight. The mixture was concentrated and the solid collected by vacuum filtration to give 0.4 g (20% yield) of 5-aminosulfonyl-2-oxindole as an off-white solid.

$^1$HNMR (360 MHz, DMSO-d6); δ 10.67 (s, 1 H, NH-1), 7.63–7.66 (m, 2 H, H-4,6), 7.13 (s, 2 H, 5-SO$_2$NH$_2$), 6.91 (d, J=8.04 Hz, 1 H, H-7), and 3.56 (s, 2 H, CH$_2$—3); MS m/z (relative intensity, %) 211 ([M−1]$^+$, 100).

4-(2-Carboxyethyl)-2-formyl-3-methylpyrrole (90.6 mg), 106 mg 5-aminosulfonyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 132 mg (70%)of the title compound as a yellow solid.

$^1$HNMR (360 MHz, DMSO-d6); δ 13.28 (s, br, 1 H, NH-1'), 12.0 (s, vbr, 1 H, COOH), 11.15 (s, br, 1 H, NH-1), 8.20 (d, J=1.60 Hz, 1 H, H-4), 7.73 (s, 1 H, H-vinyl), 7.59 (dd, J=1.60, 8.17 Hz, 1 H, H-6), 7.22 (d, J=2.85 Hz, 1 H, H-2'), 7.10 (s, 2 H, NH$_2$), 6.98 (d, J=8.17 Hz, 1 H, H-7), 2.67 (t, J=7.41 Hz, 2 H, CH$_2$CH$_2$COOH), 2.46 (t, J=7.41 Hz, 2 H, CH$_2$CH$_2$COOH), and 2.29 (s, 3 H, CH$_3$).

EXAMPLE 15

3-[4-Methyl-5-(5-methylsulfamoyl-2-oxo-1,2-dihydroindol-3-ylidenemethyl)-1H-pyrrol-3-yl]-propionic acid A suspension of 3.38 g of 5-chlorosulfonyl-2-oxindole in 10 mL 2 M methylamine in tetrahydrofuran was stirred at room temperature for 4 hours at which time a white solid was present. The precipitate was collected by vacuum filtration, washed twice with 5 mL of water and dried under vacuum at 40° C. overnight to give 3.0 g (88% yield) of 5-methylaminosulfonyl-2-oxindole.

$^1$HNMR (300 MHz, DMSO-d6): δ 10.87 (s, br, 1 H, NH-1), 7.86 (s, br, 1 H, 5-SO$_2$NHCH$_3$), 7.61 (d, J=7.80 Hz 1 H, H-6), 7.32 (d, J=4.67 Hz, 1 H, H-4), 6.97 (d, J=7.80 Hz, 1 H, H-7), 2.53 (s, 2 H, CH$_2$—3), and 2.36 (s, 3 H, 5-SO$_2$NHCH$_3$); MS m/z (relative intensity, %) 226 (M$^+$, 100).

4-(2-Carboxyethyl)-2-formyl-3-methylpyrrole (90.6 mg), 113 mg 5-methylaminosulfonyl-2-oxindole, and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven to give 163 mg (83%) of the title compound as a yellow solid.

$^1$HNMR (360 MHz, DMSO-d6): δ 13.30 (s, br, 1 H, NH-1'), 12.0 (s, vbr, 1 H, COOH), 11.19 (s, br, 1 H, NH-1), 8.18 (d, J=1.64 Hz, 1 H, H-4), 7.80 (s, 1 H, H-vinyl), 7.53 (dd, J=1.64, 8.17 Hz, 1 H, H-6), 7.23 (d, J=2.80 Hz, 1 H, H-2'), 7.13 (q, J=5.15 Hz, 1 H, NHCH$_3$), 7.02 (d, J=8.17 Hz, 1 H, H-7), 3.84 (s, 3 H, COOCH$_3$), 2.66 (t, J=7.54 Hz, 2 H, CH$_2$CH$_2$COOH), 2.47 (t, J=7.54 Hz, 2 H, CH$_2$CH$_2$COOH), 2.41 (d, J=5.15 Hz, 3 H, NCH$_3$), 2.30 (s, 3 H, CH$_3$); MS m/z 390 [M+1]$^+$.

EXAMPLE 16

3-{3-[4-(2-Carboxy-ethyl)-3-methyl-1H-pyrrol-2-ylmethylene]-2-oxo-2,3-dihydro-1H-indol-5-yl}-propionic acid 5-Chloroacetyl-2-oxindole (4.18 g) in 30 mL trifluoroacetic acid in an ice bath was treated with 4.65 g triethylsilane and stirred at room temperature for 3 hours. The mixture was poured into 150 mL of water and the precipitate collected by vacuum filtration, washed with 50 mL of water and dried to give 2.53 g (65% yield) of 5-(2-chloroethyl)-2-oxindole as a reddish-brown solid.

Potassium cyanide (2.0 g) was added to 15 mL dimethylsulfoxide and heated to 90° C. 5-Chloroethyl-2-oxindole (3.0 g) dissolved in 5 mL of dimethylsulfoxide was added slowly with stirring, and the reaction heated to 150° C. for 2 hours. The mixture was cooled, poured into ice water and the precipitate collected by vacuum filtration, washed with water, and dried to give crude product. The crude material was chromatographed on silica gel using 5% methanol in chloroform to give 1.2 g (42% yield) of the title compound.

5-Cyanoethyl-2-oxindole (4.02 g) in 10 mL water containing 25 mL of concentrated hydrochloric acid was refluxed for 4 hours. The mixture was cooled, water added and the resulting solid collected by vacuum filtration, washed with water and dried to give 1.9 g (44% yield) of 5-carboxyethyl-2-oxindole as a yellow solid.

$^1$HNMR (360 MHz, DMSO-d6): δ 12.00 (s, br, 1 H, 5—CH$_2$CH$_2$COOH), 10.21 (s, 1 H, NH-1), 7.05 (s, 1 H, H-4), 6.99 (d, J=8.68 Hz, 1 H, H-6), 6.69 (d, J=8.68 Hz, 1 H, H-7), 3.40 (s, 2 H, CH$_2$—3), 2.74 (t, J=7.44 Hz, 2 H, 5-CH$_2$CH$_2$COOH), and 2.46 (t, J=7.44 Hz, 2 H, —CH$_2$CH$_2$COOH).

4-(2-Carboxyethyl)-2-formyl-3-methylpyrrole (90.6 mg), 102.6 mg 5-carboxyethyl-2-oxindole and 75 μL piperidine in 2 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven overnight. The crude solid was purified by chromatography a silica gel column eluting with ethyl acetate-hexane-acetic acid to give 121 mg (66%) of the title compound as a yellow solid.

$^1$HNMR (360 MHz, DMSO-d6): δ 13.30 (d, J=2.38 Hz, 1 H, NH-1'), 12.0 3 (s, vbr, 2 H, 2×COOH), 10.68 (s, br, 1 H, NH-1), 7.63 (s, 1 H, H-4), 7.59 (s, 1 H, H-vinyl), 7.12 (d, J=2.64 Hz, 1 H, H- 2'), 6.96 (dd, J=1.22, 7.93 Hz, 1 H, H-6), 6.75 (d, J=7.93 Hz, 1 H, H-7), 2.81 (t, J=7.75 Hz, 2 H, $CH_2CH_2COOH$), 2.65 (t, J=7.75 Hz, 2 H, $CH_2CH_2COOH$), 2.55 (t, J=7.75 Hz, 2 H, $CH_2CH_2COOH$), 2.46 (t, J=7.42 Hz, $CH_2CH_2COOH$), and 2.26 (s, 3 H, $CH_3$).

EXAMPLE 17

3-[5-(5-Ethyl-2-oxo-1,2-dihydro-indol-3-ylidenemethyl)-4-methyl-1H-pyrrol-3-yl]-propionic acid 2-Oxindole (3 g) was suspended in 1,2-dichloroethane and slowly treated with 3.2 mL acetyl chloride. The resulting suspension was heated to 50° C. for 5 hours, cooled, and poured into water. The resulting precipitate was collected by vacuum filtration, washed copiously with water and dried under vacuum to give 2.9 g (73% yield) of 5-Acetyl-2-oxindole as a brown solid.

5-Acetyl-2-oxindole (2 g) in 15 mL trifluoroacetic acid in an ice bath was slowly treated with 1.8 g triethylsilane and then stirred at room temperature for 5 hours. One mL of riethylsilane was added and the stirring continued overnight. The reaction mixture was poured into ice water and the resulting precipitate collected by vacuum filtration, washed copiously with water and dried under vacuum to give 1.3 g (71% yield) of the title compound as a yellow solid.

$^1$HNMR (360 MHz, DMSO-d6): δ 10.25 (s, br, NH-1), 7.03 (s, 1 H, H-4), 6.97 (d, J=8.05 Hz, 1 H, H-6), 6.69 (d, J=8.05 Hz, 1 H, H-7), 3.40 (s, 2 H, $CH_2$—3), 2.51 (q, J=7.69 Hz, 2 H, $CH_2CH_3$—5), and 1.12 (t, J=7.42 Hz, 3 H, $CH_2CH_3$—5).

4-(2-Carboxyethyl)-2-formyl-3-methylpyrrole (90.6 mg), 80.5 mg 5-ethyl-2-oxindole, and 75 μL of piperidine in 2 mL of ethanol were heated at 95° C. for 5 hours. The reaction mixture was cooled and concentrated. The residue was suspended in 6 N of aqueous hydrochloric acid. The precipitate was filtered, washed with water to pH 6 and dried in a vacuum oven overnight. The crude solid was purified by a chromatography on a silica gel column eluting with ethyl acetate-hexane-acetic acid to give 52 mg (32%) of the title compound.

$^1$HNMR (360 MHz, DMSO-d6): δ 13.31 (s, br, 1 H, NH-1'), 12.0 4 (s, vbr, 1 H, COOH), 10.66 (s, 1 H, NH-1), 7.59 (s, 2 H, H-4 and H-vinyl), 7.11 (d, J=3.29 Hz, 1 H, H-2'), 6.94 (d, J=7.85 Hz, 1 H, H-6), 6.75 (d, J=7.85 Hz, 1 H, H-7), 2.65 (t, J=7.66 Hz, 2 H, $CH_2CH_2COOH$), 2.57 (q, J=7.83 Hz, 2 H, $CH_3CH_2$), 2.46 (t, J=7.66 Hz, $CH_2CH_2COOH$), 1.20 (t, J=7.83, 3 H, $CH_3CH_2$), 2.26 (s, 3 H, $CH_3$); MS m/z 325 [M+1]$^+$.

EXAMPLE 18

3-[5-(5-Methoxy-2-oxo-1,2-dihydroindol-3-ylidenemethyl)-4-methyl-1H-pyrrol-3-yl]-propionic acid Chloral hydrate (9.6 g) was dissolved in 200 mL water containing 83 g sodium sulfate. The solution was warmed to 60° C., a solution of 11.4 g hydroxylamine hydrochloride in 50 mL water was added and the mixture was held at 60° C. In a separate flask, 6.4 g 4-anisidine and 4.3 mL concentrated hydrochloric acid in 80 mL of water was warmed to 80° C. The first solution was added to the second and the resulting mixture was refluxed for 2 minutes, cooled slowly to room temperature, and then cooled in an ice bath. The tan precipitate was collected by vacuum filtration, washed with water and dried under vacuum to give 8.6 g (85% yield) of N-(2-hydroximinoacetyl)anisidine.

Concentrated sulfuric acid (45 mL) containing 5 mL water was warmed to 60° C. and 8.6 g N-(2-hydroximinoacetyl) anisidine was added in one portion. The stirred mixture was heated at 93° C. for 10 minutes and then allowed to cool to room temperature. The mixture was poured into 500 g of ice and extracted 3 times with ethyl acetate. The combined extracts were dried over anhydrous sodium sulfate and concentrated to give 5.1 g (65% yield) of 5-methoxyisatin as a dark red solid.

5-Methoxyisatin (5.0 g) and 30 mL hydrazine hydrate were heated to reflux for 15 minutes. The reaction mixture was cooled to room temperature and 50 mL water was added. The mixture was extracted 3 times with 25 mL of ethyl acetate, the organic layers were combined, dried over anhydrous sodium sulfate and concentrated to give a yellow solid. The solid was stirred in ethyl acetate and 1.1 g of insoluble material removed by vacuum filtration and saved. This material proved to be 2-hydrazinocarbonylmethyl-4-anisidine. The filtrate was concentrated and chromatographed on silica gel eluting with ethyl acetate:hexane 1:1 to give 0.7 g of 5-methoxy-2-oxindole as a dirty yellow solid. The 1.1 g of 2-hydrazinocarbonylmethyl-4-anisidine was refluxed for 1 hour in 20 mL of 1 N sodium hydroxide. The mixture was cooled, acidified to pH 2 with concentrated hydrochloric acid and extracted 3 times with 25 mL of ethyl acetate. The organic extracts were combined, washed with brine, dried over anhydrous sodium sulfate and concentrated to give 0.8 g of 5-methoxy-2-oxindole as a dirty yellow solid. The combined yield was 1.5 g or 33%.

$^1$HNMR (360 MHz, DMSO-d6): δ 10.13 (s, 1 H, NH-1), 6.84 (s, 1 H, H-4), 6.72 (d, J=8.68 Hz, 1 H, H-6), 6.69 (d, J=8.68 Hz, 1 H, H-7), 3.68 (s, 3 H, $OCH_3$—5), 3.41 (s, 2 H, $CH_2$—3). MS m/z (relative intensity, %) 163 ([M+1]$^+$, 100).

4-(2-Carboxyethyl)-2-formyl-3-methylpyrrole (90 mg), 82 mg of 5-methoxy-2-oxindole, and 2 drops piperidine in 2 mL of ethanol were heated to 95° C. overnight. The reaction mixture was cooled and concentrated. The residue was suspended in 6 N aqueous hydrochloric acid. The precipitate was filtered, washed with water to pH 6 and dried in a vacuum oven overnight to give 110 mg (67%) of the title compound as a brown solid.

$^1$HNMR (360 MHz, DMSO-d6): δ 13.38 (s, br, 1H, NH-1'), 12.03 (s, vbr, 1H, COOH), 10.57 (s, 1H, NH-1), 7.63 (s, 1H, H-vinyl), 7.42 (d, J=2.46 Hz, 1H, H-4), 7.12 (d, J=3.08 Hz, 1H, H-2'), 6.74 (d, J=8.26 Hz, 1H, H-6), 6.75 (dd, J=2.46, 8.26 Hz, 1H, H-7), 3.77 (s, 3H, $OCH_3$), 2.65 (t, J=7.40 Hz, 2H, $CH_2CH_2COOH$), 2.46 (t, J=7.40 Hz, $CH_2CH_2COOH$), 2.27 (s, 3H, $CH_3$) ; MS m/z (relative intensity, %) 327 ([M+1]$^+$, 100).

EXAMPLE 19

3-[5-(5-Bromo-2-oxo-1,2-dihydroindol-3-ylidenemethyl)-2,4-dimethyl-1H-pyrrol-3-yl]-propionic acid 3-(2-Carboxyethyl)-2,4-dimethyl-5-formylpyrrole (97.5 mg), 106 mg 5-bromo-2-oxindole, and 75 μL piperidine in 3 mL of ethanol were heated at 95° C. for 5 hours. The reaction mixture was cooled and concentrated. The residue was suspended in 6 N aqueous hydrochloric acid. The precipitate was filtered, washed with water to pH 6 and dried in a vacuum oven overnight to give 171 mg (88%) of the title compound as an orange solid.

$^1$HNMR (360 MHz, DMSO-d6): δ 12.04 (s, vbr, 1H, COOH), 10.80 (s, br, 1H, NH-1), 8.0 (d, J=2.06 Hz, 1H, H-4), 7.67 (s, 1H, H-vinyl), 7.19 (dd, J=2.06, 8.40 Hz, 1H, H-6), 6.79 (d, J=8.40 Hz, 1H, H-7), 2.65 (t, J=7.63 Hz, 2H, CH$_2$CH$_2$COOH), 2.35 (t, J=7.63 Hz, 2H, CH$_2$CH$_2$COOH), 2.29 (s, 3H, CH$_3$), 2.27 (s, 3H, CH$_3$); MS m/z (relative intensity, %) 389 ([M+1]$^+$, 100).

3-[5-(5-Iodo-2-oxo-1,2-dihydroindol-3-ylidenemethyl)-2,4-dimethyl-1H-pyrrol-3-yl]-propionic acid 3-(2-Carboxyethyl)-2,4-dimethyl-5-formylpyrrole (97.5 mg), 130 mg 5-iodo-2-oxindole, and 75 μL piperidine in 3 mL of ethanol were heated at 95 ° C. for 5 hours. The reaction mixture was cooled and concentrated. The residue was suspended in 6 N aqueous hydrochloric acid. The precipitate was filtered, washed with water to pH 6 and dried in a vacuum oven overnight to give 155 mg (71%) of the title compound as an orange solid.

$^1$HNMR (360 MHz, DMSO-d6): δ 13.41 (s, br, 1H, NH-1'), 12.03 (s, br, 1H, COOH), 10.79 (s, br, 1H, NH-1), 8.12 (d, J=1.70 Hz, 1H, H-4), 7.65 (s, 1H, H-vinyl), 7.36 (dd, J=1.70, 7.93 Hz, 1H, H-6), 6.79 (d, J=7.93 Hz, 1H, H-7), 2.64 (t, J=7.76 Hz, 2H, CH$_2$CH$_2$COOH), 2.34 (t, J=7.76 Hz, 2H, CH$_2$CH$_2$COOH), 2.29 (s, 3H, CH$_3$), 2.27 (s, 3H, CH$_3$); MS m/z (relative intensity, %) 437 ([M+1]$^+$, 100).

EXAMPLE 20

3-[5-(5-Iodo-2-oxo-1,2-dihydroindol-3-ylidenemethyl)-2,4-dimethyl-1H-pyrrol-3-yl]-propionic acid 3-(2-Carboxyethyl)-2,4-dimethyl-5-formylpyrrole (97.5 mg), 130 mg 5-iodo-2-oxindole, and 75 μL of piperidine in 3 mL of ethanol were stirred at 95 ° C. for 5 hours. The reaction mixture was cooled and concentrated. The residue was suspended in 6 N aqueous hydrochloric acid. The precipitate was filtered, washed with water to pH 6 and dried in a vacuum oven overnight to give 155 mg of the title compound (71%) as an orange solid.

$^1$HNMR (360 MHz, DMSO-d6) δ 13.41 (s, br, 1H, NH-1'), 12.03 (s, br, 1H, COOH), 10.79 (s, br, 1H, NH-1), 8.12 (d, J=1.70 Hz, 1H, H-4), 7.65 (s, 1H, H-vinyl), 7.36 (dd, J=1.70, 7.93 Hz, 1H, H-6), 6.79 (d, J=7.93 Hz, 1H, H-7), 2.64 (t, J=7.76 Hz, 2H, CH$_2$CH$_2$COOH), 2.34 (t, J=7.76 Hz, 2H, CH$_2$CH$_2$COOH), 2.29 (s, 3H, CH$_3$), 2.27 (s, 3H, CH$_3$). MS m/z (relative intensity, %) 437 ([M+1]$^+$, 100).

EXAMPLE 21

3-[2,4-Dimethyl-5-(4-methyl-2-oxo-1,2-dihydroindol-3-ylidene-methyl)-1H-pyrrol-3-yl]-propionic acid 3-(2-Carboxyethyl)-2,4-dimethyl-5-formylpyrrole (97.5 mg), 74 mg 4-methyl-2-oxindole, and 75 μL piperidine in 3 mL of ethanol were heated at 95° C. for 5 hours. The reaction mixture was cooled and concentrated. The residue was suspended in 6 N of aqueous hydrochloric acid. The precipitate was filtered, washed with water to pH 6 and dried in a vacuum oven overnight to give 60 mg (37%) of the title compound as a green solid.

$^1$HNMR (360 MHz, DMSO-d6): δ 13.41 (s, br, 1H, NH-1'), 12.03 (s, br, 1H, COOH), 10.72 (s, br, 1H, NH-1), 7.50 (s, 1H, H-vinyl), 7.01 (t, J=7.82 Hz, 1H, H-6), 6.79 (d, J=7.82 Hz, H-5), 6.74 (d, J=7.82 Hz, 1H, H-7), 2.64 (t, J=7.76 Hz, 2H, CH$_2$CH$_2$COOH), 2.56 (s, 3H, CH$_3$), 2.34 (t, J=7.76 Hz, 2H, CH$_2$CH$_2$COOH), 2.29 (s, 3H, CH$_3$), 2.18 (s, 3H, CH$_3$); MS m/z (relative intensity, %) 325 ([M+1]$^+$, 100).

EXAMPLE 22

3-[2,4-Dimethyl-5-(5-methyl-2-oxo-1,2-dihydroindol-3-ylidenemethyl)-1H-pyrrol-3-yl]-propionic acid 3-(2-Carboxyethyl)-2,4-dimethyl-5-formylpyrrole (97.5 mg), 74 mg 5-methyl-2-oxindole, and 75 μL piperidine in 3 mL of ethanol were heated at 95 ° C. for 5 hours. The reaction mixture was cooled and concentrated. The residue was suspended in 6 N aqueous hydrochloric acid. The precipitate was filtered, washed with water to pH 6 and dried in a vacuum oven overnight to give 104 mg (64%) of the title compound as a yellow solid.

$^1$HNMR (360 MHz, DMSO-d6): δ 13.38 (s, br, 1H, NH-1'), 12.02 (s, br, 1H, COOH), 10.57 (s, br, 1H, NH-1), 7.52 (s, br, 1H, H-4), 7.50 (s, 1H, H-vinyl), 6.87 (d, J=7.86 Hz, 1H, H-6), 6.73 (d, J=7.86 Hz, 1H, H-7), 2.63 (t, J=7.49 Hz, 2H, CH$_2$CH$_2$COOH), 2.34 (t, J=7.49 Hz, 2H, CH$_2$CH$_2$COOH), 2.29 (s, 3H, CH$_3$), 2.28 (s, 3H, CH$_3$), and 2.24 (s, 3H, CH$_3$); MS m/z (relative intensity, %) 325 ([M+1]$^+$, 66).

EXAMPLE 23

3-[5-(6-Hydroxy-2-oxo-1,2-dihydroindol-3-ylidenemethyl)-2,4-dimethyl-1H-pyrrol-3-yl]-propionic acid 3.26 g 6-methoxy-2-oxindole in 60 mL dichloromethane was cooled to −2° C. and 40 mL 1 M boron tribromide solution in dichloromethane was added dropwise. The reaction mixture was stirred in an ice bath for 1 hour and then at room temperature for 1 hour. It was then poured into ice water and extracted with ethyl acetate. The organic layer was washed with water and brine, dried over anhydrous sodium sulfate, concentrated, the precipitate which formed filtered and then dried in a vacuum oven overnight to give 2.56 g of the 6-hydroxy-2-oxindole (86% yield).

$^1$HNMR (360 MHz, DMSO-d6): δ 10.13 (s, 1H, NH-1), 9.22 (s, 1H, OH-6), 6.93 (d, J=7.76 Hz, 1H, H-4), 6.27–6.31 (m, 2H, H-5,7), and 3.29 (s, 2H, CH$_2$-3); MS m/z 150 [M+1]$^+$.

3-(2-carboxyethyl)-2,4-dimethyl-5-formylpyrrole (82 mg), 63 mg 6-hydroxy-2-oxindole, and 48 μL piperidine in 2 mL of ethanol were heated at 90° C. for two days. The reaction mixture was cooled, concentrated, and purified by silica gel column chromotography eluting with ethyl acetate-hexane-acetic acid to give 55 mg (40%) of the title compound as an dark brown solid.

$^1$HNMR (360 MHz, DMSO-d6): δ 13.10 (s, br, 1H, NH-1'), 12.0 (s, vbr, 1H, COOH), 10.51 (s, br, 1H, NH-1), 9.41 (s, 1H, OH), 7.44 (d, J=7.83, 1H, H-4), 7.29 (s, 1H, H-vinyl), 6.37 (dd, J=2.16, 7.83 Hz, 1H, H-5), 6.33 (d, J=2.16 Hz, 1H, H-7), 2.62 (t, J=7.75 Hz, 2H, CH$_2$CH$_2$COOH), 2.32 (t, J=7.75 Hz, 2H, CH$_2$CH$_2$COOH), 2.25 (s, 3H, CH$_3$), 2.20 (s, 3H, CH$_3$); MS m/z 325 [M+1]$^+$.

EXAMPLE 24

3-[5-(6-Methoxy-2-oxo-1,2-dihydroindol-3-ylidenemethyl)-2,4-dimethyl-1H-pyrrol-3-yl]-propionic acid 3-(2-carboxyethyl)-2,4-dimethyl-5-formylpyrrole (97.5 mg), 82 mg 6-methoxy-2-oxindole and 2 drops piperidine in 2 mL of ethanol were heated at 95° C. for overnight. The reaction mixture was cooled and concentrated. The residue was suspended in 2 N aqueous hydrochloric acid. The precipitate was filtered, washed with water to pH 6 and dried in a vacuum oven overnight to give 130 mg (76%) of the title compound as a yellow solid.

$^1$HNMR (360 MHz, DMSO-d6): δ 13.15 (s, br, 1H, NH-1'), 11.75 (s, vbr, 1H, COOH), 10.65 (s, br, 1H, NH-1), 7.58 (d, J=8.27, 1H, H-4), 7.29 (s, 1H, H-vinyl), 6.37 (dd, J=2.26, 8.27 Hz, 1H, H-5), 6.33 (d, J=2.26 Hz, 1H, H-7), 3.74 (s, 3H, OCH$_3$), 2.62 (t, J=7.67 Hz, 2H, CH$_2$CH$_2$COOH), 2.33 (t, J=7.67 Hz, 2H, CH$_2$CH$_2$COOH), 2.26 (s, 3H, CH$_3$), and 2.22 (s, 3H, CH$_3$); MS m/z (relative intensity, %) 341 ([M+1]$^+$, 100).

EXAMPLE 25

3-[5-(6-Hydroxy-2-oxo-1,2-dihydroindol-3-ylidenemethyl)-4-methyl-1H-pyrrol-3-yl]-propionic acid 4-(2-carboxyethyl)-2-formyl-3-methylpyrrole (543 mg), 450 mg 6-hydroxy-2-oxindole, and 450 μL piperidine in 10 mL of ethanol were heated at 90° C. overnight. The reaction mixture was cooled and concentrated. The residue was suspended in 2 N aqueous hydrochloric acid. The precipitate was filtered, washed with water to pH 6 and dried in a vacuum oven overnight to give a brown solid.

$^1$HNMR (360 MHz, DMSO-d6): δ 13.05 (s, br, 1H, N-H-1'), 10.60 (s, br, 1H, NH-1), 9.4 (s, 1H, OH), 7.49 (d, J=8.08, 1H, H-4), 7.35 (s, 1H, H-vinyl), 7.02 (d, J=3.22 Hz, 1H, H-2'), 6.38 (dd, J=2.28, 8.08 Hz, 1H, H-5), 6.32 (d, J=2.28 Hz, 1H, H-7), 2.62 (t, J=7.67 Hz, 2H, CH$_2$CH$_2$COOH), 2.44 (t, J=7.67 Hz, 2H, CH$_2$CH$_2$COOH), and 2.21 (s, 3H, CH$_3$); MS M/Z (relative intensity, %) 313 ([M+1]$^+$, 60).

EXAMPLE 26

3-[5-(6-Hydroxy-2-oxo-1,2-dihydroindol-3-ylidenemethyl)-4-methyl-1H-pyrrol-3-yl]-propionic acid 3,5-dimethoxy-benzyl ester 3-[5-(6-Hydroxy-2-oxo-1,2-dihydroindol-3-ylidenemethyl)-4-methyl-1H-pyrrol-3-yl]-propionic acid (100 mg), 56 mg 3,5-dimethoxy-benzylchloride and 207 mg potassium carbonate in 2 mL anhydrous dimethylformamide were heated at 90° C. overnight. The reaction mixture was cooled, poured into water and extracted with ethyl acetate. The organic layer was washed with water and brine, dried over anhydrous sodium sulfate, and concentrated. The crude product was purified by chromatography on a silica gel column eluting with ethyl acetate-hexane-acetic acid to give 39 mg of the title compound as a brown solid.

$^1$HNMR (360 MHz, DMSO-d6): δ 13.06 (s, br, 1H, NH-1'), 10.60 (s, br, 1H, NH-1), 9.4 (s, br, 1H, OH), 7.49 (d, J=8.03, 1H, H-4), 7.35 (s, 1H, H-vinyl), 7.01 (d, J=3.08 Hz, 1H, H-2'), 6.47 (d, J=2.29Hz, 2H, aromatic), 6.42 (t, J=2.29 Hz, 1H, aromatic), 6.38 (dd, J=2.15, 8.03 Hz, 1H, H-5), 6.33 (d, J=2.15 Hz, 1H, H-7), 5.01 (s, 2H, CH$_2$-Ph), 3.70 (s, 6H, 2×OCH$_3$), 2.59–2.72 (m, 4H, CH$_2$CH$_2$COOH), and 2.20 (s, 3H, CH$_3$).

EXAMPLE 27

3-{5-[6-(3-Methoxy-phenyl)-2-oxo-1,2-dihydroindol-3-ylidenemethyl]-2,4-dimethyl-1H-pyrrol-3-yl}-propionic acid Tetrakis(triphenylphosphine)palladium (0.7 g) was added to a mixture of 5 g of 3-methoxyphenylboronic acid, 3.8 g 5-bromo-2-fluoronitrobenzene and 11 mL 2 M sodium carbonate solution in 100 mL of toluene. The mixture was refluxed for 2 hours, diluted with water and extracted with ethyl acetate. The ethyl acetate was washed with saturated sodium bicarbonate and then brine, dried, and concentrated to give an oily solid. The solid was chromatographed on silica gel using ethyl acetate:hexane (1:6) to give 4.3 g (77% yield) of 4-fluoro-3'-methoxy-3-nitrobiphenyl.

Dimethyl malonate (9.7 mL) was added dropwise to 2.0 g of sodium hydride suspended in 50 mL of dimethylsulfoxide. The mixture was heated at 100° C. for 35 minutes and then cooled to room temperature. 4-Fluoro-2'-methoxy-3-nitrobiphenyl (4.2 g) in 50 mL dimethylsulfoxide was added and the mixture was heated to 100° C. for 1 hours. The reaction mixture was cooled and quenched with 300 mL of saturated ammonium chloride solution and extracted twice with ethyl acetate. The extracts were combined, washed with brine, dried over anhydrous sodium sulfate and concentrated to give crude dimethyl 3'-methoxy-3-nitrobiphenyl-4-malonate as a pale yellow solid.

Crude 3'-methoxy-3-nitro-biphenyl-4-malonate was heated at 110° C. in 45 mL of 6 N hydrochloric acid for 4 days and cooled. The precipitate was collected by filtration, washed with water and hexane, and dried to give 5.3 g of 3'-methoxy-2-nitrobiphenyl-4-acetic acid as a light tan solid.

3'-Methoxy-3-nitrobiphenyl-4-acetic acid (5.2 g) was dissolved in methanol and hydrogenated over 0.8 g 10% palladium on carbon for 3 hours at room temperature. The catalyst was removed by filtration, washed with methanol and the filtrates combined and concentrated to give a brown solid. The solid was chromatographed on silica gel in ethyl acetate:hexane:acetic acid 33:66:1 to give 3.0 g (75 % yield based on 4-fluoro-3'-methoxy-3-nitrobiphenyl) of 6-(3-methoxypheny)-2-oxindole as a pink solid.

$^1$HNMR (360 MHz, DMSO-d6): δ 10.39 (s, br, 1H, NH), 7.35 (t, J=7.85 Hz, 1H), 7.26 (d, J=7.78 Hz, 1H), 7.19 (dd, J=1.22, 7.8 HZ, 1H), 7.13–7.16 (m, 1H), 7.09–7.1 (m, 1H), 7.01 (d, J=1.48 Hz, 1H), 6.90–6.93 (m, 1H), 3.8 (s, 3H, OCH3), 3.49 (s, 2H, CH2); MS m/z (relative intensity, %) 240.0 ([M+1]$^+$, 100).

3-(2-Carboxyethyl)-2,4-dimethyl-5-formylpyrrole (117 mg), 120 mg 6-(3-methoxyphenyl)-2-oxindole and 3 drops piperidine in 3 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 190 mg (91%) of the title compound as a brown solid.

$^1$HNMR (360 MHz, DMSO-d6): δ 13.38 (s, br, 1H, NH-1'), 12.04 (s, br, 1H, COOH), 10.79 (s, br, 1H, NH-1), 7.77 (d, J=8.05, 1H, H-4), 7.58 (s, 1H, H-vinyl), 7.27 (dd, J=1.49, 8.05 Hz, 1H, H-5), 7.09 (d, J=1.49 Hz, 1H, H-7), 6.89–7.59 (m, 4H), 3.81 (s, 3H, OCH$_3$), 2.65 (t, J=7.62 Hz, 2H, CH$_2$CH$_2$COOH), 2.35 (t, J=7.62 Hz, 2H, CH$_2$CH$_2$COOH), 2.30 (s, 3H, CH$_3$), and 2.27 (s, 3H, CH$_3$); MS m/z (relative intensity, %) 417 ([M+1]$^+$, 75).

EXAMPLE 28

3-[5-(6-Bromo-2-oxo-1,2-dihydroindol-3-ylidenemethyl)-4-methyl-1H-pyrrol-3-yl]-propionic acid Dimethyl malonate (13 mL) was added dropwise to 2.7 g sodium hydride suspended in 20 mL dimethylsulfoxide. The mixture was heated to 100° C. for 10 minutes and cooled to room temperature. 5-Bromo-2-fluoronitrobenzene (5.0 g) in 25 mL dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium chloride, water and brine, dried over anhydrous sodium sulfate and concentrated to give crude dimethyl 4-bromo-2-nitrophenylmalonate as a pale yellow oil.

Crude dimethyl 4-bromo-2-nitrophenylmalonate was heated at 110° C. in 40 mL of 6 N hydrochloric acid for 24 hours and cooled. The precipitate was collected by filtration, washed with water and dried to give 5.3 g (89% yield) of 4-bromo-2-nitrophenylacetic acid as an off white solid.

4-Bromo-2-nitrophenylacetic acid 0.26 g), 0.26 g zinc powder and 3 mL 50% sulfuric acid in 5 mL ethanol was heated at 100° C. overnight. The reaction mixture was filtered, diluted with a little acetic acid, concentrated to remove ethanol, diluted with water and extracted twice with ethyl acetate. The combined extracts were washed with brine, dried over anhydrous sodium sulfate and concentrated to give 0.19 g (90% yield) of 6-bromo-2-oxindole as a yellow solid.

$^1$HNMR (360 MHz, DMSO-d6): δ 10.45 (s, br, 1H, NH-1), 7.14 (d, J=7.89 Hz, 1H, H-4), 7.09 (dd, J=1.53, 7.89 Hz, 1H, H-5), 6.93 (d, J=1.53 Hz, 1H, H-7), and 3.43 (s, 2H, $CH_2$-3); MS m/z (relative intensity, %) 210 ([M−2]$^+$, 100) and 212 (M$^+$, 100).

4-(2-carboxyethyl)-2-formyl-3-methylpyrrole (90 mg), 106 mg 6-bromo-2-oxindole, and 3 drops piperidine in 3 mL of ethanol were heated at 90° C. for 4 hours. The reaction mixture was cooled and concentrated. The residue was suspended in 6 N aqueous hydrochloric acid. The precipitate was filtered, washed with water to pH 6 and dried in a vacuum oven overnight to give 172 mg (92%) of the title compound as a yellow solid.

$^1$HNMR (360 MHz, DMSO-d6): δ 13.22 (s, br, 1H, NH-1'), 12.04 (s, br, 1H, COOH), 10.92 (s, br, 1H, NH-1), 7.73 (d, J=8.37, 1H, H-4), 7.67 (s, 1H, H-vinyl), 7.18 (d, J=3.22 Hz, 1H, H-2'), 7.14 (dd, J=1.33, 8.37 Hz, 1H, H-5), 6.99 (d, J=1.33 Hz, 1H, H-7), 2.64 (t, J=7.39 Hz, 2H, $CH_2CH_2COOH$), 2.46 (t, J=7.39 Hz, 2H, $CH_2CH_2COOH$), 2.25 (s, 3H, $CH_3$); MS (APCI) m/z 375.0 [M+1]$^+$.

EXAMPLE 29

3-{5-[6-(3-Methoxy-phenyl)-2-oxo-1,2-dihydroindol-3-ylidenemethyl]-4-methyl-1H-pyrrol-3-yl}-propionic acid 4-(2-carboxyethyl)-2-formyl-3-methylpyrrole (90.5 mg), 120 mg 6-(3-methoxyphenyl)-2-oxindole, and 3 drops piperidine in 3 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 195 mg (97%) of the title compound as a brown solid.

$^1$HNMR (360 MHz, DMSO-d6): δ 13.29 (s, br, 1H, NH-1'), 12.07 (s, br, 1H, COOH), 10.88 (s, br, 1H, NH-1), 7.82 (d, J=7.77, 1H, H-4), 7.65 (s, 1H, H-vinyl), 7.27 (dd, J=1.41, 7.77 Hz, 1H, H-5), 7.09 (d, J=1.41 Hz, 1H, H-7), 6.89–7.36 (m, 5H), 3.82 (s, 3H, $OCH_3$), 2.65 (t, J=7.55 Hz, 2H, $CH_2CH_2COOH$), 2.47 (t, J=7.55 Hz, 2H, $CH_2CH_2COOH$), 2.27 (s, 3H, $CH_3$); MS (APCI) m/z 401 [M−1]$^+$.

EXAMPLE 30

3-{5-[6-(3-Ethoxy-phenyl)-2-oxo-1,2-dihydroindol-3-ylidenemethyl]-2,4-dimethyl-1H-pyrrol-3-yl}-propionic acid Tetrakis(triphenylphosphine)palladium (0.8 g) was added to a mixture of 4.2 g of 3-ethoxyphenylboronic acid, 5.0 g 5-bromo-2-fluoronitrobenzene and 22 mL 2 M sodium carbonate solution in 50 mL toluene and 50 mL ethanol. The mixture was refluxed for 2 hours and then concentrated. Water was added and the mixture was extracted twice with ethyl acetate. The combined ethyl acetate layers were washed with water and brine brine, then dried and concentrated. The residue was chromatographed on silica gel using 5% ethyl acetate in hexane to give 5.3 g (90% yield) of crude 4-fluoro-3'-ethoxy-3-nitrobiphenyl as a yellow oil.

Dimethyl malonate (11.4 mL) was added dropwise to 4.0 g sodium hydride suspended in 20 mL dimethylsulfoxide. The mixture was heated to 100° C. for 10 minutes and cooled to room temperature. Crude 4-fluoro-3'-ethoxy-3-nitrobiphenyl (5.3 g) in 25 mL dimethylsulfoxide was added and the mixture was heated at 100° C. for 2 hours. The reaction mixture was cooled, quenched with 300 mL of saturated amonium chloride solution and extracted three times with ethyl acetate. The extracts were combined, washed with water and brine, dried over anhydrous sodium sulfate and concentrated to give crude dimethyl 3'-ethoxy-3-nitrobiphenyl-4-malonate as a yellow oil.

Crude dimethyl 3'-ethoxy-3-nitrobiphenyl-4-malonate was heated at 100° C. in 60 mL 6 N hydrochloric acid for a total of 4 days and cooled. The precipitate was collected by filtration, washed with water and hexane and dried to give 4.7 g (77% yield based on 5-bromo-2-fluoronitrobenzene) of crude 3'-ethoxy-3-nitrobiphenyl-4-acetic acid as a light tan solid.

Iron chips (2.4 g) were added in one portion to 4.6 g 3'-ethoxy-3-nitrobiphenyl-4-acetic acid in 40 mL glacial acetic acid and the mixture refluxed for 2 hours. The reaction mixture was concentrated to dryness, treated repeatedly with ethyl acetate and filtered to remove insoluble material. The filtrate was washed twice with 1 N hydrochloric acid then with brine, dried over anhydrous sodium sulfate and concentrated to give 3.5 g (91% yield) of 6-(3-ethoxyphenyl)-2-oxindole as a light brown solid.

$^1$HNMR (360 MHz, DMSO-d6): δ 10.4 (s, br, 1H, NH), 7.33 (t, J=8.4 Hz, 1H, H-3'), 7.35 (d, J=7.77 Hz, 1H), 7.19 (dd, J=1.3, 7.66 HZ, 1H), 7.13 (d, J=7.69 Hz, 1H), 7.07–7.08 (m, 1H), 7.0 (s, br, 1H), 6.9 (dd, J=2.82, 8.08 Hz, 1H), 4.08 (q, J=7 Hz, 2H, OEt), 3.49 (s, 2H, CH2), 1.34 (t, J=7 Hz, 3H, OEt); MS m/z (relative intensity, %) 254.2 ([M+1]$^+$, 100).

3-(2-carboxyethyl)-2,4-dimethyl-5-formylpyrrole (97.6 mg), 127 mg 6-(3-ethoxyphenyl)-2-oxindole, and 2 drops piperidine in 2 mL ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 227 mg of the title compound (~100%) as a brown solid.

$^1$HNMR (360 MHz, DMSO-d6): δ 13.38 ( s, br, 1H, NH-1'), 12.06 (s, br, 1H, COOH), 10.81 (s, br, 1H, NH-1), 7.77 (d, J=7.97, 1H, H-4), 7.58 (s, 1H, H-vinyl), 7.26 (dd, J=1.35, 7.97 Hz, 1H, H-5), 7.08 (d, J=1.35 Hz, 1H, H-7), 6.87–7.36 (m, 4H), 4.09 (q, J=7.0 Hz, 2H, $CH_3CH_2$), 2.65 (t, J=7.54 Hz, 2H, $CH2CH_2COOH$), 2.47 (t, J=7.54 Hz, 2H, $CH_2CH_2COOH$), 2.30 (s, 3H, $CH_3$), 2.26 (s, 3H, $CH_3$), 1.34 (t, J=7.0 Hz, 3H, $CH_3CH_2$) ; MS M/z (relative intensity, %) 431 ([M+1]$^+$, 21).

EXAMPLE 31

3-{5-[6-(3-Ethoxy-phenyl)-2-oxo-1,2-dihydroindol-3-ylidenemethyl]-4-methyl-1H-pyrrol-3-yl}-propionic acid 4-(2-carboxyethyl)-2-formyl-3-methylpyrrole (90.5 mg), 127 mg 6-(3-ethoxyphenyl)-2-oxindole and 2 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 200 mg (96%) of the title compound as a brown solid.

$^1$HNMR (360 MHz, DMSO-d6): δ 13.29 (s, br, 1H, NH-1'), 12.07 (s, vbr, 1H, COOH), 10.88 (s, br, 1H, NH-1), 7.82 (d, J=7.97, 1H, H-4), 7.65 (s, 1H, H-vinyl), 7.28 (dd, J=1.20, 7.97 Hz, 1H, H-5), 7.08 (d, J=1.20 Hz, 1H, H-7), 6.87–7.36 (m, 5H), 4.09 (q, J=6.98 Hz, 2H, CH$_3$CH$_2$), 2.65 (t, J=7.47 Hz, 2H, CH$_2$CH$_2$COOH), 2.47 (t, J=7.47 Hz, 2H, CH$_2$CH$_2$COOH), 2.27 (s, 3H, CH$_3$), 1.34 (t, J=6.98 Hz, 3H, CH$_3$CH$_2$)

EXAMPLE 32

3-[2,4-Dimethyl-5-(2-oxo-6-phenyl-1,2-dihydroindol-3-ylidenemethyl)-1H-pyrrol-3-yl]-propionic acid Tetrakis(triphenylphosphine)palladium (0.8 g) was added to a mixture of 3.1 g of benzeneboronic acid, 5 g 5-bromo-2-fluoronitrobenzene and 22 mL 2 M sodium carbonate solution in 50 mL toluene and 50 mL ethanol. The mixture was refluxed for 2 hours, concentrated, and the residue extracted twice with ethyl acetate. The ethyl acetate layer was washed with water and brine, dried, and concentrated to give a yellow oil. The oil was chromatographed on silica gel using 5% ethyl acetate in hexane to give 4.75 g (96% yield) of 4-fluoro-3-nitrobiphenyl as a yellow oil.

Dimethyl malonate (10 mL) in 25 mL of dimethylsulfoxide was added dropwise to 3.5 g sodium hydride suspended in 25 mL dimethylsulfoxide and the mixture was heated at 100° C. for 10 minutes. The mixture was cooled to room temperature and 4.7 g 4-fluoro-3-nitrobiphenyl in 25 mL dimethylsulfoxide was added. The mixture was heated at 100° C. for 2 hours, cooled and quenched with 300 mL of saturated ammonium chloride solution. The mixture was extracted three times with ethyl acetate and the combined organic layers washed with water and brine and evaporated to give a yellow oil, crude dimethyl-3-nitrobiphenyl-4-malonate.

Crude dimethyl-3-nitrobiphenyl-4-malonate was refluxed in 30 mL of 6 N hydrochloric acid for 24 hours. The precipitate was collected by filtration, washed with water and dried to give 4.5 g (80% based on 4-fluoro-3-nitrobiphenyl) of 3-nitrobiphenyl-4-acetic acid as a cream colored solid.

Iron chips (2.6 g) were added all at once to 4.5 g 3-nitrobiphenyl-4-acetic acid in 40 mL acetic acid. The mixture was refluxed for 2 hours, concentrated to dryness and taken up in ethyl acetate. The solids were removed by filtration and the filtrate washed twice with 1 N hydrochloric acid and brine and dried over anhydrous sodium sulfate. The filtrate was concentrated to give 3.4 g (93% yield) of 6-phenyl-2-oxindole as a light brown solid.

$^1$HNMR (360 MHz, DMSO-d6): δ 10.4 (s, br, 1H, NH-1), 7.57–7.6 (m, 2H), 7.42–7.46 (m, 2H), 7.32–7.37 (m, 1H), 7.27 (d, J=7.7, 1H, H-4), 7.19 (dd, J=1.6, 7.7 Hz, 1H, H-5), 7.01 (d, J=1.6 Hz, 1H, H-7), 3.49 (s, 2H, CH$_2$); MS m/z (relative intensity, %) 210 ([M+1]$^+$, 100).

3-(2-carboxyethyl)-2,4-dimethyl-5-formylpyrrole (97.6 mg), 105 mg 6-phenyl-2-oxindole and 2 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 138 mg (71%) of the title compound as a brown solid.

$^1$HNMR (360 MHz, DMSO-d6): δ 13.38 (s, br, 1H, NH-1'), 12.05 (s, br, 1H, COOH), 10.81 (s, br, 1H, NH-1), 7.78 (d, J=7.84, 1H, H-4), 7.58 (s, 1H, H-vinyl), 7.25–7.63 (m, 6H), 7.09 (s, br, 1H, H-7), 2.64 (t, J=7.71 Hz, 2H, CH$_2$CH$_2$COOH), 2.35 (t, J=7.71 Hz, 2H, CH$_2$CH$_2$COOH), 2.30 (s, 3H, CH$_3$), and 2.26 (s, 3H, CH$_3$); MS m/z (relative intensity, %) 387 ([M+1]$^+$, 100).

EXAMPLE 33

3-[4-Methyl-5-(2-oxo-6-phenyl-1,2-dihydro-indol3-ylidenemethyl)-1H-pyrrol-3-yl]-propionic acid 4-(2-Carboxyethyl)-2-formyl-3-methylpyrrole (90.5 mg), 105 mg 6-phenyl-2-oxindole and 2 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 146 mg (78%) of the title compound as a brown solid.

$^1$HNMR (360 MHz, DMSO-d6): δ 13.29 (s, br, 1H, NH-1'), 12.01 (s, vbr, 1H, COOH), 10.89 (s, br, 1H, NH-1), 7.83 (d, J=7.92, 1H, H-4), 7.65 (s, 1H, H-vinyl), 7.30–7.65 (m, 5H), 7.16 (d, J=2.83 Hz, 1H, H-2'), 7.28 (dd, J=1.58, 7.92 Hz, 1H, H-5), 7.09 (d, J=1.58 Hz, 1H, H-7), 2.66 (t, J=7.76 Hz, 2H, CH$_2$CH$_2$COOH), 2.45 (t, J=7.76 Hz, 2H, CH$_2$CH$_2$COOH), and 2.27 (s, 3H, CH$_3$); MS m/z (relative intensity, %) 373 ([M+1]$^+$, 100).

EXAMPLE 34

3-{5-[6-(4-Methoxy-phenyl)-2-oxo-1,2-dihydroindol-3-ylidenemethyl]-4-methyl-1H-pyrrol-3-yl}-propionic acid Tetrakis(triphenylphosphine)palladium (1 g) was added to a mixture of 5 g 4-methoxyphenylboronic acid, 6.6 g 5-bromo-2-fluoronitrobenzene and 30 mL 2 M sodium carbonate solution in 50 mL toluene and 50 mL ethanol. The mixture was refluxed for 2 hours, concentrated, and the residue extracted twice with ethyl acetate. The ethyl acetate layer was washed with water and brine, dried, and concentrated to give a brown oily solid. The solid was chromatographed on silica gel using 5% ethyl acetate in hexane to give crude 4-fluoro-4'-methoxy-3-nitrobiphenyl as a pale yellow solid.

Dimethyl malonate (10 mL) was added dropwise to 2.0 g of sodium hydride suspended in 60 mL dimethylsulfoxide. The mixture was heated to 100° C. for 10 minutes and cooled to room temperature. Crude 4-fluoro-2'-methoxy-3-nitrobiphenyl (5.2 g) in 50 mL dimethylsulfoxide was added and the mixture was heated at 100° C. for 2 hours. The reaction mixture was cooled and quenched with 300 mL of saturated ammonium chloride solution and extracted three times with ethyl acetate. The extracts were combined, washed with saturated ammonium chloride, water and brine, dried over anhydrous sodium sulfate and concentrated to give crude dimethyl 4'-methoxy-3-nitrobiphenyl-4-malonate as a yellow oil.

Crude 4'-methoxy-3-nitro-biphenyl-4-malonate was heated at 100° C. in 60 mL 6 N hydrochloric acid for 15 hours and cooled. The precipitate which formed was collected by filtration, washed with water and hexane, and dried to give 7.2 g of crude 4'-methoxy-3-nitrobiphenyl-4-acetic acid as a light tan solid.

Iron chips (3.6 g) were added in one portion to 7.2 g 4'-methoxy-3-nitrobiphenyl-4-acetic acid in 50 mL glacial acetic acid and heated at 100° C. overnight. The reaction mixture was concentrated to dryness, sonicated in ethyl acetate and filtered to remove the insolubles. The filtrate was washed twice with 1 N hydrochloric acid, then with brine, dried over anhydrous sodium sulfate and concentrated to give 2.7 g (54% yield based on 5-bromo-2-fluoronitrobenzene) of 6-(4-methoxyphenyl)-2-oxindole as a rose colored solid.

$^1$HNMR (360 MHz, DMSO-d6): δ 10.38 (s, br, 1H, NH-1), 7.52 (d, J=9 Hz, 2H,), 7.23 (d, J=7.3 Hz, 1H, H-4), 7.14 (d,d, J=1.38, 7.3 Hz, 1H, H-5), 7.0 (d, J=9 Hz, 2H), 6.96 (d, J=1.38 Hz, 1H, H-7), 3.78 (s, 3H, OCH$_3$ ), 3.47 (s, 2H, CH$_2$); MS m/z (relative intensity, %) 214.0 ([M+1]$^+$, 100).

4-(2-Carboxyethyl)-2-formyl-3-methylpyrrole (90.5 mg), 120 mg 6-(4-methoxyphenyl)-2-oxindole and 3 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 118 mg (59%) of the title compound as a brown solid.

$^1$HNMR (360 MHz, DMSO-d6): δ 13.26 (s, br, 1H, NH-1'), 10.83 (s, br, 1H, NH-1), 7.78 (d, J=8.07 Hz, 1H, H-4), 7.61 (s, 1H, H-vinyl), 7.56 (d, J=8.97 Hz, 2H),7.22 (dd, J=1.44, 8.07 Hz, 1H, H-5), 7.13 (d, J=3.09 Hz, 1H, H-2'), 7.04 (d, J=1.44 Hz, 1H, H-7), 7.0 (d, J=8.97 Hz, 2H), 3.79 (s, 3H, OCH$_3$), 2.65 (t, J=7.54 Hz, 2H, CH$_2$CH$_2$COOH), 2.44 (t, J=7.54 Hz, 2H, CH$_2$CH$_2$COOH), and 2.27 (s, 3H, CH$_3$); MS m/z (relative intensity, %) 404 ([M+1]$^+$, 100).

EXAMPLE 35

3-{5-[6-(4-Methoxy-phenyl)-2-oxo-1,2-dihydroindol-3-ylidenemethyl]-2,4-dimethyl-1H-pyrrol-3-yl}-propionic acid 3-(2-Carboxyethyl)-2,4-dimethyl-5-formylpyrrole (98 mg), 120 mg 6-(4-methoxyphenyl)-2-oxindole and 3 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 118 mg (57%) of the title compound as a brown solid.

$^1$HNMR (360 MHz, DMSO-d6): δ 13.35 (s, br, 1H, NH-1'), 12.02 (s, br, 1H, COOH), 10.75 (s, br, 1H, NH-1), 7.73 (d, J=6.75 Hz, 1H, H-4), 7.56 (d, J=9.01 Hz, 2H), 7.54 (s, 1H, H-vinyl), 7.21 (dd, J=1.59, 6.75 Hz, 1H, H-5), 7.04 (d, J=1.59 Hz, 1H, H-7), 7.01 (d, J=9.01 Hz, 2H), 3.79 (s, 3H, OCH$_3$), 2.65 (t, J=7.54 Hz, 2H, CH$_2$CH$_2$COOH), 2.35 (t, J=7.54 Hz, 2H, CH$_2$CH$_2$COOH), 2.29 (s, 3H, CH$_3$), and 2.26 (s, 3H, CH$_3$); MS m/z (relative intensity, %) 417 ([M+1]$^+$, 100).

EXAMPLE 36

3-{5-[6-(2-Methoxy-phenyl)-2-oxo-1,2-dihydroindol-3-ylidenemethyl]-4-methyl-1H-pyrrol-3-yl}-propionic acid Tetrakis(triphenylphosphine)palladium (1 g) was added to a mixture of 5 g of 2-methoxyphenylboronic acid, 6.6 g 5-bromo-2-fluoronitrobenzene and 30 mL 2 M sodium carbonate solution in 50 mL toluene and 50 mL ethanol. The mixture was refluxed for 2 hours, concentrated, and the residue extracted twice with ethyl acetate. The combined ethyl acetate layers were washed with water and brine, dried, and concentrated to give a dark green oil which solidified on standing to give crude 4-fluoro-2'-methoxy-3-nitrobiphenyl.

Dimethyl malonate (14 mL) was added dropwise to 2.9 g sodium hydride suspended in 50 mL dimethylsulfoxide. The mixture was heated at 100° C. for 15 minutes and cooled to room temperature.

Crude 4-fluoro-2'-methoxy-3-nitrobiphenyl in 60 mL of dimethylsulfoxide was added and the mixture was heated at 100° C. for 2 hours. The reaction mixture was cooled and quenched with 300 mL of saturated ammonium chloride solution and extracted twice with ethyl acetate. The extracts were combined, washed with saturated ammonium chloride, water, and brine, dried over anhydrous sodium sulfate and concentrated to give crude dimethyl 2'-methoxy-3-nitrobiphenyl-4-malonate as a yellow oil.

Crude 2'-methoxy-3-nitrobiphenyl-4-malonate was heated at 100° C. in 50 mL 6 N hydrochloric acid for 24 hours and cooled. The precipitate was collected by filtration, washed with water and hexane, and dried to give 9.8 of 2'-methoxy-2-nitrobiphenyl-4-acetic acid as a light tan solid.

Iron chips (5 g) were added in one portion to 9.8 g 2'-methoxy-3-nitrobiphenyl-4-acetic acid in 50 mL of glacial acetic acid and the mixture was heated to 100° C. for 3 hours. The reaction mixture was concentrated to dryness, sonicated in ethyl acetate and filtered to remove the insolubles. The filtrate was washed twice with 1 N hydrochloric acid, water and brine, dried over anhydrous sodium sulfate and concentrated. The residue was chromatographed on silica gel using ethyl acetate:hexane 1:2 to give 5.4 g (69% yield based on 5-bromo-2-fluoronitrobenzene) of 6-(2-methoxyphenyl)-2-oxindole as a rose colored solid.

$^1$HNMR (360 MHz, DMSO-d6): δ 10.32 (s, br, 1H, NH), 7.29–7.34 (m, 1H), 7.19–7.25 (m, 2H), 7.08 (d, J=8 Hz, 1H, H-4), 6.97–7.02 (m, 2H), 6.91 (d, J=1.05 Hz, 1H, H-7), 3.8 (s, 3H, OCH$_3$), 3.47 (s, 2H, CH$_2$); MS m/z (relative intensity, %) 239.8 (100, [M+1]$^+$).

4-(2-Carboxyethyl)-2-formyl-3-methylpyrrole (217 mg), 239 mg 6-(2-methoxyphenyl)-2-oxindole and 3 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight to give 348 mg (86%) of the title compound as a brown solid.

$^1$HNMR (360 MHz, DMSO-d6): δ 13.29 (s, br, 1H, NH-1'), 11.59 (s, br, 1H, COOH), 10.78 (s, br, 1H, NH-1), 7.75 (d, J=8.13 Hz, 1H, H-4), 7.62 (s, 1H, H-vinyl), 7.0–7.34 (m, 7H), 3.76 (s, 3H, OCH$_3$), 2.66 (t, J=7.46 Hz, 2H, CH$_2$CH$_2$COOH), 2.46 (t, J=7.46 Hz, 2H, CH$_2$CH$_2$COOH), and 2.27 (s, 3H, CH$_3$); MS m/z (relative intensity, %) 401 ([M+1]$^+$, 100).

EXAMPLE 37

3-{5-[6-(2-Methoxy-phenyl)-2-oxo-1,2-dihydroindol-3-ylidenemethyl]-2,4-dimethyl-1H-pyrrol-3-yl}-propionic acid 3-(2-Carboxyethyl)-2,4-dimethyl-5-formylpyrrole (234 mg), 239 mg 6-(2-methoxyphenyl)-2-oxindole and 3 drops piperidine in 2 mL of ethanol were heated at 90° C. overnight. The reaction mixture was cooled and concentrated. The residue was suspended in 6 N aqueous hydrochloric acid. The precipitate was filtered, washed with water to pH 6 and dried in a vacuum oven overnight. The crude solid was purified by chromatography on a silica gel column eluting with ethyl acetate:hexane 1:1 containing 0.1% acetic acid to give 182 mg (44%) of the title compound as a brown solid.

¹HNMR (360 MHz, DMSO-d6): δ 13.38 (s, br, 1H, NH-1'), 12.0 (s, br, 1H, COOH), 10.7 (s, br, 1H, NH-1), 7.71 (d, J=7.74 Hz, 1H, H-4), 7.55 (s, 1H, H-vinyl), 7.0–7.33 (m, 6H), 3.76 (s, 3H, OCH$_3$), 2.65 (t, J=7.6 Hz, 2H, CH$_2$CH$_2$COOH), 2.35 (t, J=7.6 Hz, 2H, CH$_2$CH$_2$COOH), 2.3 (s, 3H, CH$_3$), and 2.26 (s, 3H, CH$_3$); MS (APCI neg) m/z (relative intensity, %) 415 ([M−1], 100).

EXAMPLE 38

3-[2,4-Dimethyl-5-(6-morpholin-4-yl-2-oxo-1,2-dihydroindol-3-ylidenemethyl)-1H-pyrrol-3-yl]-propionic acid Tin chloride dihydrate (225 g) was added to a solution of 2,4-dinitrophenylacetic acid (22.6 g) in ethanol (450 mL). The mixture was heated at 90° C. for 10 hours. The reaction mixture was cooled and basified to pH 11 with 12M sodium hydroxide. The solids were removed by filtration and the filtrate was concentrated. The residue was treated with ethanol (300 mL). The insolubles were filtered and washed with ethanol (5×60 mL). The combined ethanol washes were evaporated and dried under vacuum to give 15 g of 6-amino-2-oxindole as a brown powder.

¹HNMR (360 MHz, DMSO-d6): δ 10.03 (s, br, NH), 6.78 (d, J=8.55 Hz, 1H, H-4), 6.09–6.11 (m, 2H), 4.95 (s, br, 2H, NH$_2$), 3.22 (s, 2H, H-3); MS (+APCI) m/z (relative intensity, %) 147 ([M−1]$^+$, 100).

6-Amino-2-oxindole (2.2 g), 4.0 g 2, 2'-dibromoethyl ether and 7.9 g sodium carbonate were refluxed overnight in 20 ml of ethanol, concentrated and diluted with 50 ml of water. The mixture was extracted three times with 50 ml ethyl acetate, the organic extracts were combined, washed with 20 ml of brine, dried over anhydrous sodium sulfate and concentrated to dryness. The solid was chromatographed on a column of silica gel eluting with ethyl acetate-:hexane 1:1 containing 0.7% acetic acid to give 1.2 g (37% yield) of 6-(morpholin-4-yl)-2-oxindole as a beige solid.

¹HNMR (360 MHz, DMSO-d6): δ 10.2 (s, br, 1H, NH-1), 7.02 (d, J=7.87 Hz, 1H, H-4), 6.47 (dd, J=2.11, 7.87 Hz, 1H, H-5), 6.37 (d, J=2.11 Hz, 1H, H-7), 3.69–3.72 (m, 4H), 3.32 (s, 2H, CH$_2$), 3.01–3.04 (m, 4H); MS m/z (relative intensity, %) 219 ([M+1]$^+$, 100).

3-(2-Carboxyethyl)-2,4-dimethyl-5-formylpyrrole (3.3 g), 4 g 6-(morpholin-4-yl)-2-oxindole and 1.8 mL piperidine in 60 mL of ethanol were heated at 90° C. for 7 hours. The reaction mixture was cooled and concentrated. The residue was suspended in 6 N aqueous hydrochloric acid. The precipitate was filtered, washed with water to pH 6 and dried in a vacuum oven overnight. The resulting solid was purified by chromatography on a silica gel column eluting with ethyl acetate-hexane-acetic acid to give 2.78 g (38% yield) of the title compound as a brown solid.

¹HNMR (360 MHz, DMSO-d6): δ 13.13 (s, br, 1H, NH-1'), 12.02 (s, br, 1H, COOH), 10.57 (s, br, 1H, NH-1), 7.52 (d, J=8.46 Hz, 1H, H-4), 7.32 (s, 1H, H-vinyl), 6.58 (dd, J=1.99, 8.46 Hz, 1H, H-5), 6.41 (d, J=1.99 Hz, 1H, H-7), 3.71–3.74 (m, 4H), 3.06–3.09 (m, 4H), 2.62 (t, J=7.57 Hz, 2H, CH$_2$CH$_2$COOH), 2.33 (t, J=7.57 Hz, 2H, CH$_2$CH$_2$COOH), 2.26 (s, 3H, CH$_3$), and 2.21 (s, 3H, CH$_3$); MS m/z (relative intensity, %) 396 ([M+1]$^+$, 100).

EXAMPLE 39

3-[5-(5-Chloro-4-methyl-2-oxo-1,2-dihydroindol-3-ylidenemethyl)-2,4-dimethyl-1H-pyrrol-3-yl]-propionic acid A suspension of 3.0 g 4-methyl-2-oxindole was stirred in 50 mL acetonitrile at room temperature while 3.3 g of N-chloro-succinimide was added in portions. Trifluoroacetic acid (1 mL) was then added. The suspension was stirred at room temperature for 3 days during which time solids were always present. The white solid was collected by vacuum filtration, washed with a small amount of cold acetone and dried overnight in a vacuum oven at 40° C. to give 2.5 g (68%) of 5-chloro-4-methyl-2-oxindole.

¹HNMR (360 MHz, DMSO-d6): δ 10.38 (s, br, 1H, NH), 7.19 (d, J=8 Hz, 1H, aromatic), 6.64 (d, J=8 Hz, 1H, aromatic), 3.46 (s, 2H, H-3), 2.19 (s, 3H, CH$_3$).

3-(2-Carboxyethyl)-2,4-dimethyl-5-formylpyrrole (98 mg), 91 mg 5-chloro-4-methyl-2-oxindole and 2 drops piperidine in 2 mL of ethanol were heated at 90° C. for 4 hours. The reaction mixture was cooled and concentrated. The residue was suspended in 6 N aqueous hydrochloric acid. The precipitate was filtered, washed with water to pH 6 and dried in a vacuum oven overnight to give 100 mg of the title compound.

¹HNMR (360 MHz, DMSO-d6): δ 13.47 (s, br, 1H, NH-1'), 12.03 (s, br, 1H, COOH), 10.83 (s, br, 1H, NH-1), 7.61 (s, 1H, H-vinyl), 7.14 (d, J=8.17 Hz, 1H, aromatic), 6.74 (d, J=8.17 Hz, 1H, aromatic), 2.64 (s, 3H, CH$_3$), 2.64 (t, J=7.62 Hz, 2H, CH$_2$CH$_2$COOH), 2.34 (t, J=7.62 Hz, 2H, CH$_2$CH$_2$COOH), 2.3 (s, 3H, CH$_3$), and 2.20 (s, 3H, CH$_3$).

EXAMPLE 40

3-[5-(5-Chloro-4-methyl-2-oxo-1,2-dihydroindol-3-ylidenemethyl)-4-methyl-1H-pyrrol-3-yl]-propionic acid 4-(2-Carboxyethyl)-2-formyl-3-methylpyrrole (91 mg), 91 mg 5-chloro-4-methyl-2-oxindole and 2 drops piperidine in 2 mL of ethanol were heated at 90° C. for 4 hours. The reaction mixture was cooled and concentrated. The residue was suspended in 6 N aqueous hydrochloric acid. The precipitate was filtered, washed with water to pH 6 and dried in a vacuum oven overnight to give 95 mg of the title compound.

¹HNMR (360 MHz, DMSO-d6): δ 13.36 (s, br, 1H, NH-1'), 11.98 (s, br, 1H, COOH), 10.92 (s, br, 1H, NH-1), 7.68 (s, 1H), 7.19 (d, J=7.14 Hz, 1H, aromatic), 7.17 (s, 1H), 6.75 (d, J=7.14 Hz, 1H, aromatic), 2.66 (s, 3H, CH$_3$-4), 2.66 (t, J=7.51 Hz, 2H, CH$_2$CH$_2$COOH), 2.45 (t, J=7.51 Hz, 2H, CH$_2$CH$_2$COOH), 2.21 (s, 3H, CH$_3$); MS m/z (relative intensity, %) 345 ([M+1]$^+$, 100).

EXAMPLE 41

3-[2,4-Dimethyl-5-(2-oxo-1,2-dihydroindol-3-ylidenemethyl)-1H-pyrrol-3-yl]-propionic acid, sodium salt A suspension of 8 g of 3-[2,4-dimethyl-5-(2-oxo-1,2-dihydroindol-3-ylidenemethyl)-1H-pyrrol-3-yl]-propionic acid in 60 mL of water was added to 0.98 g of sodium hydroxide in 10 ml of water. The mixture was stirred at RT for 30 minutes and filtered. The filtrate was frozen and lyophilized to give 8 g of the title compound.

Alternatively, a suspension of 117 g of 318-005 in 470 mL of water was added to 16.47 g of sodium hydroxide in 74 mL water. The mixture was stirred at room temperature for 15 minutes and filtered. The filtrate was added to 210 mL of ethanol and the resulting precipitate which formed was collected by suction filtration. After drying, a total of 106 g of the title compound was obtained.

¹HNMR (360 MHz, DMSO-d6): δ 13.34 (s, br, 1H, NH-1'), 10.82 (s, br, 1H, NH-1), 7.65 (d, J=7.52 Hz, 1H,

H-4), 7.5 (s, 1H, H-vinyl), 7.04 (t, J=7.52 Hz, 1H, H-6), 6.93 (t, J=7.52 Hz, 1H, H-5), 6.85 (d, J=7.52 Hz, 1H, H-7), 2.55 (t, J=6.95 Hz, 2H, CH$_2$CH$_2$COOH), 2.28 (s, 3H, CH$_3$), 2.24 (s, 3H, CH$_3$), and 1.99 (t, J=6.95 Hz, 2H, CH$_2$CH$_2$COOH).

EXAMPLE 42

3-[3,5-Dimethyl-4-(3-morpholin-4-ylpropyl)-1H-pyrrol-2-ylmethylene]-1,3-dihydroindol-2-one Step 1: To a suspension of 3-(2,4-dimethyl-1H-pyrrol-3-yl)-propionic acid (10 g, 60.8 mmol) in 60 ml of dichloromethane was added 1,1'-carbonyldiimidazole (11.6 g, 71.8 mmol) followed morpholine (5.5 ml, 60.8 mmol) and N,N-diisopropylethylamine (Hunig's base, 10 ml, 60.8 mmol). The dark red reaction mixture was stirred at room temperature overnight and poured into ice water. The organic layer was washed with brine until the wash had a pH of about 6, dried over anhydrous sodium sulfate, and concentrated. The crude product was purified on a silica gel column eluting with dichloromethane-methanol (98:2) to give 13.84 g (96%) of 3-(2,4-dimethyl-1H-pyrrol-3-yl)-1-morpholin-4-yl-propan-1-one.

Step 2: To a suspension of lithium aluminum hydride (2.67 g, 70 mmol) in tetrahydrofuran (100 ml) was added dropwise a solution of 3-(2,4-dimethyl-1H-pyrrol-3-yl)-1-morpholin-4-yl-propan-1-one (13.84 g, 59 mmol) in tetrahydrofuran (50 ml). The reaction mixture was stirred at 80° C. for 1 hour and cooled ins an ice bath. Ice was added to the reaction mixture slowly until gas evolution ceased. A few drops of 2N sodium hydroxide were added and the reaction mixture was stirred at room temperature for 30 minutes. The reaction mixture was then extracted with ethyl acetate, dried over anhydrous sodium sulfate and concentrated to give 10.37 g (79%) of 4-[3-(2,4-dimethyl-1H-pyrrol-3-yl)-propyl]-morpholine as a light brown oil which was used without further purification.

Step 3: To an ice-cooled solution of N,N-dimethylformamide (5.5 ml, 70 mmol) in dichloromethane (30 ml) was dropwise added phosphorus oxychloride (6.5 ml, 70 mmol). When the addition was complete, the reaction mixture was stirred at room temperature for 15 minutes after which a solution of 3,5-dimethyl-4-(3-morpholin-4-yl-propyl)-1H-pyrrole-2-carboxaldehyde (10.37 g, 46.6 mmol) in dichloromethane (20 ml) was added dropwise at 0° C. The final reaction mixture was refluxed at 60° C. for 4 hours and then cooled in an ice bath. Ice was slowly added to the reaction mixture followed by addition of 2 N sodium hydroxide until a pH to 12 was reached. The reaction mixture was stirred at room temperature for 30 min. and then extracted with ethyl acetate. The organic layer was washed with brine, dried over anhydrous sodium sulfate and concentrated to give crude product which was purified on a silica gel column eluting with dichloromethane-methanol-ammonium hydroxide (9.5:0.5) to give 4.57 g (39%) of 3,5-dimethyl-4-(3-morpholin-4-yl-propyl)-1H-pyrrole-2-carbaldehyde as a dark red oil:

$^1$HNMR (360 MHz, DMSO-d$_6$) δ 11.34 (s, br, 1H, NH-1), 9.40 (s, 1H, CHO-2), 3.55 (t, J=4.68 Hz, 4H, O(CH$_2$CH$_2$)$_2$NCH$_2$CH$_2$CH$_2$-4), 2.28–2.34 (m, 6H, O(CH$_2$CH$_2$)$_2$NCH$_2$CH$_2$CH$_2$-4), 2.21 (t, 2H, J=7.10 Hz, 2H, O(CH$_2$CH$_2$)$_2$NCH$_2$CH$_2$CH$_2$-4) CH$_3$-3), 2.19 (s, 3H, CH$_3$-5), 2.14 (s, 3H, CH$_3$-3), 1.51 (quint., J=7.10 Hz, 2H, O(CH$_2$CH$_2$)$_2$NCH$_2$CH$_2$CH$_2$-4), MS m/z (relative intensity, %) 251 ([M+1]$^+$, 100).

Step 4: A mixture of 1,3-dihydroindol-2-one (133 mg, 1.0 mmol), 3,5-dimethyl-4-(3-morpholin-4-yl-propyl)-1H-pyrrole-2-carboxaldehyde (250 mg, 1.0 mmol) and 3 drops pyrrolidine in 2.0 ml of ethanol was refluxed at 90° C. for 4 hours and then cooled to room temperature. The precipitate was filtered, washed with cold ethanol and hexane, and dried in a vacuum oven overnight to give 308.9 mg (85%) of 3-[3,5-dimethyl-4-(3-morpholin-4-yl-propyl)-1H-pyrrol-2-ylmethylene]-1,3-dihydroindol-2-one as a yellow solid:

$^1$HNMR (300 MHz, DMSO-d$_6$) δ 13.37 (s, 1H, NH-1'), 10.71 (s, 1H, NH-1), 7.68 (d, J=7.47 Hz, 1H, H-4), 7.53 (s, 1H, H-vinyl), 7.06 (dt, J=7.47 Hz, 1H,H-6), 6.94 (dt, J=7.74 Hz, 1H, H-5), 6.84 (d, J=7.47 Hz, 1H, H-7), 3.55 (t, J=4.37 Hz, 4H, O(CH$_2$CH$_2$)$_2$NCH$_2$CH$_2$CH$_2$-4'), 2.40 (t, J=7.31 Hz, 2H, O(CH$_2$CH$_2$)$_2$NCH$_2$CH$_2$CH$_2$-4'), 2.31 (t, J=4.37 Hz, 4H, O(CH$_2$CH$_2$)$_2$NCH$_2$CH$_2$CH$_2$-41), 2.28 (s, 3H, CH$_3$-3'), 2.23 (s, 3H, CH$_3$-5'), 2.23 (t, J=7.31 Hz, 2H, O(CH$_2$CH$_2$)$_2$NCH$_2$CH$_2$CH$_2$-4'), 1.56 (quint., J=7.31 Hz, 2H, O(CH$_2$CH$_2$)$_2$NCH$_2$CH$_2$CH$_2$-4'), MS m/e (relative intensity, %) 365 (M$^+$, 100).

EXAMPLE 43

5-Bromo-3-[3,5-dimethyl-4-(3-morpholin-4-yl-propyl)-1H-pyrrol-2-ylmethylene]-1,3-dihydroindol-2-one A mixture of 5-bromo-1,3-dihydroindol-2-one (212 mg, 1.0 mmol), 3,5-dimethyl-4-(3-morpholin-4-yl-propyl)-1H-pyrrole-2-carbaldehyde (250 mg, 1.0 mmol) and 3 drops pyrrolidine in 2.0 ml of ethanol was refluxed at 90° C. for 4 hours and then cooled to room temperature. The precipitate was filtered, washed with cold ethanol and hexane and dried in a vacuum oven overnight to give 399.8 mg (90%) of 5-bromo-3-[3,5-dimethyl-4-(3-morpholin-4-yl-propyl)-1H-pyrrol-2-ylmethylene]-1,3-dihydroindol-2-one as a red solid:

$^1$HNMR (300 MHz, DMSO-d$_6$) δ 13.43 (s, 1H, NH-1'), 10.81 (s, 1H, NH-1), 7.99 (d, J=2.07 Hz, 1H, H-4), 7.66 (s, 1H, H-vinyl), 7.18 (dd, J=2.07, 7.58 Hz, 1H,H-6), 6.79 (d, J=7.58 Hz, 1H, H-7), 3.55 (t, J=4.39 Hz, 4H, O(CH$_2$CH$_2$)$_2$NCH$_2$CH$_2$CH$_2$-4'), 2.40 (t, J=7.32 Hz, 2H, O(CH$_2$CH$_2$)$_2$NCH$_2$CH$_2$CH$_2$-4'), 2.31 (t, J=4.39 Hz, 4H, O(CH$_2$CH$_2$)$_2$NCH$_2$CH$_2$CH$_2$-4'), 2.29 (s, 3H, CH$_3$-3'), 2.26 (s, 3H, CH$_3$-5'), 2.23 (t, J=7.32 Hz, 2H, O(CH$_2$CH$_2$)$_2$NCH$_2$CH$_2$CH$_2$-4'), 1.56 (quint., J=7.32 Hz, 2H, O(CH$_2$CH$_2$)$_2$NCH$_2$CH$_2$CH$_2$-4'), MS m/e (relative intensity, %) 443 (M$^+$, 100), 445 ([M+2]$^+$, 100).

EXAMPLE 44

3-[3,5-Dimethyl-4-(3-morpholin-4-yl-propyl)-1H-pyrrol-2-ylmethylene]-6-phenyl-1,3-dihydroindol-2-one Using the procedure of Example 2, an 88% yield of the title compound was obtained as a yellow solid:

$^1$HNMR (300 MHz, DMSO-d$_6$) δ 13.37 (s, 1H, NH-1'), 10.81 (s, 1H, NH-1), 7.77 (d, J=8.20 Hz, 1H, H-4), 7.62 (d, J=7.39 Hz, 2H, H-2",6"), 7.58 (s, 1H, H-vinyl), 7.44 (t, J=7.39 Hz, 2H, H-3",5"), 7.32 (t, br, J=7.39 Hz, 1H, H-4"), 7.26 (dd, J=1.49, 8.29 Hz, 1H, H-5), 7.09 (d, J=1.49 Hz, 1H, H-7), 3.56 (t, J=4.48 Hz, 4H, O(CH$_2$CH$_2$)$_2$NCH$_2$CH$_2$CH$_2$-4'), 2.41 (t, J=7.18 Hz, 2H, O(CH$_2$CH$_2$)$_2$NCH$_2$CH$_2$CH$_2$-41), 2.31 (t, J=4.48 Hz, 4H, O(CH$_2$CH$_2$)$_2$NCH$_2$CH$_2$CH$_2$-4'), 2.29 (s, 3H, CH$_3$-3'), 2.26 (s, 3H, CH$_3$-5'), 2.24 (t, J=7.18 Hz, 2H, O(CH$_2$CH$_2$)$_2$NCH$_2$CH$_2$CH$_2$-4'), 1.56 (quint., J=7.18 Hz, 2H, O(CH$_2$CH$_2$)$_2$NCH$_2$CH$_2$CH$_2$-4'), MS m/e (relative intensity, %) 441 (M$^+$, 100).

EXAMPLE 45

3-[3,5-Dimethyl-4-(3-morpholin-4-yl-propyl)-1H-pyrrol-2-ylmethylene]-6-(2-methoxyphenyl)-1,3-dihydroindol-2-one Using the procedure of Example 2, an 86% yield of the title compound was obtained as a yellow solid:

¹HNMR (300 MHz, DMSO-$d_6$) δ 13.37 (s, 1H, NH-1'), 10.72 (s, 1H, NH-1), 7.71 (d, J=7.79 Hz, 1H, H-4), 7.55 (s, 1H, H-vinyl), 7.27–7.34 (m, 2H), 6.98–7.10 (m, 4H), 3.76 (s, 3H, OCH$_3$-2"), 3.56 (t, J=4.50 Hz, 4H, O(C$\underline{H}_2$CH$_2$)$_2$NCH$_2$CH$_2$CH$_2$-4'), 2.41 (t, J=7.12 Hz, 2H, O(CH$_2$CH$_2$)$_2$NCH$_2$CH$_2$C$\underline{H}_2$-4'), 2.21–2.31 (m, 6H, O(CH$_2$C$\underline{H}_2$)$_2$NC$\underline{H}_2$C$\underline{H}_2$CH$_2$-4'), 2.29 (s, 3H, CH$_3$-3'), 2.25 (s, 3H, CH$_3$-5'), 1.57 (quint., J=7.12 Hz, 2H, O(CH$_2$CH$_2$)$_2$NCH$_2$C$\underline{H}_2$CH$_2$-4'), MS m/e (relative intensity, %) 471 (M⁺, 100).

EXAMPLE 46

3-[3,5-Dimethyl-4-(3-morpholin-4-yl-propyl)-1H-pyrrol-2-ylmethylene]-6-(3-methoxyphenyl)-1,3-dihydroindol-2-one Using the procedure of Example 2, an 87% yield of the title compound was obtained as a yellow solid:

¹HNMR (300 MHz, DMSO-$d_6$) δ 13.38 (s, 1H, NH-1'), 10.80 (s, 1H, NH-1), 7.76 (d, J=7.93 Hz, 1H, H-4), 7.57 (s, 1H, H-vinyl), 7.35 (t, J=8.08 Hz, 1H, H-5"), 7.26 (dd, J=1.73, 7.93 Hz, 1H, H-5), 7.18 (d, br, J=8.08 Hz, 1H, H-4"), 7.13 (t, br, J=1.94 Hz, 1H, H-2"), 7.08 (d, J=1.73 Hz, 1H, H-7), 6.90 (dd, J=1.94, 8.08 Hz, 1H, H-6"), 3.81 (s, 3H, OCH$_3$-3"), 3.56 (t, J=4.38 Hz, 4H, O(C$\underline{H}_2$CH$_2$)$_2$NCH$_2$CH$_2$CH$_2$-4'), 2.41 (t, J=7.19 Hz, 2H, O(CH$_2$CH$_2$)$_2$NCH$_2$CH$_2$C$\underline{H}_2$-4'), 2.31 (t, J=4.38 Hz, 4H, O(CH$_2$C$\underline{H}_2$)$_2$NCH$_2$CH$_2$C$\underline{H}_2$-4'), 2.29 (s, 3H, CH$_3$-3'), 2.26 (s, 3H, CH$_3$-5'), 2.24 (t, J=7.19 Hz, 2H, O(CH$_2$CH$_2$)$_2$NCH$_2$CH$_2$CH$_2$-4'), 1.56 (quint., J=7.19 Hz, 2H, O(CH$_2$CH$_2$)$_2$NCH$_2$C$\underline{H}_2$CH$_2$-4'), MS m/e (relative intensity, %) 471 (M⁺, 100).

EXAMPLE 47

3-[3,5-Dimethyl-4-(3-morpholin-4-yl-propyl)-1H-pyrrol-2-ylmethylene]-6-(4-methoxyphenyl)-1,3-dihydroindol-2-one Using the method of Example 2, a 52% yield of the title compound was obtained as a yellow solid:

¹HNMR (300 MHz, DMSO-$d_6$) δ 13.35 (s, 1H, NH-1'), 10.77 (s, 1H, NH-1), 7.72 (d, J=7.97 Hz, 1H, H-4), 7.55 (d, J=8.57 Hz, 2H, H-2",6"), 7.54 (s, 1H, H-vinyl), 7.20 (dd, J=1.35, 7.97 Hz, 1H, H-5), 7.04 (d, J=1.35 Hz, 1H, H-7), 6.99 (d, J=8.57 Hz, 1H, H-3",5"), 3.78 (s, 3H, OCH$_3$-4"), 3.55 (t, J=4.57 Hz, 4H, O(C$\underline{H}_2$CH$_2$)$_2$NCH$_2$CH$_2$CH$_2$-4'), 2.40 (t, J=6.97 Hz, 2H, O(CH$_2$CH$_2$)$_2$NCH$_2$CH$_2$C$\underline{H}_2$-4'), 2.30 (t, J=4.57 Hz, 4H, O(CH$_2$C$\underline{H}_2$)$_2$NCH$_2$CH$_2$C$\underline{H}_2$-4'), 2.28 (s, 3H, CH$_3$-3'), 2.24 (s, 3H, CH$_3$-5'), 2.23 (t, J=6.97 Hz, 2H, O(CH$_2$CH$_2$)$_2$NC$\underline{H}_2$CH$_2$CH$_2$-4'), 1.55 (quint., J=6.97 Hz, 2H, O(CH$_2$CH$_2$)$_2$NCH$_2$C$\underline{H}_2$CH$_2$-4'), MS m/e (relative intensity, %) 471 (M⁺, 100).

EXAMPLE 48

3-[4-(3-Dimethylaminopropyl)-3,5-dimethyl-1H-pyrrol-2-ylmethylene]-1,3-dihydroindol-2-one Using Steps 1, 2, and 3 of Example 1, a 63% yield of 4-(3-dimethylaminopropyl)-3,5-dimethyl-1H-pyrrole-2-carboxaldehyde as a dark red oil:

¹HNMR (360 MHz, DMSO-$d_6$) δ 11.33 (s, br, 1H, NH-1), 9.40 (s, 1H, CHO-2), 2.30 (t, J=7.42 Hz, 2H, (CH$_3$)$_2$NCH$_2$CH$_2$C$\underline{H}_2$-4), 2.18 (s, 3H, CH$_3$-3), 2.15 (t, J=7.42 Hz, 2H, (CH$_3$)$_2$NC$\underline{H}_2$CH$_2$CH$_2$-4), 2.14 (s, 3H, CH$_3$-5), 2.10 (s, 6H, (C$\underline{H}_3$)$_2$NCH$_2$CH$_2$CH$_2$-4), 1.47 (quint., J=7.42 Hz, 2H, (CH$_3$)$_2$NCH$_2$C$\underline{H}_2$CH$_2$-4), MS m/z (relative intensity, %) 208 ([M+1]⁺, 100).

Using Stet 4 of Example 1, a 52% yield of the title compound was obtained as a yellow solid:

¹HNMR (360 MHz, DMSO-$d_6$) δ 13.38 (s, 1H, NH-1'), 10.70 (s, 1H, NH-1), 7.68 (d, J=7.54 Hz, 1H, H-4), 7.53 (s, 1H, H-vinyl), 7.06 (t, J=7.54 Hz, 1H, H-6), 6.94 (t, J=7.54 Hz, 1H, H-5), 6.85 (d, J=7.54 Hz, 1H, H-7), 2.38 (t, J=7.25 Hz, 2H, (CH$_3$)$_2$NCH$_2$CH$_2$C$\underline{H}_2$-4'), 2.27 (s, 3H, CH$_3$-3'), 2.23 (s, 3H, CH$_3$-5'), 2.17 (t, J=7.25 Hz, 2H, (CH$_3$)$_2$NC$\underline{H}_2$CH$_2$CH$_2$-4'), 2.11 (s, 6H, (CH$_3$)$_2$NCH$_2$CH$_2$C$\underline{H}_2$-4'), 1.52 (quint., J=7.25 Hz, 2H, (CH$_3$)$_2$NCH$_2$C$\underline{H}_2$CH$_2$-4), MS m/z (relative intensity, %) 323 (M⁺, 100).

EXAMPLE 49

5-Bromo-3-[4-(3-dimethylaminopropyl)-3,5-dimethyl-1H-pyrrol-2-ylmethylene]-1,3-dihydroindol-2-one Using the procedure of Example 2, a 71% yield of the title compound was obtained as a red solid:

¹HNMR (360 MHz, DMSO-$d_6$) δ 13.42 (s, 1H, NH-1'), 10.81 (s, 1H, NH-1), 7.98 (d, J=1.89 Hz, 1H, H-4), 7.66 (s, 1H, H-vinyl), 7.17 (dd, J=1.89, 8.23 Hz, 1H, H-6), 6.79 (d, J=8.23 Hz, 1H, H-7), 2.38 (t, J=7.23 Hz, 2H, (CH$_3$)$_2$NCH$_2$CH$_2$C$\underline{H}_2$-4'), 2.27 (s, 3H, CH$_3$-3'), 2.25 (s, 3H, CH$_3$-5'), 2.16 (t, J=7.23 Hz, 2H, (CH$_3$)$_2$NC$\underline{H}_2$CH$_2$CH$_2$-4'), 2.10 (s, 6H, (C$\underline{H}_3$)$_2$NCH$_2$CH$_2$C$\underline{H}_2$-4'), 1.51 (quint., J=7.23 Hz, 2H, (CH$_3$)$_2$NCH$_2$C$\underline{H}_2$CH$_2$-4'), MS m/z (relative intensity, %) 401 ([M−1]⁺, 100) and 403 ([M+1]⁺, 100).

EXAMPLE 50

3-[4-(3-Dimethylaminopropyl)-3,5-dimethyl-1H-pyrrol-2-ylmethylene]-6-phenyl-1,3-dihydroindol-2-one Using the procedure of Example 2, an 83% yield of the title compound was obtained as an orange solid:

¹HNMR (360 MHz, DMSO-$d_6$) δ 13.38 (s, 1H, NH-1'), 10.81 (s, 1H, NH-1), 7.77 (d, J=7.82 Hz, 1H, H-4), 7.62 (d, J=7.59 Hz, 2H, H-2",6"), 7.58 (s, 1H, H-vinyl), 7.44 (t, J=7.59 Hz, 2H, H-3",5"), 7.32 (t, J=7.59 Hz, 1H, H-4"), 7.27 (dd, J=1.11, 7.82 Hz, 1H, H-5), 7.09 (d, J=1.11 Hz, 1H, H-7), 2.39 (t, J=7.18 Hz, 2H, (CH$_3$)$_2$NCH$_2$CH$_2$C$\underline{H}_2$-4'), 2.29 (s, 3H, CH$_3$-3'), 2.25 (s, 3H, CH$_3$-5'), 2.17 (t, J=7.18 Hz, 2H, (CH$_3$)$_2$NC$\underline{H}_2$CH$_2$CH$_2$-4'), 2.11 (s, 6H, (C$\underline{H}_3$)$_2$NCH$_2$CH$_2$CH$_2$-4'), 1.53 (quint., J=7.18 Hz, 2H, (CH$_3$)$_2$NCH$_2$C$\underline{H}_2$CH$_2$-4'), MS m/z (relative intensity, %) 399 (M⁺, 100).

EXAMPLE 51

3-[4-(3-Dimethylaminopropyl)-3,5-dimethyl-1H-pyrrol-2-ylmethylene]-6-(2-methoxyphenyl)-1,3-dihydroindol-2-one Using the procedure of Example 2, an 83% yield of the title compound was obtained as a yellow solid:

¹HNMR (360 MHz, DMSO-$d_6$) δ 13.38 (s, 1H, NH-1'), 10.72 (s, 1H, NH-1), 7.70 (d, J=8.06 Hz, 1H, H-4), 7.55 (s, 1H, H-vinyl), 7.28–7.36 (m, 2H, H-4",5"), 7.14 (d, J=8.32

Hz, 1H, H-6"), 7.04 (dd, J=1.21, 8.06 Hz, 1H, H-5), 6.99 (d, J=7.42 Hz, 1H, H-3"), 6.99 (d, J=1.21 Hz, 1H, H-7) 3.76 (s, 3H, OCH$_3$-2"), 2.39 (t, J=7.24 Hz, 2H, (CH$_3$)$_2$NCH$_2$CH$_2$CH$_2$-4'), 2.28 (s, 3H, CH$_3$-3'), 2.25 (s, 3H, CH$_3$-5'), 2.18 (t, J=7.24 Hz, 2H, (CH$_3$)$_2$NCH$_2$CH$_2$CH$_2$-4'), 2.11 (s, 6H, (CH$_3$)$_2$NCH$_2$CH$_2$CH$_2$-4'), 1.53 (quint., J=7.24 Hz, 2H, (CH$_3$)$_2$NCH$_2$CH$_2$CH$_2$-4'), MS m/z (relative intensity, %) 429 (M$^+$, 100).

EXAMPLE 52

3-[4-(3-Dimethylaminopropyl)-3,5-dimethyl-1H-pyrrol-2-ylmethylene]-6-(3-methoxyphenyl)-1,3-dihydroindol-2-one Using the procedure of Example 2, an 83% yield of the title compound was obtained as a red solid:

$^1$HNMR (360 MHz, DMSO-d$_6$) δ 13.38 (s, 1H, NH-1'), 10.80 (s, 1H, NH-1), 7.60 (d, J=8.06 Hz, 1H, H-4), 7.57 (s, 1H, H-vinyl), 7.35 (t, J=8.15 Hz, 1H, H-5"), 7.26 (dd, J=1.39, 8.06 Hz, 1H, H-5), 7.19 (d, br, J=8.15 Hz, H-6"), 7.13 (m, 1H, H-2"), 7.09 (d, J=1.39 Hz, 1H, H-7), 6.90 (dd, J=2.57, 8.15 Hz, 1H, H-4"), 3.81 (s, 3H, OCH$_3$-3"), 2.39 (t, J=7.17 Hz, 2H, (CH$_3$)$_2$NCH$_2$CH$_2$CH$_2$-4'), 2.29 (s, 3H, CH$_3$-3'), 2.25 (s, 3H, CH$_3$-5'), 2.17 (t, J=7.17 Hz, 2H, (CH$_3$)$_2$NCH$_2$CH$_2$CH$_2$-4'), 2.11 (s, 6H, (CH$_3$)$_2$NCH$_2$CH$_2$CH$_2$-4'), 1.53 (quint., J=7.17 Hz, 2H, (CH$_3$)$_2$NCH$_2$CH$_2$CH$_2$-4), MS m/z (relative intensity, %) 429 (M$^+$, 100).

EXAMPLE 53

3-[4-(3-Dimethylaminopropyl)-3,5-dimethyl-1H-pyrrol-2-ylmethylene]-6-(4-methoxyphenyl)-1,3-dihydroindol-2-one Using the procedure of Example 2, an 83% yield of the title compound was obtained as a brown solid:

$^1$HNMR (360 MHz, DMSO-d$_6$) δ 13.35 (s, 1H, NH-1'), 10.77 (s, 1H, NH-1), 7.73 (d, J=7.82 Hz, 1H, H-4), 7.56 (d, J=8.83 Hz, 2H, H-2",6"), 7.54 (s, 1H, H-vinyl), 7.20 (dd, J=1.64, 7.82 Hz, 1H, H-5), 7.04 (d, J=1.64 Hz, 1H, H-7), 7.00 (d, J=8.83 Hz, 2H, H-3",5), 3.78 (s, 3H, OCH$_3$-4"), 2.39 (t, J=7.24 Hz, 2H, (CH$_3$)$_2$NCH$_2$CH$_2$CH$_2$-4'), 2.28 (s, 3H, CH$_3$-3'), 2.25 (s, 3H, CH$_3$-5'), 2.17 (t, J=7.24 Hz, 2H, (CH$_3$)$_2$NCH$_2$CH$_2$CH$_2$-4'), 2.11 (s, 6H, (CH$_3$)$_2$NCH$_2$CH$_2$CH$_2$-4'), 1.52 (quint., J=7.24 Hz, 2H, (CH$_3$)$_2$NCH$_2$CH$_2$CH$_2$ -4'), MS m/z (relative intensity, %) 429 (M$^+$, 100).

EXAMPLE 54

5-Chloro-3-[4-(3-dimethylaminopropyl)-3,5-dimethyl-1H-pyrrol-2-ylmethylene]-1,3-dihydroindol-2-one Using the procedure of Example 2, a 53% yield of the title compound was obtained as a brown solid:

$^1$HNMR (360 MHz, DMSO-d$_6$) δ 13.43 (s, 1H, NH-1'), 10.84 (s, 1H, NH-1), 7.87 (d, J=1.85 Hz, 1H, H-4), 7.66 (s, 1H, H-vinyl), 7.05 (dd, J=1.85, 8.15 Hz, 1H, H-6), 6.83 (d, J=8.15 Hz, 1H, H-7), 2.36–2.45 (m, 4H, (CH$_3$)$_2$NCH$_2$CH$_2$CH$_2$-4'), 2.30 (s, 6H, (CH$_3$)$_2$NCH$_2$CH$_2$CH$_2$-4'), 2.28 (s, 3H, CH$_3$-3'), 2.26 (s, 3H, CH$_3$-5'), 1.58 (quint., J=7.52 Hz, 2H, (CH$_3$)$_2$NCH$_2$CH$_2$CH$_2$-4') MS m/z (relative intensity, %) 357 ([M−1]$^+$, 100).

EXAMPLE 55

6-Chloro-3-[4-(3-dimethylaminopropyl)-3,5-dimethyl-1H-pyrrol-2-ylmethylene]-1,3-dihydroindol-2-one Using the procedure of Example 2, a 77% yield of the title compound was obtained:
MS EI 357 [M−1]$^+$.

EXAMPLE 56

3-[4-(3-Dimethylaminopropyl)-3,5-dimethyl-1H-pyrrol-2-ylmethylene]-5-methoxy-1,3-dihydroindol-2-one Using the procedure of Example 2, a 77% yield of the title compound was obtained:
MS EI 353 [M]$^+$.

EXAMPLE 57

3-[4-(3-Dimethylaminopropyl)-3,5-dimethyl-1H-pyrrol-2-ylmethylene]-6-methoxy-1,3-dihydroindol-2-one Using the procedure of Example 2, a 74% yield of the title compound was obtained.

EXAMPLE 58

3-[4-(3-Dimethylaminopropyl)-3,5-dimethyl-1H-pyrrol-2-ylmethylene]-5-methyl-1,3-dihydroindol-2-one Using the procedure of Example 2, a 45% yield of the title compound was obtained:
MS EI 337 [M]$^+$.

EXAMPLE 59

3-[4-(3-Dimethylaminopropyl)-3,5-dimethyl-1H-pyrrol-2-ylmethylene]-4-methyl-1,3-dihydroindol-2-one Using the procedure of Example 2, a 99% yield of the title compound was obtained:

$^1$HNMR (300 MHz, DMSO-d$_6$) δ 13.45 (s, br, 1H, NH), 10.78 (s, br, 1H, NH), 7.50 (s, 1H, H-vinyl), 6.98 (t, J=8.1 Hz, 1H, H-6), 6.76 (t, J=8.1 Hz, 2H, H-5 & H-7), 2.88 (m, 2H, CH$_2$), 2.64 (s, 6H, 2×CH$_3$), 2.56 (s, 3H, CH$_3$), 2.43 (t, J=7.4 Hz, 2H, CH$_2$), 2.29 (s, 3H, CH$_3$), 2.19 (s, 3H, CH$_3$), 1.65–1.75 (m, 2H, CH$_2$),

MS EI 337 [M]$^+$.

EXAMPLE 60

3-[4-(3-Dimethylaminopropyl)-3,5-dimethyl-1H-pyrrol-2-ylmethylene]-4-(2-hydroxy-ethyl)-1,3-dihydroindol-2-one Using the method of Example 2, a 98% yield of the title compound was obtained.

EXAMPLE 61

3-[4-(3-Dimethylaminopropyl)-3,5-dimethyl-1H-pyrrol-2-ylmethylene]-2-oxo-2,3-dihydro-1H-indole-5-sulfonic acid amide Using the procedure of Example 2, a 59% yield of the title compound was obtained:

$^1$HNMR (300 MHz, DMSO-d$_6$) δ 13.41 (s, 1H, NH-1'), 11.12 (s, 1H, NH-1), 8.16 (d, J=1.78 Hz, 1H, H-4), 7.66 (s, 1H, H-vinyl), 7.55 (dd, J=1.78, 8.18 Hz, 1H, H-6), 7.11 (s, br, 2H, H$_2$NSO$_2$-5), 6.98 (d, J=8.18 Hz, 1H, H-7), 2.47–2.50 (m, 2H, (CH$_3$)$_2$NCH$_2$CH$_2$CH$_2$-4'), 2.41 (t, J=7.37 Hz, 2H, (CH$_3$)$_2$NCH$_2$CH$_2$CH$_2$-4'), 2.36 (s, 6H, (C H$_3$)$_2$NCH$_2$CH$_2$CH$_2$-4') 2.30 (s, 3H, CH$_3$-3'), 2.28 (s, 3H, CH$_3$-5'), 1.61 (quint., J=7.37 Hz, 2H, (CH$_3$)$_2$NCH$_2$CH$_2$CH$_2$-4').

EXAMPLE 62

3-[4-(3-Dimethylaminopropyl)-3,5-dimethyl-1H-pyrrol-2-ylmethylene]-2-oxo-2,3-dihydro-1H-indole-5-sulfonic acid isopropylamide Using the method of Example 2, a 64% yield of the title compound was obtained:
MS EI 444 [M]$^+$.

EXAMPLE 63

3-[4-(3-Dimethylaminopropyl)-3,5-dimethyl-1H-pyrrol-2-ylmethylene]-5-(morpholine-4-sulfonyl)-1,3-dihydroindol-2-one Using the procedure of Example 2, a 90% yield of the title compound was obtained.
MS EI 472 [M]$^+$.

EXAMPLE 64

3-[4-(3-Dimethylaminopropyl)-3,5-dimethyl-1H-pyrrol-2-ylmethylene]-2-oxo-2,3-dihydro-1H-indole-5-sulfonic acid dimethylamide Using the method of claim 2, a 92% yield of the title compound was obtained:
$^1$HNMR (300 MHz, DMSO-d$_6$) δ 13.5 (s, br, 1H, NH), 12.21 (s, br, 1H, NH), 8.18 (d, J=1.8 Hz, 1H, H-4), 7.84 (s, 1H, H-vinyl), 7.44 (dd, J=1.8, 8.4 Hz, 1H, H-6), 7.05 (d, J=8.4 Hz, 1H, H-7), 2.59 (s, 6H, 2×CH$_3$), 2.59–2.64 (m, 2H, CH$_2$), 2.44 (s, 6H, 2×CH$_3$), 2.38–2.44 (m, 2H, CH$_2$), 2.31 (s, 6H, 2×CH$_3$), 1.59–1.69 (m, 2H, CH$_2$), MS EI 430 [M]$^+$.

7. BIOLOGICAL EVALUATION

It will be appreciated that, in any given series of compounds, a spectrum of biological activity will be afforded. In its presently preferred embodiments, this invention relates to novel pyrrole substituted 2-indolinones demonstrating the ability to modulate RTK, CTK, and STK activity. The following assays are employed to select those compounds demonstrating the optimal degree of the desired activity.

A. Assay Procedures.

The following in vitro assays may be used to determine the level of activity and effect of the different compounds of the present invention on one or more of the PKs. Similar assays can be designed along the same lines for any PK using techniques Well known in the art.

The cellular/catalytic assays described herein are performed in an ELISA format. The general procedure is as follows: a compound is introduced to cells expressing the test kinase, either naturally or recombinantly, for a selected period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound. The cellular/biologic assays described herein measure the amount of DNA made in response to activation of a test kinase, which is a general measure of a proliferative response. The general procedure for this assay is as follows: a compound is introduced to cells expressing the test kinase, either naturally or recombinantly, for a selected period of time after which, if the test kinase is a receptor, a ligand known to activate the receptor is added. After incubation at least overnight, a DNA labeling reagent such as Bromodeoxyuridine (BrdU) or 3H-thymidine is added. The amount of labeled DNA is detected with either an anti-BrdU antibody or by measuring radioactivity and is compared to control cells not contacted with a test compound.

Cellular/Catalytic Assays

Enzyme linked immunosorbent assays (ELISA) may be used to detect and measure the presence of PK activity. The ELISA may be conducted according to known protocols which are described in, for example, Voller, et al., 1980, "Enzyme-Linked Immunosorbent Assay," In: Manual of Clinical Immunology, 2d ed., edited by Rose and Friedman, pp 359–371 Am. Soc. Of Microbiology, Washington, D.C.

The disclosed protocol may be adapted for determining activity with respect to a specific PK. That is, the preferred protocols for conducting the ELISA experiments for specific PKs is provided below. However, adaptation of these protocols for determining a compound's activity for other members of the RTK family, as well as for CTKs and STKs, is well within the scope of knowledge of those skilled in the art.

FLK-1 Assay

An ELISA assay is conducted to measure the kinase activity of the FLK-1 receptor and more specifically, the inhibition or activation of TK activity on the FLK-1 receptor. Specifically, the following assay can be conducted to measure kinase activity of the FLK-1 receptor in cells genetically engineered to express Flk-1.

Materials and Reagents.
- a. Corning 96-well ELISA plates (Corning Catalog No. 25805-96),
- b. Cappel goat anti-rabbit IgG (catalog no. 55641),
- c. PBS (Gibco Catalog No. 450-1300EB),
- d. TBSW Buffer (50 mM Tris (pH 7.2), 150 mM NaCl and 0.1% Tween-20),
- e. Ethanolamine stock (10% ethanolamine (pH 7.0), stored at 4° C.),
- f. HNTG buffer (20 mM HEPES buffer (pH 7.5), 150 mM NaCl, 0.2% Triton X-100, and 10% glycerol),
- g. EDTA (0.5 M (pH 7.0) as a 100× stock),
- h. Sodium orthovanadate (0.5 M as a 100× stock),
- i. Sodium pyrophosphate (0.2 M as a 100× stock),
- j. NUNC 96 well V bottom polypropylene plates (Applied Scientific Catalog No. AS-72092),
- k. NIH3T3 C7#3 Cells (FLK-1 expressing cells),
- l. DMEM with 1× high glucose L-Glutamine (catalog No. 11965-050),
- m. FBS, Gibco (catalog no. 16000-028),
- n. L-glutamine, Gibco (catalog no. 25030-016),
- o. VEGF, PeproTech, Inc. (catalog no. 100-20)(kept as 1 µg/100 µl stock in Milli-Q dH$_2$O and stored at −20° C.,
- p. Affinity purified anti-FLK-1 antiserum,
- q. UB40 monoclonal antibody specific for phosphotyrosine (see, Fendley, et al., 1990, Cancer Research 50:1550–1558),
- r. EIA grade Goat anti-mouse IgG-POD (BioRad catalog no. 172-1011),
- s. 2,2-azino-bis(3-ethylbenz-thiazoline-6-sulfonic acid (ABTS) solution (100 mM citric acid (anhydrous), 250 mM Na$_2$HPO$_4$ (pH 4.0), 0.5 mg/ml ABTS (Sigma catalog no. A-1888)), solution should be stored in dark at 4° C. until ready for use, t. H$_2$O$_2$ (30% solution) (Fisher catalog no. H325), u. ABTS/ H$_2$O$_2$ (15ml ABTS solution, 2 µl H$_2$O$_2$) prepared 5 minutes before use and left at room temperature, v. 0.2 M HCl stock in H$_2$O, w. dimethylsulfoxide (100%) (Sigma Catalog No. D-8418), and y. Trypsin-EDTA (Gibco BRL Catalog No. 25200-049).

Protocol.

1. Coat Corning 96-well ELISA plates with 1.0 µg per well Cappel Anti-rabbit IgG antibody in 0.1M Na$_2$CO$_3$ pH 9.6. Bring final volume to 150 µl per well. Coat plates overnight at 4° C. Plates can be kept up to two weeks when stored at 4° C.

2. Grow cells in Growth media (DMEM, supplemented with 2.0 mM L-Glutamine, 10% FBS) in suitable culture dishes until confluent at 37° C., 5% CO$_2$.

3. Harvest cells by trypsinization and seed in Corning 25850 polystyrene 96-well round bottom cell plates, 25,000 cells/well in 200 µl of growth media.

4. Grow cells at least one day at 37° C., 5% CO$_2$.

5. Wash cells with D-PBS 1×.

6. Add 200 µl/well of starvation media (DMEM, 2.0 mM l-Glutamine, 0.1% FBS). Incubate overnight at 37° C., 5% CO$_2$.

7. Dilute Compounds 1:20 in polypropylene 96 well plates using starvation media. Dilute dimethylsulfoxide 1:20 for use in control wells.

8. Remove starvation media from 96 well cell culture plates and add 162 µl of fresh starvation media to each well.

9. Add 18 µl of 1:20 diluted compound dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 37° C., 5% CO$_2$ for two hours.

10. Remove unbound antibody from ELISA plates by inverting plate to remove liquid. Wash 3 times with TBSW+ 0.5% ethanolamine, pH 7.0. Pat the plate on a paper towel to remove excess liquid and bubbles.

11. Block plates with TBSW+0.5% ethanolamine, pH 7.0, 150 µl per well. Incubate plate thirty minutes while shaking on a microtiter plate shaker.

12. Wash plate 3 times as described in step 10.

13. Add 0.5 µg/well affinity purified anti-FLU-1 polyclonal rabbit antiserum. Bring final volume to 150 µl/well with TBSW+0.5% ethanolamine pH 7.0. Incubate plate for thirty minutes while shaking.

14. Add 180 µl starvation medium to the cells and stimulate cells with 20 µl/well 10.0 mM sodium orthovanadate and 500 ng/ml VEGF (resulting in a final concentration of 1.0 mM sodium orthovanadate and 50 ng/ml VEGF per well) for eight minutes at 37° C., 5% CO$_2$. Negative control wells receive only starvation medium.

15. After eight minutes, media should be removed from the cells and washed one time with 200 µl/well PBS.

16. Lyse cells in 150 µl/well HNTG while shaking at room temperature for five minutes. HNTG formulation includes sodium ortho vanadate, sodium pyrophosphate and EDTA.

17. Wash ELISA plate three times as described in step 10.

18. Transfer cell lysates from the cell plate to ELISA plate and incubate while shaking for two hours. To transfer cell lysate pipette up and down while scrapping the wells.

19. Wash plate three times as described in step 10.

20. Incubate ELISA plate with 0.02 µg/well UB40 in TBSW+05% ethanolamine. Bring final volume to 150 µl/well. Incubate while shaking for 30 minutes.

21. Wash plate three times as described in step 10.

22. Incubate ELISA plate with 1:10,000 diluted EIA grade goat anti-mouse IgG conjugated horseradish peroxidase in TBSW plus 0.5% ethanolamine, pH 7.0. Bring final volume to 150 µl/well. Incubate while shaking for thirty minutes.

23. Wash plate as described in step 10.

24. Add 100 µl of ABTS/H$_2$O$_2$ solution to well. Incubate ten minutes while shaking.

25. Add 100 µl of 0.2 M HCl for 0.1 M HCl final concentration to stop the color development reaction. Shake 1 minute at room temperature. Remove bubbles with slow stream of air and read the ELISA plate in an ELISA plate reader at 410 nm.

EGF Receptor-HER2 Chimeric Receptor Assay In Whole Cells.

HER2 kinase activity in whole EGFR-NIH3T3 cells are measured as described below:

Materials and Reagents.

a. EGF: stock concentration: 16.5 ILM, EGF 201, TOYOBO, Co., Ltd. Japan.

b. 05-101 (UBI) (a monoclonal antibody recognizing an EGFR extracellular domain).

c. Anti-phosphotyrosine antibody (anti-Ptyr) (polyclonal) (see, Fendley, et al., supra).

d. Detection antibody: Goat anti-rabbit lgG horseradish peroxidase conjugate, TAGO, Inc., Burlingame, Calif.

e. TBST buffer:

| Tris-HCl, pH 7.2 | 50 mN |
|---|---|
| NaCl | 150 mN |
| Triton X-100 | 0.1 | f. HNTG 5× stock:

| HEPES | 0.1M |
|---|---|
| NaCl | 0.75M |
| Glycerol | 50% |
| Triton X-100 | 1.0% | g. ABTS stock:

| Citric Acid | 100 mM |
|---|---|
| Na$_2$HPO$_4$ | 250 mM |
| HCl, conc. | 0.5 mM |
| ABTS* | 0.5 mg/ml |

*(2,2'-azinobis(3-ethylbenzthiazolinesulfonic acid)). Keep solution in dark at 4° C. until use.

h. Stock reagents of:

EDTA 100 mM pH 7.0

Na$_3$VO$_4$ 0.5 M

Na$_4$(P$_2$O$_7$) 0.2 M

Procedure.

Pre-coat ELISA Plate

1. Coat ELISA plates (Corning, 96 well, Cat. #25805-96) with 05-101 antibody at 0.5 µg per well in PBS, 100 µl final volume/well, and store overnight at 4° C. Coated plates are good for up to 10 days when stored at 4° C.

2. On day of use, remove coating buffer and replace with 100 µl blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

Seeding Cells

1. An NIH3T3 cell line overexpressing a chimeric receptor containing the EGFR extracellular domain and intracellular HER2 kinase domain can be used for this assay.

2. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.

3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μl per well, in a 96 well microtiter plate. Incubate seeded cells in 5% $CO_2$ at 37° C. for about 40 hours.

Assay Procedures

1. Check seeded cells for contamination using an inverted microscope. Dilute drug stock (10 mg/ml in DMSO) 1:10 in DMEM medium, then transfer 5 μl to a TBST well for a final drug dilution of 1:200 and a final DMSO concentration of 1%. Control wells receive DMSO alone. Incubate in 5% $CO_2$ at 37° C. for two hours.

2. Prepare EGF ligand: dilute stock EGF in DMEM so that upon transfer of 10 μl dilute EGF (1:12 dilution), 100 nM final concentration is attained.

3. Prepare fresh HNTG* sufficient for 100 μl per well, and place on ice.

HNTG* (10 ml):

| HNTG stock | 2.0 ml |
| milli-Q $H_2O$ | 7.3 ml |
| EDTA, 100 mM, pH 7.0 | 0.5 ml |
| $Na_3VO_4$ (0.5M) | 0.1 ml |
| $Na_4(P_2O_7)$ (0.2M) | 0.1 ml |

4. After 120 minutes incubation with drug, add prepared SGF ligand to cells, 10 μl per well, to a final concentration of 100 nM. Control wells receive DMEM alone. Incubate with shaking, at room temperature, for 5 minutes.

5. Remove drug, EGF, and DMEM. Wash cells twice with PBS. Transfer HNTG* to cells, 100 μl per well. Place on ice for 5 minutes. Meanwhile, remove blocking buffer from other ELISA plate and wash with TBST as described above.

6. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.

7. Remove lysate and wash 4 times with TBST. Transfer freshly diluted anti-Ptyr antibody to ELISA plate at 100 μl per well. Incubate shaking at room temperature for 30 minutes in the presence of the anti-Ptyr antiserum (1:3000 dilution in TBST).

8. Remove the anti-Ptyr antibody and wash 4 times with TBST. Transfer the freshly diluted TAGO anti-rabbit IgG antibody to the ELISA plate at 100 μl per well. Incubate shaking at room temperature for 30 minutes (anti-rabbit IgG antibody: 1:3000 dilution in TBST).

9. Remove TAGO detection antibody and wash 4 times with TBST. Transfer freshly prepared ABTS/$H_2O_2$ solution to ELISA plate, 100 μl per well. Incubate shaking at room temperature for 20 minutes. (ABTS/$H_2O_2$ solution: 1.0 μl 30% $H_2O_2$ in 10 ml ABTS stock).

10. Stop reaction by adding 50 μl 5N $H_2SO_4$ (optional), and determine O.D. at 410 nm.

11. The maximal phosphotyrosine signal is determined by subtracting the value of the negative controls from the positive controls. The percent inhibition of phosphotyrosine content for extract-containing wells is then calculated, after subtraction of the negative controls.

PDGF-R Assay

All cell culture media, glutamine, and fetal bovine serum can be purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

For ELISA assays, cells (U1242, obtained from Joseph Schlessinger, NYU) are grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium, cells are changed to serum-free medium and treated with test compound for 2 hr in a 5% $CO_2$, 37° C. incubator. Cells are then stimulated with ligand for 5–10 minute followed by lysis with HNTG (20 mM Hepes, 150 mM NaCl, 10% glycerol, 5 mM EDTA, 5 mM $Na_3VO_4$, 0.2% Triton X-100, and 2 mM NaPyr). Cell lysates (0.5 mg/well in PBS) are transferred to ELISA plates previously coated with receptor-specific antibody and which had been blocked with 5% milk in TBST (50 mM Tris-HCl pH 7.2, 150 mM NaCl and 0.1% Triton X-100) at room temperature for 30 min. Lysates are incubated with shaking for 1 hour at room temperature. The plates are washed with TBST four times and then incubated with polyclonal anti-phosphotyrosine antibody at room temperature for 30 minutes. Excess anti-phosphotyrosine antibody is removed by rinsing the plate with TBST four times. Goat anti-rabbit IgG antibody is added to the ELISA plate for 30 min at room temperature followed by rinsing with TBST four more times. ABTS (100 mM citric acid, 250 mM $Na_2HPO_4$ and 0.5 mg/mL 2,2'-azino-bis(3-ethylbenzthiazoline-6-sulfonic acid)) plus $H_2O_2$ (1.2 mL 30% $H_2O_2$ to 10 ml ABTS) is added to the ELISA plates to start color development. Absorbance at 410 nm with a reference wavelength of 630 nm is recorded about 15 to 30 min after ABTS addition.

IGF-1 RECEPTOR Assay

The following protocol may be used to measure phosphotyrosine level on IGF-1 receptor, which indicates IGF-1 receptor tyrosine kinase activity.

Materials and Reagents.

a. The cell line used in this assay is 3T3/IGF-1R, a cell line genetically engineered to overexpresses IGF-1 receptor.

b. NIH3T3/IGF-1R is grown in an incubator with 5% $CO_2$ at 37° C. The growth media is DMEM+10% FBS (heat inactivated)+2 mM L-glutamine.

c. Affinity purified anti-IGF-1R antibody 17–69.

d. D-PBS:

| $KH_2PO_4$ | 0.20 g/l |
| $KH_2PO_4$ | 2.16 g/l |
| KCl | 0.20 g/l |
| NaCl | 8.00 g/l (pH 7.2) | e. Blocking Buffer: TBST plus 5% Milk (Carnation Instant Non-Fat Dry Milk).

f. TBST buffer:

| | | |
|---|---|---|
| Tris-HCl | 50 mM | |
| NaCl | 150 mM (pH 7.2/HCl 10N) | |
| Triton X-100 | 0.1% | |

Stock solution of TBS (10×) is prepared, and Triton X-100 is added to the buffer during dilution.

g. HNTG buffer:

| | | |
|---|---|---|
| HEPES | 20 mM | |
| NaCl | 150 mN (pH 7.2/HCl 1N) | |
| Glycerol | 10% | |
| Triton X-100 | 0.2% | |

Stock solution (5×) is prepared and kept at 4° C.

h. EDTA/HCl: 0.5 M pH 7.0 (NaOH) as 100× stock.

i. $Na_3VO_4$: 0.5 M as 100× stock and aliquots are kept at 80° C.

j. $Na_4P_2O_7$: 0.2 M as 100× stock.

k. Insulin-like growth factor-1 from Promega (Cat# G5111).

l. Rabbit polyclonal anti-phosphotyrosine antiserum.

m. Goat anti-rabbit IgG, POD conjugate (detection antibody), Tago (Cat. No. 4520, Lot No. 1802): Tago, Inc., Burlingame, Calif.

n. ABTS (2,2'-azinobis(3-ethylbenzthiazolinesulfonic acid)) solution:

| | | |
|---|---|---|
| Citric acid | 100 mM | |
| $Na_2HPO_4$ | 250 mM (pH 4.0/1N HCl) | |
| ABTS | 0.5 mg/ml | |

ABTS solution should be kept in dark and 4° C. The solution should be discarded when it turns green.

o. Hydrogen Peroxide: 30% solution is kept in the dark and at 4° C.

Procedure.

All the following steps are conducted at room temperature unless specifically indicated otherwise. All ELISA plate washings are performed by rinsing the plate with tap water three times, followed by one TBST rinse. Pat plate dry with paper towels.

Cell Seeding:

1. The cells, grown in tissue culture dish (Corning 25020-100) to 80–90% confluence, are harvested with Trypsin-EDTA (0.25%, 0.5 ml/D-100, GIBCO).

2. Resuspend the cells in fresh DMEM+10% FBS+2 mM L-Glutamine, and transfer to 96-well tissue culture plate (Corning, 25806-96) at 20,000 cells/well (100 μl/well). Incubate for 1 day then replace medium to serum-free medium (90/μl) and incubate in 5% $CO_2$ and 37° C. overnight.

ELISA Plate Coating and Blocking:

1. Coat the ELISA plate (Corning 25805-96) with Anti-IGF-1R Antibody at 0.5 μg/well in 100 μl PBS at least 2 hours.

2. Remove the coating solution, and replace with 100 μl Blocking Buffer, and shake for 30 minutes. Remove the blocking buffer and wash the plate just before adding lysate.

Assay Procedures:

1. The drugs are tested under serum-free condition.

2. Dilute drug stock (in 100% DMSO) 1:10 with DMEM in 96-well poly-propylene plate, and transfer 10 μg/well of this solution to the cells to achieve final drug dilution 1:100, and final DMSO concentration of 1.0%. Incubate the cells in 5% $CO_2$ at 37° C. for 2 hours.

3. Prepare fresh cell lysis buffer (HNTG*)

| | | |
|---|---|---|
| HNTG | 2 ml | |
| EDTA | 0.1 ml | |
| $Na_3VO_4$ | 0.1 ml | |
| $Na_4(P_2O_7)$ | 0.1 ml | |
| $H_2O$ | 7.3 ml | |

4. After drug incubation for two hours, transfer 10 μl/well of 200 nM IGF-1 Ligand in PBS to the cells (Final Conc. is 20 nM), and incubate at 5% $CO_2$ at 37° C. for 10 minutes.

5. Remove media and add 100 μl/well HNTG* and shake for 10 minutes. Look at cells under microscope to see if they are adequately lysed.

6. Use a 12-channel pipette to scrape the cells from the plate, and homogenize the lysate by repeated aspiration and dispensing. Transfer all the lysate to the antibody coated ELISA plate, and shake for 1 hour.

7. Remove the lysate, wash the plate, transfer anti-pTyr (1:3,000 with TBST) 100 μl/well, and shake for 30 minutes.

8. Remove anti-pTyr, wash the plate, transfer TAGO (1:3,000 with TBST) 100 μl/well, and shake for 30 minutes.

9. Remove detection antibody, wash the plate, and transfer fresh ABTS/$H_2O_2$ (1.2 μl $H_2O_2$ to 10 ml ABTS) 100 μl/well to the plate to start color development.

Measure OD at 410 nm with a reference wavelength of 630 nm in Dynatec MR5000.

EGFR Assay

EGF Receptor kinase activity in cells genetically engineered to express human EGF-R can be measured as described below:

Materials and Reagents.

a. EGF Ligand: stock concentration=16.5 μM, EGF 201, TOYOBO, Co., Ltd. Japan.

b. 05-101 (UBI) (a monoclonal antibody recognizing an EGFR extracellular domain).

c. Anti-phosphotyosine antibody (anti-Ptyr) (polyclonal).

d. Detection antibody: Goat anti-rabbit lgG horse radish peroxidase conjugate, TAGO, Inc., Burlingame, Calif.

e. TBST buffer:

| | | |
|---|---|---|
| Tris-HCl, pH 7 | 50 mM | |
| NaCl | 150 mM | |
| Triton X-100 | 0.1 | | f. HNTG 5× stock:

| | | |
|---|---|---|
| HEPES | 0.1M | |
| NaCl | 0.75M | |
| Glycerol | 50 | |
| Triton X-100 | 1.0% | | g. ABTS stock:

| | |
|---|---|
| Citric Acid | 100 mM |
| $Na_3VO_4$ | 250 mM |
| HCl, conc. | 4.0 pH |
| ABTS* | 0.5 mg/ml |

Keep solution in dark at 4° C. until used.
h. Stock reagents of:
EDTA 100 mM pH 7.0
$Na_3VO_4$ 0.5 M
$Na_4(P_2O_7)$ 0.2 M
Procedure.
Pre-coat ELISA Plate 1. Coat ELISA plates (Corning, 96 well, Cat. #25805-96) with 05-101 antibody at 0.5 µg per well in PBS, 150 µl final volume/well, and store overnight at 4° C. Coated plates are good for up to 10 days when stored at 4° C.
2. On day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.

Seeding Cells

1. NIH 3T3/C7 cell line (Honegger, et al., Cell 51:199–209, 1987) can be use for this assay.
2. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm at room temperature for 5 minutes.
3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 µl per well, in a 96 well microtiter plate. Incubate seeded cells in 5% $CO_2$ at 37° C. for about 40 hours.

Assay Procedures.

1. Check seeded cells for contamination using an inverted microscope. Dilute test compounds stock (10 mg/ml in DMSO) 1:10 in DMEM medium, then transfer 5 µl to a test well for a test compounds drug dilution of 1:200 and a final DMSO concentration of 1%. Control wells receive DMSO alone. Incubate in 5% $CO_2$ at 37° C. for one hour.
2. Prepare EGF ligand: dilute stock EGF in DMEM so that upon transfer of 10 µl dilute EGF (1:12 dilution), 25 nM final concentration is attained.
3. Prepare fresh 10 ml HNTG* sufficient for 100 µl per well wherein HNTG* comprises: HNTG stock (2.0 ml), milli-Q $H_2O$ (7.3 ml), EDTA, 100 mM, pH 7.0 (0.5 ml), $Na_3VO_4$ 0.5 M (0.1 ml) and $Na_4(P_2O_7)$, 0.2 M (0.1 ml).
4. Place on ice.
5. After two hours incubation with drug, add prepared EGF ligand to cells, 10 µl per well, to yield a final concentration of 25 nM. Control wells receive DMEM alone. Incubate, shaking, at room temperature, for 5 minutes.
6. Remove test compound, EGF, and DMEM. Wash cells twice with PBS. Transfer HNTG* to cells, 100 µl per well. Place on ice for 5 minutes. Meanwhile, remove blocking buffer from other ELISA plate and wash with TBST as described above.
7. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.
8. Remove lysate and wash 4 times with TBST. Transfer freshly diluted anti-Ptyr antibody to ELISA plate at 100 µl per well. Incubate shaking at room temperature for 30 minutes in the presence of the anti-Ptyr antiserum (1:3000 dilution in TBST).
9. Remove the anti-Ptyr antibody and wash 4 times with TBST. Transfer the freshly diluted TAGO 30 anti-rabbit IgG antibody to the ELISA plate at 100 µl per well. Incubate shaking at room temperature for 30 minutes (anti-rabbit IgG antibody: 1:3000 dilution in TBST).
10. Remove detection antibody and wash 4 times with TBST. Transfer freshly prepared ABTS/$H_2O_2$ solution to ELISA plate, 100 µl per well. Incubate at room temperature for 20 minutes. ABTS/$H_2O_2$ solution: 1.2 µl 30% $H_2O_2$ in 10 ml ABTS stock.
11. Stop reaction by adding 50 µl 5N $H_2SO_4$ (optional), and determine O.D. at 410 nm.
12. The maximal phosphotyrosine signal is determined by subtracting the value of the negative controls from the positive controls. The percent inhibition of phosphotyrosine content for extract-containing wells is then calculated, after subtraction of the negative controls.

Met Autophosphorylation Assay

This assay determines Met tyrosine kinase activity by analyzing Met protein tyrosine kinase levels on the Met receptor.

Reagents a. HNTG (5x stock solution): Dissolve 23.83 g HEPES and 43.83 g NaCl in about 350 ml $dH_2O$. Adjust pH to 7.2 with HCl or NaOH, add 500 ml glycerol and 10 ml Triton X-100, mix, add $dH_2O$ to 1 L total volume. To make 1 L of 1x working solution add 200 ml 5x stock solution to 800 ml $dH_2O$, check and adjust pH as necessary, store at 4° C.

b. PBS (Dulbecco's Phosphate-Buffered Saline), Gibco Cat. # 450-1300EB (1x solution).

c. Blocking Buffer: in 500 ml $dH_2O$ place 100 g BSA, 12.1 g Tris-pH7.5, 58.44 g NaCl and 10 ml Tween-20, dilute to 1 L total volume.

d. Kinase Buffer: To 500 ml $dH_2O$ add 12.1 g TRIS (pH 7.2), 58.4 g NaCl, 40.7 g $MgCl_2$ and 1.9 g EGTA, bring to 1 L total volume with $dH_2O$.

e. PMSF (Phenylmethylsulfonyl fluoride), Sigma Cat. # P-7626, to 435.5 mg, add 100% ethanol to 25 ml total volume, vortex.

f. ATP (Bacterial Source), Sigma Cat. # A-7699, store powder at −20° C., to make up solution for use, dissolve 3.31 mg in 1 ml $dH_2O$.

g. RC-20H HRPO Conjugated Anti-Phosphotyrosine, Transduction Laboratories Cat. # E120H.

h. Pierce 1-Step™ Turbo TMB-ELISA (3,3',5,5'-tetramethylbenzidine, Pierce Cat. # 34022.

i. $H_2SO_4$, add 1 ml conc.(18 N) to 35 ml $dH_2O$.

j. TRIS HCL, Fischer Cat. # BP152-5, to 121.14 g of material, add 600 ml MilliQ $H_2O$, adjust pH to 7.5 (or 7.2) with HCl, bring volume to 1 L with MilliQ $H_2O$.

k. NaCl, Fischer Cat. # S271-10, make up 5M solution.

l. Tween-20, Fischer Cat. # S337-500.

m. $Na_3VO_4$, Fischer Cat. # S454-50, to 1.8 g material add 80 ml MilliQ $H_2O$, adjust pH to 10.0 with HCl or NaOH, boil in microwave, cool, check pH, repeat procedure until pH stable at 10.0, add MilliQ $H_2O$ to 100 ml total volume, make 1 ml aliquots and store at −80° C.

n. $MgCl_2$, Fischer Cat. # M33-500, make up 1M solution.

o. HEPES, Fischer Cat. X BP310-500, to 200 ml MilliQ $H_2O$, add 59.6 g material, adjust pH to 7.5, bring volume to 250 ml total, sterile filter.

p. Albumin, Bovine (BSA), Sigma Cat. # A-4503, to 30 grams material add sterile distilled water to make total volume of 300 ml, store at 4° C.

q. TBST Buffer: to approx. 900 ml $dH_2O$ in a 1 L graduated cylinder add 6.057 g TRIS and 8.766 g NaCl, when dissolved, adjust pH to 7.2 with HCl, add 1.0 ml Triton X-100 and bring to 1 L total volume with $dH_2O$.

r. Goat Affinity purified antibody Rabbit IgG (whole molecule), Cappel Cat. # 55641.

s. Anti h-Met (C-28) rabbit polyclonal IgG antibody, Santa Cruz Chemical Cat. # SC-161.

t. Transiently Transfected EGFR/Met chimeric cells (EMR) (Komada, et al., Oncogene, 8:2381–2390 (1993).

u. Sodium Carbonate Buffer, ($Na_2CO_4$, Fischer Cat. # S495): to 10.6 g material add 800 ml MilliQ $H_2O$, when dissolved adjust pH to 9.6 with NaOH, bring up to 1 L total volume with MilliQ $H_2O$, filter, store at 4° C.

Procedure

All of the following steps are conducted at room temperature unless it is specifically indicated otherwise. All ELISA plate washing is by rinsing 4× with TBST.

EMR Lysis

This procedure can be performed the night before or immediately prior to the start of receptor capture.

1. Quick thaw lysates in a 37° C. waterbath with a swirling motion until the last crystals disappear.
2. Lyse cell pellet with 1× HNTG containing 1 mM PMSF. Use 3 ml of HNTG per 15 cm dish of cells. Add ½ the calculated HNTG volume, vortex the tube for 1 min., add the remaining amount of HNTG, vortex for another min.
3. Balance tubes, centrifuge at 10,000×g for 10 min at 4° C.
4. Pool supernatants, remove an aliquot for protein determination.
5. Quick freeze pooled sample in dry ice/ethanol bath. This step is performed regardless of whether lysate will be stored overnight or used immediately following protein determination.
6. Perform protein determination using standard bicinchoninic acid (BCA) method (BCA Assay Reagent Kit from Pierce Chemical Cat. # 23225).

ELISA Procedure

1. Coat Corning 96 well ELISA plates with 5 μg per well Goat anti-Rabbit antibody in Carbonate Buffer for a total well volume of 50 μl. Store overnight at 4° C.
2. Remove unbound Goat anti-rabbit antibody by inverting plate to remove liquid.
3. Add 150 μl of Blocking Buffer to each well. Incubate for 30 min. with shaking.
4. Wash 4× with TBST. Pat plate on a paper towel to remove excess liquid and bubbles.
5. Add 1 μg per well of Rabbit anti-Met antibody diluted in TBST for a total well volume of 100 μl.
6. Dilute lysate in HNTG (90 μg lysate/100μl)
7. Add 100 μl of diluted lysate to each well. Shake for 60 min.
8. Wash 4× with TBST. Pat on paper towel to remove excess liquid and bubbles.
9. Add 50 μl of 1× lysate buffer per well.
0 10. Dilute compounds/extracts 1:10 in 1× Kinase Buffer in a polypropylene 96 well plate.
11. Transfer 5.5 μl of diluted compound to ELISA plate wells. Incubate at room temperature with shaking for 20 min.
12. Add 5.5 μl of 60 μM ATP solution per well. Negative controls do not receive any ATP. Incubate for 90 min., with shaking.
13. Wash 4× with TBST. Pat plate on paper towel to remove excess liquid and bubbles.
14. Add 100 μl per well of RC20 (1:3000 dilution in Blocking Buffer). Incubate 30 min. with shaking.
15. Wash 4× with TBST. Pat plate on paper towel to remove excess liquid and bubbles.
16. Add 100 μl per well of Turbo-TMB. Incubate with shaking for 30–60 min.
17. Add 100 μl per well of 1M $H_2SO_4$ to stop reaction.
18. Read assay on Dynatech MR7000 ELISA reader. Test Filter=450 nm, reference filter=410 nm.

Biochemical src assay

This assay is used to determine src protein kinase activity measuring phosphorylation of a biotinylated peptide as the readout.

Materials and Reagents:

a. Yeast transformed with src (Sugen, Inc., Redwood City, Calif.).

b. Cell lysates: Yeast cells expressing src are pelleted, washed once with water, re-pelleted and stored at −80° C. until use.

c. N-terminus biotinylated EEEYEEYEEEYEEEYEEEY is prepared by standard procedures well known to those skilled in the art.

d. DMSO: Sigma, St. Louis, Mo.

e. 96 Well ELISA Plate: Corning 96 Well Easy Wash, Modified flat Bottom Plate, Corning Cat. #25805-96.

f. NUNC 96-well V-bottom polypropylene plates for dilution of compounds: Applied Scientific Cat. # A-72092.

g. Vecastain ELITE ABC reagent: Vector, Burlingame, Calif.

h. Anti-src (327) mab: *Schizosaccharomyces Pombe* is used to express recombinant Src (Superti-Furga, et al., *EMBO J.*, 12:2625–2634, Superti-Furga, et al., *Nature Biochem.*, 14:600–605). *S. Pombe* strain SP200 (h-s leul.32 ura4 ade210) is grown as described and transformations are PRSP expression plasmids are done by the lithium acetate method (Superti-Furga, supra). Cells are grown in the presence of 1 μM thiamine to repress expression from the nmt1 promoter or in the absence of thiamine to induce expression.

i. Monoclonal anti-phosphotyrosine, UBI 05-321 (UB40 may be used instead).

j. Turbo TMB-ELISA peroxidase substrate: Pierce Chemical.

Buffer Solutions a. PBS (Dulbecco's Phosphate-Buffered Saline): GIBCO PBS, GIBCO Cat. # 450-1300EB.

b. Blocking Buffer: 5% Non-fat milk (Carnation) in PBS.

c. Carbonate Buffer: $Na_2CO_4$ from Fischer, Cat. # S495, make up 100 mM stock solution.

d. Kinase Buffer: 1.0 ml (from 1M stock solution) $MgCl_2$, 0.2 ml (from a 1M stock solution) $MnCl_2$, 0.2 ml (from a 1M stock solution) DTT, 5.0 ml (from a 1M stock solution) HEPES, 0.1 ml TX-100, bring to 10 ml total volume with MilliQ $H_2O$.

e. Lysis Buffer: 5.0 HEPES (from 1M stock solution.), 2.74 ml NaCl (from 5M stock solution), 10 ml glycerol, 1.0 ml TX-100, 0.4 ml EDTA (from a 100 mM stock solution), 1.0 ml PMSF (from a 100 mM stock solution), 0.1 ml $Na_3VO_4$ (from a 0.1 M stock solution), bring to 100 ml total volume with MilliQ $H_2O$.

f. ATP: Sigma Cat. # A-7699, make up 10 mM stock solution (5.51 mg/ml).

g. TRIS-HCl: Fischer Cat. # BP 152-5, to 600 ml MilliQ H2O add 121.14 g material, adjust pH to 7.5 with HCl, bring to 1 L total volume with MilliQ $H_2O$.

h. NaCl: Fischer Cat. # S271-10, Make up 5M stock solution with MilliQ $H_2O$.

i. Na$_3$VO$_4$: Fischer Cat. # S454-50, to 80 ml MilliQ H$_2$O, add 1.8 g material, adjust pH to 10.0 with HCl or NaOH, boil in a microwave, cool, check pH, repeat pH adjustment until pH remains stable after heating/cooling cycle, bring to 100 ml total volume with MilliQ H$_2$O, make 1 ml aliquots and store at −80° C.

j. MgCl$_2$: Fischer Cat. X M33-500, make up 1M stock solution with MilliQ H$_2$O.

k. HEPES: Fischer Cat. # BP 310-500, to 200 ml MilliQ H2O, add 59.6 g material, adjust pH to 7.5, bring to 250 ml total volume with MilliQ H$_2$O, sterile filter (1M stock solution).

l. TBST Buffer: TBST Buffer: To 900 ml dH$_2$O add 6.057 g TRIS and 8.766 g NaCl, adjust pH to 7.2 with HCl, add 1.0 ml Triton-X100, bring to 1 L total volume with dH$_2$O.

m. MnCl$_2$: Fischer Cat. # M87-100, make up 1M stock solution with MilliQ H$_2$O.

n. DTT: Fischer Cat. # BP172-5.

o. TBS (TRIS Buffered Saline): to 900 ml MilliQ H$_2$O add 6.057 g TRIS and 8.777 g NaCl, bring to 1 L total volume with MilliQ H$_2$O.

p. Kinase Reaction Mixture: Amount per assay plate (100 wells): 1.0 ml Kinase Buffer, 200 μg GST-ζ, bring to final volume of 8.0 ml with MilliQ H$_2$O.

q. Biotin labeled EEEYEEYEEEYEEEYEEEY: Make peptide stock solution (1 mM, 2.98 mg/ml) in water fresh just before use.

r. Vectastain ELITE ABC reagent: To prepare 14 ml of working reagent, add 1 drop of reagent A to 15 ml TBST and invert tube several times to mix. Then add 1 drop of reagent B. Put tube on orbital shaker at room temperature and mix for 30 minutes.

Procedures:

Preparation of src coated ELISA plate.

1. Coat ELISA plate with 0.5 μg/well anti-src mab in 100 μl of pH 9.6 sodium carbonate buffer, hold at 4° C. overnight.

2. Wash wells once with PBS.

3. Block plate with 0.15 ml 5% milk in PBS for 30 min. at room temperature.

4. Wash plate 5× with PBS.

5. Add 10 μg/well of src transformed yeast lysates diluted in Lysis Buffer (0.1 ml total volume per well). (Amount of lysate may vary between batches.) Shake plate for 20 minutes at room temperature.

Preparation of phosphotyrosine antibody-coated ELISA plate.

1. 4G10 plate: coat 0.5 μg/well 4G10 in 100 μl PBS overnight at 4° C. and block with 150 μl of 5% milk in PBS for 30 minutes at room temperature.

Kinase assay procedure.

1. Remove unbound proteins from plates and wash plates 5× with PBS.

2. Add 0.08 ml Kinase Reaction Mixture per well (containing 10 μl of 10× Kinase Buffer and 10 μM (final concentration) biotin-EEEYEEYEEEYEEEYEEEY per well diluted in water.

3. Add 10 μl of compound diluted in water containing 10% DMSO and pre-incubate for 15 minutes at room temperature.

4. Start kinase reaction by adding 10 μg/well of 0.05 mM ATP in water (5 μM ATP final).

5. Shake ELISA plate for 15 min. at room temperature.

6. Stop kinase reaction by adding 10 μl of 0.5 M EDTA per well.

7. Transfer 90 μl supernatant to a blocked 4G10 coated ELISA plate.

8. Incubate for 30 min. while shaking at room temperature.

9. Wash plate 5× with TBST.

10. Incubate with Vectastain ELITE ABC reagent (100 μl/well) for 30 min. at room temperature.

11. Wash the wells 5× with TBST.

12. Develop with Turbo TMB.

Biochemical lck Assay

This assay is used to determine lck protein kinase activities measuring phosphorylation of GST-ζ as the readout.

Materials and Reagents:

a. Yeast transformed with lck. *Schizosaccharomyces Pombe* is used to express recombinant Lck (Superti-Furga, et al., *EMBO J*, 12:2625–2634, Superti-Furga, et al., *Nature Biotech.*, 14:600–605). *S. Pombe* strain SP200 (h-s leu1.32 ura4 ade210) is grown as described and transformations with pRSP expression plasmids are done by the lithium acetate method (Superti-Furga, supra). Cells are grown in the presence of 1 μM thiamine to induce expression.

b. Cell lysates: Yeast cells expressing lck are pelleted, washed once in water, re-pelleted and stored frozen at −80° C. until use.

c. GST-ζ: DNA encoding for GST-ζ fusion protein for expression in bacteria obtained from Arthur Weiss of the Howard Hughes Medical Institute at the University of California, San Francisco. Transformed bacteria are grown overnight while shaking at 25° C. GST-ζ is purified by glutathione affinity chromatography, Pharmacia, Alameda, Calif.

d. DMSO: Sigma, St. Louis, Mo.

e. 96-Well ELISA plate: Corning 96 Well Easy Wash, Modified Flat Bottom Plate, Corning Cat. #25805-96.

f. NUNC 96-well V-bottom polypropylene plates for dilution of compounds: Applied Scientific Cat. # AS-72092.

g. Purified Rabbit anti-GST antiserum: Amrad Corporation (Australia) Cat. #90001605.

h. Goat anti-Rabbit-IgG-HRP: Amersham Cat. # V010301.

i. Sheep ant-mouse IgG (H+L): Jackson Labs Cat. # 5215-005-003.

j. Anti-Lck (3A5) mab: Santa Cruz Biotechnology Cat # sc-433.

k. Monoclonal anti-phosphotyrosine UBI 05-321 (UB40 may be used instead).

Buffer solutions:

a. PBS (Dulbeccols Phosphate-Buffered Saline) 1× solution: GIBCO PBS, GIBCO Cat. # 450-1300EB.

b. Blocking Buffer: 100 g. BSA, 12.1 g. TRIS (pH7.5), 58.44 g NaCl, 10 ml Tween-20, bring up to 1 L total volume with MilliQ H$_2$O.

c. Carbonate Buffer: Na$_2$CO$_4$ from Fischer, Cat. # S495, make up 100 mM solution with MilliQ H$_2$O.

d. Kinase Buffer: 1.0 ml (from 1M stock solution) MgCl$_2$, 0.2 ml (from a 1M stock solution) MnCl$_2$, 0.2 ml (from a 1M stock solution) DTT, 5.0 ml (from a 1M stock solution) HEPES, 0.1 ml TX-100, bring to 10 ml total volume with MilliQ H$_2$O.

e. Lysis Buffer: 5.0 HEPES (from 1M stock solution.), 2.74 ml NaCl (from 5M stock solution), 10 ml glycerol, 1.0 ml TX-100, 0.4 ml EDTA (from a 100 mM stock solution), 1.0 ml PMSF (from a 100 mM stock solution), 0.1 ml Na$_3$VO$_4$ (from a 0.1 M stock solution), bring to 100 ml total volume with MilliQ H$_2$O.

f. ATP: Sigma Cat. # A-7699, make up 10 mM stock solution (5.51 mg/ml).

g. TRIS-HCl: Fischer Cat. # BP 152-5, to 600 ml MilliQ H$_2$O add 121.14 g material, adjust pH to 7.5 with HCl, bring to 1 L total volume with MilliQ H$_2$O.

h. NaCl: Fischer Cat. # S271-10, Make up 5M stock solution with MilliQ $H_2O$.

i. $Na_3VO_4$: Fischer Cat. # S454-50, to 80 ml MilliQ $H_2O$, add 1.8 g material, adjust pH to 10.0 with HCl or NaOH, boil in a microwave, cool, check pH, repeat pH adjustment until pH remains stable after heating/cooling cycle, bring to 100 ml total volume with MilliQ $H_2O$, make 1 ml aliquots and store at −80° C.

j. $MgCl_2$: Fischer Cat. # M33-500, make up 1M stock solution with MilliQ $H_2O$.

k. HEPES: Fischer Cat. # BP 310-500, to 200 ml MilliQ $H_2O$, add 59.6 g material, adjust pH to 7.5, bring to 250 ml total volume with MilliQ $H_2O$, sterile filter (1M stock solution).

l. Albumin, Bovine (BSA), Sigma Cat. # A4503, to 150 ml MilliQ $H_2O$ add 30 g material, bring 300 ml total volume with MilliQ $H_2O$, filter through 0.22 μm filter, store at 4° C.

m. TBST Buffer: To 900 ml $dH_2O$ add 6.057 g TRIS and 8.766 g NaCl, adjust pH to 7.2 with HCl, add 1.0 ml Triton-X100, bring to 1 L total volume with $dH_2O$.

n. MnCl2: Fischer Cat. # M87-100, make up 1M stock solution with MilliQ $H_2O$.

o. DTT: Fischer Cat. # BP172-5.

p. TBS (TRIS Buffered Saline): to 900 ml MilliQ $H_2O$ add 6.057 g TRIS and 8.777 g NaCl, bring to 1 L total volume with MilliQ $H_2O$.

q. Kinase Reaction Mixture: Amount per assay plate (100 wells): 1.0 ml Kinase Buffer, 200 μg GST-ζ, bring to final volume of 8.0 ml with MilliQ $H_2O$.

Procedures:

Preparation of Lck coated ELISA plate.

1. Coat 2.0 μg/well Sheep anti-mouse IgG in 100 μl of pH 9.6 sodium carbonate buffer at 4° C. overnight.
2. Wash well once with PBS.
3. Block plate with 0.15 ml of blocking Buffer for 30 min. at room temp.
4. Wash plate 5× with PBS.
5. Add 0.5 μg/well of anti-lck (mab 3A5) in 0.1 ml PBS at room temperature for 1–2 hours.
6. Wash plate 5× with PBS.
7. Add 20 μg/well of lck transformed yeast lysates diluted in Lysis Buffer (0.1 ml total volume per well). Shake plate at 4° C. overnight to prevent loss of activity.

Preparation of phosphotyrosine antibody-coated ELISA plate.

1. UB40 plate: 1.0 μg/well UB40 in 100 μl of PBS overnight at 4° C. and block with 150 μl of Blocking Buffer for at least 1 hour.

Kinase assay procedure.

1. Remove unbound proteins from plates and wash plates 5× with PBS.
2. Add 0.08 ml Kinase Reaction Mixture per well (containing 10 μl of 10× Kinase Buffer and 2 μg GST-ζ per well diluted with water).
3. Add 10 μl of compound diluted in water containing 10% DMSO and pre-incubate for 15 minutes at room temperature.
4. Start kinase reaction by adding 10μg/well of 0.1 mM ATP in water (10 μM ATP final).
5. Shake ELISA plate for 60 min. at room temperature.
6. Stop kinase reaction by adding 10 μl of 0.5 M EDTA per well.
7. Transfer 90 μl supernatant to a blocked 4G10 coated ELISA plate from section B, above.
8. Incubate while shaking for 30 min. at room temperature.
9. Wash plate 5× with TBST.
10. Incubate with Rabbit anti-GST antibody at 1:5000 dilution in 100 μl TBST for 30 min. at room temperature.
11. Wash the wells 5× with TBST.
12. Incubate with Goat anti-Rabbit-IgG-HRP at 1:20,000 dilution in 100 μl of TBST for 30 min. at room temperature.
13. Wash the wells 5× with TBST.
14. Develop with Turbo TMB.

Assay measuring phosphorylating function of RAF.

The following assay reports the amount of RAF-catalyzed phosphorylation of its target protein MEK as well as MEK's target MAPK. The RAF gene sequence is described in Bonner et al., 1985, *Molec. Cell. Biol.*, 5:1400–1407, and is readily accessible in multiple gene sequence data banks. Construction of the nucleic acid vector and cell lines utilized for this portion of the invention are fully described in Morrison et al., 1988, *Proc. Natl. Acad. Sci. USA*, 85:8855–8859.

Materials and Reagents

1. Sf9 (*Spodoptera frugiperda*) cells, GIBCO-BRL, Gaithersburg, Md.
2. RIPA buffer: 20 mM Tris/HCl pH 7.4, 137 mM NaCl, 10% glycerol, 1 mM PMSF, 5 mg/L Aprotenin, 0.5% Triton X-100,
3. Thioredoxin-MEK fusion protein (T-MEK): T-MEK expression and purification by affinity chromatography are performed according to the manufacturer's procedures. Catalog# K 350-01 and R 350-40, Invitrogen Corp., San Diego, Calif.
4. His-MAPK (ERK 2), His-tagged MAPK is expressed in XL1 Blue cells transformed with pUC18 vector encoding His-MAPK. His-MAPK is purified by Ni-affinity chromatography. Cat# 27-4949-01, Pharmacia, Alameda, Calif., as described herein.
5. Sheep anti mouse IgG: Jackson laboratories, West Grove, Pa. Catalog, # 515-006-008, Lot# 28563
6. RAF-1 protein kinase specific antibody: URP2653 from UBI.
7. Coating buffer: PBS, phosphate buffered saline, GIBCO-BRL, Gaithersburg, Md.
8. Wash buffer: TBST (50 mM Tris/HCL pH 7.2, 150 mM NaCl, 0.1% Triton X-100).
9. Block buffer: TBST, 0.1% ethanolamine pH 7.4
10. DMSO, Sigma, St. Louis, Mo.
11. Kinase buffer (KB): 20 mM HEPES/HCl pH 7.2, 150 mM NaCl, 0.1% Triton X-100, 1 mM PMSF, 5 mg/L Aprotenin, 75 mM sodium orthovanadate, 0.5 MM DTT and 10 mM $MgCl_2$.
12. ATP mix: 100 mM $MgCl_2$, 300 mM ATP, 10 $\gamma^{33}P$ ATP (Dupont-NEN)/mL.
13. Stop solution: 1% phosphoric acid, Fisher, Pittsburgh, Pa.
14. Wallac Cellulose Phosphate Filter mats, Wallac, Turku, Finnland.
15. Filter wash solution: 1% phosphoric acid, Fisher, Pittsburgh, Pa.
16. Tomtec plate harvester, Wallac, Turku, Finnland.
17. Wallac beta plate reader # 1205, Wallac, Turku, Finnland.
18. NUNC 96-well V bottom polypropylene plates for compounds Applied Scientific Catalog # AS-72092.

Procedure

All of the following steps are conducted at room temperature unless specifically indicated otherwise.

1. ELISA plate coating: ELISA wells are coated with 100 ml of Sheep anti mouse affinity purified antiserum (1 mg/100 mL coating buffer) over night at 40° C. ELISA plates can be used for two weeks when stored at 40° C.

2. Invert the plate and remove liquid. Add 100 mL of blocking solution and incubate for 30 min.

3. Remove blocking solution and wash four times with wash buffer. Pat the plate on a paper towel to remove excess liquid.

4. Add 1 mg of antibody specific for RAF-1 to each well and incubate for 1 hour. Wash as described in step 3.

5. Thaw lysates from RAS/RAF infected Sf9 cells and dilute with TBST to 10 mg/100 mL. Add 10 mg of diluted lysate to the wells and incubate for 1 hour. Shake the plate during incubation. Negative controls receive no lysate. Lysates from RAS/RAF infected Sf9 insect cells are prepared after cells are infected with recombinant baculoviruses at a MOI of 5 for each virus, and harvested 48 hours later. The cells are washed once with PBS and lysed in RIPA buffer. Insoluble material is removed by centrifugation (5 min at 10,000×g). Aliquots of lysates are frozen in dry ice/ethanol and stored at −80° C. until use.

6. Remove non-bound material and wash as outlined above (step 3).

7. Add 2 mg of T-MEK and 2 mg of His-MAEPK per well and adjust the volume to 40 ml with kinase buffer. Methods for purifying T-MEK and MAPK from cell extracts are provided herein by example.

8. Pre-dilute compounds (stock solution 10 mg/ml DMSO) or extracts 20 fold in TBST plus 1% DMSO. Add 5 ml of the pre-diluted compounds/extracts to the wells described in step 6. Incubate for 20 min. Controls receive no drug.

9. Start the kinase reaction by addition of 5 ml ATP mix, Shake the plates on an ELISA plate shaker during incubation.

10. Stop the kinase reaction after 60 min by addition of 30 mL stop solution to each well.

11. Place the phosphocellulose mat and the ELISA plate in the Tomtec plate harvester. Harvest and wash the filter with the filter wash solution according to the manufacturer's recommendation. Dry the filter mats. Seal the filter mats and place them in the holder. Insert the holder into radioactive detection apparatus and quantify the radioactive phosphorous on the filter mats.

Alternatively, 40 mL aliquots from individual wells of the assay plate can be transferred to the corresponding positions on the phosphocellulose filter mat. After air drying the filters, put the filters in a tray. Gently rock the tray, changing the wash solution at 15 min intervals for 1 hour. Air-dry the filter mats. Seal the filter mats and place them in a holder suitable for measuring the radioactive phosphorous in the samples. Insert the holder into a detection device and quantify the radioactive phosphorous on the filter mats.

CDK2/Cyclin A—Inhibition Assay

This assay analyzes the protein kinase activity of CDK2 in exogenous substrate.

Reagents:

A. Buffer A: (80 mM Tris (pH 7.2), 40 mM $MgCl_2$), 4.84 g. Tris (F.W.=121.1 g/mol), 4.07 g. $MgCl_2$ (F.W.=203.31 g/mol) dissolved in 500 ml $H_2O$. Adjust pH to 7.2 with HCl.

B. Histone H1 solution (0.45 mg/ml Histone H1 and 20 mM HEPES pH 7.2: 5 mg Histone H1 (Boehinger Mannheim) in 11.111 ml 20 mM HEPES pH 7.2 (477 mg HEPES (F.W.=238.3 g/mol) dissolved in 100 ml $ddH_2O$, stored in 1 ml aliquots at −80° C.

C. ATP solution (60 $\mu$M ATP, 300 $\mu$g/ml BSA, 3 mM DTT): 120 $\mu$l 10 mM ATP, 600 $\mu$l 10 mg/ml BSA to 20 ml, stored in 1 ml aliquots at −80° C.

D. CDK2 solution: cdk2/cyclin A in 10 mM HEPES pH 7.2, 25 mM NaCl, o.5 mM DTT, 10% glycerol, stored in 9 $\mu$l aliquots at −80° C.

Protocol

1. Prepare solutions of inhibitors at three times the desired final assay concentration in $ddH_2O$/15% DMSO by volume.

2. Dispense 20 $\mu$l of inhibitors to wells of polypropylene 96-well plates (or 20 $\mu$l 15% DMSO for positive and negative controls).

3. Thaw Histone H1 solution (1 ml/plate), ATP solution (1 ml/plate plus 1 aliquot for negative control), and CDK2 solution (9 $\mu$l/plate). Keep CDK2 on ice until use. Aliquot CDK2 solution appropriately to avoid repeated freeze-thaw cycles.

4. Dilute 9 $\mu$l CDK2 solution into 2.1 ml Buffer A (per plate). Mix. Dispense 20 $\mu$l into each well.

5. Mix 1 ml Histone H1 solution with 1 ml ATP solution (per plate) into a 10 ml screw cap tube. Add $\gamma^{33}$P ATP to a concentration of 0.15 $\mu$Ci/20 $\mu$l (0.15 $\mu$Ci/well in assay). Mix carefully to avoid BSA frothing. Add 20 $\mu$l to appropriate wells. Mix plates on plate shaker. For negative control, mix ATP solution with an equal amount of 20 mM HEPES pH 7.2 and add $\gamma^{33}$P ATP to a concentration of 0.15 $\mu$Ci/20 $\mu$l solution. Add 20 $\mu$l to appropriate wells.

6. Let reactions proceed for 60 minutes.

7. Add 35 $\mu$l 10% TCA to each well. Mix plates on plate shaker.

8. Spot 40 $\mu$l of each sample onto P30 filter mat squares. Allow mats to dry (approx. 10–20 minutes).

9. Wash filter mats 4×10 minutes with 250 ml 1% phosphoric acid (10 ml phosphoric acid per liter $ddH_2O$).

10. Count filter mats with beta plate reader.

Cellular/Biologic Assays

PDGF-Induced BrdU Incorporation Assay

Materials and Reagents:

(1) PDGF: human PDGF B/B, 1276-956, Boehringer Mannheim, Germany.

(2) BrdU Labeling Reagent: 10 mM, in PBS (pH7.4), Cat. No. 1 647 229, Boehringer Mannheim, Germany.

(3) FixDenat: fixation solution (ready to use), Cat. No. 1 647 229, Boehringer Mannheim, Germany.

(4) Anti-BrdU-POD: mouse monoclonal antibody conjugated with peroxidase, Cat. No. 1 647 229, Boehringer Mannheim, Germany.

(5) TMB Substrate Solution: tetramethylbenzidine (TMB), ready to use, Cat. No. 1 647 229, Boehringer Mannheim, Germany.

(6) PBS Washing Solution : 1× PBS, pH 7.4 (Sugen, Inc., Redwood City, Calif.).

(7) Albumin, Bovine (BSA): fraction V powder, A-8551, Sigma Chemical Co., USA.

(8) 3T3 cell line genetically engineered to express human PDGF-R.

Protocol (1) Cells are seeded at 8000 cells/well in DMEM, 10% CS, 2 mM Gln in a 96 well plate. Cells are incubated overnight at 37° C. in 5% $CO_2$.

(2) After 24 hours, the cells are washed with PBS, and then are serum starved in serum free medium (0% CS DMEM with 0.1% BSA) for 24 hours.

(3) On day 3, ligand (PDGF, 3.8 nM, prepared in DMEM with 0.1% BSA) and test compounds are added to the cells simultaneously. The negative control wells receive serum free DMEM with 0.1% BSA only, the positive control cells receive the ligand (PDGF) but no test compound. Test compounds are prepared in serum free DMEM with ligand in a 96 well plate, and serially diluted for 7 test concentrations.

(4) After 20 hours of ligand activation, diluted BrdU labeling reagent (1:100 in DMEM, 0.1% BSA) is added and the cells are incubated with BrdU (final concentration=10 $\mu$M) for 1.5 hours.

(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.

(8) The antibody conjugate is thoroughly removed by decanting and rinsing the wells 5 times with PBS, and the plate is dried by inverting and tapping on a paper towel.

(9) TMB substrate solution is added (100 $\mu$g/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

EGF-Induced BrdU Incorporation Assay
Materials and Reagents
(1) EGF: mouse EGF, 201, Toyobo, Co., Ltd. Japan.
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1× PBS, pH 7.4 (Sugen, Inc., Redwood City, Calif.).
(7) Albumin, Bovine (BSA): fraction V powder, A-8551, Sigma Chemical Co., USA.
(8) 3T3 cell line genetically engineered to express human EGF-R.

Protocol
(1) Cells are seeded at 8000 cells/well in 10% CS, 2 mM Gln in DMEM, in a 96 well plate. Cells are incubated overnight at 37° C. in 5% $CO_2$.
(2) After 24 hours, the cells are washed with PBS, and then are serum starved in serum free medium (0% CS DMEM with 0.1% BSA) for 24 hours.
(3) On day 3, ligand (EGF, 2 nM, prepared in DMEM with 0.1% BSA) and test compounds are added to the cells simultaneously. The negative control wells receive serum free DMEM with 0.1% BSA only, the positive control cells receive the ligand (EGF) but no test compound. Test compounds are prepared in serum free DMEM with ligand in a 96 well plate, and serially diluted for 7 test concentrations.
(4) After 20 hours of ligand activation, diluted BrdU labeling reagent (1:100 in DMEM, 0.1% BSA) is added and the cells are incubated with BrdU (final concentration=10 $\mu$M) for 1.5 hours.
(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.

(8) The antibody conjugate is thoroughly removed by decanting and rinsing the wells 5 times with PBS, and the plate is dried by inverting and tapping on a paper towel.

(9) TMB substrate solution is added (100 $\mu$g/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

EGF-Induced Her2-Driven BrdU Incorporation
Materials and Reagents
(1) EGF: mouse EGF, 201, Toyobo, Co., Ltd. Japan
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution: 1× PBS, pH 7.4, made in house.
(7) Albumin, Bovine (BSA): fraction V powder, A-8551, Sigma Chemical Co., USA.
(8) 3T3 cell line engineered to express a chimeric receptor having the extra-cellular domain of EGF-R and the intra-cellular domain of Her2.

Protocol
(1) Cells are seeded at 8000 cells/well in DMEM, 10% CS, 2 mM Gln in a 96-well plate. Cells are incubated overnight at 37° C in 5% $CO_2$.
(2) After 24 hours, the cells are washed with PBS, and then are serum starved in serum free medium (0% CS DMEM with 0.1% BSA) for 24 hours.
(3) On day 3, ligand (EGF=2 nM, prepared in DMEM with 0.1% BSA) and test compounds are added to the cells simultaneously. The negative control wells receive serum free DMEM with 0.1% BSA only, the positive control cells receive the ligand (EGF) but no test compound. Test compounds are prepared in serum free DMEM with ligand in a 96 well plate, and serially diluted for 7 test concentrations.
(4) After 20 hours of ligand activation, diluted BrdU labeling reagent (1:100 in DMEM, 0.1% BSA) is added and the cells are incubated with BrdU (final concentration=10 $\mu$M) for 1.5 hours.
(5) After incubation with labeling reagent, the medium is removed by decanting and tapping the inverted plate on a paper towel. FixDenat solution is added (50 $\mu$l/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 μl/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 μl/well) and the plate is incubated for 90 minutes at room temperature on a plate shaker.

(8) The antibody conjugate is thoroughly removed by decanting and rinsing the wells 5 times with PBS, and the plate is dried by inverting and tapping on a paper towel.

(9) TMB substrate solution is added (100 μl/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

IGF1-Induced BrdU Incorporation Assay
Materials and Reagents (1) IGF1 Ligand: human, recombinant, G511, Promega Corp, USA.

(2) BrdU Labeling Reagent: 10 mM, in PBS (pH7.4), Cat. No. 1 647 229, Boehringer Mannheim, Germany.

(3) FixDenat: fixation solution (ready to use), Cat. No. 1 647 229, Boehringer Mannheim, Germany.

(4) Anti-BrdU-POD: mouse monoclonal antibody conjugated with peroxidase, Cat. No. 1 647 229, Boehringer Mannheim, Germany.

(5) TMB Substrate Solution: tetramethylbenzidine (TMB), ready to use, Cat. No. 1 647 229, Boehringer Mannheim, Germany.

(6) PBS Washing Solution: 1× PBS, pH 7.4 (Sugen, Inc., Redwood City, Calif.).

(7) Albumin, Bovine (BSA): fraction V powder, A-8551, Sigma Chemical Co., USA.

(8) 3T3 cell line genetically engineered to express human IGF-1 receptor.

Protocol (1) Cells are seeded at 8000 cells/well in DMEM, 10% CS, 2 mM Gln in a 96-well plate. Cells are incubated overnight at 37° C. in 5% $CO_2$.

(2) After 24 hours, the cells are washed with PBS, and then are serum starved in serum free medium (0% CS DMEM with 0.1% BSA) for 24 hours.

(3) On day 3, ligand (IGF1=3.3 nM, prepared in DMEM with 0.1% BSA) and test compounds are added to the cells simultaneously. The negative control wells receive serum free DMEM with 0.1% BSA only, the positive control cells receive the ligand (IGF1) but no test compound. Test compounds are prepared in serum free DMEM with ligand in a 96 well plate, and serially diluted for 7 test concentrations.

(4) After 16 hours of ligand activation, diluted BrdU labeling reagent (1:100 in DMEM, 0.1% BSA) is added and the cells are incubated with BrdU (final concentration=10 μM) for 1.5 hours.

(5) After incubation with labeling reagent, the medium is removed by decanting and tapping the inverted plate on a paper towel. FixDenat solution is added (50 μl/well) and the plates are incubated at room temperature for 45 minutes on a plate shaker.

(6) The FixDenat solution is thoroughly removed by decanting and tapping the inverted plate on a paper towel. Milk is added (5% dehydrated milk in PBS, 200 μl/well) as a blocking solution and the plate is incubated for 30 minutes at room temperature on a plate shaker.

(7) The blocking solution is removed by decanting and the wells are washed once with PBS. Anti-BrdU-POD solution (1:100 dilution in PBS, 1% BSA) is added (100 μl/well) and the plate is incubated for 90 minutes at room temperature on a plate shaker.

(8) The antibody conjugate is thoroughly removed by decanting and rinsing the wells 5 times with PBS, and the plate is dried by inverting and tapping on a paper towel.

(9) TMB substrate solution is added (100 μl/well) and incubated for 20 minutes at room temperature on a plate shaker until color development is sufficient for photometric detection.

(10) The absorbance of the samples are measured at 410 nm (in "dual wavelength" mode with a filter reading at 490 nm, as a reference wavelength) on a Dynatech ELISA plate reader.

FGF-Induced BrdU incorporation Assay

This assay measures FGF-induced DNA synthesis in 3Tc7/EGFr cells that express endogenous FGF receptors.

Materials and Reagents:

1. FGF: human FGF2/bFGF (Gibco BRL, No. 13256-029).

2. BrdU Labeling reagent, (10 mM PBS (pH 7.4), Boehringer Mannheim Cat No. 1 647 229).

3. Fixdenat fixation solution (Boehringer Mannheim Cat No. 1 647 229).

4. Anti-BrdU-POD (mouse monoclonal antibody conjugated with peroxidase, Boehringer Mannheim Cat. No. 1 647 229).

5. TMB (tetramethylbenzidine, Boehringer Mannheim Cat. No. 1 647 229).

6. PBS washing solution, pH 7.4 (Sugen, Inc.).

7. Albumin, bovine (BSA), fraction V powder (Sigma Chemical Co., Cat. No. A-8551)

Procedure 1. 3T3 engineered cell line: 3T3c7/EGFr.

2. Cells are seeded at 8,000 cells/well in DMEM, 10% CS and 2 mM Gln in a 96-well plate. Incubate 24 hours at 37° C. in 5% $CO_2$.

3. After 24 hours, wash cells with PBS then serum starve in serum free medium (0% DMEM, 0.1% BSA) for 24 hours.

4. Add ligand (FGF2 (1.5 nM in DMEM with 0.1% BSA) and test compound simultaneously. Negative control wells receive serum free DMEM with 0.1% BSA only, positive control wells receive FGF2 ligand but no test compound. Test compounds are prepared in serum-free DMEM with ligand in a 96-well plate and serially diluted to make seven (7) test concentrations.

5. After 20 hours, add diluted BrdU labeling reagent (1:100 BrdU:DMEM, 0.1% BSA, final concentration is 10 μM) to the cells and incubate for 1.5 hours.

6. Decant medium. Remove traces of material with paper towel. Add FixDenat (50 μl/well) and incubate at room temperature for 45 minutes on a plate shaker.

7. Remove Fixdenat solution. Add blocking solution (5% dehydrated milk in PBS (200 μl/well)) and incubate for 30 minutes at room temperature on a plate shaker.

8. Decant blocking solution, wash wells once with PBS. Add anti-BrdU-POD solution (1:100 dilution in PBS, 0.1% BSA), incubate for 90 minutes at room temperature on a plate shaker.

9. Decant antibody conjugate, rinse wells 5 times with PBS. Dry plate by inverting on paper towel and tapping.

10. Add TMB solution (100 μl/well), incubate 20 minutes at room temperature on a plate shaker until color development is sufficient for photometric detection.

11. Measure absorbance at 410 nM on a Dynatech ELISA plate reader using "Dual wavelength" mode with a filter at 490 nM.

Biochemical EGFR Assay

This assay measures the in vitro kinase activity of EGFR using ELISA.

Materials and Reagents

1. Corning 96-well Elisa plates (Corning Catalog No. 25805-96).

2. SUMO1 monoclonal anti-EGFR antibody (Biochemistry Lab, SUGEN, Inc.).

3. PBS (Dulbecco's Phosphate-Buffered Saline, Gibco Catalog No. 450-1300EB).

4. TBST Buffer

| Reagent | M.W. | Working Concentration | Amount per L |
|---|---|---|---|
| Tris | 121.14 | 50 mM | 6.057 g |
| NaCl | 58.44 | 150 mM | 8.766 g |
| Triton X-100 | NA | 0.1% | 1.0 ml |

5. Blocking Buffer:

| Reagent | M.W. | Working Concentration | Amount per 100 ml |
|---|---|---|---|
| Carnation Instant Non-Fat Milk | | 5% | 5.0 g |
| PBS | NA | NA | 100 ml |

6. A431 cell lysate (Screening Lab, SUGEN, Inc.)

7. TBS Buffer:

| Reagent | M.W. | Working Concentration | Amount per L |
|---|---|---|---|
| Tris | 121.14 | 50 mM | 6.057 g |
| NaCl | 58.44 | 150 mM | 8.766 g |

8. TBS + 10% DMSO

| Reagent | M.W. | Working Concentration | Amount per L |
|---|---|---|---|
| Tris | 121.14 | 50 mM | 1.514 g |
| NaCl | 58.44 | 150 mM | 2.192 g |
| DMSO | NA | 10% | 25 ml |

9. Adenosine-5'-triphosphate (ATP, from Equine muscle, Sigma Cat. No. A-5394).

Prepare a 1.0 mM solution in $dH_2O$. This reagent should be made up immediately prior to use and kept on ice.

10. $MnCl_2$.

Prepare a 1.0 M stock solution in $dH_2O$.

11. ATP/$MnCl_2$ $_{phosphorylation\ mix}$

| Reagent | Stock solution | Amount per 10 ml | Working Concentration |
|---|---|---|---|
| ATP | 1.0 mM | 300 μl | 30 μM |
| $MnCl_2$ | 1.0M | 500 μl | 50 mM |
| $dH_2O$ | | | 9.2 ml |

This reagent should be prepared immediately before use and kept on ice.

12. NUNC 96-well V bottom polypropylene plates (Applied Scientific Cat. No. AS-72092).

13. Ethylenediaminetetraacetic acid (EDTA)

Prepare 200 mM working solution in $dH_2O$. Adjust to pH 8.0 with 10 N NaOH.

14. Rabbit polyclonal anti-phosphotyrosine serum (Biochemistry Lab, SUGEN, Inc.)

15. Goat anti-rabbit IgG peroxidase conjugate (Biosource Cat. No. ALI0404)

16. ABTS (2,2'-azino-bis(3-ethylbenzthiazoline-6-sulfonic acid), Sigma Cat. No. A-1888).

| Reagent | M.W. | Working Concentration | Amount per L |
|---|---|---|---|
| Citric Acid | 192.12 | 100 mM | 19.21 g |
| Na2HPO4 | 141.96 | 250 mM | 35.49 g |
| ABTS | NA | 0.5 mg/ml | 500 mg |

Mix first two ingredients in about 900 ml $dH_2O$, adjust pH to 4.0 with phosphoric acid. Add ABTS, cover, let sit about 0.5 hr., filter. The solution should be kept in the dark at 40° C. until ready to use.

17. Hydrogen peroxide 30% solution (Fisher Cat. No. H325)

18. ABTS/$H_2O_2$

Mix 15 ml ABTS solution and 2.0 μl $H_2O_2$. Prepare 5 minutes before use.

19. 0.2 M HCl

Procedure

1. Coat Corning 96 well ELISA plates with 0.5 μg SUMO1 in 100 μl PBS per well, store overnight at 40° C.

2. Remove unbound SUMO1 from wells by inverting plate to remove liquid. Wash 1× with $dH_2O$. Pat the plate on a paper towel to remove excess liquid.

3. Add 150 μl of Blocking Buffer to each well. Incubate for 30 min. at room temperature with shaking.

4. Wash plate 3× with deionized water, then once with TBST. Pat plate on a paper towel to remove excess liquid and bubbles.

5. Dilute lysate in PBS (7 μg lysate/100 μl PBS).

6. Add 100 μl of diluted lysate to each well. Shake at room temperature for 60 min.

7. Wash plates as described in 4, above.

8. Add 120 μl TBS to ELISA plate containing captured EGFR.

9. Dilute test compound 1:10 in TBS in 96-well polypropylene plates (ie. 10 μl compound+90 μl TBS).

10. Add 13.5 μl diluted test compound to ELISA plate. To control wells (wells which do not receive any test compound), add 13.5 μl TBS+10% DMSO.

11. Incubate for 30 minutes while shaking at room temperature.

12. Add 15 μl phosphorylation mix directly to all wells except negative control well which does not receive ATP/

MnCl₂ (final well volume should be approximately 150 µl with 3 µM ATP/5 mM MnCl₂ final concentration in each well.) Incubate 5 minutes while shaking.

13. After 5 minutes, stop reaction by adding 16.5 µl of 200 mM EDTA (pH 8.0) to each well, shaking continuously. After the EDTA has been added, shake for 1 min.

14. Wash 4× with deionized water, twice with TBST.

15. Add 100 µl anti-phosphotyrosine (1:3000 dilution in TBST) per well. Incubate 30–45 min. at room temperature, with shaking.

16. Wash as described in 4, above.

17. Add 100 µl Biosource Goat anti-rabbit IgG peroxidase conjugate (1:2000 dilution in TBST) to each well. Incubate 30 min. at room temperature, with shaking.

18. Wash as described in 4, above.

19. Add 100 µl of ABTS/H₂O₂ solution to each well.

20. Incubate 5 to 10 minutes with shaking. Remove any bubbles.

21. If necessary stop reaction with the addition of 100 µl 0.2 M HCl per well.

22. Read assay on Dynatech MR7000 ELISA reader. Test Filter: 410 nM Reference Filter: 630 Nm.

Biochemical PDGFR Assay

This assay measures the in vitro kinase activity of PDGFR using ELISA.

Materials and Reagents

Unless otherwise noted, the preparation of working solution of the following reagents is the same as that for the Biochemical EGFR assay, above.

1. Corning 96-well Elisa plates (Corning Catalog No. 25805-96).
2. 28D4C10 monoclonal anti-PDGFR antibody (Biochemistry Lab, SUGEN, Inc.).
3. PBS (Dulbeccols Phosphate-Buffered Saline, Gibco Catalog No. 450-1300EB)
4. TBST Buffer.
5. Blocking Buffer.
6. PDGFR-β expressing NIH 3T3 cell lysate (Screening Lab, SUGEN, Inc.).
7. TBS Buffer.
8. TBS+10% DMSO.
9. Adenosine-5'-triphosphate (ATP, from Equine muscle, Sigma Cat. No. A-5394).
10. MnCl₂.
11. Kinase buffer phosphorylation mix.

| Reagent | Stock solution | Amount per 10 ml | Working Concentration |
|---|---|---|---|
| Tris | 1M | 250 µl | 25 mM |
| NaCl | 5M | 200 µl | 100 mM |
| MnCl₂ | 1M | 100 µl | 10 mM |
| TX-100 | 100 mM | 50 µl | 0.5 mM |

12. NUNC 96-well V bottom polypropylene plates (Applied Scientific Cat. No. AS-72092).
13. Ethylenediaminetetraacetic acid (EDTA).
14. Rabbit polyclonal anti-phosphotyrosine serum (Biochemistry Lab, SUGEN, Inc.).
15. Goat anti-rabbit IgG peroxidase conjugate (Biosource Cat. No. ALI0404).
16. 2,2'-azino-bis(3-ethylbenzthiazoline-6-sulfonic acid) (ABTS, Sigma Cat. No. A-1888).
17. Hydrogen peroxide 30% solution (Fisher Cat. No. H325).
18. ABTS/H₂O₂.
19. 0.2 M HCl.

Procedure

1. Coat Corning 96 well ELISA plates with 0.5 µg 28D4C10 in 100 µl PBS per well, store overnight at 40° C.

2. Remove unbound 28D4C10 from wells by inverting plate to remove liquid. Wash 1× with dH₂O. Pat the plate on a paper towel to remove excess liquid.

3. Add 150 µl of Blocking Buffer to each well. Incubate for 30 min. at room temperature with shaking.

4. Wash plate 3× with deionized water, then once with TBST. Pat plate on a paper towel to remove excess liquid and bubbles.

5. Dilute lysate in HNTG (10 µg lysate/100 µl HNTG)

6. Add 100 µl of diluted lysate to each well. Shake at room temperature for 60 min.

7. Wash plates as described in 4, above.

8. Add 80 µl working kinase buffer mix to ELISA plate containing captured PDGFR.

9. Dilute test compound 1:10 in TBS in 96-well polypropylene plates (i.e., 10 µl compound+90 µl TBS).

10. Add 10 µl diluted test compound to ELISA plate. To control wells (wells which do not receive any test compound), add 10 µl TBS+10% DMSO.

11. Incubate for 30 minutes while shaking at room temperature.

12. Add 10 µl ATP directly to all wells except negative control well (final well volume should be approximately 100 µl with 20 µM ATP in each well.) Incubate 30 minutes while shaking.

13. After 30 minutes, stop reaction by adding 10 µl of 200 mM EDTA (pH 8.0) to each well.

14. Wash 4× with deionized water, twice with TBST.

15. Add 100 µl anti-phosphotyrosine (1:3000 dilution in TBST) per well. Incubate 30–45 min. at room temperature, with shaking.

16. Wash as described in 4, above.

17. Add 100 µl Biosource Goat anti-rabbit IgG peroxidase conjugate (1:2000 dilution in TBST) to each well. Incubate 30 min. at room temperature, with shaking.

18. Wash as described in 4, above.

19. Add 100 µl of ABTS/H₂O₂ solution to each well.

20. Incubate 10 to 30 minutes with shaking. Remove any bubbles.

21. If necessary stop reaction with the addition of 100 µl 0.2 M HCl per well.

22. Read assay on Dynatech MR7000 ELISA reader: test filter: 410 nM, reference filter: 630 nM.

Biochemical FGFR Assay

This assay measures in vitro kinase activity of the Myc-GyrB-FGFR fusion protein using ELISA.

Materials and Reagents

1. HNTG

| Reagent | M.W. | 5× Stock Concentration | Amount per L | 1× Working Concentration |
|---|---|---|---|---|
| HEPES | 238.3 | 100 mM | 23.83 g | 20 mM |
| NaCl | 58.44 | 750 mM | 43.83 9 | 150 mM |
| Glycerol | NA | 50% | 500 ml | 10% |
| Triton X-100 | NA | 5% | 10 ml | 1.0% |

To make a liter of 5× stock solution, dissolve HEPES and NaCl in about 350 ml dH₂O, adjust pH to 7.2 with HCl or NaOH (depending on the HEPES that is used), add glycerol, Triton X-100 and then dH₂O to volume.

2. PBS (Dulbeccols Phosphate-Buffered Saline, Gibco Catalog # 450-1300EB).

3. Blocking Buffer.
4. Kinase Buffer.

| Reagent | M.W. | 10x Stock Concentration | 1x Working Concentration |
|---|---|---|---|
| HEPES (pH 7.2) | 238.3 | 500 mM | 50 mM |
| MnCl$_2$ | | 20 mM | 2 mM |
| MgCl$_2$ | 203.32 | 200 mM | 10 mM |
| Triton-X-100 | | 1% | 0.1% |
| DTT | 380.35 | 5 mM | 0.5 mM |

5. Phenylmethylsulfonyl fluoride (PMSF, Sigma, Cat. No. P-7626):
    Working solution: 100 mM in ethanol.
6. ATP (Bacterial source, Sigma Cat. No. A-7699)
    Use 3.31 mg per ml MilliQ H$_2$O for a stock concentration of 6 mM.
7. Biotin conjugated anti-phosphotyrosine mab (clone 4G10, Upstate Biotechnology Inc. Cat. No. 16-103, Ser. No. 14495).
8. Vectastain Elite ABC reagent (Avidin peroxidase conjugate, Vector Laboratories Cat. No. PK-6 100).
9. ABTS Solution.
10. Hydrogen peroxide 30% solution (Fisher Catalog # H325).
11. ABTS/H$_2$O$_2$.
12. 0.2 M HCl.
13. TRIS HCl (Fischer Cat. No. BP 152-5).
    Prepare 1.0 mM solution in MilliQ H$_2$O, adjust pH to 7.2 with HCl.
14. NaCl (Fisher Cat. No. S271-10).
    Prepare 5 M solution in MilliQ H$_2$O.
15. MgCl$_2$ (Fisher Cat. No. M33-500).
    Prepare 1 M solution in MilliQ H$_2$O.
16. HEPES (Fisher Cat. No. BP310-500).
    Prepare 1 M solution in MilliQ H$_2$O, adjust pH to 7.5, sterile filter.
17. TBST Buffer.
18. Sodium Carbonate Buffer (Fisher Cat. No. S495).
    Prepare 0.1 M solution in MilliQ H$_2$O, adjust pH to 9.6 with NaOH, filter.
19. Dithiothreitol (DTT, Fisher Cat. No. BP172-25).
    Prepare 0.5 mM working solution in MilliQ H$_2$O just prior to use. Store at −20° C. until used, discard any leftover.
20. MnCl$_2$.
21. Triton X-100.
22. Goat α-Rabbit IgG (Cappel).
23. Affinity purified Rabbit α GST GyrB (Biochemistry Lab. SUGEN, Inc.).

Procedure

All of the following steps are conducted at room temperature unless otherwise indicated.
1. Coat Corning 96-well ELISA plates with 2 μg Goat α-Rabbit antibody per well in Carbonate Buffer such that total well volume is 100 μl. Store overnight at 40° C.
2. Remove unbound Goat a-Rabbit antibody by inverting plate to remove liquid. Pat plate on a paper towel to remove excess liquid and bubbles.
3. Add 150 μl Blocking Buffer (5% Low Fat Milk in PBS) to each well. Incubate while shaking on a micro-titer plate shaker for 30 min.
4. Wash 4× with TBST. Pat plate on a paper towel to remove excess liquid and bubbles.
5. Add 0.5 μg Rabbit a-GyrB antibody per well. Dilute antibody in DPBS to a final volume of 100 μl per well. Incubate with shaking on a micro-titer plate shaker at room temperature for 1 hour.
6. Wash 4× with TBST as described in step 4.
7. Add 2 μg COS/FGFR cell lysate (Myc-GyrB-FGFR source) in HNTG to each well to give a final volume of 100 μl per well. Incubate with shaking on a micro-titer plate shaker for 1 hour.
8. Wash 4× with TBST as described in step 4.
9. Add 80 μl of 1× kinase buffer per well.
10. Dilute test compound 1:10 in 1× kinase buffer+1% DMSO in a polypropylene 96 well plate.
11. Transfer 10 μl of diluted test compound solution and control wells from polypropylene plate wells to the corresponding ELISA plate wells, incubate with shaking on a micro-titer plate shaker for 20 minutes.
12. Add 10 μl of 70 μM ATP diluted in kinase buffer to positive control and test wells (Final ATP concentration is 7 μM/well). Add 10 μl 1× kinase buffer to negative control wells. Incubate with shaking on a micro-titer plate shaker for 15 min.
13. Stop kinase reaction by adding 5 μl 0.5 M EDTA to all wells.
14. Wash 4× with TBST as described in step 4.
15. Add 100 μl biotin conjugated α-phosphotyrosine mab (b4G10) diluted in TBST to each well. Incubate with shaking on a micro-titer plate shaker for 30 minutes.
16. Prepare Vectastain ABC reagent. Add 1 drop reagent A to 15 ml TBST. Mix by inverting tube several times. Add 1 drop reagent B and mix again.
17. Wash 4× with TBST as described in step 4.
18. Add 100 μl ABC HRP reagent to each well. Incubate with shaking on a micro-titer plate shaker for 30 minutes.
19. Wash 4× with TBST as described in step 4.
20. Add 100 μl of ABTS/H$_2$O$_2$ solution to each well.
22. Incubate 5 to 15 minutes with shaking. Remove any bubbles.
23. If necessary stop reaction by adding 1 00 μl of 0.2M HCl/well.
24. Read assay on Dynatech MR7000 ELISA Plate Reader, test filter: 410 nM, reference filter: 630 nM.

Biochemical FLK-1 Assay

This assay evaluates flk-1 autophosphorylation activity in vitro using ELISA.

Materials and Reagents
1. 15 cm tissue culture dishes
2. Flk-l/NIH cells: NIH fibroblast line over-expressing human flk-1 clone 3 (SUGEN, Inc., obtained from MPI, Martinsried, Germany).
3. Growth medium: DMEM plus heat inactivated 10% FBS and 2 mM Glutamine (Gibco-BRL).
4. Starvation medium: DMEM plus 0.5% heat-inactivated FBS, 2 mM Glutamine (Gibco-BRL).
5. Corning 96-well ELISA plates (Corning Cat. No. 25805-96).
6. L4 or E38 monoclonal antibody specific for flk-1, Purified by Protein-A agarose affinity chromatography (SUGEN, Inc.).
7. PBS (Dulbeccols Phosphate-Buffered Saline) Gibco Cat. No. 450-1300EB).
8. HNTG (see BIOCHEMICAL FGFR for preparation).
9. Pierce BCA protein determination kit.
10. Blocking buffer
11. TBST (pH 7.0)
12. Kinase Buffer
13. Kinase Stop Solution: 200 mM EDTA.

14. Biotinylated 4G10, specific for phosphotyrosine (UBI, Cat. No. No. 16-103).
15. AB kit (Vector Laboratories Cat. No. PK 4000).
16. DMSO
17. NUNC 96-well V bottom polypropylene plates (Applied Scientific Cat. No. AS-72092).
18. Turbo-TMB (Pierce).
19. Turbo-TMB stop solution: 1 M $H_2SO_4$.
20. ATP (Sigma Cat. No. A-7699).
21. 20% DMSO in TBS (pH 7.0).

Procedure

Cell Growth and Lysate Preparation.

1. Seed cell into growth medium and grow for 2–3 days to 90–100% confluency at 37° C. and 5% $CO_2$. Do not exceed passage #20.
2. Remove the medium and wash the cells twice with PBS. Lyse with HNTG lysis buffer. Collect all lysates and vortex mix them for 20–30 seconds.
3. Remove insoluble material by centrifugation (5–10 min at 10,000×g).
4. Determine the protein concentration using BCA kit.
5. Partition lysate into 1 mg aliquots, store at −80° C.

Assay Procedure

1. Coat Corning 96-well ELISA plates with 2 µg/well purified L4 (or E 38) in 100 µl of PBS. Store overnight at 40° C.
2. Remove unbound proteins from wells by inverting the plate to remove the liquid. Wash one time with $dH_2O$, pat plate on paper towel to remove excess liquid.
3. Block plates with 150 µl blocking buffer per well. Incubate for 45–60 minutes with shaking at 40° C.
4. Remove the blocking buffer and wash the ELISA plate three times with $dH_2O$ and one time with TBST. Pat plate on paper towel to remove excess liquid.
5. Dilute lysate in PBS to give final concentration of 50 µg/100 µl. Add 100 µl of diluted lysate to each well. Incubate with shaking at 4° C. overnight.
6. Remove unbound proteins from wells by inverting the plate. Wash as in step 4.
7. Add 80 µl of kinase buffer to wells (90 µl to negative control wells).
8. Dilute test compounds (normally 10-fold) into wells of a polypropylene plate containing 20% DMSO in TBS.
9. Add 10 µl of the diluted compounds to the ELISA wells containing immobilized flk-1 and shake. Control wells receive no compounds.
10. From stock 1 mM ATP, prepare 0.3 mM ATP solution in $dH_2O$ (alternatively, kinase buffer may be used).
11. Add 10 µl of 0.3 mM ATP to all wells except the negative controls. Incubate for 60 min. at room temperature with shaking.
12. After 1 hr stop the kinase reaction by adding 11 µl 200 mM EDTA. Shake for 1–2 min.
13. Wash the ELISA plate 4 times with $dH_2O$ and twice with TBST.
14. Add 100 µl of 1:5000 biotinylated 4G10:TBST to all wells. Incubate 45 min with shaking at room temperature.
15. While the above is incubating, add 50 µl of solutions A & B from the ABC kit to 10 ml of TBST. These solutions must be combined approximately 30 min prior to use.
16. Wash plates as in step 4.
17. Add 100 µl of the preformed A & B complex to all wells. Incubate 30 min with shaking at room temperature.
18. Wash plates as in step 4.
19. Add 100 µl turbo-TMB. Shake at room temperature for 10–15 min.
20. When the color in the positive control wells reaches an absorbance of about 0.35–0.4, stop the reaction with 100 µl of turbo-TMB stop solution.
21. Read plates on Dynatech MR7000 ELISA reader, test filter: 450 nM, reference filter: 410 nM.

HUV-EC-C Assay

The following protocol may also be used to measure a compound's activity against PDGF-R, FGF-R, VEGF, aFGF or Flk-1/KDR, all of which are naturally expressed by HUV-EC cells.

DAY 0

1. Wash and trypsinize HUV-EC-C cells (human umbilical vein endothelial cells, (American Type Culture Collection, catalogue no. 1730 CRL). Wash with Dulbecco's phosphate-buffered saline (D-PBS, obtained from Gibco BRL, catalogue no. 14190-029) 2 times at about 1 ml/10 $cm^2$ of tissue culture flask. Trypsinize with 0.05% trypsin-EDTA in non-enzymatic cell dissociation solution (Sigma Chemical Company, catalogue no. C-1544). The 0.05% trypsin is made by diluting 0.25% trypsin/1 mM EDTA (Gibco, catalogue no. 25200-049) in the cell dissociation solution. Trypsinize with about 1 ml/25–30 $cm^2$ of tissue culture flask for about 5 minutes at 37° C. After cells have detached from the flask, add an equal volume of assay medium and transfer to a 50 ml sterile centrifuge tube (Fisher Scientific, catalogue no. 05-539-6).
2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 $cm^2$ of tissue culture flask. Assay medium consists of F12K medium (Gibco BRL, catalogue no. 21127-014) and 0.5% heat-inactivated fetal bovine serum. Count the cells with a Coulter Counter® (Coulter Electronics, Inc.) and add assay medium to the cells to obtain a concentration of 0.8–1.0×$10^5$ cells/ml.
3. Add cells to 96-well flat-bottom plates at 100 µl/well or 0.8–1.0×$10^4$ cells/well, incubate ~24 h at 37° C., 5% $CO_2$.

DAY 1

1. Make up two-fold test compound titrations in separate 96-well plates, generally 50 µM on down to 0 µM. Use the same assay medium as mentioned in day 0, step 2 above. Titrations are made by adding 90 µl/well of test compound at 200 µM (4× the final well concentration) to the top well of a particular plate column. Since the stock test compound is usually 20 mM in DMSO, the 200 µM drug concentration contains 2% DMSO.

A diluent made up to 2% DMSO in assay medium (F12K+0.5% fetal bovine serum) is used as diluent for the test compound titrations in order to dilute the test compound but keep the DMSO concentration constant. Add this diluent to the remaining wells in the column at 60 µl/well. Take 60 µl from the 120 µl of 200 µM test compound dilution in the top well of the column and mix with the 60 µl in the second well of the column. Take 60 µl from this well and mix with the 60 µl in the third well of the column, and so on until two-fold titrations are completed. When the next-to-the-last well is mixed, take 60 µl of the 120 µl in this well and discard it. Leave the last well with 60 µl of DMSO/media diluent as a non-test compound-containing control. Make 9 columns of titrated test compound, enough for triplicate wells each for: (1) VEGF (obtained from Pepro Tech Inc., catalogue no. 100-200, (2) endothelial cell growth factor (ECGF) (also known as acidic fibroblast growth factor, or aFGF) (obtained from Boehringer Mannheim Biochemica, catalogue no. 1439 600), or, (3) human PDGF B/B (1276-956, Boehringer Mannheim, Germany) and assay media control. ECGF comes as a preparation with sodium heparin.

2. Transfer 50 µl/well of the test compound dilutions to the 96-well assay plates containing the 0.8–1.0×$10^4$ cells/

100 μl/well of the HUV-EC-C cells from day 0 and incubate ~2 h at 37° C., 5% $CO_2$.

3. In triplicate, add 50 μl/well of 80 μg/ml VEGF, 20 ng/ml ECGF, or media control to each test compound condition. As with the test compounds, the growth factor concentrations are 4× the desired final concentration. Use the assay media from day 0 step 2 to make the concentrations of growth factors. Incubate approximately 24 hours at 37° C., 5% $CO_2$. Each well will have 50 μl test compound dilution, 50 μl growth factor or media, and 100 μl cells, which calculates to 200 μl/well total. Thus the 4× concentrations of test compound and growth factors become 1× once everything has been added to the wells.

DAY 2

1. Add $^3$H-thymidine (Amersham, catalogue no. TRK-686) at 1 μCi/well (10 μl/well of 100 μCi/ml solution made up in RPMI media+10% heat-inactivated fetal bovine serum) and incubate ~24 h at 37° C., 5% $CO_2$. RPMI is obtained from Gibco BRL, catalogue no. 11875-051.

DAY 3

1. Freeze plates overnight at −200C.

DAY 4

Thaw plates and harvest with a 96-well plate harvester (Tomtec Harvester 96®) onto filter mats (Wallac, catalogue no. 1205-401), read counts on a Wallac Betaplate™ liquid scintillation counter.

In Vivo Animal Models
Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758–760), many different human tumor cell lines (e.g., mammary, lung, genitourinary, gastro-intestinal, head and neck, glioblastoma, bone, and malignant melanomas) have been transplanted and successfully grown in nude mice. The following assays may be used to determine the level of activity, specificity and effect of the different compounds of the present invention. Three general types of assays are useful for evaluating compounds: cellular/catalytic, cellular/biological and in vivo. The object of the cellular/catalytic assays is to determine the effect of a compound on the ability of a TK to phosphorylate tyrosines on a known substrate in a cell. The object of the cellular/biological assays is to determine the effect of a compound on the biological response stimulated by a TK in a cell. The object of the in vivo assays is to determine the effect of a compound in an animal model of a particular disorder such as cancer.

Suitable cell lines for subcutaneous xenograft experiments include C6 cells (glioma, ATCC # CCL 107), A375 cells (melanoma, ATCC # CRL 1619), A431 cells (epidermoid carcinoma, ATCC # CRL 1555), Calu 6 cells (lung, ATCC # HTB 56), PC3 cells (prostate, ATCC # CRL 1435), SKOV3TP5 cells and NIH 3T3 fibroblasts genetically engineered to overexpress EGFR, PDGFR, IGF-1R or any other test kinase. The following protocol can be used to perform xenograft experiments:

Female athymic mice (BALB/c, nu/nu) are obtained from Simonsen Laboratories (Gilroy, Calif.). All animals are maintained under clean-room conditions in Micro-isolator cages with Alpha-dri bedding. They receive sterile rodent chow and water ad libitum.

Cell lines are grown in appropriate medium (for example, MEM, DMEM, Ham's F10, or Ham's F12 plus 5%–10% fetal bovine serum (FBS) and 2 mM glutamine (GLN)). All cell culture media, glutamine, and fetal bovine serum are purchased from Gibco Life Technologies (Grand Island, N.Y.) unless otherwise specified. All cells are grown in a humid atmosphere of 90–95% air and 5–10% $CO_2$ at 37° C. All cell lines are routinely subcultured twice a week and are negative for mycoplasma as determined by the Mycotect method (Gibco).

Cells are harvested at or near confluency with 0.05% Trypsin-EDTA and pelleted at 450×g for 10 min. Pellets are resuspended in sterile PBS or media (without FBS) to a particular concentration and the cells are implanted into the hindflank of the mice (8–10 mice per group, 2–10×10$^6$ cells/animal). Tumor growth is measured over 3 to 6 weeks using venier calipers. Tumor volumes are calculated as a product of length×width×height unless otherwise indicated. P values are calculated using the Students t-test. Test compounds in 50–100 μL excipient (DMSO, or VPD:D5W) can be delivered by IP injection at different concentrations generally starting at day one after implantation.

Tumor Invasion Model

The following tumor invasion model has been developed and may be used for the evaluation of therapeutic value and efficacy of the compounds identified to selectively inhibit KDR/FLK-1 receptor.

Procedure 8 week old nude mice (female) (Simonsen Inc.) are used as experimental animals. Implantation of tumor cells can be performed in a laminar flow hood. For anesthesia, Xylazine/Ketamine Cocktail (100 mg/kg ketamine and 5 mg/kg Xylazine) are administered intraperitoneally. A midline incision is done to expose the abdominal cavity (approximately 1.5 cm in length) to inject 10$^7$ tumor cells in a volume of 100 μl medium. The cells are injected either into the duodenal lobe of the pancreas or under the serosa of the colon. The peritoneum and muscles are closed with a 6-0 silk continuous suture and the skin is closed by using wound clips. Animals are observed daily.

Analysis

After 2–6 weeks, depending on gross observations of the animals, the mice are sacrificed, and the local tumor metastases to various organs (lung, liver, brain, stomach, spleen, heart, muscle) are excised and analyzed (measurement of tumor size, grade of invasion, immunochemistry, in situ hybridization determination, etc.).

Measurement Of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index, i.e., $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques as well (Mossman, 1983, *J. Immunol. Methods,* 65:55–63), by measuring the amount of LDH released (Korzeniewski and Callewaert, 1983, *J. Immunol. Methods,* 64:313, Decker and Lohmann-Matthes, 1988, *J. Immunol. Methods,* 115:61), or by measuring the lethal dose in animal models. Compounds with a large therapeutic index are preferred. The therapeutic index should be greater than 2, preferably at least 10, more preferably at least 50.

B. Examples—Biological Activity.

Examples of the in vitro potency of compounds of this invention are shown in Tables 1 and 2. The data show that the compounds are generally quite potent against a variety of PTKs in vitro. The compounds also maintain excellent activity when tested in vivo. For example several compounds of the present invention, when administered orally, exhibit a marked reduced average size of C6 glioma tumors subcutaneously implanted in mice. However, compound 5 was notably superior to the other compounds of this invention. In one experiment, C6 human glioma cells ($3 \times 10^6$ cells, n=10–20 animals/group) were implanted subcutaneously in the hindflank of female BALB/c nu/nu mice on day 0. Oral administration of compounds 3, 5, 19 and 20 in aqueous labrasol at 200 mg/kg/day commenced one day post-implantation. Tumor growth was measured using vernier calipers and tumor volumes were calculated as the product of length×width×height.

3

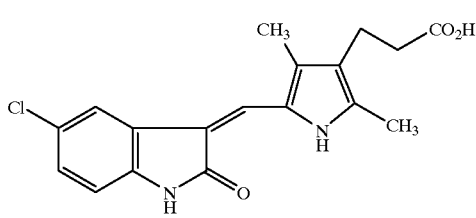

5

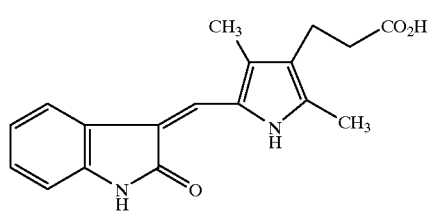

19

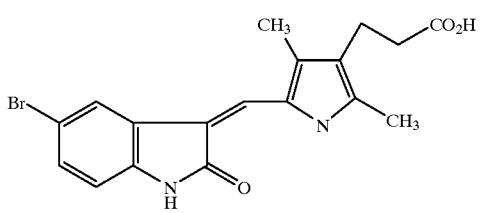

21

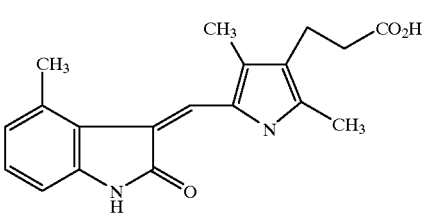

As shown in the following graph, all of the compounds tested show a marked inhibition compared to the vehicle-only control. However, compound 5 clearly and, considering the close structural similarity of the compounds tested, surprisingly stands out from the rest. That is, while compounds 3, 19 and 21 cluster around 40–45% inhibition of tumor growth at day 18 post-implantation, compound 5 inhibits tumor growth by 80–85% at that point.

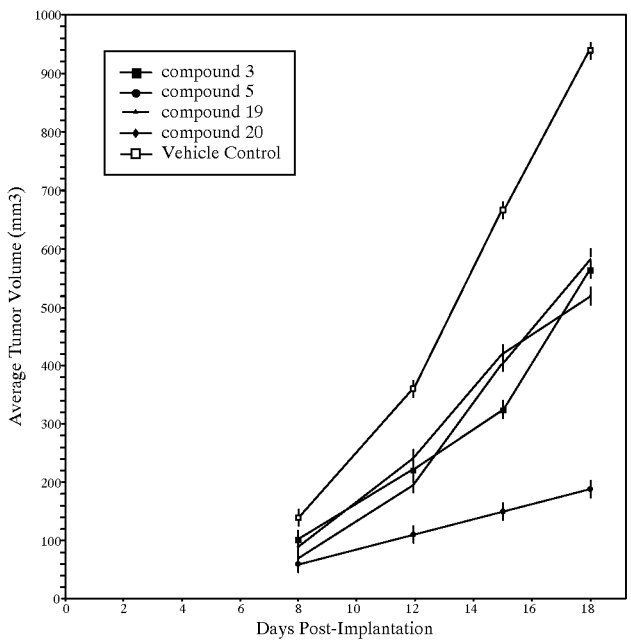

The unexpected efficacy of compound 5 in vivo, particularly upon oral administration, is further demonstrated when it is compared to compound 65:

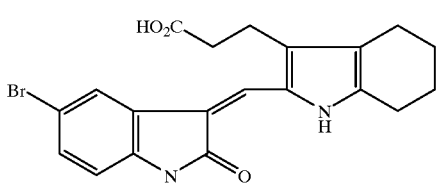

65

Compound 65 manifests almost an order of magnitude greater potency in vitro than compound 5 (data not shown). However, when tested interpertitoneally in mice against two different tumor cells lines, SF763T and SF767T, compound 5 is from slightly (5% greater inhibition at 21 days) to notably (14% greater inhibition at 21 days) more efficacious than compound 65.

The difference in activity between compound 5 and compound 65 is even greater when the two compounds are administered orally. The oral efficacy of compound 65 and several of its analogs, compounds 66–69, is shown graphically below:

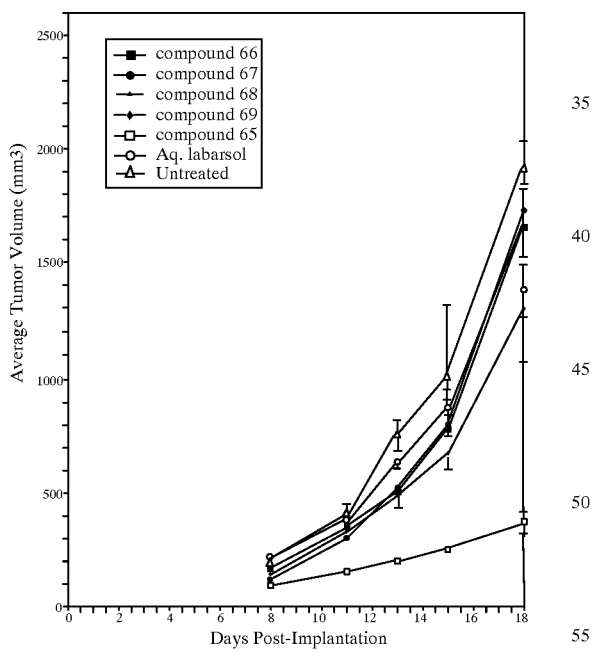

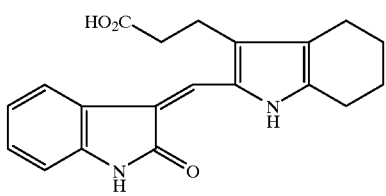

66

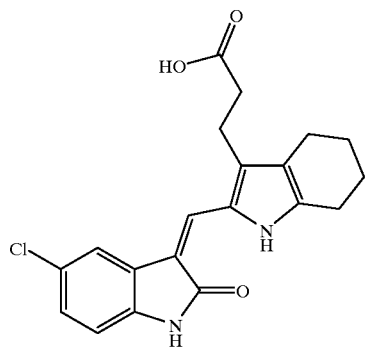

67

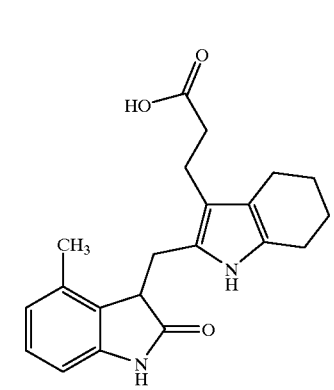

68

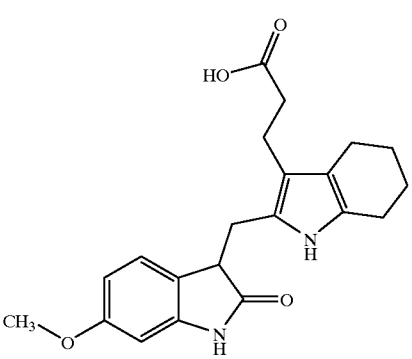

69

As can be seen from the graph, compound 65, administered orally at 200 mg/kg/day, shows approximately 65% inhibition of C6 tumors at 18 days post subcutaneous implantation in mice, which is clearly superior to its own analogs, which average about 14–16% inhibition of tumor growth. Surprisingly, however, the oral efficacy of compound 65 is still remarkably less than that of compound 5, which, as noted above, demonstrates 80–85% inhibition at the same time in the same tumor model.

When compared to compound 70, compound 5 shows significantly smaller (i.e., greater potency) $K_i$'s (inhibition constants) against FGF-R1 (1.2 for compound 5 versus 19.49 for compound 70) and PDGFR (data not shown).

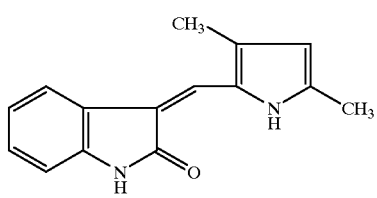

The unexpected superiority of compound 5 is further demonstrated when its oral efficacy is compared to that of a close analog, compound 71:

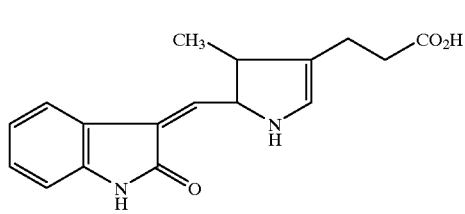

Despite the structural similarity, when tested orally at 200 mg/kg/day against subcutaneously implanted C6 human melanoma tumors in BALB/c nu/nu mice, at 18 days post implantation compound 71 shows only a 57% inhibition of tumor growth (data not shown) compared, again, to the 80–85% inhibition demonstrated by compound 5.

Based on the above surprising efficacy of compound 5 when administered orally, compound 5 is presently a preferred embodiment of this invention.

CONCLUSION

Thus, it will be appreciated that the compounds, methods and pharmaceutical compositions of the present invention are effective in modulating PK activity and therefore are expected to be effective as therapeutic agents against RTK, CTK-, and STK-related disorders.

One skilled in the art would readily appreciate that the present invention is well adapted to carry out the objects and obtain the ends and advantages mentioned, as well as those inherent herein. The molecular complexes and the methods, procedures, treatments, molecules, specific compounds described herein are presently representative of preferred embodiments, are exemplary, and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are within the following claims.

What is claimed:

1. A pyrrole substituted 2-indolinone having the chemical structure:

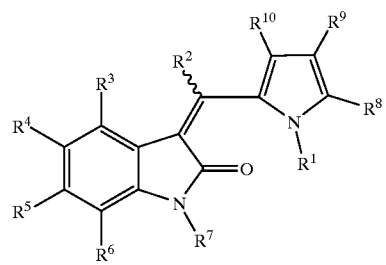

wherein: $R^1$, $R^2$ and $R^7$ are hydrogen;

$R^3$, $R^4$, and $R^6$ are independently selected from the group consisting of:
hydrogen;
hydroxy;
halo;
unsubstituted lower alkyl;
lower alkyl substituted with a carboxylic acid;
unsubstituted lower alkoxy;
carboxylic acid;
unsubstituted aryl;
aryl substituted with one or more unsubstituted lower alkyl alkoxy; and
morpholino;

$R^8$ is unsubstituted lower alkyl;

$R^9$ is —$(CH_2)(CH_2)C(=O)OH$; and $R^{10}$ is unsubstituted lower alkyl.

2. A compound having the structure:

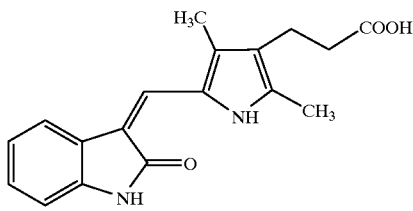

named as 3-[2,4-Dimethyl-5-(2-oxo-1,2-dihydroindol-3-ylidenemethyl)-1 H-pyrrol-3-yl]-propionic acid.

3. A pharmaceutical composition comprising a compound of claim 1 and a physiologically acceptable carrier or excipient.

4. A pharmaceutical composition comprising a compound of claim 2 and a physiologically acceptable carrier or excipient.

5. A method for treating a protein kinase related disorder in an organism, comprising administering a therapeutically effective amount of a compound of claim 1 to said organism.

6. A method for treating a protein kinase related disorder in an organism, comprising administering a therapeutically effective amount of a compound of claim 2 to said organism.

7. The method of claim 5, wherein said protein kinase related disorder is selected from the group consisting of a receptor tyrosine related disorder, a non-receptor tyrosine kinase related disorder and a serine-threonine kinase related disorder.

8. The method of claim 6, wherein said protein kinase related disorder is selected from the group consisting of a receptor tyrosine related disorder, a non-receptor tyrosine kinase related disorder and a serine-threonine kinase related disorder.

9. The method of claim 5, wherein said protein kinase related disorder is selected from the group consisting of a EGFR related disorder, a PGFR related disorder, and IGFR related disorder and a flk related disorder.

10. The method of claim 6, wherein said protein kinase related disorder is selected from the group consisting of an EGFR related disorder, a PGFR related disorder, an IGFR related disorder and a flk related disorder.

11. The method of claim 5, wherein said protein kinase related disorder is selected from the group consisting of a squamous cell carcinoma, astrocytoma, Kaposi's sarcoma, glioblastoma, lung cancer, bladder cancer, head and neck cancer, melanoma, ovarian cancer, prostate cancer, breast cancer, small cell lung cancer, glioma, colorectal cancer, genitourinary cancer and gastrointestinal cancer.

12. The method of claim 6, wherein said protein kinase related disorder is selected from the group consisting of a squamous cell carcinoma, astrocytoma, Kaposi's sarcoma, glioblastoma, lung cancer, bladder cancer, head and neck cancer, melanoma, ovarian cancer, prostate cancer, breast cancer, small cell lung cancer, glioma, colorectal cancer, genitourinary cancer and gastrointestinal cancer.

13. The method of claim 5, wherein said protein kinase related disorder is selected from the group consisting of diabetes, a hyperproliferation disorder, angiogenesis, an inflammatory disorder, an immunological disorder and a cardiovascular disorder.

14. The method of claim 6, wherein said protein kinase related disorder is selected from the group consisting of diabetes, a hyperproliferation disorder, angiogenesis, an inflammatory disorder, an immunological disorder and a cardiovascular disorder.

15. The method of claim 11, wherein said organism is a mammal.

16. The method of claim 12, wherein said organism is a mammal.

17. A compound selected from the group consisting of:

3-[5-(5-Chloro-2-oxo-1,2-dihydroindol-3-ylidenemethyl)-2,4-dimethyl-1H-pyrrol-3-yl]-propionic acid, 3-[2,4-Dimethyl-5-(2-oxo-1,2-dihydroindol-3-ylidenemethyl)-1H-pyrrol-3-yl]-propionic acid, 3-[5-(5-Bromo-2-oxo-1,2-dihydroindol-3-ylidenemethyl)-2,4-dimethyl-1H-pyrrol-3-yl]-propionic acid, 3-[5-(5-Iodo-2-oxo-1,2-dihydroindol-3-ylidenemethyl)-2,4-dimethyl-1H-pyrrol-3-yl]-propionic acid, 3-[2,4-Dimethyl-5-(4-methyl-2-oxo-1,2-dihydroindol-3-ylidenemethyl)-1H-pyrrol-3-yl]-propionic acid, 3-[2,4-Dimethyl-5-(5-methyl-2-oxo-1,2-dihydroindol-3-ylidenemethyl)-1H-pyrrol-3-yl]-propionic acid, 3-[5-(6-Hydroxy-2-oxo-1,2-dihydroindol-3-ylidenemethyl)-2,4-dimethyl-1H-pyrrol-3-yl]-propionic acid, 3-[5-(6-Methoxy-2-oxo-1,2-dihydroindol-3-ylidenemethyl)-2,4-dimethyl-1H-pyrrol-3-yl]-propionic acid, 3-{5-[6-(3-Methoxy-phenyl)-2-oxo-1,2-dihydroindol-3-ylidenemethyl]-2,4-dimethyl-1H-pyrrol-3-yl}-propionic acid, 3-{5-[6-(3-Ethoxy-phenyl)-2-oxo-1,2-dihydroindol-3-ylidenemethyl]-2,4-dimethyl-1H-pyrrol-3-yl}-propionic acid, 3-[2,4-Dimethyl-5-(2-oxo-6-phenyl-1,2-dihydroindol-3-ylidenemethyl)-1H-pyrrol-3-yl]-propionic acid, 3-{5-[6-(4-Methoxy-phenyl)-2-oxo-1,2-dihydroindol-3-ylidenemethyl]-2,4-dimethyl-1H-pyrrol-3-yl}-propionic acid, 3-{5-[6-(2-Methoxy-phenyl)-2-oxo-1,2-dihydronidol-3-ylidenemethyl]-2,4-dimethyl-1H-pyrrol-3-yl}-propionic acid, 3-[2,4-Dimethyl-5-(6-morpholin-4-yl-2-oxo-1,2-dihydroindol-3-ylidenemethyl)-1H-pyrrol-3-yl]-propionic acid, and 3-[5-Chloro-4-methyl-2-oxo-1,2-dihydroindol-3-ylidenemethyl)-2,4-dimethyl-1H-pyrrol-3-yl]-propionic acid.

18. The method of claim 13, wherein said hyperproliferation disorder is selected from the group consisting of restenosis, fibrosis and psoriasis.

19. The method of claim 13, wherein said inflammatory disorder is selected from the group consisting of osteoarthritis and rheumatoid arthritis.

20. The method of claim 14, wherein said hyperproliferation disorder is selected from the group consisting of restenosis, fibrosis and psoriasis.

21. The method of claim 14, wherein said inflammatory disorder is selected from the group consisting of osteoarthritis and rheumatoid arthritis.

22. The method of claim 13, wherein said immunological disorder is an autoimmune disease.

23. The method of claim 14, wherein said immunological disorder is an autoimmune disease.

* * * * *

UNITED STATES PATENT AND TRADEMARK OFFICE
CERTIFICATE OF CORRECTION

PATENT NO.   : 6,395,734 B1
DATED        : May 28, 2002
INVENTOR(S)  : Peng Cho Tang, Li Sun and Gerald McMahon It is certified that error appears in the above-identified patent and that said Letters Patent is hereby corrected as shown below:

<u>Column 168,</u>
Line 50, should read -- $R^3$, $R^4$, $R^5$ and $R^6$ are independently selected from the group --.

Signed and Sealed this

Thirteenth Day of July, 2004

JON W. DUDAS
*Acting Director of the United States Patent and Trademark Office*